US009212360B2

(12) United States Patent
Tuschl et al.

(10) Patent No.: US 9,212,360 B2
(45) Date of Patent: Dec. 15, 2015

(54) HUMAN MICRORNAS AND METHODS FOR INHIBITING SAME

(71) Applicant: Rockefeller University, New York, NY (US)

(72) Inventors: Thomas Tuschl, Brooklyn, NY (US); Pablo Landgraf, Duesseldorf (DE)

(73) Assignee: The Rockefeller University, New York, NY (US)

( * ) Notice: Subject to any disclaimer, the term of this patent is extended or adjusted under 35 U.S.C. 154(b) by 32 days.

(21) Appl. No.: 13/959,064

(22) Filed: Aug. 5, 2013

(65) Prior Publication Data

US 2014/0045258 A1 Feb. 13, 2014

Related U.S. Application Data

(62) Division of application No. 13/469,689, filed on May 11, 2012, now Pat. No. 8,754,203, which is a division of application No. 11/919,393, filed as application No. PCT/US2006/016767 on May 1, 2006, now Pat. No. 8,247,543.

(60) Provisional application No. 60/714,519, filed on Apr. 29, 2005.

(51) Int. Cl.
*C07H 21/02* (2006.01)
*C07H 21/04* (2006.01)
*C12N 15/63* (2006.01)
*C12N 15/113* (2010.01)

(52) U.S. Cl.
CPC .......... *C12N 15/113* (2013.01); *C12N 2310/14* (2013.01); *C12N 2330/10* (2013.01)

(58) Field of Classification Search
CPC .................................................. C12N 15/113
See application file for complete search history.

(56) References Cited

U.S. PATENT DOCUMENTS

| | | | |
|---|---|---|---|
| 7,217,807 B2 | 5/2007 | Bentwich | |
| 7,365,058 B2 | 4/2008 | Stoffel et al. | |
| 2003/0108923 A1 | 6/2003 | Tuschl et al. | |
| 2005/0222067 A1 | 10/2005 | Pfeffer et al. | |
| 2006/0166910 A1 | 7/2006 | Tuschl et al. | |
| 2006/0257851 A1 | 11/2006 | Bentwich | |
| 2007/0039072 A1 | 2/2007 | Khvorova et al. | |
| 2007/0042381 A1 | 2/2007 | Bentwich et al. | |
| 2007/0287179 A1 | 12/2007 | Tuschl et al. | |
| 2008/0114162 A1 | 5/2008 | Khvorova et al. | |
| 2008/0188428 A1 | 8/2008 | Bentwich | |
| 2008/0318210 A1 | 12/2008 | Bentwich | |
| 2009/0275729 A1 | 11/2009 | Stoffel et al. | |

FOREIGN PATENT DOCUMENTS

| | | |
|---|---|---|
| EP | 1777301 A2 | 4/2007 |
| WO | WO03029459 A2 | 4/2003 |
| WO | WO2004007718 A2 | 1/2004 |
| WO | WO2004044123 A2 | 5/2004 |
| WO | WO2004048511 A2 | 6/2004 |
| WO | WO2005013001 A2 | 2/2005 |
| WO | WO2005013901 A2 | 2/2005 |
| WO | WO2005078397 A1 | 8/2005 |
| WO | WO2005079397 A2 | 9/2005 |
| WO | WO2006033020 A2 | 3/2006 |
| WO | WO2006047454 A2 | 5/2006 |
| WO | WO2006137941 A2 | 12/2006 |
| WO | WO2007073737 A1 | 7/2007 |
| WO | WO2007081204 A2 | 7/2007 |
| WO | WO2007090073 A2 | 8/2007 |
| WO | WO2007109350 A2 | 9/2007 |

OTHER PUBLICATIONS

Fu et al., "Identification of Human Fetal Liver miRNAs by a Novel Method" FEBS Letters 579, 3849-3854 (2005).
Gong et al., "The Role of Small RNAs in Human Diseases: Potential Troublemaker and Therapeutic Tools", Medicinal Research Reviews, vol. 25, No. 3, 361-381 (2005).
Avavin et al., "The Small RNA Profile During *Drosophila Melanagester* Development", Developmental Cell, vol. 5, p. 337-350 (2003).
Beigelman et al., "Chemical Modification of Hammerhead Ribozymes", The Journal of Biological Chemistry, vol. 270, No. 43, p. 25702-25708 (1995).
Liang et al., "Inhibitor RNA Blocks the Protein Translation Mediated by Hepatitis C Virus Internal Ribosome Entry Site in Vivo", World J. Gastroenterol, 10(5), p. 664-667 (2004).
Amarzguioui, Mohammed, et al., "Tolerance for mutations and chemical modifications in a sIRNA", Nucleic Acids Research 2003, 31(2):589-595.
Bartel, David P., "MicroRNAs: Genomics, Biogenesis, Mechanism, and Function", Cell 2004, 116:281-297.
Elbashir, Sayda M., et al., "Duplexes of 21-nucleotide RNAs mediate RNA Interference in cultured mammalian cells", Nature 2001, 411:494-498.
Holen, Torgeir, et al., "Positional effects of short Interfering RNAs targeting the human coagulation trigger Tissue Factor", Nucleic Acids Research 2002, 30(8):1757-1766.
Holen, Torgeir, et al., "Similar behaviour of single-strand and double-strand sIRNAs suggests they act through a common RNAi pathway", Nucleic Acids Research 2003, 31(9)2401-2407.
Howard, Ken, "Unlocking the money-making potential of RNAi", Nature Biotechnology 2003, 21(12):1441-1446.
Kurreck, Jens, "Antisense technologies Improvement through novel chemical modifications", Eur. J. Biochem. 2003, 270:1628-1644.

(Continued)

*Primary Examiner* — Amy Bowman
(74) *Attorney, Agent, or Firm* — Hoffmann & Baron, LLP

(57) ABSTRACT

The invention relates to isolated DNA or RNA molecules comprising at least ten contiguous bases having a sequence in a microRNA shown in SEQ ID NOs: 1-94; 281-374; 467-481; 497-522; or 549, except that up to thirty percent of the bases may be wobble bases, and up to 10% of the contiguous bases may be non-complementary. The invention further relates to modified single stranded microRNA molecules, isolated single stranded anti-microRNA molecules and isolated microRNP molecules. In another embodiment, the invention relates to a method for inhibiting microRNP activity in a cell.

29 Claims, 2 Drawing Sheets

(56) References Cited

OTHER PUBLICATIONS

Meister, Gunter, et al., "Sequence-specific inhibition of microRNA- and sIRNA-induced RNA silencing", RNA 2004, 10:544-550.
Nelson, Peter, et al., "The microRNA world: small is mighty", Trends in Biochemical Sciences 2003, 28(10):534-540.
Database EMBL (Online), 'Homo Sapiens Genomic Sequence Surrounding Notl site, clone NR3-1307C, XP002451881 retrieved from EBI accession No. EMBL: AJ332626: 21/22 residues match Seq Id No: 1; Oct. 2001, abstract.
Database EMBL (Online), 'NISC_is08a05.w1 Soares NMBP1 Mus Musculus cDNA clone Image: 4314537 5', mRNA sequence, XP002451882 retrieved from EBI accession No. EMBL: CB057718; 22/22 residues match Seq Id No. 3; Jan. 2003, abstract.
Database EMBL (Online), CH4#001_G02T7 Canine Heart Normalized CDNA Library in pBluescript Canis familaris CDNA clone CH4#001_,G02 5', mRNA sequence. XP002451883 retrieved from EBI accession No. EMBL: BU751380: 22/22 residues match Seq Id No. 4; Oct. 2002, abstract.
Berezikov et al., "Phylogenetic Shadowing and Computational Identification of Human MicroRNA Genes", Cell, vol. 120, pp. 21-24 (2005).
Seitz, et al., "A Large Imprinted MicroRNA Gene Cluster at the Mouse Elki-Gtl2 Domain", Genome Research, pp. 2. 1-8 (2004).
Xie et al., "Systematic Discovery of Regulatory Motifs in Human Promoters and 3' UTR's by Comparison of Several Mammals", Nature, pp. 1-8 (2005).
Analysis and accompanying remarks by Rosetta Genomics of the sequences presented in Table A2 of the specification of the instant application (Jun. 28, 2007).
Table of information provided by Rosetta regarding the applications submitted in IDS dated Jul. 12, 2007 (Jun. 28, 2007).
Analysis by Rosetta of the sequences of Table A2 compared to those disclosed in Rosetta's patent applications (Jun. 28, 2007).
AC146999, Murphy et al. Oct. 31, 2003, p. 1-67.
Murphy et al., "Coding Potential of Laboratory and Clinical Strains of Human Cytomegalovirus", PNAS, vol. 100, No. 25, p. 14976-14981 (2003).
Tallansky et al., "An Umbraviral Protein, Involved in Long-Distance RNA Movement, Binds Viral RNA and Forms Unique, Protective Ribonudeoprotin Complexes", Journal of Virology, vol. 77, No. 5, p. 3031-3040 (2003).
Paddison et al., "Short Hairpin RNAs (shRNAs) Induce Sequence-Specific Silencing in Mammalian Cells", Genes & Development, 18:948-958 (2002).
Wiebusch et al., "inhibition of Human Cytomegalovirus Replication by Small Interfering RNAs", Journal of General Virology, 85, p. 179-184 (2004).
Vanitharani et al., "Short Interfering RNA-Mediated Interference of Gene Expression and Viral DNA Accumulation in Cultured Plant Cells", PNAS, vol. 100, No. 16, p. 9632-9636 (2003).
Pfitzner et al., "Isolation and Characterization of cDNA Clones Corresponding to Transcripts from the BamHI H and F Regions of the Epstein-Barr Virus Genome", Journal of Virology, vol. 51, No. 9, p. 2902-2909 (1987).
Pfeffer et al., "Indentification of Virus-Encoded microRNAs", Science, vol. 304, p. 734-736 (2004).
Pfeffer et al., "Identification of microRNAs of the Herpesvirus Family", Nature Methods, Published Online DOI:10.1038/NMETH746, p. 1-8.
Zeng, et al., "MicroRNAs and Small Interfering RNAs Can Inhibit mRNA Expression by Similar Mechanisms", PNAS, vol. 100, No. 17, p. 9779-9784 (2003).
U.S. Appl. No. 10/604,945, filed Aug. 27, 2003.
U.S. Appl. No. 10/604,984, filed Aug. 29, 2003.
Boutla et al., "Developmental Defects by Antisense-Mediated Inactivation of Micr-RNAs 2 and 13 in *Drosophila* and the Identification of Putative Target Genes", Nucleic Acids Research, vol. 31, No. 17, pp. 4973-4980 (2003).
Kawasaki et al., "Hes1 is a Target of MicroRNA-23 During Retinoic-Acid-Induced Neutonal Differentiation of NT2 Cells", Nature, vol. 423, No. 6942, pp. 838-842 (2003).
Mourelatos et al., "MiRNPs: A Novel Class of Ribonucleoproteins Containing Numerous microRNAs", Genes and Development, vol. 16, No. 6, pp. 720-728 (2002).
Hutvagner et al., "Sequence-Specific Inhibition of Small HRN function", PLOS Biology, Public Library of Science, vol. 2, No. 4, pp. 465-475 (2004).
Database EMBL (Online), "*Homosapiens* MicroRNAs hsa-RG-33, Complete Sequence", XP002598630 retrieved from EBI Accession No. EMBL:AY785943, Nov. 2004.
Dostie et al., "Numerous MicroRNPs in Neuronal Cells Containing Novel MicroRNAs", RNA, Cold Spring Habor Laboratory Press, vol. 9, No. 2, pp. 180-186 (Feb. 2003).
Cupido, Marinus, Supplementary European Search Report for corresponding European Application No. EP06752071, Aug. 31, 2010, pp. 1-10.
Fu et al., "Identification of Human Fetal Liver miRNAs by a Novel Method", FEBS Letters, Elsevier, vol. 579, No. 17, pp. 3849-3854 (2005).
Oh et al., "Genomic Loss of miR-486 Regulates Tumor Progression and the OLFM4 Antiapoptotic Factor in Gastric Cancer", Clinical Cancer Research, vol. 17, No. 9, pp. 2657-2667 (2011).
Database EMBL [online] "*Homo Sapiens* MicroRNA HSA-MIR-RG-47 Variant 2, Complete Sequence, XP002712280, retrieved from EBI" accession No. EMBL: AY882276, 1 page (Feb. 2005).
Bentwich et al., "Identification of Hundreds of Conserved and Nonconserved Human MicroRNAs", Nature Genetics, vol. 37, No. 7, pp. 766-770 (Jul. 2005).0.
He et al., "The Role of MicroRNA Genes in Papillary Thyroid Carcinoma", PNAS, vol. 102, No. 52, pp. 19075-19080 (Dec. 2005).
Zhang et al., "Selective Suppression of Cervical Cancer Hela Cells by 2-O-β-D-Glucopyranosyl-L-Ascorbic Acid Isolated from the Fruit of *Lycium Barbarum* L", Cell Biol Toxicol 27:102-121 (2011).
U.S. Appl. No. 10/604,945, filed Aug. 27, 2003, Bentwich et al.
U.S. Appl. No. 10/604,984, filed Aug. 29, 2003, Bentwich et al.
U.S. Appl. No. 10/708,952, filed Apr. 2, 2004, Bentwich et al.
U.S. Appl. No. 10/707,003, filed Oct. 30, 2003, Bentwich et al.
U.S. Appl. No. 10/310,188, filed Dec. 5, 2002, Bentwich et al.
U.S. Appl. No. 10/605,840, filed Oct. 30, 2003, Bentwich et al.
U.S. Appl. No. 10/303,778, filed Nov. 26, 2002, Bentwich et al.
U.S. Appl. No. 60/457,788, filed Mar. 27, 2003, Bentwich et al.

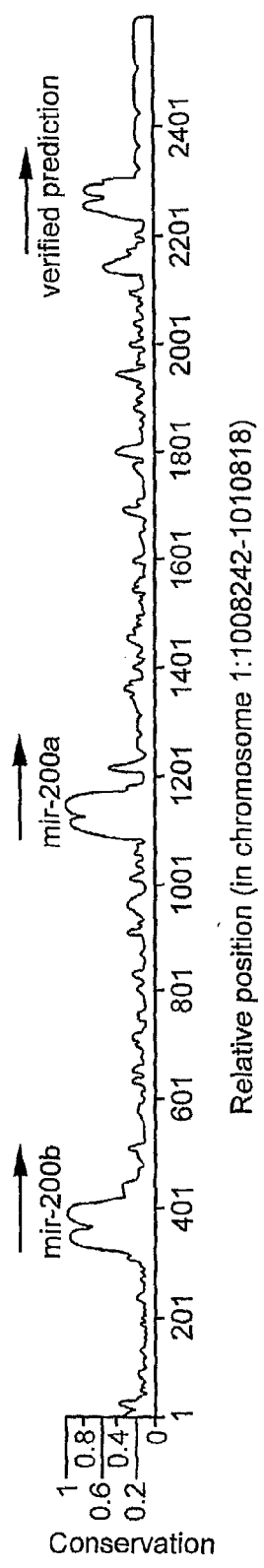
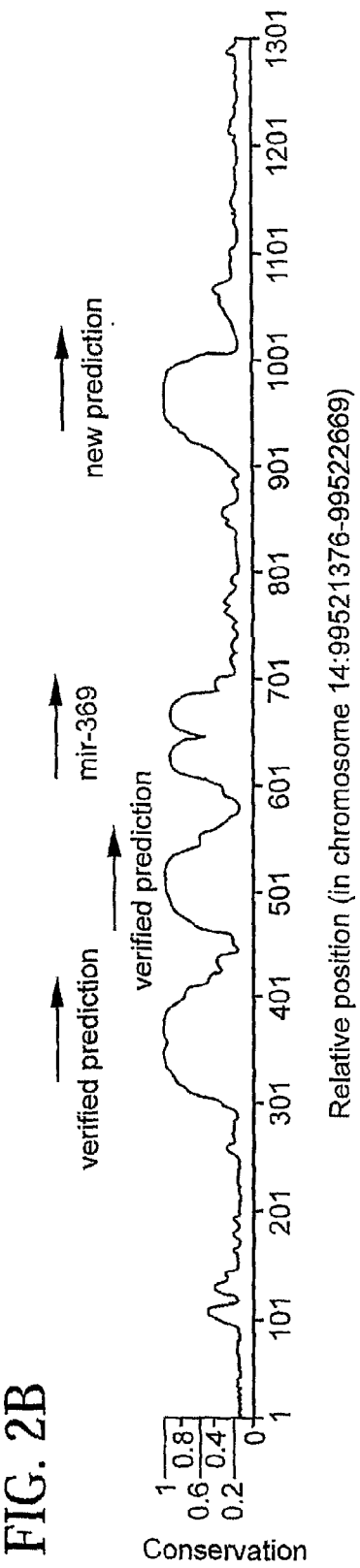
FIG. 2A
FIG. 2B

SEQUENCE LISTING

<160> NUMBER OF SEQ ID NOS: 686

<210> SEQ ID NO 1
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1
caaagugcuc auagugcagg uag                                              23

<210> SEQ ID NO 2
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 2
uaaggugcau cuagugcagu uag                                              23

<210> SEQ ID NO 3
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 3
caacuagacu gugagcuucu ag                                               22

<210> SEQ ID NO 4
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 4
ucgaggagcu cacagucuag ac                                               22

<210> SEQ ID NO 5
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 5
gugcauugcu guugcauugc                                                  20

<210> SEQ ID NO 6
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 6
uggcagugua uuguuagcug gu                                               22

<210> SEQ ID NO 7
<211> LENGTH: 22
<212> TYPE: RNA
<213> ORGANISM: Artificial Sequence

```
<220> FEATURE:
<223> OTHER INFORMATION: Synthetic Sequence

<400> SEQUENCE: 7
aggcagugua uuguuagcug gc                                              22

<210> SEQ ID NO 8
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 8
uauugcacuc gucccggccu cc                                              22

<210> SEQ ID NO 9
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 9
uaauacuguc ugguaaaacc gu                                              22

<210> SEQ ID NO 10
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 10
gugugcggaa augcuucugc ua                                              22

<210> SEQ ID NO 11
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 11
aaaucucugc aggcaaaugu ga                                              22

<210> SEQ ID NO 12
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 12
cagugcaaug auauugucaa agca                                            24

<210> SEQ ID NO 13
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 13
aaaagcugag uugagaggg                                                  19
```

```
<210> SEQ ID NO 14
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 14
auauaauaca accugcuaag ug                                            22

<210> SEQ ID NO 15
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 15
uuuccggcuc gcugggugu gu                                             22

<210> SEQ ID NO 16
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 16
acuguaguau gggcacuucc ag                                            22

<210> SEQ ID NO 17
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 17
aacacaccug guuaaccucu uu                                            22

<210> SEQ ID NO 18
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 18
aucaacagac auuaauuggg cg                                            22

<210> SEQ ID NO 19
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 19
ugucuugcag gccgucaugc ag                                            22

<210> SEQ ID NO 20
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 20
aucaugaugg gcuccucggu gu                                              22

<210> SEQ ID NO 21
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 21
aaaccguuac cauuacugag uu                                              22

<210> SEQ ID NO 22
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 22
uguuugcaga ggaaacugag ac                                              22

<210> SEQ ID NO 23
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 23
agguuguccg uggugaguuc gc                                              22

<210> SEQ ID NO 24
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 24
uagugcaaua uugcuuauag ggu                                             23

<210> SEQ ID NO 25
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 25
ugcggggcua gggcuaacag ca                                              22

<210> SEQ ID NO 26
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 26
caugccuuga guguaggacc gu                                              22

<210> SEQ ID NO 27
```

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 27
uuaauaugua cugacaaagc gu                                              22

<210> SEQ ID NO 28
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 28
auguugggag cgggcagguu gg                                              22

<210> SEQ ID NO 29
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 29
uccgagccug ggucucccuc uu                                              22

<210> SEQ ID NO 30
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 30
cgugggccug auguggugcu gg                                              22

<210> SEQ ID NO 31
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 31
aguaccacgu gucagggcca ca                                              22

<210> SEQ ID NO 32
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 32
aaacauucgc ggugcacuuc uu                                              22

<210> SEQ ID NO 33
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 33
```

```
aaaggauucu gcugucgguc cc                                              22

<210> SEQ ID NO 34
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 34
aaucguacag ggucauccac uu                                              22

<210> SEQ ID NO 35
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 35
aaucauacag ggacauccag uu                                              22

<210> SEQ ID NO 36
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 36
uaugugccuu uggacuacau cg                                              22

<210> SEQ ID NO 37
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 37
uuuugcgaug uguuccuaau au                                              22

<210> SEQ ID NO 38
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 38
gcaggaacuu gugagucucc                                                 20

<210> SEQ ID NO 39
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 39
aauggcgcca cuagguugu gc                                               22

<210> SEQ ID NO 40
<211> LENGTH: 22
<212> TYPE: RNA
```

```
<213> ORGANISM: Artificial Sequence
<220> FEATURE:
<223> OTHER INFORMATION: Synthetic Sequence

<400> SEQUENCE: 40
uuggggaaac ggccgcugag ug                                               22

<210> SEQ ID NO 41
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 41
cuguaugccc ucaccgcuca gc                                               22

<210> SEQ ID NO 42
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 42 aggggggaaag uucuauaguc cu                                              22

<210> SEQ ID NO 43
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 43
uccauuacac uacccugccu cu                                               22

<210> SEQ ID NO 44
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 44
gcggcggcgg cggaggcugc ug                                               22

<210> SEQ ID NO 45
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 45
cggcggcggc ggcggcggcu gu                                               22

<210> SEQ ID NO 46
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 46
ggagaaauua uccuuggugu gu                                               22
```

<210> SEQ ID NO 47
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 47
uugugacaga uugauaacug aa                                              22

<210> SEQ ID NO 48
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 48
ucggggauca ucaugucacg ag                                              22

<210> SEQ ID NO 49
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 49
auugacacuu cugugaguag ag                                              22

<210> SEQ ID NO 50
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 50
augcugacau auuuacuaga gg                                              22

<210> SEQ ID NO 51
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 51
ucuaguaaga guggcagucg aa                                              22

<210> SEQ ID NO 52
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 52
gagcuuauuc auaaaagugc ag                                              22

<210> SEQ ID NO 53
<211> LENGTH: 22
<212> TYPE: RNA
<213> ORGANISM: Artificial Sequence
<220> FEATURE:

<223> OTHER INFORMATION: Synthetic Sequence

<400> SEQUENCE: 53
uaauuuuaug uauaagcuag uc                                        22

<210> SEQ ID NO 54
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 54
uggggcggag cuuccggagg cc                                        22

<210> SEQ ID NO 55
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 55
ccauggaucu ccaggugggu ca                                        22

<210> SEQ ID NO 56
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 56
ugaaggucua cugugugcca gg                                        22

<210> SEQ ID NO 57
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 57
aggaagcccu ggaggggcug ga                                        22

<210> SEQ ID NO 58
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 58
uccgguucuc agggcuccac cu                                        22

<210> SEQ ID NO 59
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 59
accaggaggc ugaggcnccu ca                                        22

```
<210> SEQ ID NO 60
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 60
ucaggcucag uccccucccg au                                              22

<210> SEQ ID NO 61
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 61
uccuguacug agcugccccg a                                               21

<210> SEQ ID NO 62
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 62
cggggcagcu caguacagga u                                               21

<210> SEQ ID NO 63
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 63
ucgaccggac cucgaccggc u                                               21

<210> SEQ ID NO 64
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 64
cucggcgugg cgucggucgu gg                                              22

<210> SEQ ID NO 65
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 65
uuugaaaggc uauuucuugg uc                                              22

<210> SEQ ID NO 66
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 66
cgaaaacagc aauuaccuuu gc                                              22

<210> SEQ ID NO 67
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 67
aaagcaugcu ccaguggcgc a                                               21

<210> SEQ ID NO 68
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 68
cggcucuggg ucugugggga gc                                              22

<210> SEQ ID NO 69
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 69
cagagaggac cacuauggcg gg                                              22

<210> SEQ ID NO 70
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 70
auugccaucc ccuauggacc ag                                              22

<210> SEQ ID NO 71
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 71
ugucuacuac uggagacacu gg                                              22

<210> SEQ ID NO 72
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 72
uuagggcccu ggcuccaucu cc                                              22

<210> SEQ ID NO 73
<211> LENGTH: 22
```

```
<212> TYPE: RNA
<213> ORGANISM: Artificial Sequence
<220> FEATURE:
<223> OTHER INFORMATION: Synthetic Sequence

<400> SEQUENCE: 73
gugaacgggc gccaucccga gg                                              22

<210> SEQ ID NO 74
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 74
ucagcaaaca uuuauugugu gc                                              22

<210> SEQ ID NO 75
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 75
ugggaucucc gggucuugg uu                                               22

<210> SEQ ID NO 76
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 76
cugcccuggc ccgagggacc ga                                              22

<210> SEQ ID NO 77
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 77
ugagugugug ugugagug ug                                                22

<210> SEQ ID NO 78
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 78
cacgcucaug cacacaccca ca                                              22

<210> SEQ ID NO 79
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 79
```
aaggcagggc ccccgcuccc cg                                              22

<210> SEQ ID NO 80
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 80 ugugggccg cagaacaugu gc                                               22

<210> SEQ ID NO 81
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 81
cgggucggag uuagcucaag cgg                                             23

<210> SEQ ID NO 82
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 82
cuaucugucc aucucugugc ug                                              22

<210> SEQ ID NO 83
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 83
ugaaacauac acgggaaacc uc                                              22

<210> SEQ ID NO 84
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 84
auucugcauu uuuagcaagu uc                                              22

<210> SEQ ID NO 85
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 85
gcgacccaua cuugguuuca ga                                              22

<210> SEQ ID NO 86
<211> LENGTH: 22
<212> TYPE: RNA
<213> ORGANISM: Artificial Sequence

```
<220> FEATURE:
<223> OTHER INFORMATION: Synthetic Sequence

<400> SEQUENCE: 86
aacaucacag caagucugug cu                                              22

<210> SEQ ID NO 87
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 87
uauaccucag uuuuaucagg ug                                              22

<210> SEQ ID NO 88
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 88
ccuggaaaca cugagguugu gu                                              22

<210> SEQ ID NO 89
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 89
agacccuggu cugcacucua uc                                              22

<210> SEQ ID NO 90
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 90 agugggaac ccuuccauga gg                                               22

<210> SEQ ID NO 91
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 91
guguugaaac aaucucuacu ga                                              22

<210> SEQ ID NO 92
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 92
auggauuucu uugugaauca cc                                              22
```

<210> SEQ ID NO 93
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 93
aagacgggag gaaagaaggg aa                                             22

<210> SEQ ID NO 94
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 94
gugacaucac auauacggca gc                                             22

<210> SEQ ID NO 95
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 95
cuuguguuaa ggugcaucua gugcaguuag ugaagcagcu uagaaucuac ugcccuaaau     60
gccccuucug gcacagg                                                   77

<210> SEQ ID NO 96
<211> LENGTH: 111
<212> TYPE: RNA
<213> ORGANISM: Artificial Sequence
<220> FEATURE:
<223> OTHER INFORMATION: Synthetic Sequence

<400> SEQUENCE: 96
gauaagauug gguccuagua guaccaaagu gcucauagug cagguaguuu uggcaugacu     60
cuacuguagu augggcacuu ccaguacucu uggauaacaa aucucuuguu g              111

<210> SEQ ID NO 97
<211> LENGTH: 108
<212> TYPE: RNA
<213> ORGANISM: Artificial Sequence
<220> FEATURE:
<223> OTHER INFORMATION: Synthetic Sequence

<400> SEQUENCE: 97
gggguccccc cugcuggccg caggugcucu gacgagguug cacuacugug cucugagaag     60
cagugcaaug auauugucaa agcaucuggg accagccuug gggaucuc                 108

<210> SEQ ID NO 98
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 98
gguaccugaa gagagguuuu cugggguuucu guuucuuuaa ugaggacgaa acacaccugg    60
uuaaccucuu uuccaguauc                                                80

<210> SEQ ID NO 99
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 99
gugguaccug aagagagguu uucuggguuu cuguuucuuu auugaggacg aaacacaccu    60
gguuaaccuc uuuuccagua ucaa    84

<210> SEQ ID NO 100
<211> LENGTH: 70
<212> TYPE: RNA
<213> ORGANISM: Artificial Sequence
<220> FEATURE:
<223> OTHER INFORMATION: Synthetic Sequence

<400> SEQUENCE: 100
acucggaugg auauaauaca accugcuaag uguccuagca cuuagcaggu uguauuauca    60
uuguccgugu    70

<210> SEQ ID NO 101
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 101
cacauuguag gccucauuaa auguuuguug aaugaaaaaa ugaaucauca acagacauua    60
auggggcgcc ugcucugug    79

<210> SEQ ID NO 102
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 102
ccagauccua gaacccuauc aauauugucu cugcugugua aauaguucug aguagugcaa    60
uauugcuuau aggguuuugg uguuugg    87

<210> SEQ ID NO 103
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 103
ggcggccccg cggugcauug cuguugcauu gcacgugugu gaggcgggug cagugccucg    60
gcagugcagc ccggagccgg c    81

<210> SEQ ID NO 104
<211> LENGTH: 80
<212> TYPE: RNA
<213> ORGANISM: Artificial Sequence
<220> FEATURE:
<223> OTHER INFORMATION: Synthetic Sequence

```
<400> SEQUENCE: 104
ggguugggca aggugcgggg cuagggcuaa cagcagucuu acugaagguu uccuggaaac    60
cacgcacaug cguugccac                                                 80

<210> SEQ ID NO 105
<211> LENGTH: 62
<212> TYPE: RNA
<213> ORGANISM: Artificial Sequence
<220> FEATURE:
<223> OTHER INFORMATION: Synthetic Sequence

<400> SEQUENCE: 105
cuccaugccu ugaguguagg accguuggca ucuuaauuac ccucccacac ccaaggcuug    60
ca                                                                   62

<210> SEQ ID NO 106
<211> LENGTH: 97
<212> TYPE: RNA
<213> ORGANISM: Artificial Sequence
<220> FEATURE:
<223> OTHER INFORMATION: Synthetic Sequence

<400> SEQUENCE: 106
uuauugugaa auaugucauu aauauguacu gacaaagcgu aucuguguaa uaaauaugcu    60
uuuugucagu acauguuaau gguauauuuc auaacaa                             97

<210> SEQ ID NO 107
<211> LENGTH: 75
<212> TYPE: RNA
<213> ORGANISM: Artificial Sequence
<220> FEATURE:
<223> OTHER INFORMATION: Synthetic Sequence

<400> SEQUENCE: 107
gcggcugcug gacccacccg gccgggaaua gugcuccugg uuguuccgg cucgcguggg     60 ugugucggcg gcggg                                                     75

<210> SEQ ID NO 108
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 108
cgcccccacg uggccccgcc cccugaggcc ggcgcugccg ccauguuggg agcgggcagg    60
uugggagcg                                                            69

<210> SEQ ID NO 109
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 109
ggggcgggag gggggucccc ggugcucgga ucucgagggu gcuuauuguu cggaccgagc    60
cugggucucc cucuucccccc c                                             81

<210> SEQ ID NO 110
<211> LENGTH: 118
```

```
<212> TYPE: RNA
<213> ORGANISM: Artificial Sequence
<220> FEATURE:
<223> OTHER INFORMATION: Synthetic Sequence

<400> SEQUENCE: 110
ugcucuggau accugugugu gaugagcugg caguguauug uuagcgguu gaauauguga        60 auggcaucgg cuaacaugca acugcugucu uauugcauau acaaugaaca ucagagug        118

<210> SEQ ID NO 111
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 111
ugaaucaggu aggcagugua uuguuagcug gcugcuuggg ucaagucagc agccacaacu        60
acccugccac uugcuucu                                                    78

<210> SEQ ID NO 112
<211> LENGTH: 89
<212> TYPE: RNA
<213> ORGANISM: Artificial Sequence
<220> FEATURE:
<223> OTHER INFORMATION: Synthetic Sequence

<400> SEQUENCE: 112
gccaccuucc gagccuccag uaccacgugu cagggccaca ugagcugggc cucgugggcc        60
ugauguggug cugggggccuc agggggucug                                      89

<210> SEQ ID NO 113
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 113
gcgguacuua augagaaguu gcccguguuu uuucgcuuu auuugugacg aaacauucgc        60
ggugcacuuc uuuuucagua uccu                                             84

<210> SEQ ID NO 114
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 114
ccaacgucag ggaaaggauu cugcugucgg ucccacucca aaguucacag aauggguggu       60
gggcacagaa ucuggacucu                                                  80

<210> SEQ ID NO 115
<211> LENGTH: 158
<212> TYPE: RNA
<213> ORGANISM: Artificial Sequence
<220> FEATURE:
<223> OTHER INFORMATION: Synthetic Sequence

<400> SEQUENCE: 115
cggccgaugg gcgucuuacc agacauggu agaccuggcc cucugcuaa uacugucugg        60
```

| | |
|---|---|
| uaaaaccguc cauccgcugc ggccgauggg cgucuuacca gacaugguua gaccuggccc | 120 |
| ucugucuaau acugucuggu aaaaccgucc auccgcug | 158 |

<210> SEQ ID NO 116
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 116

| | |
|---|---|
| ugcuucugug ugauauguuu gauauugggu uguuuaauua ggaaccaacu aaaugucaaa | 60 |
| cauauucuua cagcagca | 78 |

<210> SEQ ID NO 117
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 117

| | |
|---|---|
| gcagacugga aaaucucugc aggcaaaugu gaugucacug aggaaaucac acacuuaccc | 60 |
| guagagauuc uacagucuga | 80 |

<210> SEQ ID NO 118
<211> LENGTH: 111
<212> TYPE: RNA
<213> ORGANISM: Artificial Sequence
<220> FEATURE:
<223> OTHER INFORMATION: Synthetic Sequence

<400> SEQUENCE: 118

| | |
|---|---|
| cuuucuuuuc cgugcuaacc uuugguacuu ggagaguggu uaucccuguc cuguucguuu | 60 |
| ugcucauguc gaaucguaca gggucaucca cuuuucagu aucaagagcg c | 111 |

<210> SEQ ID NO 119
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 119

| | |
|---|---|
| ugaagagugg uuaucccugc uguguucgcu uaauuauga cgaaucauac agggacaucc | 60 |
| aguuuuuca | 69 |

<210> SEQ ID NO 120
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 120

| | |
|---|---|
| cccuggcgug aggguaugug ccuuuggacu acaucgugga agccagcacc augcagucca | 60 |
| ugggcauaua cacuugccuc aagg | 84 |

<210> SEQ ID NO 121
<211> LENGTH: 162
<212> TYPE: RNA
<213> ORGANISM: Artificial Sequence

```
<220> FEATURE:
<223> OTHER INFORMATION: Synthetic Sequence

<400> SEQUENCE: 121
gaugcuaaac uauuuuugcg auguguuccu aauauguaau auaaauguau uggggacauu      60
uugcauucau aguuuuguau cgaugcuaaa cuauuuuugc gauguguucc aauauguaa       120 uauaaaugua uuggggacau uuugcauuca uaguuuugua uc                        162

<210> SEQ ID NO 122
<211> LENGTH: 72
<212> TYPE: RNA
<213> ORGANISM: Artificial Sequence
<220> FEATURE:
<223> OTHER INFORMATION: Synthetic Sequence

<400> SEQUENCE: 122
cuugggaaug gcaaggaaac cguuaccauu acugaguuua guaaugguaa gguucucuu       60 gcuauaccca ga                                                         72

<210> SEQ ID NO 123
<211> LENGTH: 93
<212> TYPE: RNA
<213> ORGANISM: Artificial Sequence
<220> FEATURE:
<223> OTHER INFORMATION: Synthetic Sequence

<400> SEQUENCE: 123
ccggggagaa guacggugag ccugucauua uucagagagg cuagauccuc uguguugaga      60
aggaucauga ugggcucccuc gguguucucc agg                                 93

<210> SEQ ID NO 124
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 124
uccugcuugu ccugcgaggu gucuugcagg ccgucaugca ggccacacug acgguaacgu      60
ugcaggucgu cuugcagggc uucucgcaag acgacauccu caucaccaac gacg           114

<210> SEQ ID NO 125
<211> LENGTH: 85
<212> TYPE: RNA
<213> ORGANISM: Artificial Sequence
<220> FEATURE:
<223> OTHER INFORMATION: Synthetic Sequence

<400> SEQUENCE: 125
gcuaagcacu uacaacuguu ugcagaggaa acugagacuu uguaacuaug ucucagucuc      60
aucugcaaag aaguaagugc uuugc                                           85

<210> SEQ ID NO 126
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 126
gcaggaaugc ugcgagcagu gccaccucau gguacucgga gggagguugu ccguggugag      60
```
uucgcauuau uuaaugaugc                                                    80

<210> SEQ ID NO 127
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 127
gugcauuugc aggaacuugu gagucuccua uugaaaauga acaggagacu gaugaguucc        60
cgggaacac                                                                69

<210> SEQ ID NO 128
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 128
cuaugcacug cacaacccua ggagagggug ccauucacau agacuauaau ugaauggcgc        60
cacuaggguu gugcagugca caa                                                83

<210> SEQ ID NO 129
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 129
ggguuugggg aaacggccgc ugagugaggc gucggcugug uuucucaccg cggucuuuuc        60
cucccacuc                                                                69

<210> SEQ ID NO 130
<211> LENGTH: 97
<212> TYPE: RNA
<213> ORGANISM: Artificial  Sequence
<220> FEATURE:
<223> OTHER INFORMATION: Synthetic Sequence

<400> SEQUENCE: 130
cuuggugacg cuguaugccc ucaccgcuca gccccugggg cuggcuuggc agacaguaca        60
gcauccaggg gagucaaggg caugggcga gaccaga                                  97

<210> SEQ ID NO 131
<211> LENGTH: 94
<212> TYPE: RNA
<213> ORGANISM: Artificial Sequence
<220> FEATURE:
<223> OTHER INFORMATION: Synthetic Sequence

<400> SEQUENCE: 131
gguaagggua gagggaugag ggggaaaguu cuauaguccu guaauuagau cucaggacua        60
uagaacuuuc ccccucaucc cucugcccuc uacc                                    94

<210> SEQ ID NO 132
<211> LENGTH: 94
<212> TYPE: RNA
<213> ORGANISM: Artificial Sequence
<220> FEATURE:
<223> OTHER INFORMATION: Synthetic Sequence

```
<400> SEQUENCE: 132
guagagggca gagggaugag ggggaaaguu cuauaguccu gagaucuaau uacaggacua    60
uagaacuuuc ccccucaucc cucuacccuu acca                                94

<210> SEQ ID NO 133
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 133
ggcccgcacu cucccauua cacucccug ccucuucucc augagaggca gcggggugua     60
guggauagag cacggguu                                                  78

<210> SEQ ID NO 134
<211> LENGTH: 86
<212> TYPE: RNA
<213> ORGANISM: Artificial Sequence
<220> FEATURE:
<223> OTHER INFORMATION: Synthetic Sequence

<400> SEQUENCE: 134
gcggcggcgg cggaggcugc ugcugggggcg gcugcugcug gggcggcugc ggcggcggcu  60
gcugcggggg cugcugcugc uguugc                                        86

<210> SEQ ID NO 135
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 135
gcggcugcgg cggcggcgga ggcugcggcg gcgaccgugg cagaggcggu ggcggaggcc   60
uccguggcgg aggcggaagc                                                80

<210> SEQ ID NO 136
<211> LENGTH: 86
<212> TYPE: RNA
<213> ORGANISM: Artificial Sequence
<220> FEATURE:
<223> OTHER INFORMATION: Synthetic Sequence

<400> SEQUENCE: 136
acucuauaaa ucuaguggaa acauuucugc acaaacuaga uucuggacac cagugugcgg   60
aaaugcuucu gcuacauuuu uagggu                                         86

<210> SEQ ID NO 137
<211> LENGTH: 88
<212> TYPE: RNA
<213> ORGANISM: Artificial Sequence
<220> FEATURE:
<223> OTHER INFORMATION: Synthetic Sequence

<400> SEQUENCE: 137
guuucauacu ugaggagaaa uuaccuugg uguuucgcu uuauuuauga ugaaucauac     60
aaggacaauu ucuuuuugag uaucaaau                                      88

<210> SEQ ID NO 138
```

```
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 138
ucucagacau cucggggauc aucaugucac gagauaccag ugugcacuug ugacagauug    60
auaacugaaa ggucuggga                                                 79

<210> SEQ ID NO 139
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 139
uugucugugg uacccuacuc uggagaguga caaucaugua uaacuaaauu ugauugacac    60
uucugugagu agaguaacgc augacac                                        87

<210> SEQ ID NO 140
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 140
uugucugugg uacccuacuc uggagaguga caaucaugua uaauuaaauu ugauugacac    60
uucugugagu agaguaacgc augacac                                        87

<210> SEQ ID NO 141
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 141
cuuccucaug cugacauauu uacuagaggg uaaaauuaau aaccuucuag uaagaguggc    60
agucgaaggg aag                                                       73

<210> SEQ ID NO 142
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 142
cagucagaaa ugagcuuauu cauaaaagug caguagguga aagucaaucu guaauuuuau    60
guauaagcua gucucugauu g                                              81

<210> SEQ ID NO 143
<211> LENGTH: 153
<212> TYPE: RNA
<213> ORGANISM: Artificial Sequence
<220> FEATURE:
<223> OTHER INFORMATION: Synthetic Sequence

<400> SEQUENCE: 143
gcuccgcccc acgucgcaug cgccccggga acgcguggggg cggagcuucc ggaggcccccg   60
```
cucugcugcc gacccugugg agcggagggu gaagccuccg gaugccaguc ccucaucgcu    120
ggccuggucg cgcuguggcg aaggggggcgg agc                                153

<210> SEQ ID NO 144
<211> LENGTH: 153
<212> TYPE: RNA
<213> ORGANISM: Artificial Sequence
<220> FEATURE:
<223> OTHER INFORMATION: Synthetic Sequence

<400> SEQUENCE: 144
gcuccgcccc acgucgcaug cgccccggga acgcgugggg cggagcuucc ggaggccccg    60
cccugcugcc gacccugugg agcggagggu gaagccuccg gaugccaguc ccucaucgcu   120
ggcccggucg cgcuguggcg aaggggggcgg agc                                153

<210> SEQ ID NO 145
<211> LENGTH: 154
<212> TYPE: RNA
<213> ORGANISM: Artificial Sequence
<220> FEATURE:
<223> OTHER INFORMATION: Synthetic Sequence

<400> SEQUENCE: 145
cgcuccgccc cacgucgcau gcgccccggg aaagcguggg gcggagcuuc cggaggcccc    60
gcccugcugc cgacccugug gagcggaggg ugaagccucc ggaugccagu cccucaucgc   120
uggcccgguc gcgcugugc gaaggggggcg gagc                                154

<210> SEQ ID NO 146
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 146
auuguucgac accauggauc uccaggugg ucaaguuuag agaugcacca accuggagga    60
cuccaugcug uugagcugu                                                 79

<210> SEQ ID NO 147
<211> LENGTH: 75
<212> TYPE: RNA
<213> ORGANISM: Artificial Sequence
<220> FEATURE:
<223> OTHER INFORMATION: Synthetic Sequence

<400> SEQUENCE: 147
cagggcuuug uacaugguag gcuuucauuc auucguuugc acauucggug aaggcuacu    60 gugugccagg cccug                                                     75

<210> SEQ ID NO 148
<211> LENGTH: 100
<212> TYPE: RNA
<213> ORGANISM: Artificial Sequence
<220> FEATURE:
<223> OTHER INFORMATION: Synthetic Sequence

<400> SEQUENCE: 148
cuggcaggcc aggaagagga ggaagcccug gaggggcugg aggugaugga uguuuccuc    60 cgguucucag ggcuccaccu cuuucgggcc guagagccag                         100

```
<210> SEQ ID NO 149
<211> LENGTH: 91
<212> TYPE: RNA
<213> ORGANISM: Artificial Sequence
<220> FEATURE:
<223> OTHER INFORMATION: Synthetic Sequence

<400> SEQUENCE: 149
agaggagggu cccucgagg ggucucugcc ucuacccagg acucuuucau gaccaggagg     60
cugaggcccc ucacaggcgg cuucuuacuc u                                  91

<210> SEQ ID NO 150
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 150
ucgucaggcu caguccccuc ccgauaaacc ccuaaauagg gacuuucccg gggggugacc     60
cuggcuuuuu uggcga                                                   76

<210> SEQ ID NO 151
<211> LENGTH: 105
<212> TYPE: RNA
<213> ORGANISM: Artificial Sequence
<220> FEATURE:
<223> OTHER INFORMATION: Synthetic Sequence

<400> SEQUENCE: 151
cugacuccca ccccgaguau ccuguacuga gcugccccga gcugggcagc augaagggcc     60
ucggggcagc ucaguacagg augccccagg gaggauggag aucag                   105

<210> SEQ ID NO 152
<211> LENGTH: 100
<212> TYPE: RNA
<213> ORGANISM: Artificial Sequence
<220> FEATURE:
<223> OTHER INFORMATION: Synthetic Sequence

<400> SEQUENCE: 152
cuccauccuc ccuggggcau ccuguacuga gcugccccga ggcccuucau gcugcccagc     60
ucggggcagc ucaguacagg auacucgggg ugggagucag                         100

<210> SEQ ID NO 153
<211> LENGTH: 151
<212> TYPE: RNA
<213> ORGANISM: Artificial Sequence
<220> FEATURE:
<223> OTHER INFORMATION: Synthetic Sequence

<400> SEQUENCE: 153
uucaucaaga cccagcugag ucacugucac ugccuaccaa ucucgaccgg accucgaccg     60
gcucgucugu guugccaauc gacucggcgu ggcgucgguc gugguagaua ggcggucaug    120
cauacgaauu uucagcucuu guucggguga c                                  151

<210> SEQ ID NO 154
<211> LENGTH: 81
<212> TYPE: RNA
<213> ORGANISM: Artificial Sequence
<220> FEATURE:
<223> OTHER INFORMATION: Synthetic Sequence
```

```
<400> SEQUENCE: 154
agaaucaucu cucccagaua auggcacucu caaacaaguu uccaaauugu uugaaaggcu      60
auuucuuggu cagaugacuc u                                                81

<210> SEQ ID NO 155
<211> LENGTH: 104
<212> TYPE: RNA
<213> ORGANISM: Artificial Sequence
<220> FEATURE:
<223> OTHER INFORMATION: Synthetic Sequence

<400> SEQUENCE: 155
ccuagauaag uuauuaggug ggugcaaagg uaauugcagu uuucccauu auuuaauug       60 cgaaaacagc aauuaccuuu gcaccaaccu gauggagucc cccu                     104

<210> SEQ ID NO 156
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 156
gcccucaagg agcuuacaau cuagcugggg guaaaugacu ugcacaugaa cacaacuaga    60
cugugagcuu cuagagggc                                                 79

<210> SEQ ID NO 157
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 157
cgcgaggccg ggguucgagcg cuucaguagc ucauggcucu guagagugcg cauggccaag   60
caaaggaaag caugcuccag uggcgca                                        87

<210> SEQ ID NO 158
<211> LENGTH: 66
<212> TYPE: RNA
<213> ORGANISM: Artificial Sequence
<220> FEATURE:
<223> OTHER INFORMATION: Synthetic Sequence

<400> SEQUENCE: 158
aguaaccacu uaguguguau ugacuugca gaauuuucag aauuuaaagc augcuccagu     60
ggcgca                                                               66

<210> SEQ ID NO 159
<211> LENGTH: 86
<212> TYPE: RNA
<213> ORGANISM: Artificial Sequence
<220> FEATURE:
<223> OTHER INFORMATION: Synthetic Sequence

<400> SEQUENCE: 159
cggggcgcgu cgcccccuc aguccaccag agcccggaua cccagaaaau ucggcucugg     60 gucuguggg agcgaaaugc aaccca                                          86

<210> SEQ ID NO 160
```

```
<211> LENGTH: 95
<212> TYPE: RNA
<213> ORGANISM: Artificial Sequence
<220> FEATURE:
<223> OTHER INFORMATION: Synthetic Sequence

<400> SEQUENCE: 160
uuacuguguc auuguugcug ucauugcuac ugaggaguac ugaccagaau caucugcaac    60
ucuuaguugg cagagaggac cacuauggcg gguag                              95

<210> SEQ ID NO 161
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 161
ugggccagau ugccaucccc uauggaccag aagccaagga ucucucuagu gauggucaga    60
gggcccaaau ggcagggaua ccca                                          84

<210> SEQ ID NO 162
<211> LENGTH: 65
<212> TYPE: RNA
<213> ORGANISM: Artificial Sequence
<220> FEATURE:
<223> OTHER INFORMATION: Synthetic Sequence

<400> SEQUENCE: 162
gcuucugucu acacuggag acacugguag uauaaaaccc agagucucca guaauggacg     60
ggagc                                                               65

<210> SEQ ID NO 163
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 163
cuggguuagg gcccuggcuc caucuccuuu aggaaaaccu ucugugggga gugggcuuc     60 gacccuaacc cag                                                      73

<210> SEQ ID NO 164
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 164
gcagauccuu gggagcccug uuagacucug gauuuuacac uuggagugaa cgggcgccau    60
cccgaggcuu ugc                                                      73

<210> SEQ ID NO 165
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 165
aguaggccuc aguaaauguu uauuagauga auaaaugaau gacucaucag caaacauuua    60
```

```
uugugugccu gcu                                                     73

<210> SEQ ID NO 166
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 166
ccugggcucu gaccugagac cucugggouc ugagcuguga uguugcucuc gagcugggau    60
cuccgggguc uugguucagg g                                            81

<210> SEQ ID NO 167
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 167
gguguuagcc cugcggcccc acgcaccagg guaagagaga cucucgcuuc cugcccuggc    60
ccgagggacc gacuggcugg gcc                                          83

<210> SEQ ID NO 168
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 168
ugggugcggg cgugugagug ugugugugug aguguguguc gcuccggguc cacgcucaug    60
cacacaccca cacgcccaca cuca                                         84

<210> SEQ ID NO 169
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 169
ugggugcggg cgugugagug ugugugugug aguguguguc gcuccggguc cacgcucaug    60
cacacaccca cacgcccaca cuca                                         84

<210> SEQ ID NO 170
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 170
gggcccggcc ccaggagcgg ggccugggca gccccgugug uugaggaagg aaggcagggc    60
ccccgcuccc cgggccu                                                 77

<210> SEQ ID NO 171
<211> LENGTH: 50
<212> TYPE: RNA
<213> ORGANISM: Artificial Sequence
<220> FEATURE:
```

<223> OTHER INFORMATION: Synthetic Sequence

<400> SEQUENCE: 171
ccuucucuuc ucaguucuuc cccaaguuag gaaaagcuga guugagaggg          50

<210> SEQ ID NO 172
<211> LENGTH: 66
<212> TYPE: RNA
<213> ORGANISM: Artificial Sequence
<220> FEATURE:
<223> OTHER INFORMATION: Synthetic Sequence

<400> SEQUENCE: 172
gucucucuuc agggcucccg agacacagaa acagacaccu gcccucgagg agcucacagu          60
cuagac          66

<210> SEQ ID NO 173
<211> LENGTH: 63
<212> TYPE: RNA
<213> ORGANISM: Artificial Sequence
<220> FEATURE:
<223> OTHER INFORMATION: Synthetic Sequence

<400> SEQUENCE: 173
aaagauggug ggccgcagaa caugugcuga guucgugcca uaugucugcu gaccaucacc          60
uuu          63

<210> SEQ ID NO 174
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 174
uccuacccgg gucggaguua gcucaagcgg uuaccuccuc augccggacu uucuaucugu          60
ccaucucugu gcuggggsuuc gagacccgcg ggugcuuacu gacccuuuua ugca          114

<210> SEQ ID NO 175
<211> LENGTH: 102
<212> TYPE: RNA
<213> ORGANISM: Artificial Sequence
<220> FEATURE:
<223> OTHER INFORMATION: Synthetic Sequence

<400> SEQUENCE: 175
ccgggccccg ggcgggcggg agggacggga cgcggugcag uguuguuuuu uccccgcca          60 auauugcacu cgucccggcc uccggccccc ccggcccccc gg          102

<210> SEQ ID NO 176
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 176
gauacucgaa ggagagguug uccguguugu cuucucuuua uuuaugauga aacauacacg          60
ggaaaccucu uuuuaguau c          81

<210> SEQ ID NO 177
<211> LENGTH: 91

```
<212> TYPE: RNA
<213> ORGANISM: Artificial Sequence
<220> FEATURE:
<223> OTHER INFORMATION: Synthetic Sequence

<400> SEQUENCE: 177 auuucauca ccuagggauc uuguuaaaaa gcagauucug auucagggac caagauucug      60 cauuuuagc aaguucucaa gugaugcuaa u                                    91

<210> SEQ ID NO 178
<211> LENGTH: 93
<212> TYPE: RNA
<213> ORGANISM: Artificial Sequence
<220> FEATURE:
<223> OTHER INFORMATION: Synthetic Sequence

<400> SEQUENCE: 178
gugcucuccu ggcccaugaa aucaagcgug ggugagaccu ggucagaac gggaaggcga      60 cccauacuug guuucagagg cugugagaau aac                                 93

<210> SEQ ID NO 179
<211> LENGTH: 110
<212> TYPE: RNA
<213> ORGANISM: Artificial Sequence
<220> FEATURE:
<223> OTHER INFORMATION: Synthetic Sequence

<400> SEQUENCE: 179
ccccugugcc uugggcgggc ggcuguuaag acuugcagug auguuaacu ccucuccacg      60 ugaacaucac agcaagucug ugcugcuucc cgucccuacg cugccugggc               110

<210> SEQ ID NO 180
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 180
guuuaguggu acuauaccuc aguuuuauca gguguucuua aaaucaccug gaaacacuga     60
gguugugucu cacugaac                                                  78

<210> SEQ ID NO 181
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 181
gcugcuguug ggagacccug gucugcacuc uaucuguauu cuuacugaag ggagugcagg     60
gcaggguuuc ccauacagag ggc                                            83

<210> SEQ ID NO 182
<211> LENGTH: 92
<212> TYPE: RNA
<213> ORGANISM: Artificial Sequence
<220> FEATURE:
<223> OTHER INFORMATION: Synthetic Sequence

<400> SEQUENCE: 182
ggaauugacu uagcugggua gugggggaacc cuuccaugag gaguagaaca cuccuuaugc    60
```

```
aagauuccccu ucuaccuggc uggguuggag uc                                    92

<210> SEQ ID NO 183
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 183
ucauuccuuc aguguugaaa caaucucuac ugaaccagcu caaacaagu cacuggagu         60 uuguuucaau auugcaagaa uga                                              83

<210> SEQ ID NO 184
<211> LENGTH: 96
<212> TYPE: RNA
<213> ORGANISM: Artificial Sequence
<220> FEATURE:
<223> OTHER INFORMATION: Synthetic Sequence

<400> SEQUENCE: 184
cacaaacugu gaagugcugu ggauuucuuu gugaaucacc auaucuaagc uaauguggug       60
gugguuuaca aaguaauuca uagugcuuca caggug                                96

<210> SEQ ID NO 185
<211> LENGTH: 92
<212> TYPE: RNA
<213> ORGANISM: Artificial Sequence
<220> FEATURE:
<223> OTHER INFORMATION: Synthetic Sequence

<400> SEQUENCE: 185
gcggcugcgg cggcggcggc ggcggcggcg gcggcuguug cuguugcugc ugcugcugcu       60
gcugcuguug cugcugcugc ugcugcugcu gc                                    92

<210> SEQ ID NO 186
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 186 gaggggggaag acgggaggaa agaagggagu gguuccauca cgccuccuca cuccucuccu      60
cccgucuucu ccucuc                                                      76

<210> SEQ ID NO 187
<211> LENGTH: 110
<212> TYPE: RNA
<213> ORGANISM: Artificial Sequence
<220> FEATURE:
<223> OTHER INFORMATION: Synthetic Sequence

<400> SEQUENCE: 187
cuacugcugu ugguggcagc uugguggucg uaugugugac gccauuuacu ugaaccuuua      60
ggagugacau cacauauacg gcagcuaaac ugcuacaugg acaacaauu                 110

<210> SEQ ID NO 188
<211> LENGTH: 23
<212> TYPE: RNA
<213> ORGANISM: Artificial Sequence
<220> FEATURE:
<223> OTHER INFORMATION: Synthetic Sequence
```

```
<400> SEQUENCE: 188
cuaacugcac uagaugcacc uua                                            23

<210> SEQ ID NO 189
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 189
cuggaagugc ccauacuaca gu                                             22

<210> SEQ ID NO 190
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 190
cuaccugcac uaugagcacu uug                                            23

<210> SEQ ID NO 191
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 191
ugcuuugaca auaucauugc acug                                           24

<210> SEQ ID NO 192
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 192
aaagagguua accaggugug uu                                             22

<210> SEQ ID NO 193
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 193
cacuuagcag guuguauuau au                                             22

<210> SEQ ID NO 194
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 194
cgcccaauua augucuguug au                                             22

<210> SEQ ID NO 195
```

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 195
acccuauaag caauauugca cua                                           23

<210> SEQ ID NO 196
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 196
gcaaugcaac agcaaugcac                                               20

<210> SEQ ID NO 197
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 197
ugcuguuagc ccuagccccg ca                                            22

<210> SEQ ID NO 198
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 198
acgguccuac acucaaggca ug                                            22

<210> SEQ ID NO 199
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 199
acgcuuuguc aguacauauu aa                                            22

<210> SEQ ID NO 200
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 200
acacacccac gcgagccgga aa                                            22

<210> SEQ ID NO 201
<211> LENGTH: 22
<212> TYPE: RNA
<213> ORGANISM: Artificial Sequence
<220> FEATURE:
<223> OTHER INFORMATION: Synthetic  Sequence

<400> SEQUENCE: 201
```
ccaaccugcc cgcucccaac au                                              22

<210> SEQ ID NO 202
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 202
aagagggaga cccaggcucg ga                                              22

<210> SEQ ID NO 203
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 203
accagcuaac aauacacugc ca                                              22

<210> SEQ ID NO 204
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 204
gccagcuaac aauacacugc cu                                              22

<210> SEQ ID NO 205
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 205
ccagcaccac aucaggccca cg                                              22

<210> SEQ ID NO 206
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 206
uguggcccug acacguggua cu                                              22

<210> SEQ ID NO 207
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 207
aagaagugca ccgcgaaugu uu                                              22

<210> SEQ ID NO 208
<211> LENGTH: 22
<212> TYPE: RNA

<213> ORGANISM: Artificial Sequence
<220> FEATURE:
<223> OTHER INFORMATION: Synthetic Sequence

<400> SEQUENCE: 208
gggaccgaca gcagaauccu uu                                      22

<210> SEQ ID NO 209
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 209
acgguuuuac cagacaguau ua                                      22

<210> SEQ ID NO 210
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 210
ucacauuugc cugcagagau uu                                      22

<210> SEQ ID NO 211
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 211
aaguggauga cccuguacga uu                                      22

<210> SEQ ID NO 212
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 212
aacuggaugu cccuguauga uu                                      22

<210> SEQ ID NO 213
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 213
cgauguaguc caaaggcaca ua                                      22

<210> SEQ ID NO 214
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 214
auauuaggaa cacaucgcaa aa                                      22

<210> SEQ ID NO 215
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 215
acucaguaau gguaacgguu u                                            21

<210> SEQ ID NO 216
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 216
acaccgagga gcccaucaug au                                           22

<210> SEQ ID NO 217
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 217
cugcaugacg gccugcaaga ca                                           22

<210> SEQ ID NO 218
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 218
gucucaguuu ccucugcaaa ca                                           22

<210> SEQ ID NO 219
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 219
gcgaacucac cacggacaac cu                                           22

<210> SEQ ID NO 220
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 220
ggagacucac aaguuccugc                                              20

<210> SEQ ID NO 221
<211> LENGTH: 22
<212> TYPE: RNA
<213> ORGANISM: Artificial Sequence
<220> FEATURE:

```
<223> OTHER INFORMATION: Synthetic Sequence

<400> SEQUENCE: 221
gcacaacccu aguggcgcca uu                                    22

<210> SEQ ID NO 222
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 222
cacucagcgg ccguuccccc aa                                    22

<210> SEQ ID NO 223
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 223
gcugagcggu gagggcauac ag                                    22

<210> SEQ ID NO 224
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 224
aggacuauag aacuuccccc cu                                    22

<210> SEQ ID NO 225
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 225
agaggcaggg uaguguaaug ga                                    22

<210> SEQ ID NO 226
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 226
cagcagccuc cgccgccgcc gc                                    22

<210> SEQ ID NO 227
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 227
uagcagaagc auuccgcac ac                                     22
```

```
<210> SEQ ID NO 228
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 228
acacaccaag gauaauuucu cc                                              22

<210> SEQ ID NO 229
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 229
uucaguuauc aaucugucac aa                                              22

<210> SEQ ID NO 230
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 230
cucgugacau gaugaucccc ga                                              22

<210> SEQ ID NO 231
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 231
cucuacucac agaaguguca au                                              22

<210> SEQ ID NO 232
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 232
uucgacugcc acucuuacua ga                                              22

<210> SEQ ID NO 233
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 233
ccucuaguaa auaugucagc au                                              22

<210> SEQ ID NO 234
<211> LENGTH: 22
<212> TYPE: RNA
<213> ORGANISM: Artificial Sequence
<220> FEATURE:
<223> OTHER INFORMATION: Synthetic Sequence
```

<400> SEQUENCE: 234
cugcacuuuu augaauaagc uc                                            22

<210> SEQ ID NO 235
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 235
gacuagcuua uacauaaaau ua                                            22

<210> SEQ ID NO 236
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 236
ggccuccgga agcuccgccc ca                                            22

<210> SEQ ID NO 237
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 237
ugacccaccu ggagauccau gg                                            22

<210> SEQ ID NO 238
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 238
ccuggcacac aguagaccuu ca                                            22

<210> SEQ ID NO 239
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 239
uccagccccu ccagggcuuc cu                                            22

<210> SEQ ID NO 240
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 240
agguggagcc cugagaaccg ga                                            22

<210> SEQ ID NO 241
<211> LENGTH: 22

```
<212> TYPE: RNA
<213> ORGANISM: Artificial Sequence
<220> FEATURE:
<223> OTHER INFORMATION: Synthetic Sequence

<400> SEQUENCE: 241
ugaggggccu cagccuccug gu                                                22

<210> SEQ ID NO 242
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 242
aucgggaggg gacugagccu ga                                                22

<210> SEQ ID NO 243
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 243
ucggggcagc ucaguacagg a                                                 21

<210> SEQ ID NO 244
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 244
auccuguacu gagcugcccc g                                                 21

<210> SEQ ID NO 245
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 245
ccacgaccga cgccacgccg ag                                                22

<210> SEQ ID NO 246
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 246
agccggucga gguccggucg a                                                 21

<210> SEQ ID NO 247
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 247
```
gaccaagaaa uagccuuuca aa                                          22

<210> SEQ ID NO 248
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 248
gcaaagguaa uugcuguuuu cg                                          22

<210> SEQ ID NO 249
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 249
cuagaagcuc acagucuagu ug                                          22

<210> SEQ ID NO 250
<211> LENGTH: 21
<212> TYPE: RNA
<213> ORGANISM: Artificial Sequence
<220> FEATURE:
<223> OTHER INFORMATION: Synthetic  Sequence

<400> SEQUENCE: 250
ugcgccacug gagcaugcuu u                                           21

<210> SEQ ID NO 251
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 251
gcuccccaca gacccagagc cg                                          22

<210> SEQ ID NO 252
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 252
cccgccauag ugguccucuc ug                                          22

<210> SEQ ID NO 253
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 253
cugguccaua ggggauggca au                                          22

<210> SEQ ID NO 254
<211> LENGTH: 22
<212> TYPE: RNA
<213> ORGANISM: Artificial Sequence

```
<220> FEATURE:
<223> OTHER INFORMATION: Synthetic Sequence

<400> SEQUENCE: 254
ccagugucuc caguaguaga ca                                              22

<210> SEQ ID NO 255
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 255
ccucgggaug gcgcccguuc ac                                              22

<210> SEQ ID NO 256
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 256
gcacacaaua aauguuugcu ga                                              22

<210> SEQ ID NO 257
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 257
aaccaagacc ccggagaucc ca                                              22

<210> SEQ ID NO 258
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 258
ucggucccuc gggccagggc ag                                              22

<210> SEQ ID NO 259
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 259
ugugggugug ugcaugagcg ug                                              22

<210> SEQ ID NO 260
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 260
cacacucaca cacacacacu ca                                              22
```

```
<210> SEQ ID NO 261
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 261
cggggagcgg gggcccugcc uu                                              22

<210> SEQ ID NO 262
<211> LENGTH: 19
<212> TYPE: RNA
<213> ORGANISM: Artificial NSequence
<220> FEATURE:
<223> OTHER INFORMATION: Synthetic Sequence

<400> SEQUENCE: 262
cccucucaac ucagcuuuu                                                  19

<210> SEQ ID NO 263
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 263
gucuagacug ugagcuccuc ga                                              22

<210> SEQ ID NO 264
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 264
gcacauguuc ugcggcccac ca                                              22

<210> SEQ ID NO 265
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 265
cagcacagag auggacagau ag                                              22

<210> SEQ ID NO 266
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 266
ccgcuugagc uaacuccgac ccg                                             23

<210> SEQ ID NO 267
<211> LENGTH: 22
<212> TYPE: RNA
<213> ORGANISM: Artificial Sequence
<220> FEATURE:
<223> OTHER INFORMATION: Synthetic Sequence
```

<400> SEQUENCE: 267
ggaggccggg acgagugcaa ua                                              22

<210> SEQ ID NO 268
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 268
gcugccguau augugauguc ac                                              22

<210> SEQ ID NO 269
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 269
gagguuuccc guguauguuu ca                                              22

<210> SEQ ID NO 270
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 270
gaacuugcua aaaugcaga au                                               22

<210> SEQ ID NO 271
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 271
acugaaacca aguauggguc gc                                              22

<210> SEQ ID NO 272
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 272
agcacagacu ugcugugaug uu                                              22

<210> SEQ ID NO 273
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 273
caccugauaa aacugaggua ua                                              22

<210> SEQ ID NO 274

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 274
acacaaccuc aguguuucca gg                                              22

<210> SEQ ID NO 275
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 275
gauagagugc agaccagggu cu                                              22

<210> SEQ ID NO 276
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 276
ccucauggaa ggguucccca cu                                              22

<210> SEQ ID NO 277
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 277
ucaguagaga uuguuucaac ac                                              22

<210> SEQ ID NO 278
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 278
ggugauucac aaagaaaucc au                                              22

<210> SEQ ID NO 279
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 279
acagccgccg ccgccgccgc cg                                              22

<210> SEQ ID NO 280
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 280
```

```
uucccuucuu uccucccguc uu                                              22

<210> SEQ ID NO 281
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 281
uacucaaaaa gcugucaguc a                                               21

<210> SEQ ID NO 282
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 282
ugcggggcua gggcuaacag ca                                              22

<210> SEQ ID NO 283
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 283
caugccuuga guguaggacc gu                                              22

<210> SEQ ID NO 284
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 284
uccgagccug ggucucccuc uu                                              22

<210> SEQ ID NO 285
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 285
aagguuacuu guuaguucag g                                               21

<210> SEQ ID NO 286
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 286
cgugggccug auguggugcu gg                                              22

<210> SEQ ID NO 287
<211> LENGTH: 22
<212> TYPE: RNA
```

```
<213> ORGANISM: Artificial Sequence
<220> FEATURE:
<223> OTHER INFORMATION: Synthetic Sequence

<400> SEQUENCE: 287
aaacauucgc ggugcacuuc uu                                              22

<210> SEQ ID NO 288
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 288
aaggauucug cugucggucc c                                               21

<210> SEQ ID NO 289
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 289
ugauauguuu gauauugggu u                                               21

<210> SEQ ID NO 290
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 290
gcacugagau gggaguggug ua                                              22

<210> SEQ ID NO 291
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 291
gcaggaacuu gugagucucc u                                               21

<210> SEQ ID NO 292
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 292
aauggcgcca cuaggguugu gu                                              22

<210> SEQ ID NO 293
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 293 aggggggaaag uucuauaguc c                                              21
```

-continued

<210> SEQ ID NO 294
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 294
uccauuacac uacccugccu cu                                            22

<210> SEQ ID NO 295
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 295
ggagaaauua uccuuggugu gu                                            22

<210> SEQ ID NO 296
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 296
ugugacagau ugauaacuga aa                                            22

<210> SEQ ID NO 297
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 297
ucggggauca ucaugucacg aga                                           23

<210> SEQ ID NO 298
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 298
uaauuuuaug uauaagcuag u                                             21

<210> SEQ ID NO 299
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 299
aggaagcccu ggaggggcug gag                                           23

<210> SEQ ID NO 300
<211> LENGTH: 22
<212> TYPE: RNA
<213> ORGANISM: Artificial Sequence
<220> FEATURE:

<223> OTHER INFORMATION: Synthetic Sequence

<400> SEQUENCE: 300
cgaaaacagc aauuaccuuu gc                                            22

<210> SEQ ID NO 301
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 301
caacuagacu gugagcuucu ag                                            22

<210> SEQ ID NO 302
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 302
aaggagcuua caaucuagcu ggg                                           23

<210> SEQ ID NO 303
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 303
cggcucuggg ucugugggga g                                             21

<210> SEQ ID NO 304
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 304
gugaacgggc gccaucccga gg                                            22

<210> SEQ ID NO 305
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 305
ucagcaaaca uuuauugugu gc                                            22

<210> SEQ ID NO 306
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 306
cugcccuggc ccgagggacc ga                                            22

```
<210> SEQ ID NO 307
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 307
cacgcucaug cacacaccca ca                                              22

<210> SEQ ID NO 308
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 308
ugagugugug ugugugagug ugu                                             23

<210> SEQ ID NO 309
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 309
uaugucugcu gaccaucacc uu                                              22

<210> SEQ ID NO 310
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 310
uggugggccg cagaacaugu gc                                              22

<210> SEQ ID NO 311
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 311
cgcgggugcu uacugacccu u                                               21

<210> SEQ ID NO 312
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 312
cgggucggag uuagcucaag cgg                                             23

<210> SEQ ID NO 313
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 313
gcgacccaua cuugguuuca g                                              21

<210> SEQ ID NO 314
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 314
ccuggaaaca cugagguugu gu                                             22

<210> SEQ ID NO 315
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 315
uauaccucag uuuuaucagg ug                                             22

<210> SEQ ID NO 316
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 316
uggugguuua caaaguaauu ca                                             22

<210> SEQ ID NO 317
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 317
uggauuucuu ugugaaucac ca                                             22

<210> SEQ ID NO 318
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 318
accaggaggc ugaggccccu                                                20

<210> SEQ ID NO 319
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 319
ugagaacuga auuccauagg cu                                             22

<210> SEQ ID NO 320
<211> LENGTH: 22
```

```
<212> TYPE: RNA
<213> ORGANISM: Artificial Sequence
<220> FEATURE:
<223> OTHER INFORMATION: Synthetic Sequence

<400> SEQUENCE: 320
gugugcggaa augcuucugc ua                                            22

<210> SEQ ID NO 321
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 321
aacauucauu guugucggug ggu                                           23

<210> SEQ ID NO 322
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 322
uaaggugcau cuagugcagu uag                                           23

<210> SEQ ID NO 323
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 323
aacuggcccu caaagucccg cu                                            22

<210> SEQ ID NO 324
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 324
ugcaacgaac cugagccacu ga                                            22

<210> SEQ ID NO 325
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 325
auaauacaug guuaaccucu uu                                            22

<210> SEQ ID NO 326
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 326
```
uacuuggaaa ggcaucaguu g                                       21

<210> SEQ ID NO 327
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 327
ugcaacuuac cugagucauu ga                                      22

<210> SEQ ID NO 328
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 328
guagaggaga uggcgcaggg                                         20

<210> SEQ ID NO 329
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 329
uacccauugc auaucggagu u                                       21

<210> SEQ ID NO 330
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 330
caaagugcuc auagugcagg uag                                     23

<210> SEQ ID NO 331
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 331
acuguaguau gggcacuucc ag                                      22

<210> SEQ ID NO 332
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 332
aaaucucugc aggcaaaugu ga                                      22

<210> SEQ ID NO 333
<211> LENGTH: 24
<212> TYPE: RNA
<213> ORGANISM: Artificial Sequence

```
<220> FEATURE:
<223> OTHER INFORMATION: Synthetic Sequence

<400> SEQUENCE: 333
cagugcaaug auauugucaa agca                                           24

<210> SEQ ID NO 334
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 334
aacacaccug guuaaccucu uu                                             22

<210> SEQ ID NO 335
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 335
gugcauugcu guugcauugc                                                20

<210> SEQ ID NO 336
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 336
auauaauaca accugcuaag ug                                             22

<210> SEQ ID NO 337
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 337
uuuguucguu cggcucgcgu ga                                             22

<210> SEQ ID NO 338
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 338
aucauagagg aaaauccacg u                                              21

<210> SEQ ID NO 339
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 339
aucauagagg aaaauccaug uu                                             22
```

```
<210> SEQ ID NO 340
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 340
aaucguacag ggucauccac uu                                              22

<210> SEQ ID NO 341
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 341
aaucguacag ggucauccac uu                                              22

<210> SEQ ID NO 342
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 342
aucacacaaa ggcaacuuuu gu                                              22

<210> SEQ ID NO 343
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 343
acuggacuug gagucagaag g                                               21

<210> SEQ ID NO 344
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 344
ugguagacua uggaacguag g                                               21

<210> SEQ ID NO 345
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 345
uauguaauau gguccacauc uu                                              22

<210> SEQ ID NO 346
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 346
aauauaacac agauggccug u                                            21

<210> SEQ ID NO 347
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 347
aucaacagac auuaauuggg cg                                           22

<210> SEQ ID NO 348
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 348
uaauacuguc ugguaaaacc gu                                           22

<210> SEQ ID NO 349
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 349
ugucuugcag gccgucaugc a                                            21

<210> SEQ ID NO 350
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 350
ucuuggagua ggucauuggg ugg                                          23

<210> SEQ ID NO 351
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 351
aucaugaugg gcuccucggu gu                                           22

<210> SEQ ID NO 352
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 352
uggcagugua uuguuagcug gu                                           22

<210> SEQ ID NO 353
```

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 353
aggcagugua uuguuagcug gc                                              22

<210> SEQ ID NO 354
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 354
uuuugcgaug uguccuaau au                                               22

<210> SEQ ID NO 355
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 355
aaaccguuac cauuacugag uu                                              22

<210> SEQ ID NO 356
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 356
aacuguuugc agaggaaacu ga                                              22

<210> SEQ ID NO 357
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 357
agguuguccg uggugaguuc gca                                             23

<210> SEQ ID NO 358
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 358
uagugcaaua uugcuuauag ggu                                             23

<210> SEQ ID NO 359
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 359
```
uaugugccuu uggacuacau cg                                                22

<210> SEQ ID NO 360
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 360
ucaggcucag uccccucccg au                                                22

<210> SEQ ID NO 361
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 361
gucauacacg gcucuccucu cu                                                22

<210> SEQ ID NO 362
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 362
agaggcuggc cgugaugaau uc                                                22

<210> SEQ ID NO 363
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 363
cggggcagcu caguacagga u                                                 21

<210> SEQ ID NO 364
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 364
aaucauacag ggacauccag uu                                                22

<210> SEQ ID NO 365
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 365
uugaaaggcu auuucuuggu cu                                                22

<210> SEQ ID NO 366
<211> LENGTH: 20
<212> TYPE: RNA

```
<213> ORGANISM: Artificial Sequence
<220> FEATURE:
<223> OTHER INFORMATION: Synthetic Sequence

<400> SEQUENCE: 366
ccauggaucu ccagguggu                                                      20

<210> SEQ ID NO 367
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 367
ugaaggucua cugugugcca gg                                                  22

<210> SEQ ID NO 368
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 368
cagcagcaca cugugguuug u                                                   21

<210> SEQ ID NO 369
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 369
aaugcaccug ggcaaggauu ca                                                  22

<210> SEQ ID NO 370
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 370
uagcagcggg aacaguucug cag                                                 23

<210> SEQ ID NO 371
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 371
cgucaacacu ugcugguuuc cu                                                  22

<210> SEQ ID NO 372
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 372
ugauugguac gucugugggu ag                                                  22
```

```
<210> SEQ ID NO 373
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 373
auugacacuu cugugaguag a                                              21

<210> SEQ ID NO 374
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 374
uauugcacuc gucccggccu cc                                             22

<210> SEQ ID NO 375
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 375
ggcagugcuc uacucaaaaa gcugucaguc acuuagauua caugugacug acaccucuuu    60
gggugaagga aggcuca                                                   77

<210> SEQ ID NO 376
<211> LENGTH: 98
<212> TYPE: RNA
<213> ORGANISM: Artificial Sequence
<220> FEATURE:
<223> OTHER INFORMATION: Synthetic Sequence

<400> SEQUENCE: 376
uugggcaagg ugcggggcua gggcuaacag cagucuuacu gaagguuucc uggaaaccac    60
gcacaugcug uugccacuaa ccucaaccuu acucgguc                            98

<210> SEQ ID NO 377
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 377
uucucuccuc caugccuuga guguaggacc guuggcaucu uaauuacccu cccacaccca    60
aggcuugcaa aaaagcgag                                                 79

<210> SEQ ID NO 378
<211> LENGTH: 86
<212> TYPE: RNA
<213> ORGANISM: Artificial Sequence
<220> FEATURE:
<223> OTHER INFORMATION: Synthetic Sequence

<400> SEQUENCE: 378
aggggcggga gggggguccc cggugcucgg aucucgaggg ugcuuauugu ucgguccgag    60
```

```
ccugggucuc ccucuucccc ccaacc                                            86

<210> SEQ ID NO 379
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 379
aacuuguuag aagguuacuu guuaguucag gaccucauua cuuucugccu gaacuauugc        60
aguagccucc uaacugguua u                                                 81

<210> SEQ ID NO 380
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 380
ccgagccucc aguaccacgu gucagggcca caugagcugg gccucguggg ccugaugugg        60
ugcuggggcc ucaggg                                                       76

<210> SEQ ID NO 381
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 381
uacuuaauga aaguugccc guguuuuuuu cgcuuuauuu gugacgaaac auucgcggug         60
cacuucuuuu ucaguauc                                                     78

<210> SEQ ID NO 382
<211> LENGTH: 84
<212> TYPE: RNA
<213> ORGANISM: Artificial  Sequence
<220> FEATURE:
<223> OTHER INFORMATION: Synthetic Sequence

<400> SEQUENCE: 382
acgucaggga aaggauucug cugucggucc cacuccaaag uucacagaau ggguggugggg       60 cacagaaucu ggacucugcu ugug                                              84

<210> SEQ ID NO 383
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 383
ugcuucugug ugauauguuu gauauugggu uguuuaauua ggaaccaacu aaaugucaaa        60
cauauucuua cagcagcag                                                    79

<210> SEQ ID NO 384
<211> LENGTH: 77
<212> TYPE: RNA
<213> ORGANISM: Artificial Sequence
<220> FEATURE:
<223> OTHER INFORMATION: Synthetic Sequence
```

<400> SEQUENCE: 384
ccugagccuu gcacugagau gggaguggug uaaggcucag guaugcacag cucccaucuc    60
agaacaaggc ucggguq                                                   77

<210> SEQ ID NO 385
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 385
gugugcauuu gcaggaacuu gugagucucc uauugaaaau gaacaggaga cugaugaguu    60
cccgggaaca cccacaa                                                   77

<210> SEQ ID NO 386
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 386
augcacugca caacccuagg agagggugcc auucacauag acuauaauug aauggcgcca    60 cuagqguugu gcagugcaca a                                              81

<210> SEQ ID NO 387
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 387
uagagggaug aggggggaaag uucuauaguc cuguaauuag aucucaggac uauagaacuu    60 uccccccucau cccucugcc                                                79

<210> SEQ ID NO 388
<211> LENGTH: 74
<212> TYPE: RNA
<213> ORGANISM: Artificial Sequence
<220> FEATURE:
<223> OTHER INFORMATION: Synthetic Sequence

<400> SEQUENCE: 388
ccgcacucuc uccauuacac uacccugccu cuucuccaug agaggcagcg ggguguagug    60
gauagagcac gggu                                                      74

<210> SEQ ID NO 389
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 389
ucauacuuga ggagaaauua uccuuggugu guucgcuuua uuuaugauga aucauacaag    60
gacaauuucu uuuugaguau caaa                                           84

<210> SEQ ID NO 390

```
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 390
cucagacauc ucggggauca ucaugucacg agauaccagu gugcacuugu gacagauuga    60
uaacugaaag gucugggag                                                 79

<210> SEQ ID NO 391
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 391
agucagaaau gagcuuauuc auaaaagugc aguaugguga agucaaucug uaauuuuaug    60
uauaagcuag ucucugauug a                                              81

<210> SEQ ID NO 392
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 392
caggaagagg aggaagcccu ggaggggcug gaggugaugg auguuuccu ccgguucuca     60 gggcuccacc ucuuucgggc c                                              81

<210> SEQ ID NO 393
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 393
aggugggugc aaagguaauu gcaguuuuuc ccauuauuuu aauugcgaaa acagcaauua    60
ccuuugcacc aaccuga                                                   77

<210> SEQ ID NO 394
<211> LENGTH: 88
<212> TYPE: RNA
<213> ORGANISM: Artificial Sequence
<220> FEATURE:
<223> OTHER INFORMATION: Synthetic Sequence

<400> SEQUENCE: 394
aacugcccuc aaggagcuua caaucuagcu ggggguaaau gacuugcaca ugaacacaac    60
uagacuguga gcuucuagag ggcaggga                                       88

<210> SEQ ID NO 395
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 395
ggcgcgucgc cccccucagu ccaccagagc ccggauaccu cagaaauucg gcucugdguc    60
``` ugugggagc gaaaugcaac                                                  80

<210> SEQ ID NO 396
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 396
gugcagaucc uugggagccc uguuagacuc uggauuuuac acuuggagug aacgggcgcc      60
aucccgaggc uuugcacag                                                   79

<210> SEQ ID NO 397
<211> LENGTH: 82
<212> TYPE: RNA
<213> ORGANISM: Artificial Sequence
<220> FEATURE:
<223> OTHER INFORMATION: Synthetic Sequence

<400> SEQUENCE: 397
cauuaguagg ccucaguaaa uguuuauuag augaauaaau gaaugacuca ucagcaaaca      60
uuuauugugu gccugcuaaa gu                                               82

<210> SEQ ID NO 398
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 398
uuagcccugc ggccccacgc accaggguaa gagagacucu cgcuuccugc ccuggcccga      60
gggaccgacu ggcugggc                                                    78

<210> SEQ ID NO 399
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 399
ugcgggcgug ugagugugug uguugagug ugucgcuc cgguccacg cucaugcaca         60 cacccacacg cccacacu                                                    78

<210> SEQ ID NO 400
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 400
uaaguggaaa gaugugggc cgcagaacau gugcugaguu cgugccauau gucugcugac      60
caucaccuuu agaagcccc                                                   79

<210> SEQ ID NO 401
<211> LENGTH: 121
<212> TYPE: RNA
<213> ORGANISM: Artificial Sequence
<220> FEATURE:

<223> OTHER INFORMATION: Synthetic Sequence

<400> SEQUENCE: 401
cacuccuacc cgggucggag uuagcucaag cgguuaccuc cucaugccgg acuuucuauc    60
uguccaucuc ugugcugggg uucgagaccc gcgggugcuu acugacccuu uuaugcaaua   120
a                                                                  121

<210> SEQ ID NO 402
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 402
ccuggcccau gaaaucaagc ugggugaga ccuggugcag aacgggaagg cgacccauac     60
uugguuucag aggcugugag                                                80

<210> SEQ ID NO 403
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 403 uuaggguac uauaccucag uuuuaucagg uguucuuaaa aucaccugga aacacugagg     60
uugugucuca cugaac                                                    76

<210> SEQ ID NO 404
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 404
ugaagugcug uggauuucuu ugugaaucac cauaucuaag cuaaugugu gguggucuuac    60 aaaguaauuc auagugcuuc a                                              81

<210> SEQ ID NO 405
<211> LENGTH: 72
<212> TYPE: RNA
<213> ORGANISM: Artificial Sequence
<220> FEATURE:
<223> OTHER INFORMATION: Synthetic Sequence

<400> SEQUENCE: 405
ucuccucgag gggucucugc cucuacccag gacucuuuca ugaccaggag gcugaggccc    60
cucacaggcg gc                                                        72

<210> SEQ ID NO 406
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 406
caccuggcac ugagaacuga auccauagg cugugagcuc uagcaaugcc cuguggacuc     60
aguucuggug cccggcagu                                                 79

<210> SEQ ID NO 407
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 407
uauaaaucua guggaaacau uucugcacaa acuagauucu ggacaccagu gugcggaaau    60
gcuucugcua cauuuuuagg                                                80

<210> SEQ ID NO 408
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 408
ggucacaauc aacauucauu guugucggug gguugugagg acugaggcca gacccaccgg    60
gggaugaaug ucacuguggc uggg                                           84

<210> SEQ ID NO 409
<211> LENGTH: 85
<212> TYPE: RNA
<213> ORGANISM: Artificial Sequence
<220> FEATURE:
<223> OTHER INFORMATION: Synthetic Sequence

<400> SEQUENCE: 409
ucucuugugu uaaggugcau cuagugcagu uagugaagca gcuuagaauc uacugcccua    60
aaugccccuu cuggcacagg cugcc                                          85

<210> SEQ ID NO 410
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 410
gucucagaau cggggguuuug agggcgagau gaguuuaugu uuuauccaac uggcccucaa    60
agucccgcuu uugggguca                                                 79

<210> SEQ ID NO 411
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 411
ccuuaauccu ugcaacgaac cugagccacu gauucaguaa aauacucagu ggcacauguu    60
uguugugagg gucaaaaga                                                 79

<210> SEQ ID NO 412
<211> LENGTH: 80
<212> TYPE: RNA
<213> ORGANISM: Artificial Sequence
<220> FEATURE:
<223> OTHER INFORMATION: Synthetic Sequence

```
<400> SEQUENCE: 412
auauuugagg agagguuauc cguguuaugu ucgcuucauu caucaugaau aauacauggu    60
uaaccucuuu uugaauauca                                                80

<210> SEQ ID NO 413
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 413
ggaagugccc uacuuggaaa ggcaucaguu gcuuagauua cauguaacua uucccuuucu    60
gaguagagua agucuua                                                   77

<210> SEQ ID NO 414
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 414
ccuuaauccu ugcaacuuac cgagucauu gauucaguaa aacauucaau ggcacauguu     60
uguuguuagg gucaaaaga                                                 79

<210> SEQ ID NO 415
<211> LENGTH: 103
<212> TYPE: RNA
<213> ORGANISM: Artificial Sequence
<220> FEATURE:
<223> OTHER INFORMATION: Synthetic Sequence

<400> SEQUENCE: 415
gcuagagaag guagaggaga uggcgcaggg gacacgggca aagacuuggg gguuccuggg    60
acccucagac guguguccuc uucucccucc ucccaggugu aug                     103

<210> SEQ ID NO 416
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 416
ccuucuccca uacccauugc auaucggagu ugugaauucu caaaacaccu ccugugugca    60
uggauuacag gaggguga                                                  78

<210> SEQ ID NO 417
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 417
cuaguaguac caaagugcuc auagugcagg uaguuuggc augacucuac uguaguaugg     60
gcacuuccag uacucuugga                                                80

<210> SEQ ID NO 418
<211> LENGTH: 82
```

```
<212> TYPE: RNA
<213> ORGANISM: Artificial Sequence
<220> FEATURE:
<223> OTHER INFORMATION: Synthetic Sequence

<400> SEQUENCE: 418
gcagacugga aaaucucugc aggcaaaugu gaugucacug aggaaaucac acacuuaccc    60
guagagauuc uacagucuga ca                                            82

<210> SEQ ID NO 419
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 419
gccgcaggug cucugacgag guugcacuac ugugcucuga gaagcagugc aaugauauug    60
ucaaagcauc ugggacca                                                 78

<210> SEQ ID NO 420
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 420
guaccugaag agagguuuuc uggguuucug uuucuuuaau gaggacgaaa cacaccuggu    60
uaaccucuuu uccaguauca                                               80

<210> SEQ ID NO 421
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 421
guaccugaag agagguuuuc uggguuucug uuucuuuauu gaggacgaaa cacaccuggu    60
uaaccucuuu uccaguauca                                               80

<210> SEQ ID NO 422
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 422
cggccccgcg gugcauugcu guugcauugc acguguguga ggcgggugca gugccucggc    60
agugcagccc ggagccggcc                                               80

<210> SEQ ID NO 423
<211> LENGTH: 72
<212> TYPE: RNA
<213> ORGANISM: Artificial Sequence
<220> FEATURE:
<223> OTHER INFORMATION: Synthetic Sequence

<400> SEQUENCE: 423
acucggaugg auauaauaca accugcuaag ugccuagca cuuagcaggu uguauuauca    60
```

```
uuguccgugu cu                                                             72

<210> SEQ ID NO 424
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 424
cucccgcccc gcgacgagcc ccucgcacaa accggaccug agcguuuugu ucguucggcu         60
cgcgugaggc aggggcg                                                        77

<210> SEQ ID NO 425
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 425
uauuuaaaag guagauucuc cuucuaugag uacauuauuu augauuaauc auagaggaaa         60
auccacguuu ucaguauc                                                       78

<210> SEQ ID NO 426
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 426
uauuuaaaag guagauuuuc cuucuauggu uacguguuug augguuaauc auagaggaaa         60
auccacguuu ucaguauc                                                       78

<210> SEQ ID NO 427
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 427
guauuuaaaa cguggauauu ccuucuaugu uuacgugauu ccugguuaau cauagaggaa         60
aauccauguu uucaguauca                                                     80

<210> SEQ ID NO 428
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 428
uauuuaaaag guggauauuc cuucuauguu uauguuauuu augguuaaac auagaggaaa         60
uuccacguuu ucaguauc                                                       78

<210> SEQ ID NO 429
<211> LENGTH: 78
<212> TYPE: RNA
<213> ORGANISM: Artificial Sequence
<220> FEATURE:
<223> OTHER INFORMATION: Synthetic Sequence
```

<400> SEQUENCE: 429
uauuuaaaag guggauauuc cuucuauguu uauguuauuu augguuaaac auagaggaaa    60
uuccacguuu ucaguauc                                                 78

<210> SEQ ID NO 430
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 430
acccuugagc agagguugcc cuuggugaau ucgcuuuauu uauguugaau cacacaaagg    60
caacuuuugu uugaguauca                                               80

<210> SEQ ID NO 431
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 431
cacccagggc uccugacucc agguccugug uguuaccuag aaauagcacu ggacuuggag    60
ucagaaggcc ugagugga                                                 78

<210> SEQ ID NO 432
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 432
ccugaagaga ugguagacua uggaacguag gcguuaugau uucugaccua uguaacaugg    60
uccacuaacu cucaguauc                                                79

<210> SEQ ID NO 433
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 433
accugaaaag augguugacc auagaacaug cgcuaucucu gugucguaug uaauaugguc    60
cacaucuucu caauauca                                                 78

<210> SEQ ID NO 434
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 434
accugagaag agguugucug ugaugaguuc gcuuuuauua augacgaaua uaacacagau    60
ggccuguuuu caguacc                                                  77

<210> SEQ ID NO 435

```
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 435
cauuguaggc ucauuaaau guuuguugaa ugaaaaaaug aaucaucaac agacauuaau      60
ugggcgccug cucugu                                                     76

<210> SEQ ID NO 436
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 436
gccgaugggc gucuuaccag acaugguuag accggcccu cugucuaaua cugucgguaa      60
aaaccgucca uccgcug                                                    77

<210> SEQ ID NO 437
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 437
uccugcgagg ugucuugcag gccgucaugc aggccacacu gacgguaacg uugcaggucg     60
ucuugcaggg cuucucgcaa gacg                                            84

<210> SEQ ID NO 438
<211> LENGTH: 89
<212> TYPE: RNA
<213> ORGANISM: Artificial Sequence
<220> FEATURE:
<223> OTHER INFORMATION: Synthetic Sequence

<400> SEQUENCE: 438
cuccuccagg ucuggaguag ggucauuggg uggauccucu auuccuuac gugggccacu      60 ggauggcucc uccaugucuu ggaguagau                                       89

<210> SEQ ID NO 439
<211> LENGTH: 94
<212> TYPE: RNA
<213> ORGANISM: Artificial Sequence
<220> FEATURE:
<223> OTHER INFORMATION: Synthetic Sequence

<400> SEQUENCE: 439
cggggagaag uacggugagc cugucauuau ucagagaggc uagauccucu guguugagaa     60
ggaucaugau gggcuccucg guguucucca ggua                                 94

<210> SEQ ID NO 440
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 440
ugugaugagc uggcagugua uuguuagcug guugaauaug ugaauggcau cggcuaacau     60
```

```
gcaacugcug ucuuauugca u                                                 81

<210> SEQ ID NO 441
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 441
ugaaucaggu aggcagugua uuguuagcug gcugcuuggg ucaagucagc agccacaacu       60
acccugccac uugcuucugg a                                                 81

<210> SEQ ID NO 442
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 442
acuaaacugu uuuugcgaug uguuccuaau augcacuaua aauauauugg gaacauuuug       60
cauguauagu uuuguau                                                      77

<210> SEQ ID NO 443
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 443
gcuaaacuau uuuugcgaug uguuccuaau auguaauaua aauguauugg ggacauuuug       60
cauucauagu uuuguau                                                      77

<210> SEQ ID NO 444
<211> LENGTH: 62
<212> TYPE: RNA
<213> ORGANISM: Artificial Sequence
<220> FEATURE:
<223> OTHER INFORMATION: Synthetic Sequence

<400> SEQUENCE: 444
aauggcaagg aaaccguuac cauuacugag uuuaguaaug guaaugguuc ucuugcuaua       60
cc                                                                      62

<210> SEQ ID NO 445
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 445
aagcacuuac aacuguuugc agaggaaacu gagacuuugu aacuaugucu cagucucauc       60
ugcaaagaag uaagugcuuu gcc                                               83

<210> SEQ ID NO 446
<211> LENGTH: 81
<212> TYPE: RNA
<213> ORGANISM: Artificial Sequence
<220> FEATURE:
```

<223> OTHER INFORMATION: Synthetic Sequence

<400> SEQUENCE: 446
agaagaugca ggaaugcugc gagcagugcc accucauggu acucggaggg agguuguccg    60
uggugaguuc gcauuauuua a                                               81

<210> SEQ ID NO 447
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 447
auccuagaac ccuaucaaua uugucucugc uguguaaaua guucugagua gugcaauauu    60
gcuuauaggg uuuuggiguguu u                                             81

<210> SEQ ID NO 448
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 448
ggcgugaggg uaugugccuu uggacuacau cguggaagcc agcaccaugc aguccauggg    60
cauauacacu ugccucaag                                                  79

<210> SEQ ID NO 449
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 449
cugggaaccc cggggggggc ggggccucgc ggcccugcag ccucgucagg cucagucccc    60
ucccgauaaa ccccuaa                                                    77

<210> SEQ ID NO 450
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 450
guacuuggag agaggcuggc cgugaugaau ucgauucauc aaagcgaguc auacacggcu    60
cuccucucuu uuaguguca                                                  79

<210> SEQ ID NO 451
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 451
cccuggggca uccuguacug agcugccccg aggcccuuca ugcugcccag cucggggcag    60
cucaguacag gauaucuggg gugg                                            84

<210> SEQ ID NO 452
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 452
uacuugaaga gugguuaucc cugcuguguu cgcuuaauuu augacgaauc auacagggac    60
auccaguuuu ucaguauc                                                 78

<210> SEQ ID NO 453
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 453
aaucaucucu cccagauaau ggcacucuca aacaaguuuc caaauuguuu gaaaggcuau    60
uucuugguca gaugacucu                                                79

<210> SEQ ID NO 454
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 454
uuguucgaca ccauggaucu ccagguggu caaguuuaga gaugcaccaa ccuggaggac    60
uccaugcugu ugagcuguu                                                79

<210> SEQ ID NO 455
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 455
cuccagggcu uuguacaugg uaggcuuuca uucauucguu ugcacauucg gugaaggucu    60
acugugugcc aggcccugug cca                                           83

<210> SEQ ID NO 456
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 456
gcucccgccc cagcagcaca cuguggauug uacggcacug uggccacguc caaaccacac    60
ugugguguua gagcgagggu gggggag                                       87

<210> SEQ ID NO 457
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 457

```
cccucucucua auccuugcua ucugggugcu agugcuggcu caaugcaaug caccgggca      60 aggauucaga gaggggga                                                    78
```

<210> SEQ ID NO 458
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 458

```
agccgugccc uagcagcggg aacaguucug cagugagcga ucggugcucu gggguauugu      60
uuccgcugcc aggguaaguc ugg                                              83
```

<210> SEQ ID NO 459
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 459

```
acccaguggg ggagccagga aguauugaug uuucugccag uuuagcguca acacuugcug      60
guuuccucuc uggagca                                                     77
```

<210> SEQ ID NO 460
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 460

```
gugguacccu acugcagaca guggcaauca uguauaauua aaaugauug guacgucugu       60 ggguagagua cugcau                                                      76
```

<210> SEQ ID NO 461
<211> LENGTH: 75
<212> TYPE: RNA
<213> ORGANISM: Artificial Sequence
<220> FEATURE:
<223> OTHER INFORMATION: Synthetic Sequence

<400> SEQUENCE: 461

```
gugguacccu acugcagacg uggcaaucau guauaauuaa aaaugauugg uacgucugug      60
gguagaguac ugcau                                                       75
```

<210> SEQ ID NO 462
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 462

```
gugguacccu acugcagaca guggcaauca uguauaauua aaaugauuug guacgucugu      60
ggguagagua cugcau                                                      76
```

<210> SEQ ID NO 463
<211> LENGTH: 80
<212> TYPE: RNA
<213> ORGANISM: Artificial Sequence

```
<220> FEATURE:
<223> OTHER INFORMATION: Synthetic Sequence

<400> SEQUENCE: 463
cugugguacc cuacucugga gagugacaau cauguauaau uaaauuugau ugacacuucu    60
gugaguagag uaacgcauga                                                80

<210> SEQ ID NO 464
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 464
cugugguacc cuacucugga gagugacaau cauguauaac uaaauuugau ugacacuucu    60
gugaguagag uaacgcauga                                                80

<210> SEQ ID NO 465
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 465
cugugguacc cuacucugga gagugacaau cauguauaac uaaauuugau ugacacuucu    60
gugaguagag uaacgcauga                                                80

<210> SEQ ID NO 466
<211> LENGTH: 83
<212> TYPE: RNA
<213> ORGANISM: Artificial Sequence
<220> FEATURE:
<223> OTHER INFORMATION: Synthetic Sequence

<400> SEQUENCE: 466
ggcgggcggg agggacggga cgcggugcag uguuguuuuu uccccccgcca auauugcacu   60 cgucccggcc uccggccccc ccg                                            83

<210> SEQ ID NO 467
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 467
uacucaaaaa gcugucaguc a                                              21

<210> SEQ ID NO 468
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 468
aagguuacuu guuaguucag g                                              21

<210> SEQ ID NO 469
<211> LENGTH: 22
<212> TYPE: RNA
```

<213> ORGANISM: Artificial Sequence
<220> FEATURE:
<223> OTHER INFORMATION: Synthetic Sequence

<400> SEQUENCE: 469
gcacugagau gggaguggug ua                                    22

<210> SEQ ID NO 470
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 470
gcgacccaua cuugguuuca g                                     21

<210> SEQ ID NO 471
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 471
ccuggaaaca cugagguugu gu                                    22

<210> SEQ ID NO 472
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 472
uauaccucag uuuuaucagg ug                                    22

<210> SEQ ID NO 473
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 473
uggugguuua caaaguaauu ca                                    22

<210> SEQ ID NO 474
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 474
uggauuucuu ugugaaucac ca                                    22

<210> SEQ ID NO 475
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 475
ugcaacgaac cugagccacu ga                                    22

```
<210> SEQ ID NO 476
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 476
auaauacaug guuaaccucu uu                                              22

<210> SEQ ID NO 477
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 477
uacuuggaaa ggcaucaguu g                                               21

<210> SEQ ID NO 478
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 478
ugcaacuuac cugagucauu ga                                              22

<210> SEQ ID NO 479
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 479
guagaggaga uggcgcaggg                                                 20

<210> SEQ ID NO 480
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 480
uacccauugc auaucggagu u                                               21

<210> SEQ ID NO 481
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 481
cggggcagcu caguacagga u                                               21

<210> SEQ ID NO 482
<211> LENGTH: 77
<212> TYPE: RNA
<213> ORGANISM: Artificial Sequence
<220> FEATURE:
```

<223> OTHER INFORMATION: Synthetic Sequence

<400> SEQUENCE: 482
ggcagugcuc uacucaaaaa gcugucaguc acuuagauua caugugacug acaccucuuu    60
gggugaagga aggcuca                                                   77

<210> SEQ ID NO 483
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 483
aacuuguuag aagguuacuu guuaguucag gaccucauua cuuucugccu gaacuauugc    60
aguagccucc uaacugguua u                                              81

<210> SEQ ID NO 484
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 484
ccugagccuu gcacugagau gggaguggug uaaggcucag guaugcacag cucccaucuc    60
agaacaaggc ucgggug                                                   77

<210> SEQ ID NO 485
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 485
ccuggcccau gaaaucaagc gugggugaga ccuggugcag aacgggaagg cgacccauac    60
uugguuucag aggcugugag                                                80

<210> SEQ ID NO 486
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 486 uuaguggüac uauaccucag uuuuaucagg uguucuuaaa aucaccugga aacacugagg    60 uuguğucuca cugaac                                                    76

<210> SEQ ID NO 487
<211> LENGTH: 76
<212> TYPE: RNA
<213> ORGANISM: Artificial Sequence
<220> FEATURE:
<223> OTHER INFORMATION: Synthetic Sequence

<400> SEQUENCE: 487 uuaguggüac uauaccucag uuuuaucagg uguucuuaaa aucaccugga aacacugagg    60 uuguğucuca cugaac                                                    76

```
<210> SEQ ID NO 488
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 488
ugaagugcug uggauuucuu ugugaaucac cauaucuaag cuaauguggu ggugguuuac    60
aaaguaauuc auagugcuuc a                                             81

<210> SEQ ID NO 489
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 489
ugaagugcug uggauuucuu ugugaaucac cauaucuaag cuaauguggu ggugguuuac    60
aaaguaauuc auagugcuuc a                                             81

<210> SEQ ID NO 490
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 490
ccuuaauccu ugcaacgaac cugagccacu gauucaguaa aauacucagu ggcacauguu    60
uguugugagg gucaaaaga                                                79

<210> SEQ ID NO 491
<211> LENGTH: 80
<212> TYPE: RNA
<213> ORGANISM: Artificial Sequence
<220> FEATURE:
<223> OTHER INFORMATION: Synthetic Sequence

<400> SEQUENCE: 491
auauuugagg agagguuauc cguguuaugu ucgcuucauu caucaugaau aauacauggu    60
uaaccucuuu uugaauauca                                               80

<210> SEQ ID NO 492
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 492
ggaagugccc uacuuggaaa ggcaucaguu gcuuagauua cauguaacua uucccuuucu    60
gaguagagua agucuua                                                  77

<210> SEQ ID NO 493
<211> LENGTH: 79
<212> TYPE: RNA
<213> ORGANISM: Artificial Sequence
<220> FEATURE:
<223> OTHER INFORMATION: Synthetic Sequence

<400> SEQUENCE: 493
```

```
ccuuaauccu ugcaacuuac cugagucauu gauucaguaa aacauucaau ggcacauguu    60
uguuguuagg gucaaaaga                                                 79

<210> SEQ ID NO 494
<211> LENGTH: 103
<212> TYPE: RNA
<213> ORGANISM: Artificial Sequence
<220> FEATURE:
<223> OTHER INFORMATION: Synthetic Sequence

<400> SEQUENCE: 494
gcuagagaag guagaggaga uggcgcaggg gacacgggca aagacuuggg gguuccuggg    60
acccucagac guguguccuc uucucccucc ucccaggugu aug                     103

<210> SEQ ID NO 495
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 495
ccuucuccca uacccauugc auaucggagu ugugaauucu caaaacaccu ccugugugca    60
uggauuacag gaggguga                                                  78

<210> SEQ ID NO 496
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 496
cccuggggca uccuguacug agcugccccg aggcccuuca ugcugcccag cucggggcag    60
cucaguacag gauacucggg gugg                                           84

<210> SEQ ID NO 497
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 497
cugcccuaaa ugccccuucu ggc                                            23

<210> SEQ ID NO 498
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 498
uuaauaugua cugacaaagc gu                                             22

<210> SEQ ID NO 499
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 499
```

```
uuuccggcuc gcguggguqu gu                                              22

<210> SEQ ID NO 500
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 500
auguugggag cgggcagguu gg                                              22

<210> SEQ ID NO 501
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 501
aguaccacgu gucagggcca cauga                                           25

<210> SEQ ID NO 502
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 502
uuggggaaac ggccgcugag uga                                             23

<210> SEQ ID NO 503
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 503
cuguaugccc ucaccgcuca gc                                              22

<210> SEQ ID NO 504
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 504
gcggcggcgg cggaggcu                                                   18

<210> SEQ ID NO 505
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 505
gcggcggcgg cggaggcu                                                   18

<210> SEQ ID NO 506
<211> LENGTH: 21
<212> TYPE: RNA
```

<213> ORGANISM: Artificial Sequence
<220> FEATURE:
<223> OTHER INFORMATION: Synthetic Sequence

<400> SEQUENCE: 506
ucuaguaaga guggcagucg a                                           21

<210> SEQ ID NO 507
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 507
augcugacau auuuacuaga gg                                          22

<210> SEQ ID NO 508
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 508 ugggggcggag cuuccggagg cc                                         22

<210> SEQ ID NO 509
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 509 ugggcggag cuuccggagg cc                                           22

<210> SEQ ID NO 510
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 510 ugggcggag cuuccggagg cc                                           22

<210> SEQ ID NO 511
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 511
acucggcgug gcgucggucg ugg                                         23

<210> SEQ ID NO 512
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 512
ucgaccggac cucgaccggc uc                                          22

<210> SEQ ID NO 513
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 513
aaagcaugcu ccaguggcgc                                               20

<210> SEQ ID NO 514
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 514
aaagcaugcu ccaguggcgc                                               20

<210> SEQ ID NO 515
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 515
cagagaggac cacuauggcg gg                                            22

<210> SEQ ID NO 516
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 516
auugccaucc ccuauggacc ag                                            22

<210> SEQ ID NO 517
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 517
ugucuacuac uggagacacu gg                                            22

<210> SEQ ID NO 518
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 518
uuagggcccu ggcuccaucu cc                                            22

<210> SEQ ID NO 519
<211> LENGTH: 22
<212> TYPE: RNA
<213> ORGANISM: Artificial Sequence
<220> FEATURE:

<223> OTHER INFORMATION: Synthetic Sequence

<400> SEQUENCE: 519
ugggaucucc ggggucuugg uu                                         22

<210> SEQ ID NO 520
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 520
aaggcagggc ccccgcuccc cgg                                        23

<210> SEQ ID NO 521
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 521
aaaagcugag uugagagg                                              18

<210> SEQ ID NO 522
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 522
ucgaggagcu cacagucuag a                                          21

<210> SEQ ID NO 523
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 523
cuuguguuaa ggugcaucua gugcaguuag ugaagcagcu agaaucuac ugcccuaaau  60 gccccuucug gcacagg                                               77

<210> SEQ ID NO 524
<211> LENGTH: 97
<212> TYPE: RNA
<213> ORGANISM: Artificial Sequence
<220> FEATURE:
<223> OTHER INFORMATION: Synthetic Sequence

<400> SEQUENCE: 524
uuauugugaa auaugucauu aauauguacu gacaaagcgu aucuguguaa uaaauaugcu  60
uuuugucagu acauguuaau gguauauuuc auaacaa                          97

<210> SEQ ID NO 525
<211> LENGTH: 75
<212> TYPE: RNA
<213> ORGANISM: Artificial Sequence
<220> FEATURE:
<223> OTHER INFORMATION: Synthetic Sequence

<400> SEQUENCE: 525

```
gcggcugcug gacccacccg gccgggaaua gugcuccugg uuguuccgg cucgcguggg    60 ugugucggcg gcggg                                                   75

<210> SEQ ID NO 526
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 526
cgcccccacg uggccccgcc cccugaggcc ggcgcugccg ccauguuggg agcgggcagg   60
uugggagcg                                                          69

<210> SEQ ID NO 527
<211> LENGTH: 89
<212> TYPE: RNA
<213> ORGANISM: Artificial Sequence
<220> FEATURE:
<223> OTHER INFORMATION: Synthetic Sequence

<400> SEQUENCE: 527
gccaccuucc gagccuccag uaccacgugu cagggccaca ugagcugggc cucgugggcc   60
ugauguggug cugggccuc aggggucug                                     89

<210> SEQ ID NO 528
<211> LENGTH: 69
<212> TYPE: RNA
<213> ORGANISM: Artificial Sequence
<220> FEATURE:
<223> OTHER INFORMATION: Synthetic Sequence

<400> SEQUENCE: 528
ggguuugggg aaacggccgc ugagugaggc gucggcugug uuucucaccg cggucuuuuc   60
cucccacuc                                                          69

<210> SEQ ID NO 529
<211> LENGTH: 97
<212> TYPE: RNA
<213> ORGANISM: Artificial Sequence
<220> FEATURE:
<223> OTHER INFORMATION: Synthetic Sequence

<400> SEQUENCE: 529
cuuggugacg cuguaugccc ucaccgcuca gccccugggg cuggcuuggc agacaguaca   60
gcauccaggg gagucaaggg caugggcga gaccaga                            97

<210> SEQ ID NO 530
<211> LENGTH: 86
<212> TYPE: RNA
<213> ORGANISM: Artificial Sequence
<220> FEATURE:
<223> OTHER INFORMATION: Synthetic Sequence

<400> SEQUENCE: 530
gcggcggcgg cggaggcugc ugcuggggcg gcugcugcug gggcggcugc ggcggcggcu   60
gcugcggggg cugcugcugc uguugc                                       86

<210> SEQ ID NO 531
<211> LENGTH: 80
<212> TYPE: RNA
```

```
<213> ORGANISM: Artificial Sequence
<220> FEATURE:
<223> OTHER INFORMATION: Synthetic Sequence

<400> SEQUENCE: 531
gcggcugcgg cggcggcgga ggcugcggcg gcgaccgugg cagaggcggu ggcggaggcc    60
uccguggcgg aggcggaagc                                                80

<210> SEQ ID NO 532
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 532
cuuccucaug cugacauauu uacuagaggg uaaaauuaau aaccuucuag uaagaguggc    60
agucgaaggg aag                                                       73

<210> SEQ ID NO 533
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 533
cuuccucaug cugacauauu uacuagaggg uaaaauuaau aaccuucuag uaagaguggc    60
agucgaaggg aag                                                       73

<210> SEQ ID NO 534
<211> LENGTH: 153
<212> TYPE: RNA
<213> ORGANISM: Artificial Sequence
<220> FEATURE:
<223> OTHER INFORMATION: Synthetic Sequence

<400> SEQUENCE: 534
gcuccgcccc acgucgcaug cgccccggga acgcgugggg cggagcuucc ggaggccccg    60
cucugcugcc gacccugugg agcggagggu gaagccuccg gaugccaguc ccucaucgcu   120
ggccuggucg cgcuguggcg aaggggcgg agc                                 153

<210> SEQ ID NO 535
<211> LENGTH: 153
<212> TYPE: RNA
<213> ORGANISM: Artificial Sequence
<220> FEATURE:
<223> OTHER INFORMATION: Synthetic Sequence

<400> SEQUENCE: 535
gcuccgcccc acgucgcaug cgccccggga acgcgugggg cggagcuucc ggaggccccg    60
cccugcugcc gacccugugg agcggagggu gaagccuccg gaugccaguc ccucaucgcu   120
ggcccggucg cgcuguggcg aaggggcgg agc                                 153

<210> SEQ ID NO 536
<211> LENGTH: 154
<212> TYPE: RNA
<213> ORGANISM: Artificial Sequence
<220> FEATURE:
<223> OTHER INFORMATION: Synthetic Sequence

<400> SEQUENCE: 536
```

```
cgcuccgccc cacgucgcau gcgccccggg aaagcguggg gcggagcuuc cggaggcccc    60
gcccugcugc cgacccugug gagcggaggg ugaagccucc ggaugccagu cccucaucgc   120
uggcccgguc gcgcugtggc gaaggggcg gagc                                154
```

```
<210> SEQ ID NO 537
<211> LENGTH: 151
<212> TYPE: RNA
<213> ORGANISM: Artificial Sequence
<220> FEATURE:
<223> OTHER INFORMATION: Synthetic Sequence

<400> SEQUENCE: 537
uucaucaaga cccagcugag ucacugucac ugccuaccaa ucucgaccgg accucgaccg    60
gcucgucugu guugccaauc gacucggcgu ggcgucgguc gugguagaua ggcggucaug   120
cauacgaauu uucagcucuu gucugguga c                                   151
```

```
<210> SEQ ID NO 538
<211> LENGTH: 151
<212> TYPE: RNA
<213> ORGANISM: Artificial Sequence
<220> FEATURE:
<223> OTHER INFORMATION: Synthetic Sequence

<400> SEQUENCE: 538
uucaucaaga cccagcugag ucacugucac ugccuaccaa ucucgaccgg accucgaccg    60
gcucgucugu guugccaauc gacucggcgu ggcgucgguc gugguagaua ggcggucaug   120
cauacgaauu uucagcucuu gucugguga c                                   151
```

```
<210> SEQ ID NO 539
<211> LENGTH: 87
<212> TYPE: RNA
<213> ORGANISM: Artificial Sequence
<220> FEATURE:
<223> OTHER INFORMATION: Synthetic Sequence

<400> SEQUENCE: 539
cgcgaggccg ggducgagcg cuucaguagc ucauggcucu guagagugcg cauggccaag    60
caaaggaaag caugcuccag uggcgca                                        87
```

```
<210> SEQ ID NO 540
<211> LENGTH: 66
<212> TYPE: RNA
<213> ORGANISM: Artificial Sequence
<220> FEATURE:
<223> OTHER INFORMATION: Synthetic Sequence

<400> SEQUENCE: 540
aguaaccacu uaguguguau ugacuuguca gaauuuucag aauuuaaagc augcuccagu    60
ggcgca                                                               66
```

```
<210> SEQ ID NO 541
<211> LENGTH: 95
<212> TYPE: RNA
<213> ORGANISM: Artificial Sequence
<220> FEATURE:
<223> OTHER INFORMATION: Synthetic Sequence

<400> SEQUENCE: 541
uuacuguguc auuguugcug ucauugcuac ugaggaguac ugaccagaau caucugcaac    60
```

```
ucuuaguugg cagagaggac cacuauggcg gguag                                    95

<210> SEQ ID NO 542
<211> LENGTH: 84
<212> TYPE: RNA
<213> ORGANISM: Artificial Sequence
<220> FEATURE:
<223> OTHER INFORMATION: Synthetic Sequence

<400> SEQUENCE: 542
ugggccagau ugccaucccc uauggaccag aagccaagga ucucucuagu gauggucaga        60
gggcccaaau ggcagggaua ccca                                               84

<210> SEQ ID NO 543
<211> LENGTH: 65
<212> TYPE: RNA
<213> ORGANISM: Artificial Sequence
<220> FEATURE:
<223> OTHER INFORMATION: Synthetic Sequence

<400> SEQUENCE: 543
gcuucugucu acuacuggag acacugguag uauaaaaccc agagucucca guaauggacg        60
ggagc                                                                    65

<210> SEQ ID NO 544
<211> LENGTH: 73
<212> TYPE: RNA
<213> ORGANISM: Artificial Sequence
<220> FEATURE:
<223> OTHER INFORMATION: Synthetic Sequence

<400> SEQUENCE: 544
cuggguuagg gcccuggcuc caucuccuuu aggaaaaccu ucugugggga gugggcuuc         60 gacccuaacc cag                                                           73

<210> SEQ ID NO 545
<211> LENGTH: 81
<212> TYPE: RNA
<213> ORGANISM: Artificial Sequence
<220> FEATURE:
<223> OTHER INFORMATION: Synthetic Sequence

<400> SEQUENCE: 545
ccugggcucu gaccugagac cucugggpuc ugagcuguga uguugcucuc gagcugggau        60 cuccggggluc uugguucagg g                                                 81

<210> SEQ ID NO 546
<211> LENGTH: 77
<212> TYPE: RNA
<213> ORGANISM: Artificial Sequence
<220> FEATURE:
<223> OTHER INFORMATION: Synthetic Sequence

<400> SEQUENCE: 546
gggcccggcc ccaggagcgg ggccugggca gccccgugug uugaggaagg aaggcagggc        60
ccccgcuccc cgggccu                                                       77

<210> SEQ ID NO 547
<211> LENGTH: 50
<212> TYPE: RNA
<213> ORGANISM: Artificial Sequence
<220> FEATURE:
<223> OTHER INFORMATION: Synthetic Sequence
```

<400> SEQUENCE: 547
ccuucucuuc ucaguucuuc cccaaguuag gaaaagcuga guugagaggg       50

<210> SEQ ID NO 548
<211> LENGTH: 66
<212> TYPE: RNA
<213> ORGANISM: Artificial Sequence
<220> FEATURE:
<223> OTHER INFORMATION: Synthetic Sequence

<400> SEQUENCE: 548
gucucucuuc agggcucccg agacacagaa acagacaccu gcccucgagg agcucacagu       60
cuagac                                                                 66

<210> SEQ ID NO 549
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 549
auucugcauu uuuagcaagu uc                                               22

<210> SEQ ID NO 550
<211> LENGTH: 78
<212> TYPE: RNA
<213> ORGANISM: Artificial Sequence
<220> FEATURE:
<223> OTHER INFORMATION: Synthetic Sequence

<400> SEQUENCE: 550
caccuaggga ucuuguuaaa aagcagauuc ugauucaggg accaagauuc ugcauuuuua       60
gcaaguucuc aagugaug                                                    78

<210> SEQ ID NO 551
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 551
ugacugacag cuuuuugagu a                                                21

<210> SEQ ID NO 552
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 552
ugcuguuagc ccuagccccg ca                                               22

<210> SEQ ID NO 553
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 553
acgguccuac acucaaggca ug                                                22

<210> SEQ ID NO 554
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 554
aagagggaga cccaggcucg ga                                                22

<210> SEQ ID NO 555
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 555
ccugaacuaa caaguaaccu u                                                 21

<210> SEQ ID NO 556
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 556
ccagcaccac aucaggccca cg                                                22

<210> SEQ ID NO 557
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 557
aagaagugca ccgcgaaugu uu                                                22

<210> SEQ ID NO 558
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 558
gggaccgaca gcagaauccu u                                                 21

<210> SEQ ID NO 559
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 559
aacccaauau caaacauauc a                                                 21

<210> SEQ ID NO 560
<211> LENGTH: 22
<212> TYPE: RNA
<213> ORGANISM: Artificial Sequence

```
<220> FEATURE:
<223> OTHER INFORMATION: Synthetic Sequence

<400> SEQUENCE: 560
uacaccacuc ccaucucagu gc                                                  22

<210> SEQ ID NO 561
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 561
aggagacuca caaguuccug c                                                   21

<210> SEQ ID NO 562
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 562
acacaacccu aguggcgcca uu                                                  22

<210> SEQ ID NO 563
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 563
ggacuauaga acuuccccc u                                                    21

<210> SEQ ID NO 564
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 564
agaggcaggg uaguguaaug ga                                                  22

<210> SEQ ID NO 565
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 565
acacaccaag gauaauuucu cc                                                  22

<210> SEQ ID NO 566
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 566
uuucaguuau caaucuguca ca                                                  22
```

```
<210> SEQ ID NO 567
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 567
ucucgugaca ugaugauccc cga                                              23

<210> SEQ ID NO 568
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 568
acuagcuuau acauaaaauu a                                                21

<210> SEQ ID NO 569
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 569
cuccagcccc uccagggcuu ccu                                              23

<210> SEQ ID NO 570
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 570
gcaaagguaa uugcuguuuu cg                                               22

<210> SEQ ID NO 571
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 571
cuagaagcuc acagucuagu ug                                               22

<210> SEQ ID NO 572
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 572
cccagcuaga uuguaagcuc cuu                                              23

<210> SEQ ID NO 573
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 573
cuccccacag acccagagcc g                                              21

<210> SEQ ID NO 574
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 574
ccucgggaug gcgcccguuc ac                                             22

<210> SEQ ID NO 575
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 575
gcacacaaua aauguuugcu ga                                             22

<210> SEQ ID NO 576
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 576
ucgguccduc gggccagggc ag                                             22

<210> SEQ ID NO 577
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 577
ugugggugug ugcaugagcg ug                                             22

<210> SEQ ID NO 578
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 578
acacacucac acacacacac uca                                            23

<210> SEQ ID NO 579
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 579
aaggugaugg ucagcagaca ua                                             22

<210> SEQ ID NO 580
```

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 580
gcacauguuc ugcggcccac ca                                                  22

<210> SEQ ID NO 581
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 581
aagggucagu aagcacccgc g                                                   21

<210> SEQ ID NO 582
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 582
ccgcuugagc uaacuccgac ccg                                                 23

<210> SEQ ID NO 583
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 583
cugaaaccaa guauggucg c                                                    21

<210> SEQ ID NO 584
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 584
acacaaccuc aguguuucca gg                                                  22

<210> SEQ ID NO 585
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 585
caccugauaa aacugaggua ua                                                  22

<210> SEQ ID NO 586
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 586
```
ugaauuacuu uguaaaccac ca				22

<210> SEQ ID NO 587
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 587
uggugauuca caaagaaauc ca				22

<210> SEQ ID NO 588
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 588
aggggccuca gccuccuggu				20

<210> SEQ ID NO 589
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 589
agccuaugga auucaguucu ca				22

<210> SEQ ID NO 590
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 590
uagcagaagc auuccgcac ac				22

<210> SEQ ID NO 591
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 591
acccaccgac aacaaugaau guu				23

<210> SEQ ID NO 592
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 592
cuaacugcac uagaugcacc uua				23

<210> SEQ ID NO 593
<211> LENGTH: 22
<212> TYPE: RNA

```
<213> ORGANISM: Artificial Sequence
<220> FEATURE:
<223> OTHER INFORMATION: Synthetic Sequence

<400> SEQUENCE: 593
agcgggacuu ugagggccag uu                                          22

<210> SEQ ID NO 594
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 594
ucaguggcuc agguucguug ca                                          22

<210> SEQ ID NO 595
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 595
aaagagguua accauguauu au                                          22

<210> SEQ ID NO 596
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 596
caacugaugc cuuccaagu a                                            21

<210> SEQ ID NO 597
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 597
ucaaugacuc agguaaguug ca                                          22

<210> SEQ ID NO 598
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 598
cccugcgcca ucuccucuac                                             20

<210> SEQ ID NO 599
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 599
aacuccgaua ugcaaugggu a                                           21
```

```
<210> SEQ ID NO 600
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 600
cuaccugcac uaugagcacu uug                                              23

<210> SEQ ID NO 601
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 601
cuggaagugc ccauacuaca gu                                               22

<210> SEQ ID NO 602
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 602
ucacauuugc cugcagagau uu                                               22

<210> SEQ ID NO 603
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 603
ugcuuugaca auaucauugc acug                                             24

<210> SEQ ID NO 604
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 604
aaagagguua accaggugug uu                                               22

<210> SEQ ID NO 605
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 605
gcaaugcaac agcaaugcac                                                  20

<210> SEQ ID NO 606
<211> LENGTH: 20
<212> TYPE: RNA
<213> ORGANISM: Artificial Sequence
<220> FEATURE:
```

```
<223> OTHER INFORMATION: Synthetic Sequence

<400> SEQUENCE: 606
gcaaugcaac agcaaugcac                                              20

<210> SEQ ID NO 607
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 607
ucacgcgagc cgaacgaaca aa                                           22

<210> SEQ ID NO 608
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 608
acguggauuu uccucuauga u                                            21

<210> SEQ ID NO 609
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 609
aacauggauu uccucuaug au                                            22

<210> SEQ ID NO 610
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 610
aaguggauga cccuguacga uu                                           22

<210> SEQ ID NO 611
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 611
aaguggauga cccuguacga uu                                           22

<210> SEQ ID NO 612
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 612
acaaaaguug ccuuugugug au                                           22
```

```
<210> SEQ ID NO 613
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 613
ccuucugacu ccaaguccag u                                              21

<210> SEQ ID NO 614
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 614
ccuacguucc auagucuacc a                                              21

<210> SEQ ID NO 615
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 615
aagaugugga ccauauuaca ua                                             22

<210> SEQ ID NO 616
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 616
acaggccauc uguguuauau u                                              21

<210> SEQ ID NO 617
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 617
cgcccaauua augucuguug au                                             22

<210> SEQ ID NO 618
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 618
acgguuuuac cagacaguau ua                                             22

<210> SEQ ID NO 619
<211> LENGTH: 21
<212> TYPE: RNA
<213> ORGANISM: Artificial Sequence
<220> FEATURE:
<223> OTHER INFORMATION: Synthetic Sequence
```

<400> SEQUENCE: 619
ugcaugacgg ccugcaagac a                                           21

<210> SEQ ID NO 620
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 620
ccacccaaug accuacucca aga                                         23

<210> SEQ ID NO 621
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 621
acaccgagga gcccaucaug au                                          22

<210> SEQ ID NO 622
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 622
accagcuaac aauacacugc ca                                          22

<210> SEQ ID NO 623
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 623
gccagcuaac aauacacugc cu                                          22

<210> SEQ ID NO 624
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 624
auauuaggaa cacaucgcaa aa                                          22

<210> SEQ ID NO 625
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 625
aacucaguaa ugguaacggu uu                                          22

<210> SEQ ID NO 626
<211> LENGTH: 22

```
<212> TYPE: RNA
<213> ORGANISM: Artificial Sequence
<220> FEATURE:
<223> OTHER INFORMATION: Synthetic Sequence

<400> SEQUENCE: 626
ucaguucccu cugcaaacag uu                                              22

<210> SEQ ID NO 627
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 627
ugcgaacuca ccacggacaa ccu                                             23

<210> SEQ ID NO 628
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 628
acccuauaag caauauugca cua                                             23

<210> SEQ ID NO 629
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 629
cgauguaguc caaaggcaca ua                                              22

<210> SEQ ID NO 630
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 630
aucgggaggg gacugagccu ga                                              22

<210> SEQ ID NO 631
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 631
agagaggaga gccguguaug ac                                              22

<210> SEQ ID NO 632
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 632
```

```
gaauucauca cggccagccu cu                                              22

<210> SEQ ID NO 633
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 633
auccuguacu gagcugcccc g                                               21

<210> SEQ ID NO 634
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 634
aacuggaugu cccuguauga uu                                              22

<210> SEQ ID NO 635
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 635
agaccaagaa auagccuuuc aa                                              22

<210> SEQ ID NO 636
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 636
acccaccugg agauccaugg                                                 20

<210> SEQ ID NO 637
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 637
ccuggcacac aguagaccuu ca                                              22

<210> SEQ ID NO 638
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 638
acaaaccaca gugugcugcu g                                               21

<210> SEQ ID NO 639
<211> LENGTH: 22
<212> TYPE: RNA
<213> ORGANISM: Artificial Sequence
```

```
<220> FEATURE:
<223> OTHER INFORMATION: Synthetic Sequence

<400> SEQUENCE: 639
ugaauccuug cccaggugca uu                                              22

<210> SEQ ID NO 640
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 640
cugcagaacu guucccgcug cua                                             23

<210> SEQ ID NO 641
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 641
aggaaaccag caaguguuga cg                                              22

<210> SEQ ID NO 642
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 642
cuacccacag acguaccaau ca                                              22

<210> SEQ ID NO 643
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 643
ucuacucaca gaagugucaa u                                               21

<210> SEQ ID NO 644
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 644
gaggccggga cgagugcaau a                                               21

<210> SEQ ID NO 645
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 645
ugacugacag cuuuuugagu a                                               21
```

<210> SEQ ID NO 646
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 646
ccugaacuaa caaguaaccu u                                           21

<210> SEQ ID NO 647
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 647
uacaccacuc ccaucucagu gc                                          22

<210> SEQ ID NO 648
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 648
cugaaaccaa guaugggucg c                                           21

<210> SEQ ID NO 649
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 649
acacaaccuc aguguuucca gg                                          22

<210> SEQ ID NO 650
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 650
caccugauaa aacugaggua ua                                          22

<210> SEQ ID NO 651
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 651
ugaauuacuu uguaaaccac ca                                          22

<210> SEQ ID NO 652
<211> LENGTH: 22
<212> TYPE: RNA
<213> ORGANISM: Artificial Sequence
<220> FEATURE:
<223> OTHER INFORMATION: Synthetic Sequence

```
<400> SEQUENCE: 652
uggugauuca caaagaaauc ca                                           22

<210> SEQ ID NO 653
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 653
ucaguggcuc agguucguug ca                                           22

<210> SEQ ID NO 654
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 654
aaagagguua accauguauu au                                           22

<210> SEQ ID NO 655
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 655
caacugaugc cuuccaagu a                                             21

<210> SEQ ID NO 656
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 656
ucaaugacuc agguaaguug ca                                           22

<210> SEQ ID NO 657
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 657
cccugcgcca ucuccucuac                                              20

<210> SEQ ID NO 658
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 658
aacuccgaua ugcaaugggu a                                            21

<210> SEQ ID NO 659
```

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 659
uccuguacug agcugccccg                                                     20

<210> SEQ ID NO 660
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 660
gccagaaggg gcauuuaggg cag                                                 23

<210> SEQ ID NO 661
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 661
acgcuuuguc aguacauauu aa                                                  22

<210> SEQ ID NO 662
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 662
acacacccac gcgagccgga aa                                                  22

<210> SEQ ID NO 663
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 663
ccaaccugcc cgcucccaac au                                                  22

<210> SEQ ID NO 664
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 664
ucauguggcc cugacacgug guacu                                               25

<210> SEQ ID NO 665
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 665
```
ucacucagcg gccguuuccc caa 23

<210> SEQ ID NO 666
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 666
gcugagcggu gagggcauac ag 22

<210> SEQ ID NO 667
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 667
agccuccgcc gccgccgc 18

<210> SEQ ID NO 668
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 668
agccuccgcc gccgccgc 18

<210> SEQ ID NO 669
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 669
ucgacugcca cucuuacuag a 21

<210> SEQ ID NO 670
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 670
ccucuaguaa auaugucagc au 22

<210> SEQ ID NO 671
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 671
ggccuccgga agcuccgccc ca 22

<210> SEQ ID NO 672
<211> LENGTH: 22
<212> TYPE: RNA

```
<213> ORGANISM: Artificial Sequence
<220> FEATURE:
<223> OTHER INFORMATION: Synthetic Sequence

<400> SEQUENCE: 672
ggccuccgga agcuccgccc ca                                              22

<210> SEQ ID NO 673
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 673
ggccuccgga agcuccgccc ca                                              22

<210> SEQ ID NO 674
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 674
ccacgaccga cgccacgccg agu                                             23

<210> SEQ ID NO 675
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 675
gagccggucg agguccgguc ga                                              22

<210> SEQ ID NO 676
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 676
gcgccacugg agcaugcuuu                                                 20

<210> SEQ ID NO 677
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 677
gcgccacugg agcaugcuuu                                                 20

<210> SEQ ID NO 678
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 678
cccgccauag ugguccucuc ug                                              22
```

<210> SEQ ID NO 679
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 679
cugguccaua ggggauggca au                                            22

<210> SEQ ID NO 680
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 680
ccagugucuc caguaguaga ca                                            22

<210> SEQ ID NO 681
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 681
ggagauggag ccagggcccu aa                                            22

<210> SEQ ID NO 682
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 682
aaccaagacc ccggagaucc ca                                            22

<210> SEQ ID NO 683
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 683
ccggggagcg ggggcccugc cuu                                           23

<210> SEQ ID NO 684
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 684
ccucucaacu cagcuuuu                                                 18

<210> SEQ ID NO 685
<211> LENGTH: 20
<212> TYPE: RNA
<213> ORGANISM: Artificial Sequence
<220> FEATURE:

```
<223> OTHER INFORMATION: Synthetic Sequence

<400> SEQUENCE: 685
cuagacugug agcuccucga                                                    20

<210> SEQ ID NO 686
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 686
auucugcauu uuuagcaagu uc                                                 22
```

HUMAN MICRORNAS AND METHODS FOR INHIBITING SAME

CROSS-REFERENCE TO RELATED APPLICATIONS

This application is a divisional of U.S. application Ser. No. 13/469,689, filed on May 11, 2012, which is a divisional of U.S. application Ser. No. 11/919,393, filed on Oct. 26, 2007, which is a National Phase application of International Application No. PCT/US06/16767 filed May 1, 2006, which claims priority based on U.S. Provisional Application No. 60/714,519 filed Apr. 29, 2005, which are incorporated herein by reference.

This application asserts priority to U.S. Provisional Application Ser. No. 60/714,519 filed on Apr. 29, 2005, the specification of which is hereby incorporated by reference in its entirety.

The invention described in this application was made with funds from the National Institutes of Health/NIGMS, Grant Numbers 1 P01 GM073047-01 and 1 R01 GM068476-01. The United States government has certain rights in this invention.

BACKGROUND OF THE INVENTION

MicroRNAs are typically small RNA molecules of generally about nineteen to twenty-five nucleotides in length. These microRNAs are non-coding RNAs which are cleaved from hairpin precursors. Several microRNAs have been identified in the genomes of a wide range of multicellular life forms.

MicroRNAs in animals are found in diverse genomic locations. Typically, most microRNAs are encoded in intergenic regions. Other microRNAs are hosted within the introns of mRNAs or within non-coding RNA transcripts.

Many microRNAs are conserved in sequence between distantly related organisms, and exhibit tissue-specific or developmental stage-specific expression. The conservation of the sequence between organisms indicates that microRNAs may play important roles in biological processes.

MicroRNA molecules have been reported to control gene expression in a sequence specific manner in a wide variety of organisms by blocking translation after partially hybridizing to the non-coding 3' region of mRNAs of target genes. The genes targeted by microRNAs largely remain to be characterized.

However, there is growing evidence that microRNAs are implicated in various diseases and illnesses. For instance, Drosophila microRNAs have been shown to target genes involved in apoptosis. Also, B-cell chronic lymphocytic leukemia has been linked to the deletion of two microRNAs.

Therefore, it is important to elucidate the mechanisms involved in mediating genes which play a role in the regulation of various diseases and illnesses. Thus, there is a need for materials and methods that can help elucidate the function of regulators, such as microRNAs, in various diseases and illnesses.

Further, due to the ability of microRNAs to induce RNA degradation or repress translation of mRNA which encode important proteins, there is also a need for novel molecules that inhibit microRNA-induced cleavage or promote expression by inhibiting translational repression of target mRNAs.

SUMMARY OF THE INVENTION

In one embodiment, the invention relates to an isolated DNA or RNA molecule comprising at least ten contiguous bases having a sequence in a microRNA shown in SEQ ID NOs:1-94, except that up to thirty percent of the bases may be wobble bases, and up to 10% of the contiguous bases may be non-complementary.

In another embodiment, the invention relates to a modified single stranded microRNA molecule comprising a minimum of ten moieties and a maximum of fifty moieties on a molecular backbone, the molecular backbone comprising backbone units, each moiety comprising a base bonded to a backbone unit, wherein at least ten contiguous bases have the same sequence as a contiguous sequence of bases in a microRNA molecule shown in SEQ ID NOs:1-94, except that up to thirty percent of the bases pairs may be wobble base pairs, and up to 10% of the contiguous bases may be additions, deletions, mismatches, or combinations thereof; no more than fifty percent of the contiguous moieties contain deoxyribonucleotide backbone units, and at least one moiety is not an unmodified deoxyribonucleotide moiety or an unmodified ribonucleotide moiety.

In a further embodiment, the invention relates to an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases have a sequence complementary to a contiguous sequence of bases in any one of the microRNA molecules shown in SEQ ID NOs; 1-94, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units; and the molecule is capable of inhibiting microRNP activity.

In yet another embodiment, the invention relates to a method for inhibiting microRNP activity in a cell, the microRNP comprising a microRNA molecule, the method comprising introducing into the cell a single-stranded anti-microRNA molecule according to claim 18, wherein the anti-microRNA is complementary to the microRNA molecule.

In yet a further embodiment, the invention relates to an isolated microRNP comprising an isolated DNA or RNA molecule described herein.

In another embodiment, the invention relates to an isolated microRNP comprising an isolated single stranded microRNA molecule described herein.

In another embodiment, the invention relates to an isolated DNA or RNA molecule comprising at least ten contiguous bases having a sequence in a microRNA shown in SEQ. ID. NOs:281-374, except that up to thirty percent of the bases may be wobble bases, and up to 10% of the contiguous bases may be wobble bases, and up to 10% of the contiguous bases may be non-complementary.

In another embodiment, the invention relates to an isolated DNA or RNA molecule comprising at least ten contiguous bases having a sequence in a microRNA shown in SEQ. ID. NOs:467-481, except that up to thirty percent of the bases may be wobble bases, and up to 10% of the contiguous bases may be wobble bases, and up to 10% of the contiguous bases may be non-complementary.

In another embodiment, the invention relates to an isolated DNA or RNA molecule comprising at least ten contiguous bases having a sequence in a microRNA shown in SEQ. ID. NOs:497-522, except that up to thirty percent of the bases may be wobble bases, and up to 10% of the contiguous bases may be wobble bases, and up to 10% of the contiguous bases may be non-complementary.

In another embodiment, the invention relates to an isolated DNA or RNA molecule comprising at least ten contiguous bases having a sequence in a microRNA shown in SEQ. ID. NO:549, except that up to thirty percent of the bases may be wobble bases, and up to 10% of the contiguous bases may be wobble bases, and up to 10% of the contiguous bases may be non-complementary.

In another embodiment, the invention relates to a modified single stranded microRNA molecule comprising a minimum of ten moieties and a maximum of fifty moieties on a molecular backbone, the molecular backbone comprising backbone unites, each moiety comprising a base bonded to a backbone unit, wherein at least ten contiguous bases have the same sequence as a contiguous sequence of bases in a microRNA molecule shown in SEQ. ID. NOs: 281-374, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units, and at least one moiety is not an unmodified deoxyribonucleotide moiety or an unmodified ribonucleotide moiety.

In another embodiment, the invention relates to a modified single stranded microRNA molecule comprising a minimum of ten moieties and a maximum of fifty moieties on a molecular backbone, the molecular backbone comprising backbone unites, each moiety comprising a base bonded to a backbone unit, wherein at least ten contiguous bases have the same sequence as a contiguous sequence of bases in a microRNA molecule shown in SEQ. ID. NOs:467-481, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units, and at least one moiety is not an unmodified deoxyribonucleotide moiety or an unmodified ribonucleotide moiety.

In another embodiment, the invention relates to a modified single stranded microRNA molecule comprising a minimum of ten moieties and a maximum of fifty moieties on a molecular backbone, the molecular backbone comprising backbone unites, each moiety comprising a base bonded to a backbone unit, wherein at least ten contiguous bases have the same sequence as a contiguous sequence of bases in a microRNA molecule shown in SEQ. ID. NOs: 497-522, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units, and at least one moiety is not an unmodified deoxyribonucleotide moiety or an unmodified ribonucleotide moiety.

In another embodiment, the invention relates to a modified single stranded microRNA molecule comprising a minimum of ten moieties and a maximum of fifty moieties on a molecular backbone, the molecular backbone comprising backbone unites, each moiety comprising a base bonded to a backbone unit, wherein at least ten contiguous bases have the same sequence as a contiguous sequence of bases in a microRNA molecule shown in SEQ. ID. NO: 549, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units, and at least one moiety is not an unmodified deoxyribonucleotide moiety or an unmodified ribonucleotide moiety.

In another embodiment, the invention relates to an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases have a sequence complementary to a contiguous sequence of bases in any one of the microRNA molecules shown in SEQ ID NOs; 281-374, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units; and the molecule is capable of inhibiting microRNP activity.

In another embodiment, the invention relates to an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases have a sequence complementary to a contiguous sequence of bases in any one of the microRNA molecules shown in SEQ ID NOs; 467-481, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units; and the molecule is capable of inhibiting microRNP activity.

In another embodiment, the invention relates to an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases have a sequence complementary to a contiguous sequence of bases in any one of the microRNA molecules shown in SEQ ID NOs: 497-522, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units; and the molecule is capable of inhibiting microRNP activity.

In another embodiment, the invention relates to an isolated single stranded anti-microRNA molecule comprising a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases have a sequence complementary to a contiguous sequence of bases in any one of the microRNA molecules shown in SEQ ID NO: 549, except that up to thirty percent of the base pairs may be wobble base pairs, and up to 10% of the contiguous bases may be additions, deletions, mismatches, or combinations thereof; no more than fifty percent of the contiguous moieties contain deoxyribonucleotide backbone units; and the molecule is capable of inhibiting microRNP activity.

DESCRIPTION OF THE FIGURES

FIG. 2: Conservation patterns of known and predicted human microRNAs. The conservation patterns are based on the UCSC phastCons scores (http://genome.ucsc.edu). The chromosomal regions of the microRNAs with additional 3000 flanking nucleotides on both sides are presented. The chromosomal coordinates follow the build 34 assembly (hg16) of the human genome from UCSC (http://genome.ucsc.edu/). For simplicity the X-axis displays the relative positions. Known microRNAs are designated by their Rfam name omitting the "hsa" prefix. The predicted microRNAs fall into two categories: verified predictions—these predictions were verified experimentally in this study. New predictions—these predictions have not been verified. The microRNA orientation is marked by an arrow. A: example of a microRNA prediction that extends a known pair cluster. B: Unraveling a new multi-member cluster. (The figures are not plotted to scale, and therefore the conserved region width is a function of the length of the presented region; the longer the region, the narrower is the presented profile).

DETAILED DESCRIPTION OF THE INVENTION

MicroRNA Molecules

Figure 1:
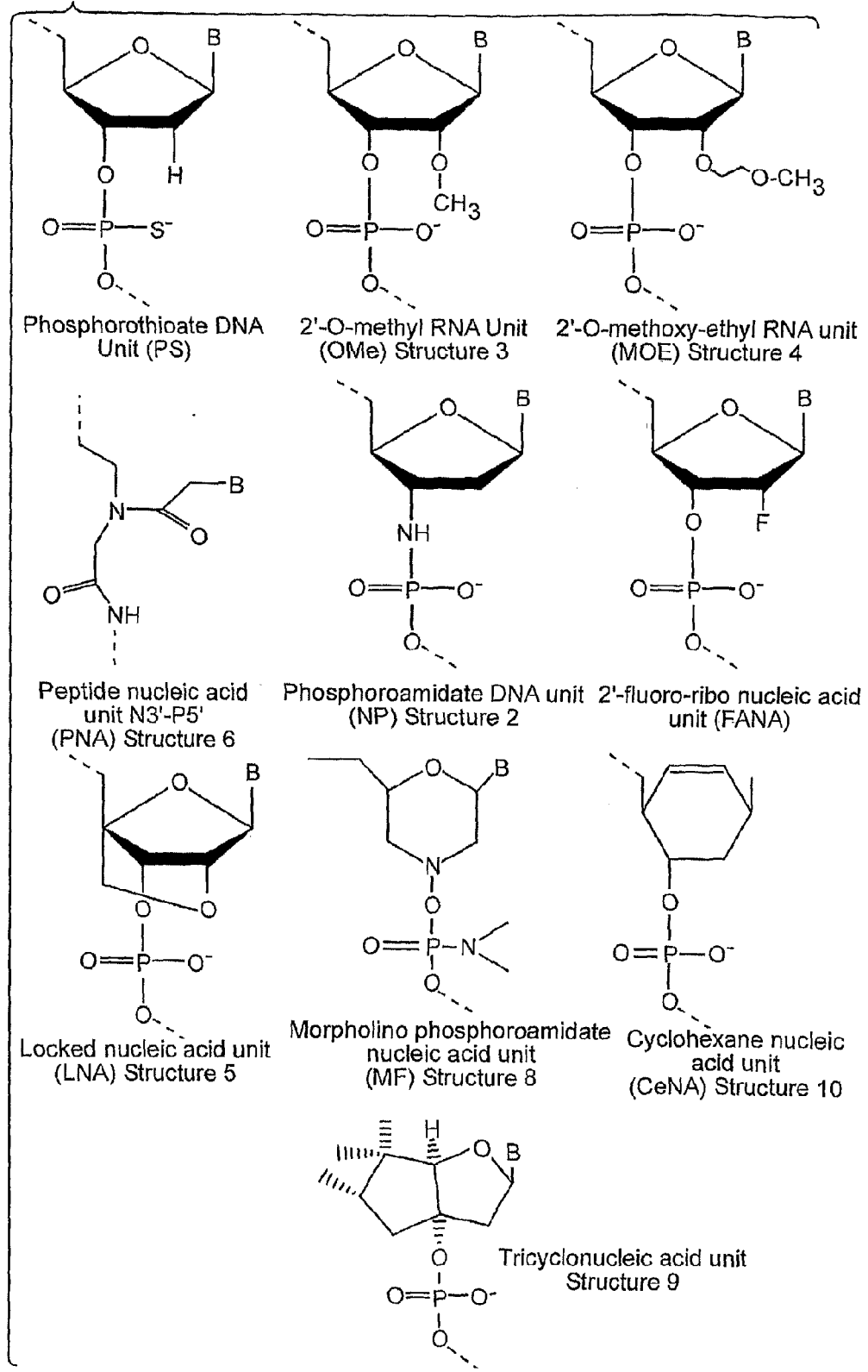
FIG. 1 shows the modified nucleotide units discussed in the specification. B denotes any one of the following nucleic acid bases: adenosine, cytidine, guanosine, thymine, or uridine

In one embodiment, the invention relates to an isolated single stranded microRNA molecule having any one of SEQ. ID. NOs:1-94.

In another embodiment, the invention relates to an isolated single stranded microRNA molecule having any one of SEQ. ID. NOs: 281-374.

In yet another embodiment, the invention relates to an isolated single stranded microRNA molecule having any one of SEQ. ID. NOs: 467-481.

In a further embodiment, the invention relates to an isolated single stranded microRNA molecule having any one of SEQ. ID. NOs: 497-522.

In yet a further embodiment, the invention relates to an isolated single stranded microRNA molecule having any one of SEQ. ID. NO: 549

MicroRNA molecules are known in the art (see, for example, Bartel, *Cell,* 2004, 116, 281-297 for a review on microRNA molecules). The definitions and characterizations of microRNA molecules in the article by Bartel is hereby incorporated by reference. Such molecules are derived from genomic loci and are produced from specific microRNA genes.

Mature microRNA molecules are processed from precursor transcripts that form local hairpin structures. The hairpin structures are typically cleaved by an enzyme known as Dicer, generating thereby one microRNA duplex. See the above reference by Bartel.

Usually, one of the two strands of a microRNA duplex is packaged in a microRNA ribonucleoprotein complex (microRNP). A microRNP in, for example, humans, also includes the proteins eIF2C2/Argonaute (Ago)2, the helicase Gemin3, and Gemin 4. Other members of the Argonaute protein family, such as Ago1, 3, and 4, also associate with microRNAs and form microRNPs.

In humans, microRNP containing Agog typically guide microRNA cleavage of a target RNA sequence. MicroRNP complexes containing other Ago proteins (e.g., Ago 1, 3, and 4) generally repress translation of target mRNAs.

In one embodiment, the invention relates to an isolated DNA or RNA molecule comprising at least ten contiguous bases having a sequence shown in SEQ ID NOs:1-94 in Table A, and equivalents thereof. Preferably, the isolated DNA or RNA molecule comprises at least thirteen, more preferably at least fifteen, and even more preferably at least twenty contiguous bases.

In another embodiment, the invention relates to an isolated DNA or RNA molecule comprising at least ten contiguous bases having a sequence shown in SEQ ID NOs:281-374 in Table A2, and equivalents thereof. Preferably, the isolated DNA or RNA molecule comprises at least thirteen, more preferably at least fifteen, and even more preferably at least twenty contiguous bases.

In yet another embodiment, the invention relates to an isolated DNA or RNA molecule comprising at least ten contiguous bases having a sequence shown in SEQ ID NOs:467-481 in Table A4, and equivalents thereof. Preferably, the isolated DNA or RNA molecule comprises at least thirteen, more preferably at least fifteen, and even more preferably at least twenty contiguous bases.

In a further embodiment, the invention relates to an isolated DNA or RNA molecule comprising at least ten contiguous bases having a sequence shown in SEQ ID NOs:497-522 in Table A6, and equivalents thereof. Preferably, the isolated DNA or RNA molecule comprises at least thirteen, more preferably at least fifteen, and even more preferably at least twenty contiguous bases.

In yet a further embodiment, the invention relates to an isolated DNA or RNA molecule comprising at least ten contiguous bases having a sequence shown in SEQ ID NO:549 in Table A8, and equivalents thereof. Preferably, the isolated DNA or RNA molecule comprises at least thirteen, more preferably at least fifteen, and even more preferably at least twenty contiguous bases.

TABLE A

| MicroRNAs Sequences. | |
|---|---|
| Name | Mature MicroRNA (5'→ 3') |
| miR-20b-5p | CAAAGUGCUCAUAGUGCAGGUAG (SEQ. ID. NO: 1) |
| miR-18b | UAAGGUGCAUCUAGUGCAGUUAG (SEQ. ID. NO: 2) |
| miR-843 | CAACUAGACUGUGAGCUUCUAG (SEQ. ID. NO: 3) |
| miR-867 | UCGAGGAGCUCACAGUCUAGAC (SEQ. ID. NO: 4) |
| miR-504 | GUGCAUUGCUGUUGCAUUGC (SEQ. ID. NO: 5) |
| miR-720a | UGGCAGUGUAUUGUUAGCUGGU (SEQ. ID. NO: 6) |
| miR-720b | AGGCAGUGUAUUGUUAGCUGGC (SEQ. ID. NO: 7) |
| miR-92b | UAUUGCACUCGUCCCGGCCUCC (SEQ. ID. NO: 8) |
| miR-429 | UAAUACUGUCUGGUAAAACCGU (SEQ. ID. NO: 9) |
| miR-822 | GUGUGCGGAAAUGCUUCUGCUA (SEQ. ID. NO: 10) |

TABLE A-continued

MicroRNAs Sequences.

| Name | Mature MicroRNA (5'→ 3') |
|---|---|
| miR-755# | AAAUCUCUGCAGGCAAAUGUGA (SEQ. ID. NO: 11) |
| miR-301b | CAGUGCAAUGAUAUUGUCAAAGCA (SEQ. ID. NO: 12) |
| miR-864 | AAAAGCUGAGUUGAGAGGG SEQ. ID. NO: 13) |
| miR-374b | AUAUAAUACAACCUGCUAAGUG (SEQ. ID. NO: 14) |
| miR-619 | UUUCCGGCUCGCGUGGGUGUGU (SEQ. ID. NO: 15) |
| miR-20b-3p | ACUGUAGUAUGGGCACUUCCAG (SEQ. ID. NO: 16) |
| miR-329 | AACACACCUGGUUAACCUCUUU (SEQ. ID. NO: 17) |
| miR-421 | AUCAACAGACAUUAAUUGGGCG (SEQ. ID. NO: 18) |
| miR-431 | UGUCUUGCAGGCCGUCAUGCAG (SEQ. ID. NO: 19) |
| miR-433 | AUCAUGAUGGGCUCCUCGGUGU (SEQ. ID. NO: 20) |
| miR-451 | AAACCGUUACCAUUACUGAGUU (SEQ. ID. NO: 21) |
| miR-452 | UGUUUGCAGAGGAAACUGAGAC (SEQ. ID. NO: 22) |
| miR-453 | AGGUUGUCCGUGGUGAGUUCGC (SEQ. ID. NO: 23) |
| miR-500 | UAGUGCAAUAUUGCUUAUAGGGU (SEQ. ID. NO: 24) |
| miR-604 | UGCGGGGCUAGGGCUAACAGCA (SEQ. ID. NO: 25) |
| miR-610 | CAUGCCUUGAGUGUAGGACCGU (SEQ. ID. NO: 26) |
| miR-618 | UUAAUAUGUACUGACAAAGCGU (SEQ. ID. NO: 27) |
| miR-620 | AUGUUGGGAGCGGGCAGGUUGG (SEQ. ID. NO: 28) |
| miR-631# | UCCGAGCCUGGGUCUCCCUCUU (SEQ. ID. NO: 29) |
| miR-723-3p# | CGUGGGCCUGAUGUGGUGCUGG (SEQ. ID. NO: 30) |
| miR-723-5p# | AGUACCACGUGUCAGGGCCACA (SEQ. ID. NO: 31) |
| miR-730# | AAACAUUCGCGGUGCACUUCUU (SEQ. ID. NO: 32) |
| miR-732# | AAAGGAUUCUGCUGUCGGUCCC (SEQ. ID. NO: 33) |
| miR-800a | AAUCGUACAGGGUCAUCCACUU (SEQ. ID. NO: 34) |
| miR-800b | AAUCAUACAGGGACAUCCAGUU (SEQ. ID. NO: 35) |
| miR-803 | UAUGUGCCUUUGGACUACAUCG (SEQ. ID. NO: 36) |
| miR-805 | UUUUGCGAUGUGUUCCUAAUAU (SEQ. ID. NO: 37) |
| miR-814 | GCAGGAACUUGUGAGUCUCC (SEQ. ID. NO: 38) |
| miR-815 | AAUGGCGCCACUAGGGUUGUGC (SEQ. ID. NO: 39) |
| miR-816 | UUGGGGAAACGGCCGCUGAGUG (SEQ. ID. NO: 40) |
| miR-817 | CUGUAUGCCCUCACCGCUCAGC (SEQ. ID. NO: 41) |
| miR-818 | AGGGGGAAAGUUCUAUAGUCCU (SEQ. ID. NO: 42) |
| miR-819 | UCCAUUACACUACCCUGCCUCU (SEQ. ID. NO: 43) |
| miR-821 | GCGGCGGCGGCGGAGGCUGCUG (SEQ. ID. NO: 44) |
| miR-892 | CGGCGGCGGCGGCGGCGGCUGU (SEQ. ID. NO: 45) |
| miR-824 | GGAGAAAUUAUCCUUGGUGUGU (SEQ. ID. NO: 46) |
| miR-825-3p | UUGUGACAGAUUGAUAACUGAA (SEQ. ID. NO: 47) |
| miR-825-5p | UCGGGGAUCAUCAUGUCACGAG (SEQ. ID. NO: 48) |
| miR-826 | AUUGACACUUCUGUGAGUAGAG (SEQ. ID. NO: 49) |
| miR-828-5p | AUGCUGACAUAUUUACUAGAGG (SEQ. ID. NO: 50) |
| miR-828-3p | UCUAGUAAGAGUGGCAGUCGAA (SEQ. ID. NO: 51) |
| miR-829-5p | GAGCUUAUUCAUAAAAGUGCAG (SEQ. ID. NO: 52) |
| miR-829-3p | UAAUUUUAUGUAUAAGCUAGUC (SEQ. ID. NO: 53) |
| miR-831 | UGGGGCGGAGCUUCCGGAGGCC (SEQ. ID. NO: 54) |
| miR-832 | CCAUGGAUCUCCAGGUGGGUCA (SEQ. ID. NO: 55) |
| miR-834 | UGAAGGUCUACUGUGUGCCAGG (SEQ. ID. NO: 56) |
| miR-835-5p | AGGAAGCCCUGGAGGGGCUGGA (SEQ. ID. NO: 57) |
| miR-835-3p | UCCGGUUCUCAGGGCUCCACCU (SEQ. ID. NO: 58) |
| miR-837 | ACCAGGAGGCUGAGGCCCCUCA (SEQ. ID. NO: 59) |
| miR-838 | UCAGGCUCAGUCCCCUCCCGAU (SEQ. ID. NO: 60) |

TABLE A-continued

MicroRNAs Sequences.

| Name | Mature MicroRNA (5'→ 3') |
|---|---|
| miR-839-5p | UCCUGUACUGAGCUGCCCCGA (SEQ. ID. NO: 61) |
| miR-839-3p | CGGGGCAGCUCAGUACAGGAU (SEQ. ID. NO: 62) |
| miR-840-5p | UCGACCGGACCUCGACCGGCU (SEQ. ID. NO: 63) |
| miR-840-3p | CUCGGCGUGGCGUCGGUCGUGG (SEQ. ID. NO: 64) |
| miR-841 | UUUGAAAGGCUAUUUCUUGGUC (SEQ. ID. NO: 65) |
| miR-842 | CGAAAACAGCAAUUACCUUUGC (SEQ. ID. NO: 66) |
| miR-845 | AAAGCAUGCUCCAGUGGCGCA (SEQ. ID. NO: 67) |
| miR-846 | CGGCUCUGGGUCUGUGGGGAGC (SEQ. ID. NO: 68) |
| miR-847 | CAGAGAGGACCACUAUGGCGGG (SEQ. ID. NO: 69) |
| mIR-848 | AUUGCCAUCCCCUAUGGACCAG (SEQ. ID. NO: 70) |
| miR-849 | UGUCUACUACUGGAGACACUGG (SEQ. ID. NO: 71) |
| miR-850 | UUAGGGCCCUGGCUCCAUCUCC (SEQ. ID. NO: 72) |
| miR-851 | GUGAACGGGCGCCAUCCCGAGG (SEQ. ID. NO: 73) |
| miR-852 | UCAGCAAACAUUUAUUGUGUGC (SEQ. ID. NO: 74) |
| miR-853 | UGGGAUCUCCGGGGUCUUGGUU (SEQ. ID. NO: 75) |
| miR-854 | CUGCCCUGGCCCGAGGGACCGA (SEQ. ID. NO: 76) |
| miR-855-5p | UGAGUGUGUGUGUGUGAGUGUG (SEQ. ID. NO: 77) |
| miR-855-3p | CACGCUCAUGCACACACCCACA (SEQ. ID. NO: 78) |
| miR-857 | AAGGCAGGGCCCCCGCUCCCCG (SEQ. ID. NO: 79) |
| miR-869 | UGGUGGGCCGCAGAACAUGUGC (SEQ. ID. NO: 80) |
| miR-871-5p | CGGGUCGGAGUUAGCUCAAGCGG (SEQ. ID. NO: 81) |
| miR-871-3p | CUAUCUGUCCAUCUCUGUGCUG (SEQ. ID. NO: 82) |
| miR-883 | UGAAACAUCACGGGAAACCUC (SEQ. ID. NO: 83) |
| miR-884 | AUUCUGCAUUUUUAGCAAGUUC (SEQ. ID. NO: 84) |
| miR-885 | GCGACCCAUACUUGGUUUCAGA (SEQ. ID. NO: 85) |

TABLE A-continued

MicroRNAs Sequences.

| Name | Mature MicroRNA (5'→ 3') |
|---|---|
| miR-886 | AACAUCACAGCAAGUCUGUGCU (SEQ. ID. NO: 86) |
| miR-887-5p | UAUACCUCAGUUUUAUCAGGUG (SEQ. ID. NO: 87) |
| miR-887-3p | CCUGGAAACACUGAGGUUGUGU (SEQ. ID. NO: 88) |
| miR-888 | AGACCCUGGUCUGCACUCUAUC (SEQ. ID. NO: 89) |
| miR-889 | AGUGGGGAACCCUUCCAUGAGG (SEQ. ID. NO: 90) |
| miR-890 | GUGUUGAAACAAUCUCUACUGA (SEQ. ID. NO: 91) |
| miR-891 | AUGGAUUUCUUUGUGAAUCACC (SEQ. ID. NO: 92) |
| miR-893 | AAGACGGGAGGAAAGAAGGGAA (SEQ. ID. NO: 93) |
| miR-894 | GUGACAUCACAUAUACGGCAGC (SEQ. ID. NO: 94) |

TABLE A1

MicroRNA Hairpin Precursor Sequences.

>hsa-mir-18b
CUUGUGUUAAGGUGCAUCUAGUGCAGUUAGUGAAGCAGCUUAGAAUCUA
CUGCCCUAAAUGCCCCUUCUGGCACAGG (SEQ. ID. NO: 95)

>hsa-mir-20b
GAUAAGAUUGGGUCCUAGUAGUACCAAAGUGCUCAUAGUGCAGGUAGUU
UUGGCAUGACUCUACUGUAGUAUGGGCACUUCCAGUACUCUUGGAUAAC
AAAUCUCUUGUUG (SEQ. ID. NO: 96)

>hsa-mir-301b
GGGGUCCCCCCUGCUGGCCGCAGGUGCUCUGACGAGGUUGCACUACUGU
GCUCUGAGAAGCAGUGCAAUGAUAUUUGUCAAAGCAUCUGGGACCAGCCU
UGGGGAUCUC (SEQ. ID. NO: 97)

>hsa-mir-329-1
GGUACCUGAAGAGAGGUUUUCUGGGUUUCUGUUUCUUUAAUGAGGACGA
AACACACCUGGUUAACCUCUUUUCCAGUAUC (SEQ. ID. NO: 98)

>hsa-mir-329-2
GUGGUACCUGAAGAGAGGUUUUCUGGGUUUCUGUUUCUUUAUUGAGGAC
GAAACACACCUGGUUAACCUCUUUUCCAGUAUCAA
(SEQ. ID. NO: 99)

>hsa-mir-374b
ACUCGGAUGGAUAUAAUACAACCUGCUAAGUGUCCUAGCACUUAGCAGG
UUGUAUUAUCAUUGUCCGUGU (SEQ. ID. NO: 100)

>hsa-mir-421
CACAUUGUAGGCCUCAUUAAAUGUUUGUUGAAUGAAAAAAUGAAUCAUC
AACAGACAUUAAUUGGGCGCCUGCUCUGUG (SEQ. ID. NO: 101)

>hsa-mir-500
CCAGAUCCUAGAACCCUAUCAAUAUUGUCUCUGCUGUGUAAAUAGUUCU
GAGUAGUGCAAUAUUGCUUAUAGGGUUUUGGUGUUUGG
(SEQ. ID. NO: 102)

>hsa-mir-504
GGCGGCCCCGCGGUGCAUUGCUGUUGCAUUGCACGUGUGUGAGGCGGGU
GCAGUGCCUCGGCAGUGCAGCCCGGAGCCGGC
(SEQ. ID. NO: 103)

TABLE A1-continued

MicroRNA Hairpin Precursor Sequences.

>hsa-mir-604
GGGUUGGGCAAGGUGCGGGGCUAGGGCUAACAGCAGUCUUACUGAAGGU
UUCCUGGAAACCACGCACAUGCUGUUGCCAC
(SEQ. ID. NO: 104)

>hsa-mir-610
CUCCAUGCCUUGAGUGUAGGACCGUUGGCAUCUUAAUUACCCUCCCACA
CCCAAGGCUUGCA (SEQ. ID. NO: 105)

>hsa-mir-618
UUAUUGUGAAAUAUGUCAUUAAUAUGUACUGACAAAGCGUAUCUGUGUA
AUAAAUAUGCUUUUUGUCAGUACAUGUUAAUGGUAUAUUUCAUAACAA
(SEQ. ID. NO: 106)

>hsa-mir-619
GCGGCUGCUGGACCCACCCGGCCGGGAAUAGUGCUCCUGGUUGUUUCCG
GCUCGCGUGGGUGUGUCGGCGCGCGGG (SEQ. ID. NO: 107)

>hsa-mir-620
CGCCCCCACGUGGCCCCGCCCCUGAGGCCGGCGCUGCCGCCAUGUUGG
GAGCGGGCAGGUUGGGAGCG (SEQ. ID. NO: 108)

>hsa-mir-631
GGGGCGGGAGGGGGUCCCCGGUGCUCGGAUCUCGAGGGUGCUUAUUGU
UCGGUCCGAGCCUGGGUCUCCCUCUUCCCCCC
(SEQ. ID. NO: 109)

>hsa-mir-720A
UGCUCUGGAUACCUGUGUGUGAUGAGCUGGCAGUGUAUUGUUAGCUGGU
UGAAUAUGUGAAUGGCAUCGGCUAACAUGCAACUGCUGUCUUAUUGCAU
AUACAAUGAACAUCAGAGUG (SEQ. ID. NO: 110)

>hsa-mir-720b
UGAAUCAGGUAGGCAGUGUAUUGUUAGCUGGCUGCUUUGGGUCAAGUCAG
CAGCCACAACUACCCUGCCACUUGCUUCU (SEQ. ID. NO: 111)

>hsa-mir-723
GCCACCUUCCGAGCCUCCAGUACCACGUGUCAGGGCCACAUGAGCUGGG
CCUCGUGGGCCUGAUGUGGUGCUGGGGCCUCAGGGGUCUG
(SEQ. ID. NO: 112)

>hsa-mir-730
GCGGUACUUAAUGAGAAGUUGCCCGUGUUUUUUCGCUUUAUUUGUGAC
GAAACAUUCGCGGUGCACUUCUUUUUCAGUAUCCU
(SEQ. ID. NO: 113)

>hsa-mir-732
CCAACGUCAGGGAAAGGAUUCUGCUGUCGGUCCCACUCCAAAGUUCACA
GAAUGGGUGGUGGGCACAGAAUCUGGACUCU
(SEQ. ID. NO: 114)

>hsa-mir-429
CGGCCGAUGGGCGUCUUACCAGACAUGGUUAGACCUGGCCCUCUGUCUA
AUACUGUCUGGUAAAACCGUCCAUCCGCUG (SEQ. ID. NO: 115)

>hsa-mir-754
UGCUUCUGUGUGAUAUGUUUGAUAUUGGGUUGUUUAAUUAGGAACCAAC
UAAAUGUCAAACAUAUUCUUACAGCAGCA (SEQ. ID. NO: 116)

>hsa-mir-755
GCAGACUGGAAAAUCUCUGCAGGCAAAUGUGAUGUCACUGAGGAAAUCA
CACACUUACCCGUAGAGAUUCUACAGUCUGA
(SEQ. ID. NO: 117)

>hsa-mir-800A
CUUUCUUUUCCGUGCUAACCUUUGGUACUUGGAGAGUGGUUUAUCCCUGU
CCUGUUCGUUUUGCUCAUGUCGAAUCGUACAGGGUCAUCCACUUUUUCA
GUAUCAAGAGCGC (SEQ. ID. NO: 118)

>hsa-mir-800b
UGAAGAGUGGUUAUCCCUGCUGUGUUCGCUUAAUUUAUGACGAAUCAUA
CAGGGACAUCCAGUUUUUCA (SEQ. ID. NO: 119)

>hsa-mir-803
CCCUGGCGUGAGGGUAUGUGCCUUUGGACUACAUCGUGGAAGCCAGCAC
CAUGCAGUCCAUGGGCAUAUACACUUGCCUCAAGG
(SEQ. ID. NO: 120)

>hsa-mir-805-2
GAUGCUAAACUAUUUUUGCGAUGUGUUCCUAAUAUGUAAUAUAAAUGUA
UUGGGGACAUUUUGCAUUCAUAGUUUUGUAUC
(SEQ. ID. NO: 121)

>hsa-mir-451
CUUGGGAAUGGCAAGGAAACCGUUACCAUUACUGAGUUUAGUAAUGGUA
AUGGUUCUCUUGCUAUACCCAGA (SEQ. ID. NO: 122)

>hsa-mir-433
CCGGGGAGAAGUACGUGAGCCGUCAUUAUUCAGAGAGGCUAGAUCCU
CUGUGUUGAGAAGGAUCAUGAUGGGCUCCUCGGUGUUCUCCAGG
(SEQ. ID. NO: 123)

>hsa-mir-431
UCCUGCUUGUCCUGCGAGGUGUCUUGCAGGCCGUCAUGCAGGCCACACU
GACGGUAACGUUGCAGGUCGUCUUGCAGGGCUUCUCGCAAGACGACAUC
CUCAUCACCAACGACG (SEQ. ID. NO: 124)

>hsa-mir-452
GCUAAGCACUUACAACUGUUUGCAGAGGAAACUGAGACUUUGUAACUAU
GUCUCAGUCUCAUCUGCAAAGAAGUAAGUGCUUUGC
(SEQ. ID. NO: 125)

>hsa-mir-453
GCAGGAAUGCUGCGAGCAGUGCCACCUCAUGGUACUCGGAGGGAGGUUG
UCCGUGGUGAGUUCGCAUUAUUUAAUGAUGC
(SEQ. ID. NO: 126)

>hsa-mir-814
GUGCAUUUGCAGGAACUUGUGAGUCUCCUAUUGAAAAUGAACAGGAGAC
UGAUGAGUUCCCGGGAACAC (SEQ. ID. NO: 127)

>hsa-mir-815
CUAUGCACUGCACAACCCUAGGAGAGGGUGCCAUUCACAUAGACUAUAA
UUGAAUGGCGCCACUAGGGUUGUGCAGUGCACAA
(SEQ. ID. NO: 128)

>hsa-mir-816
GGGUUUGGGGAAACGGCCGCUGAGUGAGGCGUCGGCUGUGUUUCUCACC
GCGGUCUUUUCCUCCCACUC (SEQ. ID. NO: 129)

>hsa-mir-817
CUUGGUGACGCUGUAUGCCCUCACCGCUCAGCCCCUGGGGCUGGCUUGG
CAGACAGUACAGCAUCCAGGGGAGUCAAGGGCAUGGGGCGAGACCAGA
(SEQ. ID. NO: 130)

>hsa-mir-818-1
GGUAAGGUAGAGGGAUGAGGGGGAAAGUUCUAUAGUCCUGUAAUUAGA
UCUCAGGACUAUAGAACUUUCCCCCUCAUCCCUCUGCCCUCUACC
(SEQ. ID. NO: 131)

>hsa-mir-818-2
GUAGAGGGCAGAGGGAUGAGGGGGAAAGUUCUAUAGUCCUGAGAUCUAA
UUACAGGACUAUAGAACUUUCCCCCUCAUCCCUCUACCCUUACCA
(SEQ. ID. NO: 132)

>hsa-mir-819
GGCCCGCACUCUCUCCAUUACACUACCCUGCCUCUUUCUCCAUGAGAGGC
AGCGGGGUGUAGUGGAUAGAGCACGGGUU (SEQ. ID. NO: 133)

>hsa-mir-821-1
GCGGCGGCGGCGGAGGCUGCUGCUGGGGCGGCUGCUGCUGGGGCGGCUG
CGGCGGCGGCUGCUGCGGGGGCUGCUGCUGCUGUUGC
(SEQ. ID. NO: 134)

>hsa-mir-821-2/-3
GCGGCUGCGGCGGCGGCGGAGGCUGCGGCGGCGACCGUGGCAGAGGCGG
UGGCGGAGGCCUCCGUGGCGGAGGCGGAAGC
(SEQ. ID. NO: 135)

>hsa-mir-822
ACUCUAUAAAUCUAGUGGAAACAUUUCUGCACAAACUAGAUUCUGGACA
CCAGUGUGCGGAAAUGCUUUCUGCUACAUUUUUAGGGU
(SEQ. ID. NO: 136)

TABLE A1-continued

MicroRNA Hairpin Precursor Sequences.

>hsa-mir-824
GUUUCAUACUUGAGGAGAAAUUAUCCUUGGUGUGUUCGCUUUAUUUAUG
AUGAAUCAUACAAGGACAAUUUCUUUUUGAGUAUCAAAU
(SEQ. ID. NO: 137)

>hsa-mir-825
UCUCAGACAUCUCGGGGAUCAUCAUGUCACGAGAUACCAGUGUGCACUU
GUGACAGAUUGAUAACUGAAAGGUCUGGGA (SEQ. ID. NO: 138)

>hsa-mir-826-2
UUGUCUGUGGUACCCUACUCUGGAGAGUGACAAUCAUGUAUAACUAAAU
UUGAUUGACACUUCUGUGAGUAGAGUAACGCAUGACAC
(SEQ. ID. NO: 139)

>hsa-mir-826-3
UUGUCUGUGGUACCCUACUCUGGAGAGUGACAAUCAUGUAUAAUUAAAU
UUGAUUGACACUUCUGUGAGUAGAGUAACGCAUGACAC
(SEQ. ID. NO: 140)

>hsa-mir-828
CUUCCUCAUGCUGACAUAUUUACUAGAGGGUAAAAUUAAUAACCUUCUA
GUAAGAGUGGCAGUCGAAGGGAAG (SEQ. ID. NO: 141)

>hsa-mir-829
CAGUCAGAAAUGAGCUUAUUCAUAAAAGUGCAGUAUGGUGAAGUCAAUC
UGUAAUUUUAUGUAUAAGCUAGUCUCUGAUUG
(SEQ. ID. NO: 142)

>hsa-mir-831-1
GCUCCGCCCCACGUCGCAUGCGCCCCGGGAACGCGUGGGGCGGAGCUUC
CGGAGGCCCCGCCUCUGCUGCCGACCCUGUGGAGCGGAGGGUGAAGCCUC
CGGAUGCCAGUCCUCAUCGCUGGCCUGGUCGCGCUGUGGCGAAGGGGG
CGGAGC (SEQ. ID. NO: 143)

>hsa-mir-831-2
GCUCCGCCCCACGUCGCAUGCGCCCCGGGAACGCGUGGGGCGGAGCUUC
CGGAGGCCCCGCCCUGCUGCCGACCCUGUGGAGCGGAGGGUGAAGCCUC
CGGAUGCCAGUCCCUCAUCGCUGGCCCGGUCGCGCUGUGGCGAAGGGGG
CGGAGC (SEQ. ID. NO: 144)

>hsa-mir-831-3/-4/-5
CGCUCCGCCCCACGUCGCAUGCGCCCCGGGAAAGCGUGGGGCGGAGCUU
CCGGAGGCCCCGCCCUGCUGCCGACCCUGUGGAGCGGAGGGUGAAGCCU
CCGGAUGCCAGUCCCUCAUCGCUGGCCCGGUCGCGCUGUGGCGAAGGGGG
GCGGAGC (SEQ. ID. NO: 145)

>hsa-mir-832
AUUGUUCGACACCAUGGAUCUCCAGGUGGGUCAAGUUUAGAGAUGCACC
AACCUGGAGGACUCCAUGCUGUUGAGCUGU (SEQ. ID. NO: 146)

>hsa-mir-834
CAGGGCUUUGUACAUGGUAGGCUUUCAUUCAUUCGUUUGCACAUUCGGU
GAAGGUCUACUGUGUGCCAGGCCCUG (SEQ. ID. NO: 147)

>hsa-mir-835
CUGGCAGGCCAGGAAGAGGAGGAAGCCCUGGAGGGGCUGGAGGUGAUGG
AUGUUUUCCUCCGGUUCUCAGGGCUCCACCUCUUUCGGGCCGUAGAGCC
AG (SEQ. ID. NO: 148)

>hsa-mir-837
AGAGGAGGGUCUCCUCGAGGGGUCUCUGCCUCUACCCAGGACUCUUUCA
UGACCAGGAGGCUGAGGCCCCUCACAGGCGGCUUCUUACUCU
(SEQ. ID. NO: 149)

>hsa-mir-838
UCGUCAGGCUCAGUCCCCUCCCGAUAAACCCCUAAAUAGGGACUUUCCC
GGGGGGUGACCCUGGCUUUUUGGCGA (SEQ. ID. NO: 150)

>hsa-mir-839
CUGACUCCCACCCCGAGUAUCCUGUACUGAGCUGCCCCGAGCUGGGCAG
CAUGAAGGGCUCGGGGCAGCUCAGUACAGGAUGCCCCAGGGAGGAUGG
AGAUCAG (SEQ. ID. NO: 151)

>hsa-mir-839-2
CUCCAUCCUCCCCUGGGGCAUCCUGUACUGAGCUGCCCCGAGGCCCUUCA
UGCUGCCCAGCUCGGGGCAGCUCAGUACAGGAUACUCGGGGUGGGAGUC
AG (SEQ. ID. NO: 152)

>hsa-mir-840
UUCAUCAAGACCCAGCUGAGUCACUGUCACUGCCUACCAAUCUCGACCG
GACCUCGACCGGCUCGUCUGUGUUGCCAAUCGACUCGGCGUGGCGUCGG
UCGUGGUAGAUAGGCGGUCAUGCAUACGAAUUUUCAGCUCUUGUUCUGG
UGAC (SEQ. ID. NO: 153)

>hsa-mir-841
AGAAUCAUCUCUCCCAGAUAAUGGCACUCUCAAACAAGUUUCCAAAUUG
UUUGAAAGGCUAUUUCUUGGUCAGAUGACUCU
(SEQ. ID. NO: 154)

>hsa-mir-842
CCUAGAUAAGUUAUUAGGUGGGUGCAAAGGUAAUUGCAGUUUUUCCCAU
UAUUUUAAUUGCGAAAACAGCAAUUACCUUUGCACCAACCUGAUGGAGU
CCCCCU (SEQ. ID. NO: 155)

>hsa-mir-843
GCCCUCAAGGAGCUUACAAUCUAGCUGGGGGUAAAUGACUUGCACAUGA
ACACAACUAGACUGUGAGCUUCUAGAGGGC (SEQ. ID. NO: 156)

>hsa-mir-845-1
CGCGAGGCCGGGGUCGAGCGCUUCAGUAGCUCAUGGCUCUGUAGAGUGC
GCAUGGCCAAGCAAAGGAAAGCAUGCUCCAGUGGCGCA
(SEQ. ID. NO: 157)

>hsa-mir-845-2
AGUAACCACUUAGUGUGUAUUGACUUGUCAGAAUUUUCAGAAUUUAAAG
CAUGCUCCAGUGGCGCA (SEQ. ID. NO: 158)

>hsa-mir-846
CGGGGCGCGUCGCCCCCCUCAGUCCACCAGAGCCCGGAUACCCUCAGAAA
UUCGGCUCUGGGUCUGUGGGGAGCGAAAUGCAACCCA
(SEQ. ID. NO: 159)

>hsa-mir-847
UUACUGUGUCAUUGUUGCUGUCAAUUGCUACUGAGGAGUACUGACCAGAA
UCAUCUGCAACUCUUAGUUGGCAGAGAGGACCACUAUGGCGGGUAG
(SEQ. ID. NO: 160)

>hsa-mir-848
UGGGCCAGAUUGCCAUCCCCUAUGGACCAGAAGCCAAGGAUCUCUCUAG
UGAUGGUCAGAGGGCCCAAAUGGCAGGGAUACCCA
(SEQ. ID. NO: 161)

>hsa-mir-849
GCUUCUGUCUACUACUGGAGACACUGGUAGUAUAAAACCCAGAGUCUCC
AGUAAUGGACGGGAGC (SEQ. ID. NO: 162)

>hsa-mir-850
CUGGGUUAGGGCCCUGGCUCCAUCUCCUUUAGGAAAACCUUCUGUGGGG
AGUGGGCUUCGACCCUAACCCAG (SEQ. ID. NO: 163)

>hsa-mir-851
GCAGAUCCUUGGGAGCCCUGUUAGACUCUGGAUUUUACACUUGGAGUGA
ACGGGCGCCAUCCCGAGGCUUUGC (SEQ. ID. NO: 164)

>hsa-mir-852
AGUAGGCCUCAGUAAAUGUUUAUUAGAUGAAUAAAUGAAUGACUCAUCA
GCAAACAUUUAUUGUGUGCCUGCU (SEQ. ID. NO: 165)

>hsa-mir-853
CCUGGGCUCUGACCUGAGACCUCUGGGUUCUGAGCUGUGAUGUUGCUCU
CGAGCUGGGAUCUCCGGGGUCUUGGUUCAGGG
(SEQ. ID. NO: 166)

>hsa-mir-854
GGUGUUAGCCCUGCGGCCCCACGCACCAGGGUAAGAGAGACUCUCGCUU
CCUGCCCUGGCCCGAGGGACCGACUGGCUGGGCC
(SEQ. ID. NO: 167)

>hsa-mir-855
UGGGUGCGGGCGUGUGAGUGUGUGUGUGAGUGUGUGUCGCUCCGGGU
CCACGCUCAUGCACACACCCACACGCCCACACUCA
(SEQ. ID. NO: 168)

TABLE A1-continued

MicroRNA Hairpin Precursor Sequences.

>hsa-mir-855
UGGGUGCGGGCGUGUGAGUGUGUGUGUGAGUGUGUGUCGCUCCGGGU
CCACGCUCAUGCACACACCCACACGCCCACACUCA
(SEQ. ID. NO: 169)

>hsa-mir-857
GGGCCCGGCCCCAGGAGCGGGGCCUGGGCAGCCCCGUGUGUUGAGGAAG
GAAGGCAGGGCCCCCGCUCCCCGGGCCU (SEQ. ID. NO: 170)

>hsa-mir-864
CCUUCUCUUCUCAGUUCUUCCCCAAGUUAGGAAAAGCUGAGUUGAGAGG
G (SEQ. ID. NO: 171)

>hsa-mir-151
GUCUCUCUUCAGGGCUCCCGAGACACAGAAACAGACACCUGCCCUCGAG
GAGCUCACAGUCUAGAC (SEQ. ID. NO: 172)

>hsa-mir-869
AAAGAUGGUGGGCCGCAGAACAUGUGCUGAGUUCGUGCCAUAUGUCUGC
UGACCAUCACCUUU (SEQ. ID. NO: 173)

>hsa-mir-871-1
UCCUACCCGGGUCGGAGUUAGCUCAAGCGGUUACCUCCUCAUGCCGGAC
UUUCUAUCUGUCCAUCUCUGUGCUGGGGUUCGAGACCCGCGGGUGCUUA
CUGACCCUUUUAUGCA (SEQ. ID. NO: 174)

>hsa-mir-92b
CCGGGCCCCGGGCGGGCGGGAGGGACGGGACGCGGUGCAGUGUUGUUUU
UUCCCCCGCCAAUAUUGCACUCGUCCCGGCCUCCGGCCCCCCCGGCCCC
CCGG (SEQ. ID. NO: 175)

>hsa-mir-883
GAUACUCGAAGGAGAGGUUGUCCGUGUUGUCUUCUCUUUAUUUAUGAUG
AAACAUACACGGGAAACCUCUUUUUUAGUAUC
(SEQ. ID. NO: 176)

>hsa-mir-884
AUUUUCAUCACCUAGGGAUCUUGUUAAAAAGCAGAUUCUGAUUCAGGGA
CCAAGAUUCUGCAUUUUUAGCAAGUUCUCAAGUGAUGCUAAU
(SEQ. ID. NO: 177)

>hsa-miR-885
GUGCUCUCCUGGCCCAUGAAAUCAAGCGUGGGUGAGACCUGGUGCAGAA
CGGGAAGGCGACCCAUACUUGGUUUCAGAGGCUGUGAGAAUAAC
(SEQ. ID. NO: 178)

>hsa-mir-886
CCCCUGUGCCUUGGGCGGGCGGCUGUUAAGACUUGCAGUGAUGUUUAAC
UCCUCUCCACGUGAACAUCACAGCAAGUCUGUGCUGCUUCCCGUCCCUA
CGCUGCCUGGGC (SEQ. ID. NO: 179)

>hsa-mir-887
GUUUAGUGGUACUAUACCUCAGUUUUAUCAGGUGUUCUUAAAAUCACCU
GGAAACACUGAGGUUGUGUCUCACUGAAC (SEQ. ID. NO: 180)

>hsa-mir-888
GCUGCUGUUGGGAGACCCUGGUCUGCACUCUAUCUGUAUUCUUACUGAA
GGGAGUGCAGGGCAGGGUUUCCCAUACAGAGGGC
(SEQ. ID. NO: 181)

>hsa-mir-889
GGAAUUGACUUAGCUGGGUAGUGGGGAACCCUUCCAUGAGGAGUAGAAC
ACUCCUUAUGCAAGAUUCCCUUCUACCUGGCUGGGUUGGAGUC
(SEQ. ID. NO: 182)

>hsa-mir-890
UCAUUCCUUCAGUGUUGAAACAAUCUCUACUGAACCAGCUUCAAACAAG
UUCACUGGAGUUUGUUUCAAUAUUGCAAGAAUGA
(SEQ. ID. NO: 183)

>hsa-mir-891
CACAAACUGUGAAGUGCUGUGGAUUUCUUUGUGAAUCACCAUAUCUAAG
CUAAUGUGGUGGUGGUUUACAAAGUAAUUCAUAGUGCUUCACAGGUG
(SEQ. ID. NO: 184)

>hsa-mir-892
GCGGCUGCGGCGGCGGCGGCGGCGGCGGCUGUUGCUGUUGCUG
CUGCUGCUGCUGCUGUUGCUGCUGCUGCUGCUGCUGC
(SEQ. ID. NO: 185)

>hsa-mir-893
GAGGGGGAAGACGGGAGGAAAGAAGGGAGUGGUUCCAUCACGCCUCCUC
ACUCCUCUCCUCCCGUCUUCUCCCUCUC (SEQ. ID. NO: 186)

>hsa-mir-894
CUACUGCUGUUGGUGGCAGCUUGGUGGUCGUAUGUGUGACGCCAUUUAC
UUGAACCUUUAGGAGUGACAUCACAUAUACGGCAGCUAAACUGCUACAU
GGGACAACAAUU (SEQ. ID. NO: 187)

TABLE A2

MicroRNA Sequences

| Name | Mature MicroRNA (5' -> 3') |
|---|---|
| hsa-miR-100516 | UACUCAAAAAGCUGUCAGUCA (SEQ. ID. NO: 281) |
| hsa-miR-100604 | UGCGGGGCUAGGGCUAACAGCA (SEQ. ID. NO: 282) |
| hsa-miR-100610-5p | CAUGCCUUGAGUGUAGGACCGU (SEQ. ID. NO: 283) |
| hsa-miR-100631 | UCCGAGCCUGGGUCUCCCUCUU (SEQ. ID. NO: 284) |
| hsa-miR-100701 | AAGGUUACUUGUUAGUUCAGG (SEQ. ID. NO: 285) |
| hsa-miR-100723 | CGUGGGCCUGAUGUGGUGCUGG (SEQ. ID. NO: 286) |
| hsa-miR-100730 | AAACAUUCGCGGUGCACUUCUU (SEQ. ID. NO: 287) |
| hsa-miR-100732 | AAGGAUUCUGCUGUCGGUCCC (SEQ. ID. NO: 288) |
| hsa-miR-100754 | UGAUAUGUUUGAUAUUGGGUU (SEQ. ID. NO: 289) |
| hsa-miR-100760 | GCACUGAGAUGGGAGUGGUGUA (SEQ. ID. NO: 290) |
| hsa-miR-100814 | GCAGGAACUUGUGAGUCUCCU (SEQ. ID. NO: 291) |
| hsa-miR-100815 | AAUGGCGCCACUAGGGUUGUGU (SEQ. ID. NO: 292) |

TABLE A2-continued

MicroRNA Sequences

| Name | Mature MicroRNA (5' -> 3') |
|---|---|
| hsa-miR-100818 | AGGGGGAAAGUUCUAUAGUCC (SEQ. ID. NO: 293) |
| hsa-miR-100819 | UCCAUUACACUACCCUGCCUCU (SEQ. ID. NO: 294) |
| hsa-miR-100824 | GGAGAAAUUAUCCUUGGUGUGU (SEQ. ID. NO: 295) |
| hsa-miR-100825-3p | UGUGACAGAUUGAUAACUGAAA (SEQ. ID. NO: 296) |
| hsa-miR-100825-5p | UCGGGGAUCAUCAUGUCACGAGA (SEQ. ID. NO: 297) |
| hsa-miR-100829-3p | UAAUUUUAUGUAUAAGCUAGU (SEQ. ID. NO: 298) |
| hsa-miR-100835-5p | AGGAAGCCCUGGAGGGGCUGGAG (SEQ. ID. NO: 299) |
| hsa-miR-100842 | CGAAAACAGCAAUUACCUUUGC (SEQ. ID. NO: 300) |
| hsa-miR-100843-3p | CAACUAGACUGUGAGCUUCUAG (SEQ. ID. NO: 301) |
| hsa-miR-100843-5p | AAGGAGCUUACAAUCUAGCUGGG (SEQ. ID. NO: 302) |
| hsa-miR-100846 | CGGCUCUGGGUCUGUGGGGAG (SEQ. ID. NO: 303) |
| hsa-miR-100851 | GUGAACGGGCGCCAUCCCGAGG (SEQ. ID. NO: 304) |
| hsa-miR-100852 | UCAGCAAACAUUUAUUGUGUGC (SEQ. ID. NO: 305) |
| hsa-miR-100854 | CUGCCCUGGCCCGAGGGACCGA (SEQ. ID. NO: 306) |
| hsa-miR-100855-3p | CACGCUCAUGCACACACCCACA (SEQ. ID. NO: 307) |
| hsa-miR-100855-5p | UGAGUGUGUGUGUGUGAGUGUGU (SEQ. ID. NO: 308) |
| hsa-miR-100869-3p | UAUGUCUGCUGACCAUCACCUU (SEQ. ID. NO: 309) |
| hsa-miR-100869-5p | UGGUGGGCCGCAGAACAUGUGC (SEQ. ID. NO: 310) |
| hsa-miR-100871-3p | CGCGGGUGCUUACUGACCCUU (SEQ. ID. NO: 311) |
| hsa-miR-100871-5p | CGGGUCGGAGUUAGCUCAAGCGG (SEQ. ID. NO: 312) |
| hsa-miR-100885 | GCGACCCAUACUUGGUUUCAG (SEQ. ID. NO: 313) |
| hsa-miR-100887-3p | CCUGGAAACACUGAGGUUGUGU (SEQ. ID. NO: 314) |
| hsa-miR-100887-5p | UAUACCUCAGUUUUAUCAGGUG (SEQ. ID. NO: 315) |
| hsa-miR-100891-3p | UGGUGGUUUACAAAGUAAUUCA (SEQ. ID. NO: 316) |
| hsa-miR-100891-5p | UGGAUUUCUUUGUGAAUCACCA (SEQ. ID. NO: 317) |
| hsa-miR-101001 | ACCAGGAGGCUGAGGCCCCU (SEQ. ID. NO: 318) |
| hsa-miR-146b | UGAGAACUGAAUUCCAUAGGCU (SEQ. ID. NO: 319) |
| hsa-miR-147b | GUGUGCGGAAAUGCUUCUGCUA (SEQ. ID. NO: 320) |
| hsa-miR-181d | AACAUUCAUUGUUGUCGGUGGGU (SEQ. ID. NO: 321) |
| hsa-miR-18b | UAAGGUGCAUCUAGUGCAGUUAG (SEQ. ID. NO: 322) |
| hsa-miR-193b | AACUGGCCCUCAAAGUCCCGCU (SEQ. ID. NO: 323) |
| hsa-miR-200001 | UGCAACGAACCUGAGCCACUGA (SEQ. ID. NO: 324) |
| hsa-miR-200002 | AUAAUACAUGGUUAACCUCUUU (SEQ. ID. NO: 325) |
| hsa-miR-200003 | UACUUGGAAAGGCAUCAGUUG (SEQ. ID. NO: 326) |
| hsa-miR-200004 | UGCAACUUACCUGAGUCAUUGA (SEQ. ID. NO: 327) |
| hsa-miR-200007 | GUAGAGGAGAUGGCGCAGGG (SEQ. ID. NO: 328) |
| hsa-miR-200008 | UACCCAUUGCAUAUCGGAGUU (SEQ. ID. NO: 329) |
| hsa-miR-20b | CAAAGUGCUCAUAGUGCAGGUAG (SEQ. ID. NO: 330) |

TABLE A2-continued

MicroRNA Sequences

| Name | Mature MicroRNA (5' -> 3') |
|---|---|
| hsa-miR-20b-3p | ACUGUAGUAUGGGCACUUCCAG (SEQ. ID. NO: 331) |
| hsa-miR-216b | AAAUCUCUGCAGGCAAAUGUGA (SEQ. ID. NO: 332) |
| hsa-miR-301b | CAGUGCAAUGAUAUUGUCAAAGCA (SEQ. ID. NO: 333) |
| hsa-miR-329 | AACACACCUGGUUAACCUCUUU (SEQ. ID. NO: 334) |
| hsa-miR-33b | GUGCAUUGCUGUUGCAUUGC (SEQ. ID. NO: 335) |
| hsa-miR-374b | AUAUAAUACAACCUGCUAAGUG (SEQ. ID. NO: 336) |
| hsa-miR-375 | UUUGUUCGUUCGGCUCGCGUGA (SEQ. ID. NO: 337) |
| hsa-miR-376a | AUCAUAGAGGAAAAUCCACGU (SEQ. ID. NO: 338) |
| hsa-miR-376b | AUCAUAGAGGAAAAUCCAUGUU (SEQ. ID. NO: 339) |
| hsa-miR-376c | AAUCGUACAGGGUCAUCCACUU (SEQ. ID. NO: 340) |
| hsa-miR-376c | AAUCGUACAGGGUCAUCCACUU (SEQ. ID. NO: 341) |
| hsa-miR-377 | AUCACACAAAGGCAACUUUUGU (SEQ. ID. NO: 342) |
| hsa-miR-378 | ACUGGACUUGGAGUCAGAAGG (SEQ. ID. NO: 343) |
| hsa-miR-379 | UGGUAGACUAUGGAACGUAGG (SEQ. ID. NO: 344) |
| hsa-miR-380 | UAUGUAAUAUGGUCCACAUCUU (SEQ. ID. NO: 345) |
| hsa-miR-410 | AAUAUAACACAGAUGGCCUGU (SEQ. ID. NO: 346) |
| hsa-miR-421-3p | AUCAACAGACAUUAAUUGGGCG (SEQ. ID. NO: 347) |
| hsa-miR-429 | UAAUACUGUCUGGUAAAACCGU (SEQ. ID. NO: 348) |
| hsa-miR-431 | UGUCUUGCAGGCCGUCAUGCA (SEQ. ID. NO: 349) |
| hsa-miR-432 | UCUUGGAGUAGGUCAUUGGGUGG (SEQ. ID. NO: 350) |
| hsa-miR-433 | AUCAUGAUGGGCUCCUCGGUGU (SEQ. ID. NO: 351) |
| hsa-miR-449a | UGGCAGUGUAUUGUUAGCUGGU (SEQ. ID. NO: 352) |
| hsa-miR-449b | AGGCAGUGUAUUGUUAGCUGGC (SEQ. ID. NO: 353) |
| hsa-miR-450a | UUUUGCGAUGUGUUCCUAAUAU (SEQ. ID. NO: 354) |
| hsa-miR-451 | AAACCGUUACCAUUACUGAGUU (SEQ. ID. NO: 355) |
| hsa-miR-452 | AACUGUUUGCAGAGGAAACUGA (SEQ. ID. NO: 356) |
| hsa-miR-453 | AGGUUGUCCGUGGUGAGUUCGCA (SEQ. ID. NO: 357) |
| hsa-miR-454 | UAGUGCAAUAUUGCUUAUAGGGU (SEQ. ID. NO: 358) |
| hsa-miR-455-5p | UAUGUGCCUUUGGACUACAUCG (SEQ. ID. NO: 359) |
| hsa-miR-484 | UCAGGCUCAGUCCCCUCCCGAU (SEQ. ID. NO: 360) |
| hsa-miR-485-3p | GUCAUACACGGCUCUCCUCUCU (SEQ. ID. NO: 361) |
| hsa-miR-485-5p | AGAGGCUGGCCGUGAUGAAUUC (SEQ. ID. NO: 362) |
| hsa-mir-486_os | CGGGGCAGCUCAGUACAGGAU (SEQ. ID. NO: 3603) |
| hsa-miR-487 | AAUCAUACAGGGACAUCCAGUU (SEQ. ID. NO: 364) |
| hsa-miR-488 | UUGAAAGGCUAUUUCUUGGUCU (SEQ. ID. NO: 365) |
| hsa-miR-490 | CCAUGGAUCUCCAGGUGGGU (SEQ. ID. NO: 366) |
| hsa-miR-493 | UGAAGGUCUACUGUGUGCCAGG (SEQ. ID. NO: 367) |
| hsa-miR-497 | CAGCAGCACACUGUGGUUUGU (SEQ. ID. NO: 368) |

TABLE A2-continued

MicroRNA Sequences

| Name | Mature MicroRNA (5' -> 3') |
|---|---|
| hsa-miR-502 | AAUGCACCUGGGCAAGGAUUCA (SEQ. ID. NO: 369) |
| hsa-miR-503 | UAGCAGCGGGAACAGUUCUGCAG (SEQ. ID. NO: 370) |
| hsa-miR-505 | CGUCAACACUUGCUGGUUUCCU (SEQ. ID. NO: 371) |
| hsa-miR-509-3p | UGAUUGGUACGUCUGUGGGUAG (SEQ. ID. NO: 372) |
| hsa-miR-514 | AUUGACACUUCUGUGAGUAGA (SEQ. ID. NO: 373) |
| hsa-miR-92b | UAUUGCACUCGUCCCGGCCUCC (SEQ. ID. NO: 374) |

TABLE A3

MicroRNA Hairpin Precursor Sequences

| Name | Hairpin Precursor (5' → 3') |
|---|---|
| hsa-mir-100516 | GGCAGUGCUCUACUCAAAAAGCUGUCAGUCACUUAGAUUACAUGUGACUG ACACCUCUUUGGGUGAAGGAAGGCUCA (SEQ. ID. NO: 375) |
| hsa-mir-100604 | UUGGGCAAGGUGCGGGGCUAGGGCUAACAGCAGUCUUACUGAAGGUUUC CUGGAAACCACGCACAUGCUGUUGCCACUAACCUCAACCUUACUCGGUC (SEQ. ID. NO: 376) |
| hsa-mir-100610 | UUCUCUCCUCCAUGCCUUGAGUGUAGGACCGUUGGCAUCUUAAUUACCCU CCCACACCCAAGGCUUGCAAAAAAGCGAG (SEQ. ID. NO: 377) |
| hsa-mir-100631 | AGGGGCGGGAGGGGGUCCCCGGUGCUCGGAUCUCGAGGGUGCUUAUU GUUCGGUCCGAGCCUGGGUCUCCCUCUUCCCCCCAACC (SEQ. ID. NO: 378) |
| hsa-mir-100701 | AACUUGUUAGAAGGUUACUUGUUAGUUCAGGACCUCAUUACUUUCUGCCU GAACUAUUGCAGUAGCCUCCUAACUGGUUAU (SEQ. ID. NO: 379) |
| hsa-mir-100723 | CCGAGCCUCCAGUACCACGUGUCAGGGCCACAUGAGCUGGGCCUCGUGG GCCUGAUGUGGUGCUGGGGCCUCAGGG (SEQ. ID. NO: 380) |
| hsa-mir-100730 | UACUUAAUGAGAAGUUGCCCGUGUUUUUUUCGCUUUAUUUGUGACGAAAC AUUCGCGGUGCACUUCUUUUUCAGUAUC (SEQ. ID. NO: 381) |
| hsa-mir-100732 | ACGUCAGGGAAAGGAUUCUGCUGUCGGUCCCACUCCAAAGUUCACAGAAU GGGUGGUGGGCACAGAAUCUGGACUCUGCUUGUG (SEQ. ID. NO: 382) |
| hsa-mir-100754 | UGCUUCUGUGUGAUAUGUUUGAUAUUGGGUUGUUUAAUUAGGAACCAAC UAAAAUGUCAAACAUAUUCUUACAGCAGCAG (SEQ. ID. NO: 383) |
| hsa-mir-100760 | CCUGAGCCUUGCACUGAGAUGGGAGUGGUGUAAGGCUCAGGUAUGCACA GCUCCCAUCUCAGAACAAGGCUCGGGUG (SEQ. ID. NO: 384) |
| hsa-mir-100814 | GUGUGCAUUUGCAGGAACUUGUGAGUCUCCUAUUGAAAAUGAACAGGAGA CUGAUGAGUUCCCGGGAACACCCACAA (SEQ. ID. NO: 385) |
| hsa-mir-100815 | AUGCACUGCACAACCCUAGGAGAGGGUGCCAUUCACAUAGACUAUAAUUG AAUGGCGCCACUAGGGUUGUGCAGUGCACAA (SEQ. ID. NO: 386) |
| hsa-mir-100818 | UAGAGGGAUGAGGGGGAAAGUUCUAUAGUCCUGUAAUUAGAUCUCAGGA CUAUAGAACUUUCCCCCUCAUCCCUCUGCC (SEQ. ID. NO: 387) |
| hsa-mir-100819 | CCGCACUCUCUCCAUUACACUACCCUGCCUCUUCUCCAUGAGAGGCAGCG GGGUGUAGUGGAUAGAGCACGGGU (SEQ. ID. NO: 388) |
| hsa-mir-100824 | UCAUACUUGAGGAGAAAUUAUCCUUGGUGUGUUCGCUUUAUUUAUGAUG AAUCAUACAAGGACAAUUUCUUUUUGAGUAUCAAA (SEQ. ID. NO: 389) |
| hsa-mir-100825 | CUCAGACAUCUCGGGGAUCAUCAUGUCACGAGAUACCAGUGUGCACUUGU GACAGAUUGAUAACUGAAAGGUCUGGGAG (SEQ. ID. NO: 390) |
| hsa-mir-100829 | AGUCAGAAAUGAGCUUAUUCAUAAAAGUGCAGUAUGGUGAAGUCAAUCUG UAAUUUUAUGUAUAAGCUAGUCUCUGAUUGA (SEQ. ID. NO: 391) |
| hsa-mir-100835 | CAGGAAGAGGAGGAAGCCCUGGAGGGGCUGGAGGUGAUGGAUGUUUCC UCCGGUUCUCAGGGCUCCACCUCUUUCGGGCC (SEQ. ID. NO: 392) |

TABLE A3-continued

MicroRNA Hairpin Precursor Sequences

| Name | Hairpin Precursor (5' → 3') |
|---|---|
| hsa-mir-100842 | AGGUGGGUGCAAAGGUAAUUGCAGUUUUUCCCAUUAUUUUAAUUGCGAAA ACAGCAAUUACCUUUGCACCAACCUGA (SEQ. ID. NO: 393) |
| hsa-mir-100843 | AACUGCCCUCAAGGAGCUUACAAUCUAGCUGGGGGUAAAUGACUUGCACA UGAACACAACUAGACUGUGAGCUUCUAGAGGGCAGGGA (SEQ. ID. NO: 394) |
| hsa-mir-100846 | GGCGCGUCGCCCCCCUCAGUCCACCAGAGCCCGGAUACCUCAGAAAUUCG GCUCUGGGUCUGUGGGGAGCGAAAUGCAAC (SEQ. ID. NO: 395) |
| hsa-mir-100851 | GUGCAGAUCCUUGGGAGCCCUGUUAGACUCUGGAUUUUACACUUGGAGU GAACGGGCGCCAUCCCGAGGCUUUGCACAG (SEQ. ID. NO: 396) |
| hsa-mir-100852 | CAUUAGUAGGCCUCAGUAAAUGUUUAUUAGAUGAAUAAAUGAAUGACUCA UCAGCAAACAUUUAUUGUGUGCCUGCUAAAGU (SEQ. ID. NO: 397) |
| hsa-mir-100854 | UUAGCCCUGCGGCCCCACGCACCAGGGUAAGAGAGACUCUCGCUUCCUGC CCUGGCCCGAGGGACCGACUGGCUGGGC (SEQ. ID. NO: 398) |
| hsa-mir-100855 | UGCGGGCGUGUGAGUGUGUGUGUGAGUGUGUGUCGCUCCGGGUCCA CGCUCAUGCACACACCCACACGCCCACACU (SEQ. ID. NO: 399) |
| hsa-mir-100869 | UAAGUGGAAAGAUGGUGGGCCGCAGAACAUGUGCUGAGUUCGUGCCAUA UGUCUGCUGACCAUCACCUUUAGAAGCCCC (SEQ. ID. NO: 400) |
| hsa-mir-100871 | CACUCCUACCCGGGUCGGAGUUAGCUCAAGCGGUUACCUCCUCAUGCCGG ACUUUCUAUCUGUCCAUCUCUGUGCUGGGGUUCGAGACCCGCGGGUGCU UACUGACCCUUUUAUGCAAUAA (SEQ. ID. NO: 401) |
| hsa-mir-100885 | CCUGGCCCAUGAAAUCAAGCGUGGGUGAGACCUGGUGCAGAACGGGAAG GCGACCCAUACUUGGUUUCAGAGGCUGUGAG (SEQ. ID. NO: 402) |
| hsa-mir-100887 | UUAGUGGUACUAUACCUCAGUUUUAUCAGGUGUUCUUAAAAUCACCUGGA AACACUGAGGUUGUGUCUCACUGAAC (SEQ. ID. NO: 403) |
| hsa-mir-100891 | UGAAGUGCUGUGGAUUUCUUUGUGAAUCACCAUAUCUAAGCUAAUGUGG UGGUGGUUUACAAAGUAAUUCAUAGUGCUUCA (SEQ. ID. NO: 404) |
| hsa-mir-101001 | UCUCCUCGAGGGGUCUCUGCCUCUACCCAGGACUCUUUCAUGACCAGGAG GCUGAGGCCCCUCACAGGCGGC (SEQ. ID. NO: 405) |
| hsa-mir-146b | CACCUGGCACUGAGAACUGAAUUCCAUAGGCUGUGAGCUCUAGCAAUGCC CUGUGGACUCAGUUCUGGUGCCCGGCAGU (SEQ. ID. NO: 406) |
| hsa-mir-147b | UAUAAAUCUAGUGGAAACAUUUCUGCACAAACUAGAUUCUGGACACCAGU GUGCGGAAAUGCUUCUGCUACAUUUUUAGG (SEQ. ID. NO: 407) |
| hsa-mir-181d | GGUCACAAUCAACAUUCAUUGUUGUCGGUGGGUUGUGAGGACUGAGGCC AGACCCACCGGGGAUGAAUGUCACUGUGGCUGGG (SEQ. ID. NO: 408) |
| hsa-mir-18b | UCUCUUGUGUUAAGGUGCAUCUAGUGCAGUUAGUGAAGCAGCUUAGAAU CUACUGCCCUAAAUGCCCCUUCUGGCACAGGCUGCC (SEQ. ID. NO: 409) |
| hsa-mir-193b | GUCUCAGAAUCGGGGUUUUGAGGGCGAGAUGAGUUUAUGUUUUAUCCAA CUGGCCCUCAAAGUCCCGCUUUUGGGUCA (SEQ. ID. NO: 410) |
| hsa-mir-200001 | CCUUAAUCCUUGCAACGAACCUGAGCCACUGAUUCAGUAAAAUACUCAGU GGCACAUGUUUGUUGUGAGGGUCAAAGA (SEQ. ID. NO: 411) |
| hsa-mir-200002 | AUAUUUGAGGAGAGGUUAUCCGUGUUAUGUUCGCUUCAUUCAUCAUGAAU AAUACAUGGUUAACCUCUUUUUGAAUAUCA (SEQ. ID. NO: 412) |
| hsa-mir-200003 | GGAAGUGCCCUACUUGGAAAGGCAUCAGUUGCUUAGAUUACAUGUAACUA UUCCCUUUCUGAGUAGAGUAAGUCUUA (SEQ. ID. NO: 413) |
| hsa-mir-200004 | CCUUAAUCCUUGCAACUUACCUGAGUCAUUGAUUCAGUAAAACAUUCAAU GGCACAUGUUUGUUGUUAGGGUCAAAGA (SEQ. ID. NO: 414) |
| hsa-mir-200007 | GCUAGAGAAGGUAGAGGAGAUGGCGCAGGGGACACGGGCAAAGACUUGG GGGUUCCUGGGACCCUCAGACGUGUGUCCUCUUCUCCCUCCUCCCAGGU GUAUG (SEQ. ID. NO: 415) |
| hsa-mir-200008 | CCUUCUCCCAUACCCAUUGCAUAUCGGAGUUGUGAAUUCUCAAAACACCU CCUGUGUGCAUGGAUUACAGGAGGGUGA (SEQ. ID. NO: 416) |

TABLE A3-continued

MicroRNA Hairpin Precursor Sequences

| Name | Hairpin Precursor (5' → 3') |
|---|---|
| hsa-mir-20b | CUAGUAGUACCAAAGUGCUCAUAGUGCAGGUAGUUUUGGCAUGACUCUAC UGUAGUAUGGGCACUUCCAGUACUCUUGGA (SEQ. ID. NO: 417) |
| hsa-mir-216b | GCAGACUGGAAAAUCUCUGCAGGCAAAUGUGAUGUCACUGAGGAAAUCAC ACACUUACCCGUAGAGAUUCUACAGUCUGACA (SEQ. ID. NO: 418) |
| hsa-mir-301b | GCCGCAGGUGCUCUGACGAGGUUGCACUACUGUGCUCUGAGAAGCAGUG CAAUGAUAUUGUCAAAGCAUCUGGGACCA (SEQ. ID. NO: 419) |
| hsa-mir-329-1 | GUACCUGAAGAGAGGUUUUCUGGGUUUCUGUUUCUUUAAUGAGGACGAA ACACACCUGGUUAACCUCUUUUCCAGUAUCA (SEQ. ID. NO: 420) |
| hsa-mir-329-2 | GUACCUGAAGAGAGGUUUUCUGGGUUUCUGUUUCUUUAUUGAGGACGAA ACACACCUGGUUAACCUCUUUUCCAGUAUCA (SEQ. ID. NO: 421) |
| hsa-mir-33b | CGGCCCCGCGGUGCAUUGCUGUUGCAUUGCACGUGUGUGAGGCGGGUGC AGUGCCUCGGCAGUGCAGCCCGGAGCCGGCC (SEQ. ID. NO: 422) |
| hsa-mir-374b | ACUCGGAUGGAUAUAAUACAACCUGCUAAGUGUCCUAGCACUUAGCAGGU UGUAUUAUCAUUGUCCGUGUCU (SEQ. ID. NO: 423) |
| hsa-mir-375 | CUCCCGCCCCGCGACGAGCCCCUCGCACAAACCGGACCUGAGCGUUUUGU UCGUUCGGCUCGCGUGAGGCAGGGGCG (SEQ. ID. NO: 424) |
| hsa-mir-376a-1 | UAUUUAAAAGGUAGAUUCUCCUUCUAUGAGUACAUUAUUUAUGAUUAAUC AUAGAGGAAAAUCCACGUUUUCAGUAUC (SEQ. ID. NO: 425) |
| hsa-mir-376a-2 | UAUUUAAAAGGUAGAUUUUCCUUCUAUGGUUACGUGUUUGAUGGUUAAUC AUAGAGGAAAAUCCACGUUUUCAGUAUC (SEQ. ID. NO: 426) |
| hsa-mir-376b | GUAUUUAAACGUGGAUAUUCCUUCUAUGUUUACGUGAUUCCUGGUUAAU CAUAGAGGAAAAUCCAUGUUUUCAGUAUCA (SEQ. ID. NO: 427) |
| hsa-mir-376c | UAUUUAAAAGGUGGAUAUUCCUUCUAUGUUUAUGUUAUUUAUGGUUAAAC AUAGAGGAAAUUCCACGUUUUCAGUAUC (SEQ. ID. NO: 428) |
| hsa-mir-376c | UAUUUAAAGGUGGAUAUUCCUUCUAUGUUUAUGUUAUUUAUGGUUAAAC AUAGAGGAAAUUCCACGUUUUCAGUAUC (SEQ. ID. NO: 429) |
| hsa-mir-377 | ACCCUUGAGCAGAGGUUGCCCUUGGUGAAUUCGCUUUAUUUAUGUUGAA UCACACAAAGGCAACUUUUGUUUGAGUAUCA (SEQ. ID. NO: 430) |
| hsa-mir-378 | CACCCAGGGCUCCUGACUCCAGGUCCUGUGUGUUACCUAGAAAUAGCACU GGACUUGGAGUCAGAAGGCCUGAGUGGA (SEQ. ID. NO: 431) |
| hsa-mir-379 | CCUGAAGAGAUGGUAGACUAUGGAACGUAGGCGUUAUGAUUUCUGACCUA UGUAACAUGGUCCACUAACUCUCAGUAUC (SEQ. ID. NO: 432) |
| hsa-mir-380 | ACCUGAAAAGAUGGUUGACCAUAGAACAUGCGCUAUCUCUGUGUCGUAUG UAAUAUGGUCCACAUCUUCUCAAUAUCA (SEQ. ID. NO: 433) |
| hsa-mir-410 | ACCUGAGAAGAGGUUGUCUGUGAUGAGUUCGCUUUUAUUAAUGACGAAUA UAACACAGAUGGCCUGUUUUCAGUACC (SEQ. ID. NO: 434) |
| hsa-mir-421 | CAUUGUAGGCCUCAUUAAAUGUUUGUUGAAUGAAAAAAUGAAUCAUCAAC AGACAUUAAUUGGGCGCCUGCUCUGU (SEQ. ID. NO: 435) |
| hsa-mir-429 | GCCGAUGGGCGUCUUACCAGACAUGGUUAGACCUGGCCCUCUGUCUAAUA CUGUCUGGUAAAACCGUCCAUCCGCUG (SEQ. ID. NO: 436) |
| hsa-mir-431 | UCCUGCGAGGUGUCUUGCAGGCCGUCAUGCAGGCCACACUGACGGUAAC GUUGCAGGUCGUCUUGCAGGGCUUCUCGCAAGACG (SEQ. ID. NO: 437) |
| hsa-mir-432 | CUCCUCCAGGUCUUGGAGUAGGUCAUUGGGUGGAUCCUCUAUUUCCUUA CGUGGGCCACUGGAUGGCUCCUCCAUGUCUUGGAGUAGAU (SEQ. ID. NO: 438) |
| hsa-mir-433 | CGGGGAGAAGUACGGUGAGCCUGUCAUUAUUCAGAGAGGCUAGAUCCUC UGUGUUGAGAAGGAUCAUGAUGGGCUCCUCGGUGUUCUCCAGGUA (SEQ. ID. NO: 439) |
| hsa-mir-449a | UGUGAUGAGCUGGCAGUGUAUUGUUAGCUGGUUGAAUAUGUGAAUGGCA UCGGCUAACAUGCAACUGCUGUCUAUUGCAUA (SEQ. ID. NO: 440) |
| hsa-mir-449b | UGAAUCAGGUAGGCAGUGUAUUGUUAGCUGGCUGCUUGGGUCAAGUCAG CAGCCACAACUACCCUGCCACUUGCUUCUGGA (SEQ. ID. NO: 441) |

TABLE A3-continued

MicroRNA Hairpin Precursor Sequences

| Name | Hairpin Precursor (5' → 3') |
|---|---|
| hsa-mir-450a-1 | ACUAAACUGUUUUUGCGAUGUGUUCCUAAUAUGCACUAUAAAUAUAUUGG GAACAUUUUGCAUGUAUAGUUUUGUAU (SEQ. ID. NO: 442) |
| hsa-mir-450a-2 | GCUAAACUAUUUUUGCGAUGUGUUCCUAAUAUGUAAUAUAAAUGUAUUGG GGACAUUUUGCAUUCAUAGUUUUGUAU (SEQ. ID. NO: 443) |
| hsa-mir-451 | AAUGGCAAGGAAACCGUUACCAUUACUGAGUUUAGUAAUGGUAAUGGUUC UCUUGCUAUACC (SEQ. ID. NO: 444) |
| hsa-mir-452 | AAGCACUUACAACUGUUUGCAGAGGAAACUGAGACUUUGUAACUAUGUCU CAGUCUCAUCUGCAAAGAAGUAAGUGCUUUGCC (SEQ. ID. NO: 445) |
| hsa-mir-453 | AGAAGAUGCAGGAAUGCUGCGAGCAGUGCCACCUCAUGGUACUCGGAGG GAGGUUGUCCGUGGUGAGUUCGCAUUAUUUAA (SEQ. ID. NO: 446) |
| hsa-mir-454 | AUCCUAGAACCCUAUCAAUAUUGUCUCUGCUGUGUAAAUAGUUCUGAGUA GUGCAAUAUUGCUUAUAGGGUUUUGGUGUUU (SEQ. ID. NO: 447) |
| hsa-mir-455 | GGCGUGAGGGUAUGUGCCUUUGGACUACAUCGUGGAAGCCAGCACCAUG CAGUCCAUGGGCAUAUACACUUGCCUCAAG (SEQ. ID. NO: 448) |
| hsa-mir-484 | CUGGGAACCCCGGGGGGGCGGGGCCUCGCGGCCCUGCAGCCUCGUCAG GCUCAGUCCCCUCCCGAUAAACCCCUAA (SEQ. ID. NO: 449) |
| hsa-mir-485 | GUACUUGGAGAGAGGCUGGCCGUGAUGAAUUCGAUUCAUCAAAGCGAGU CAUACACGGCUCUCCUCUCUUUUAGUGUCA (SEQ. ID. NO: 450) |
| hsa-mir-486_os | CCCUGGGGCAUCCUGUACUGAGCUGCCCCGAGGCCCUUCAUGCUGCCCAG CUCGGGGCAGCUCAGUACAGGAUACUCGGGGUGG (SEQ. ID. NO: 451) |
| hsa-mir-487 | UACUUGAAGAGUGGUUAUCCCUGCUGUGUUCGCUUAAUUUAUGACGAAUC AUACAGGGACAUCCAGUUUUUCAGUAUC (SEQ. ID. NO: 452) |
| hsa-mir-488 | AAUCAUCUCUCCCAGAUAAUGGCACUCUCAAACAAGUUUCCAAAUUGUUU GAAAGGCUAUUUCUUGGUCAGAUGACUCU (SEQ. ID. NO: 453) |
| hsa-mir-490 | UUGUUCGACACCAUGGAUCUCCAGGUGGGUCAAGUUUAGAGAUGCACCAA CCUGGAGGACUCCAUGCUGUUGAGCUGUU (SEQ. ID. NO: 454) |
| hsa-mir-493 | CUCCAGGGCUUUGUACAUGGUAGGCUUUCAUUCAUUCGUUUGCACAUUCG GUGAAGGUCUACUGUGUGCCAGGCCCUGUGCCA (SEQ. ID. NO: 455) |
| hsa-mir-497 | GCUCCCGCCCCAGCAGCACACUGUGGUUUGUACGGCACUGUGGCCACGUC CAAACCACACUGUGGUGUUAGAGCGAGGGUGGGGAG (SEQ. ID. NO: 456) |
| hsa-mir-502 | CCCCUCUCUAAUCCUUGCUAUCUGGGUGCUAGUGCUGGCUCAAUGCAAUG CACCUGGGCAAGGAUUCAGAGAGGGGGA (SEQ. ID. NO: 457) |
| hsa-mir-503 | AGCCGUGCCCUAGCAGCGGGAACAGUUCUGCAGUGAGCGAUCGGUGCUC UGGGGUAUUGUUUCCGCUGCCAGGGUAAGUCUGG (SEQ. ID. NO: 458) |
| hsa-mir-505 | ACCCAGUGGGGGAGCCAGGAAGUAUUGAUGUUUCUGCCAGUUUAGCGUC AACACUUGCUGGUUUCCUCUCUGGAGCA (SEQ. ID. NO: 459) |
| hsa-mir-509-1 | GUGGUACCCUACUGCAGACAGUGGCAAUCAUGUAUAAUUAAAAAUGAUUG GUACGUCUGUGGGUAGAGUACUGCAU (SEQ. ID. NO: 460) |
| hsa-mir-509-2 | GUGGUACCCUACUGCAGACGUGGCAAUCAUGUAUAAUUAAAAAUGAUUGG UACGUCUGUGGGUAGAGUACUGCAU (SEQ. ID. NO: 461) |
| hsa-mir-509-3 | GUGGUACCCUACUGCAGACAGUGGCAAUCAUGUAUAAUUAAAAAUGAUUG GUACGUCUGUGGGUAGAGUACUGCAU (SEQ. ID. NO: 462) |
| hsa-mir-514-1 | CUGUGGUACCCUACUCUGGAGAGUGACAAUCAUGUAUAAUUAAAUUUGAU UGACACUUCUGUGAGUAGAGUAACGCAUGA (SEQ. ID. NO: 463) |
| hsa-mir-514-2 | CUGUGGUACCCUACUCUGGAGAGUGACAAUCAUGUAUAACUAAAUUUGAU UGACACUUCUGUGAGUAGAGUAACGCAUGA (SEQ. ID. NO: 464) |

TABLE A3-continued

MicroRNA Hairpin Precursor Sequences

| Name | Hairpin Precursor (5' → 3') |
|---|---|
| hsa-mir-514-3 | CUGUGGUACCCUACUCUGGAGAGUGACAAUCAUGUAUAACUAAAUUUGAU UGACACUUCUGUGAGUAGAGUAACGCAUGA (SEQ. ID. NO: 465) |
| hsa-mir-92b | GGCGGGCGGGAGGGACGGGACGCGGUGCAGUGUUGUUUUUCCCCCGCC AAUAUUGCACUCGUCCCGGCCUCCGGCCCCCCG (SEQ. ID. NO: 466) |

TABLE A4

MicroRNA Sequences

| Name | Mature MicroRNA (5' to 3') |
|---|---|
| hsa-miR-100516 | UACUCAAAAAGCUGUCAGUCA (SEQ. ID. NO: 467) |
| hsa-miR-100701 | AAGGUUACUUGUUAGUUCAGG (SEQ. ID. NO: 468) |
| hsa-miR-100760 | GCACUGAGAUGGGAGUGGUGUA (SEQ. ID. NO: 469) |
| hsa-miR-100885 | GCGACCCAUACUUGGUUUCAG (SEQ. ID. NO: 470) |
| hsa-miR-100887-3p | CCUGGAAACACUGAGGUUGUGU (SEQ. ID. NO: 471) |
| hsa-miR-100887-5p | UAUACCUCAGUUUUAUCAGGUG (SEQ. ID. NO: 472) |
| hsa-miR-100891-3p | UGGUGGUUUACAAAGUAAUUCA (SEQ. ID. NO: 473) |
| hsa-miR-100891-5p | UGGAUUUCUUUGUGAAUCACCA (SEQ. ID. NO: 474) |
| hsa-miR-200001 | UGCAACGAACCUGAGCCACUGA (SEQ. ID. NO: 475) |
| hsa-miR-200002 | AUAAUACAUGGUUAACCUCUUU (SEQ. ID. NO: 476) |
| hsa-miR-200003 | UACUUGGAAAGGCAUCAGUUG (SEQ. ID. NO: 477) |
| hsa-miR-200004 | UGCAACUUACCUGAGUCAUUGA (SEQ. ID. NO: 478) |
| hsa-miR-200007 | GUAGAGGAGAUGGCGCAGGG (SEQ. ID. NO: 479) |
| hsa-miR-200008 | UACCCAUUGCAUAUCGGAGUU (SEQ. ID. NO: 480) |
| hsa-mir-486_os | CGGGGCAGCUCAGUACAGGAU (SEQ. ID. NO: 481) |

TABLE A5

MicroRNA Hairpin Precursor Sequences

| Name | Hairpin Precursor (5' → 3') |
|---|---|
| hsa-miR-100516 | GGCAGUGCUCUACUCAAAAAGCUGUCAGUCACUUAGA UUACAUGUGACUGACACCUCUUUGGGUGAAGGAAGGCUCA (SEQ. ID. NO: 482) |
| hsa-miR-100701 | AACUUGUUAGAAGGUUACUUGUUAGUUCAGGACCUCAUU ACUUUCUGCCUGAACUAUUGCAGUAGCCUCCUAACUGGUUAU (SEQ. ID. NO: 483) |
| hsa-miR-100760 | CCUGAGCCUUGCACUGAGAUGGGAGUGGUGUAAGGCUCAGG UAUGCACAGCUCCCAUCUCAGAACAAGGCUCGGGUG (SEQ. ID. NO: 484) |
| hsa-miR-100885 | CCUGGCCCAUGAAAUCAAGCGUGGGUGAGACCUGGUGCAG AACGGGAAGGCGACCCAUACUUGGUUUCAGAGGCUGUGAG (SEQ. ID. NO: 485) |
| hsa-miR-100887-3p | UUAGUGGUACUAUACCUCAGUUUUAUCAGGUGUUCUUAAA AUCACCUGGAAACACUGAGGUUGUGUCUCACUGAAC (SEQ. ID. NO: 486) |
| hsa-miR-100887-5p | UUAGUGGUACUAUACCUCAGUUUUAUCAGGUGUUCUUAAA AUCACCUGGAAACACUGAGGUUGUGUCUCACUGAAC (SEQ. ID. NO: 487) |

TABLE A5-continued

MicroRNA Hairpin Precursor Sequences

| Name | Hairpin Precursor (5' → 3') |
|---|---|
| hsa-miR-100891-3p | UGAAGUGCUGUGGAUUUCUUUGUGAAUCACCAUAUCUAAGC UAAUGUGGUGGUGGUUUACAAAGUAAUUCAUAGUGCUUCA (SEQ. ID. NO: 488) |
| hsa-miR-100891-5p | UGAAGUGCUGUGGAUUUCUUUGUGAAUCACCAUAUCUAAGC UAAUGUGGUGGUGGUUUACAAAGUAAUUCAUAGUGCUUCA (SEQ. ID. NO: 489) |
| hsa-miR-200001 | CCUUAAUCCUUGCAACGAACCUGAGCCACUGAUUCAGUAAAA UACUCAGUGGCACAUGUUUGUUGUGAGGGUCAAAAGA (SEQ. ID. NO: 490) |
| hsa-miR-200002 | AUAUUUGAGGAGAGGUUAUCCGUGUUAUGUUCGCUUCAUUCA UCAUGAAUAAUACAUGGUUAACCCUCUUUUUGAAUAUCA (SEQ. ID. NO: 491) |
| hsa-miR-200003 | GGAAGUGCCCUACUUGGAAAGGCAUCAGUUGCUUAGAUUACAU GUAACUAUUCCCUUUCUGAGUAGAGUAAGUCUUA (SEQ. ID. NO: 492) |
| hsa-miR-200004 | CCUUAAUCCUUGCAACUUACCUGAGUCAUUGAUUCAGUAAAAC AUUCAAUGGCACAUGUUUGUUGUUAGGGUCAAAAGA (SEQ. ID. NO: 493) |
| hsa-miR-200007 | GCUAGAGAAGGUAGAGGAGAUGGCGCAGGGGACACGGGCAAAG ACUUGGGGGUUCCUGGGACCCUCAGACGUGUGUCCUCUUCUCCC UCCUCCCAGGUGUAUG (SEQ. ID. NO: 494) |
| hsa-miR-200008 | CCUUCUCCCAUACCCAUUGCAUAUCGGAGUUGUGAAUUCUC AAAACACCUCCUGUGUGCAUGGAUUACAGGAGGGUGA (SEQ. ID. NO: 495) |
| hsa-mir-486_os | CCCUGGGGCAUCCUGUACUGAGCUGCCCCGAGGCCCUUCAU GCUGCCCAGCUCGGGGCAGCUCAGUACAGGAUACUCGGGUGG (SEQ. ID. NO: 496) |

TABLE A6

MicroRNA Sequences

| name | MicroRNA (5' → 3') |
|---|---|
| hsa-mir-18b-3p | CUGCCCUAAAUGCCCCUUCUGGC (SEQ. ID. NO: 497) |
| hsa-miR-618 | UUAAUAUGACUGACAAAGCGU (SEQ. ID. NO: 498) |
| hsa-miR-619 | UUUCCGGCUCGCGUGGGUGUGU (SEQ. ID. NO: 499) |
| hsa-miR-620 | AUGUUGGGAGCGGGCAGGUUGG (SEQ. ID. NO: 500) |
| hsa-miR-723-5p | AGUACCACGUGUCAGGGCCACAUGA (SEQ. ID. NO: 501) |
| hsa-mir-816 | UUGGGGAAACGGCCGCUGAGUGA (SEQ. ID. NO: 502) |
| hsa-mir-817 | CUGUAUGCCCUCACCGCUCAGC (SEQ. ID. NO: 503) |
| hsa-mir-821-1 | GCGGCGGCGGCGGAGGCU (SEQ. ID. NO: 504) |
| hsa-mir-821-2/3 | GCGGCGGCGGCGGAGGCU (SEQ. ID. NO: 505) |
| hsa-mir-828-3p | UCUAGUAAGAGUGGCAGUCGA (SEQ. ID. NO: 506) |
| hsa-mir-828-5p | AUGCUGACAUAUUUACUAGAGG (SEQ. ID. NO: 507) |
| hsa-mir-831-1 | UGGGGCGGAGCUUCCGGAGGCC (SEQ. ID. NO: 508) |
| hsa-mir-831-2 | UGGGGCGGAGCUUCCGGAGGCC (SEQ. ID. NO: 509) |
| hsa-mir-831-3/-4/-5 | UGGGGCGGAGCUUCCGGAGGCC (SEQ. ID. NO: 510) |
| hsa-mir-840-3p | ACUCGGCGUGGCGUCGGUCGUGG (SEQ. ID. NO: 511) |

TABLE A6-continued

MicroRNA Sequences

| name | MicroRNA (5' → 3') |
|---|---|
| hsa-mir-840-5p | UCGACCGGACCUCGACCGGCUC (SEQ. ID. NO: 512) |
| hsa-mir-845-1 | AAAGCAUGCUCCAGUGGCGC (SEQ. ID. NO: 513) |
| hsa-mir-845-2 | AAAGCAUGCUCCAGUGGCGC (SEQ. ID. NO: 514) |
| hsa-mir-847 | CAGAGAGGACCACUAUGGCGGG (SEQ. ID. NO: 515) |
| hsa-mir-848 | AUUGCCAUCCCCUAUGGACCAG (SEQ. ID. NO: 516) |
| hsa-mir-849 | UGUCUACUACUGGAGACACUGG (SEQ. ID. NO: 517) |
| hsa-mir-850 | UUAGGGCCCUGGCUCCAUCUCC (SEQ. ID. NO: 518) |
| hsa-mir-853 | UGGGAUCUCCGGGGUCUUGGUU (SEQ. ID. NO: 519) |
| hsa-mir-857 | AAGGCAGGGCCCCCGCUCCCCGG (SEQ. ID. NO: 520) |
| hsa-mir-864 | AAAAGCUGAGUUGAGAGG (SEQ. ID. NO: 521) |
| hsa-mir-151 | UCGAGGAGCUCACAGUCUAGA (SEQ. ID. NO: 522) |

TABLE A7

MicroRNA Hairpin Precursor Sequences.

| name | Hairpin Precursor (5' → 3') |
|---|---|
| >hsa-mir-18b-3p | CUUGUGUUAAGGUGCAUCUAGUGCAGUUAGUGAAGCAGCUUAGA AUCUACUGCCCUAAAUGCCCCUUCUGGCACAGG (SEQ. ID. NO: 523) |
| >hsa-miR-618 | UUAUUGUGAAAUAUGUCAUUAAUAUGUACUGACAAAGCGUAUCUG UGUAAUAAAUAUGCUUUUUGUCAGUACAUGUUAAUGGUAUAUUUC AUAACAA (SEQ. ID. NO: 524) |
| >hsa-miR-619 | GCGGCUGCUGGACCCACCCGGCCGGGAAUAGUGCUCCUGGUUGUU UCCGGCUCGCGUGGGUGUGUCGGCGGCGGG (SEQ. ID. NO: 525) |
| >hsa-miR-620 | CGCCCCCACGUGGCCCCGCCCCUGAGGCCGGCGCUGCCGCCAUGU UGGGAGCGGGCAGGUUGGGAGCG (SEQ. ID. NO: 526) |
| >hsa-miR-723-5p | GCCACCUUCCGAGCCUCCAGUACCACGUGUCAGGGCCACAUGAGCUG GGCCUCGUGGGCCUGAUGUGGUGCUGGGGCCUCAGGGGUCUG (SEQ. ID. NO: 527) |
| >hsa-mir-816 | GGGUUUGGGGAAACGGCCGCUGAGUGAGGCGUCGGCUGUGUUUCUC ACCGCGGUCUUUUCCUCCCACUC (SEQ. ID. NO: 528) |
| >hsa-mir-817 | CUUGGUGACGCUGUAUGCCCUCACCGCUCAGCCCCUGGGGCUGGCUU GGCAGACAGUACAGCAUCCAGGGGAGUCAAGGGCAUGGGGCGAGACC AGA (SEQ. ID. NO: 529) |
| >hsa-mir-821-1 | GCGGCGGCGGCGGAGGCUGCUGCUGGGGCGGCUGCUGCUGGGGCGG CUGCGGCGGCGGCUGCUGCGGGGGCUGCUGCUGCUGUUGC (SEQ. ID. NO: 530) |
| >hsa-mir-821-2/3 | GCGGCUGCGGCGGCGGCGGAGGCUGCGGCGGCGACCGUGGCAGAGGC GGUGGCGGAGGCCUCCGUGGCGGAGGCGGAAGC (SEQ. ID. NO: 531) |
| >hsa-mir-828-3p | CUUCCUCAUGCUGACAUAUUUACUAGAGGGUAAAAUUAAUAACCUUCUA GUAAGAGUGGCAGUCGAAGGGAAG (SEQ. ID. NO: 532) |
| >hsa-mir-828-5p | CUUCCUCAUGCUGACAUAUUUACUAGAGGGUAAAAUUAAUAACCUUCUA GUAAGAGUGGCAGUCGAAGGGAAG (SEQ. ID. NO: 533) |
| >hsa-mir-831-1 | GCUCCGCCCCACGUCGCAUGCGCCCCGGGAACGCGUGGGGCGGAGC UUCCGGAGGCCCCGCUCUGCUGCCGACCCUGUGGAGCGGAGGGUGA AGCCUCCGGAUGCCAGUCCCUCAUCGCUGGCCUGGUCGCGCUGUGG CGAAGGGGGCGGAGC (SEQ. ID. NO: 534) |

TABLE A7-continued

MicroRNA Hairpin Precursor Sequences.

| name | Hairpin Precursor (5' → 3') |
|---|---|
| >hsa-mir-831-2 | GCUCCGCCCCACGUCGCAUGCGCCCCGGGAACGCGUGGGGCGGAGC UUCCGGAGGCCCCGCCCUGCUGCCGACCCUGUGGAGCGGAGGGUGA AGCCUCCGGAUGCCAGUCCCUCAUCGCUGGCCCGGUCGCGCUGUGG CGAAGGGGGCGGAGC (SEQ. ID. NO: 535) |
| >hsa-mir-831-3/-4/-5 | CGCUCCGCCCCACGUCGCAUGCGCCCCGGGAAAGCGUGGGGCGGAG CUUCCGGAGGCCCCGCCCUGCUGCCGACCCUGUGGAGCGGAGGGUG AAGCCUCCGGAUGCCAGUCCCUCAUCGCUGGCCCGGUCGCGCUGUG GCGAAGGGGGCGGAGC (SEQ. ID. NO: 536) |
| >hsa-mir-840-3p | UUCAUCAAGACCCAGCUGAGUCACUGUCACUGCCUACCAAUCUCGAC CGGACCUCGACCGGCUCGUCUGUGUUGCCAAUCGACUCGGCGUGGC GUCGGUCGUGGUAGAUAGGCGGUCAUGCAUACGAAUUUUCAGCUCU UGUUCUGGUGAC (SEQ. ID. NO: 537) |
| >hsa-mir-840-5p | UUCAUCAAGACCCAGCUGAGUCACUGUCACUGCCUACCAAUCUCGAC CGGACCUCGACCGGCUCGUCUGUGUUGCCAAUCGACUCGGCGUGGC GUCGGUCGUGGUAGAUAGGCGGUCAUGCAUACGAAUUUUCAGCUCU UGUUCUGGUGAC (SEQ. ID. NO: 538) |
| >hsa-mir-845-1 | CGCGAGGCCGGGUCGAGCGCUUCAGUAGCUCAUGGCUCUGUAGAG UGCGCAUGGCCAAGCAAAGGAAAGCAUGCUCCAGUGGCGCA (SEQ. ID. NO: 539) |
| >hsa-mir-845-2 | AGUAACCACUUAGUGUGUAUUGACUUGUCAGAAUUUUCAGAAUUUAA AGCAUGCUCCAGUGGCGCA (SEQ. ID. NO: 540) |
| >hsa-mir-847 | UUACUGUGUCAUUGUUGCUGUCAUUGCUACUGAGGAGUACUGACCAG AAUCAUCUGCAACUCUUAGUUGGCAGAGAGGACCACUAUGGCGGGUAG (SEQ. ID. NO: 541) |
| >hsa-mir-848 | UGGGCCAGAUUGCCAUCCCCUAUGGACCAGAAGCCAAGGAUCUCUCUA GUGAUGGUCAGAGGGCCCAAAUGGCAGGGAUACCCA (SEQ. ID. NO: 542) |
| >hsa-mir-849 | GCUUCUGUCUACUACUGGAGACACUGGUAGUAUAAAACCCAGAGUCUC CAGUAAUGGACGGGAGC (SEQ. ID. NO: 543) |
| >hsa-mir-850 | CUGGGUUAGGGCCCUGGCUCCAUCUCCUUUAGGAAAACCUUCUGUGGG GAGUGGGGCUUCGACCCUAACCCAG (SEQ. ID. NO: 544) |
| >hsa-mir-853 | CCUGGGCUCUGACCUGAGACCUCUGGGUUCUGAGCUGUGAUGUUGCUC UCGAGCUGGGAUCUCCGGGGUCUUGGUUCAGGG (SEQ. ID. NO: 545) |
| >hsa-mir-857 | GGGCCCGGCCCCAGGAGCGGGGCCUGGGCAGCCCCGUGUGUUGAGGAA GGAAGGCAGGGCCCCCGCUCCCCGGGCCU (SEQ. ID. NO: 546) |
| >hsa-mir-864 | CCUUCUCUUCUCAGUUCUUCCCCAAGUUAGGAAAAGCUGAGUUGAGAGGG (SEQ. ID. NO: 547) |
| >hsa-mir-151 | GUCUCUCUUCAGGGCUCCCGAGACACAGAAACAGACACCUGCCCUCGAG GAGCUCACAGUCUAGAC (SEQ. ID. NO: 548) |

TABLE A8

MicroRNA Sequence and Hairpin Precursor Sequence

| Name | Mature MicroRNA (5' → 3') | Hairpin Precursor Sequence |
|---|---|---|
| hsa-miR-544 | AUUCUGCAU UUUUAGCAA GUUC (SEQ. ID. NO: 549) | CACCUAGGGAUCUUGUUAAAAAGCAGAUUC UGAUUCAGGGACCAAGAUUCUGCAUUUUUA GCAAGUUCUCAAGUGAUG (SEQ. ID. NO: 550) |

In this specification, a base refers to any one of the nucleotide bases normally found in naturally occurring DNA or RNA. The bases can be purines or pyrimidines. Examples of purine bases include adenine (A) and guanine (G). Examples of pyrimidine bases include thymine (T), cytosine (C) and uracil (U). The adenine can be replaced with 2,6-diaminopurine.

Sequences of nucleic acid molecules disclosed in this specification are shown having uracil bases. Uracil bases occur in RNA molecules. The invention also includes DNA molecules. The sequence of bases of the DNA molecule is the same as the RNA molecule, except that in the DNA molecule, the uracil bases are replaced with thymine bases.

Each base in the sequence can form a Watson-Crick base pair with a complementary base. Watson-Crick base pairs as used herein refer to the hydrogen bonding interaction between, for example, the following bases: adenine and thymine (A-T); adenine and uracil (A-U); and cytosine and guanine (C-G).

Equivalents refer to molecules wherein up to thirty percent of the contiguous bases in, for example, SEQ. ID. NOS:1-94 are wobble bases, and/or up to ten percent, and preferably up to five percent of the contiguous bases are non-complementary.

As used herein, wobble bases refer to either: 1) substitution of a cytosine with a uracil, or 2) the substitution of an adenine with a guanine, in the sequence of the molecule. These wobble base substitutions are generally referred to as UG or GU wobbles. Table B shows the number of contiguous bases and the maximum number of wobble bases in the molecule.

TABLE B

Number of contiguous Bases and Maximum Number of Wobble Bases

| No. of Contiguous Bases | 10 | 11 | 12 | 13 | 14 | 15 | 16 | 17 | 18 | 19 | 20 | 21 | 22 | 23 |
|---|---|---|---|---|---|---|---|---|---|---|---|---|---|---|
| Max. No. of Wobble Base Pairs | 3 | 3 | 3 | 3 | 4 | 4 | 4 | 5 | 5 | 5 | 6 | 6 | 6 | 6 |

The term "non-complementary" as used herein refers to additions, deletions, mismatches or combinations thereof. Additions refer to the insertion in the contiguous sequence of any base described above. Deletions refer to the removal of any moiety present in the contiguous sequence. Mismatches refer to the substitution of one of the bases in the contiguous sequence with a different base.

The additions, deletions or mismatches can occur anywhere in the contiguous sequence, for example, at either end of the contiguous sequence or within the contiguous sequence of the molecule. Typically, the additions, deletions or mismatches occur at the end of the contiguous sequence if the contiguous sequence is relatively short, such as, for example, from about ten to about fifteen bases in length. If the contiguous sequence is relatively long, such as, for example, a minimum of sixteen contiguous sequences, the additions, deletions, or mismatches may occur anywhere in the contiguous sequence.

For example, none or one of the contiguous bases may be additions, deletions, or mismatches when the number of contiguous bases is ten to nineteen; and none, or one or two additions, deletions, or mismatches are permissible when the number of contiguous bases is twenty or more.

In addition to the at least ten contiguous nucleotides of the microRNA, the isolated DNA or RNA molecule may also have one or more additional nucleotides. There is no upper limit to the additional number of nucleotides. Typically, no more than about 500 nucleotides, and preferably no more than about 300 nucleotides are added to the at least ten contiguous bases of a microRNA.

Any nucleotide can be added. The additional nucleotides can comprise any base described above. Thus, for example, the additional nucleotides may be any one or more of A, G, C, T, or U.

In one embodiment, the microRNA is part of a hairpin precursor sequence or fragment thereof. For example, suitable hairpin precursor sequences are shown in Table A1 as SEQ ID NOs:95-187. Further hairpin precursor sequences are shown in the following: Table A3 as SEQ. ID, NOs: 375-466; Table A5 as SEQ. ID. NOs: 482-496; Table A7 as SEQ. ID. NOs: 523-548; and Table A8 as SEQ. ID. NO: 550.

The fragment can be any fragment of the hairpin precursor sequence containing at least ten, preferably at least fifteen, more preferably at least twenty nucleotides at the 5' end and/or nucleotides at the 3' end. Preferably the sequence of nucleotides is in the hairpin precursor in which the microRNA is present.

The microRNA or haipin precursor can be inserted into a vector, such as, for example, a recombinant vector. Typically, to construct a recombinant vector containing a microRNA, the hairpin precursor sequence which contains the microRNA sequence is incorporated into the vector. See for example, Chen et al. *Science* 2004, 303:83-86.

The recombinant vector may be any recombinant vector, such as a plasmid, a cosmid or a phage. Recombinant vectors generally have an origin of replication. The vector may be, for example, a viral vector, such as an adenovirus vector or an adeno-associated virus (AAV) vector. See for example: Ledley 1996, *Pharmaceutical Research* 13:1595-1614 and Verma et al. *Nature* 1997, 387:239-242.

The vector may further include a selectable marker. Suitable selectable markers include a drug resistance marker, such as tetracycline or gentamycin, or a detectable gene marker, such as β-galactosidase or luciferase.

In a preferred embodiment, the isolated DNA or RNA molecule consists of any one of the microRNA sequences or a hairpin precursor sequence shown in SEQ ID NOs:1-187.

In another preferred embodiment, the isolated DNA or RNA molecule consists of any one of the microRNA sequences or a hairpin precursor sequence shown in SEQ ID NOs:281-466.

In a further preferred embodiment, the isolated DNA or RNA molecule consists of any one of the microRNA sequences or a hairpin precursor sequence shown in SEQ ID NOs:467-496.

In yet a further preferred embodiment, the isolated DNA or RNA molecule consists of any one of the microRNA sequences or a hairpin precursor sequence shown in SEQ ID NOs:497-548.

In yet a further preferred embodiment, the isolated DNA or RNA molecule consists of any one of the microRNA sequences or a hairpin precursor sequence shown in SEQ ID NOs:549-550.

In this specification, "isolated" means that the molecule is essentially free of other nucleic acids. Essentially free from other nucleic acids means that the molecule is at least about 90%, preferably at least about 95%, and more preferably at least about 98% free of other nucleic acids.

Preferably, the molecule is essentially pure, which means that the molecules are free not only of other nucleic acids, but also of other materials used in the synthesis and isolation of the molecule. Materials used in synthesis include, for example, enzymes. Materials used in isolation include, for example, gels, such as SDS-PAGE. The molecule is at least about 90% free, preferably at least about 95% free and, more preferably at least about 98% free of such materials.

The sequence of bases in a microRNA or hairpin precursor is highly conserved. Due to the high conservation, the sequence can be from a cell of any mammal. Examples of mammals include pet animals, such as dogs and cats, farm animals, such as cows, horses and sheeps, laboratory animals, such as rats, mice and rabbits, and primates, such as monkeys and humans. Preferably, the mammal is human or mouse.

Modified Single Stranded MicroRNA Molecules

In another embodiment, the invention relates to a modified single stranded microRNA molecule. The modified single stranded microRNA molecule can be any of the microRNA molecules, hairpin precursor molecules, or equivalents thereof described above, except that the modified molecule comprises at least one modified moiety (i.e., at least one moiety is not an unmodified deoxyribonucleotide moiety or an unmodified ribonucleotide moiety). In this embodiment, the modified microRNA molecule comprises a minimum number of ten moieties, preferably a minimum of thirteen, more preferably a minimum of fifteen, even more preferably a minimum of eighteen, and most preferably a minimum of twenty-one moieties.

The modified microRNA molecules preferably comprise a maximum number of fifty moieties, more preferably a maximum of forty, even more preferably a maximum of thirty, most preferably a maximum of twenty-five, and optimally a maximum of twenty-three moieties. A suitable range of minimum and maximum numbers of moieties may be obtained by combining any of the above minima with any of the above maxima.

Each modified moiety comprises a base bonded to a backbone unit. The backbone unit may be any molecular unit that is able to stably bind to a base and to form an oligomeric chain. In this specification, the backbone units of a modified moiety do not include the backbone units commonly found in naturally occurring DNA or RNA molecules.

Such modified microRNA molecules have increased nuclease resistance. Therefore, the nuclease resistance of the molecule is increased compared to a sequence containing only unmodified ribonucleotide moieties, unmodified deoxyribonucleotide moieties or both. Such modified moieties are well known in the art, and were reviewed, for example, by Kurreck, Eur. J. Biochem. 270, 1628-1644 (2003).

The nuclease resisted can be an exonuclease, an endonuclease, or both. The exonuclease can be a 3'→5' exonuclease or a 5'→43' exonuclease. Examples of 3'→5' human exonuclease include PNPT1, Werner syndrome helicase, RRP40, RRP41, RRP42, RRP45, and RRP46. Examples of 5'→' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

A modified moiety can occur at any position in the microRNA molecule. For example, to protect microRNA molecules against 3'→5' exonucleases, the molecules can have at least one modified moiety at the 3' end of the molecule and preferably at least two modified moieties at the 3' end. If it is desirable to protect the molecule against 5'→3' exonuclease, the microRNA molecules can have at least one modified moiety and preferably at least two modified moieties at the 5' end of the molecule. The microRNA molecules can also have at least one and preferably at least two modified moieties between the 5' and 3' end of the molecule to increase resistance of the molecule to endonucleases. Preferably, at least about 10%, more preferably at least about 25%, even more preferably at least about 50%, and further more preferably at least about 75%, and most preferably at least about 95% of the moieties are modified. In one embodiment, all of the moieties are modified (e.g., nuclease resistant).

In one example of a modified microRNA molecule, the molecule comprises at least one modified deoxyribonucleotide moiety. Suitable modified deoxyribonucleotide moieties are known in the art. Such modified deoxyribonucleotide moieties comprise, for example, phosphorothioate deoxyribose groups as the backbone unit. See structure 1 in FIG. 1. A modified microRNA molecule comprising phosphorothioate deoxyribonucleotide moieties is generally referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety, which comprises an N'3-N'5 phosphoroamidate deoxyribose group as the backbone unit. See structure 2 in FIG. 1. An oligonucleotide molecule comprising phosphoroamidate deoxyribonucleotide moieties is generally referred to as phosphoroamidate (NP) DNA. See, for example, Gryaznov et al., J. Am. Chem. Soc. 116, 3143-3144 (1994).

In another example of a modified microRNA molecule, the molecule comprises at least one modified ribonucleotide moiety. A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. See structure 3 in FIG. 1. An oligoribonucleotide molecule comprising ribonucleotide moieties substituted at the 2' position with a $C_1$ to $C_4$ alkyl group is generally referred to as a 2'-O—($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy $C_1$ to $C_4$ alkyl group. The $C_1$ to $C_4$ alkoxy (alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. See structure 4 in FIG. 1. An oligonucleotide molecule comprising more than one ribonucleotide moiety that is substituted at the 2' position with a $C_1$ to $C_4$ alkoxy-$C_1$ to $C_4$ alkyl group is referred to as a 2'-O—($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. See structure 5 in FIG. 1. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Ørum et al., Curr. Opinion Mol. Ther. 3, 239-243 (2001); Koshkin et al., Tetrahedron 54, 3607-3630 (1998); Obika et al., Tetrahedron Lett. 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. Such 2'-fluororibonucleotide moieties are known in the art. Molecules comprising 2'-fluororibonucleotide moieties are generally referred to herein as 2'-fluororibo nucleic acids (FANA). See structure 7 in FIG. 1. Damha et al., J. Am. Chem. Soc. 120, 12976-12977 (1998).

In another example of a modified microRNA molecule, the molecule comprises at least one modified moiety comprising a base bonded to an amino acid residue as the backbone unit. Modified moieties that have at least one base bonded to an amino acid residue will be referred to herein as peptide nucleic acid (PNA) moieties. Such moieties are nuclease resistance, and are known in the art. Molecules having PNA moieties are generally referred to as peptide nucleic acids.

See structure 6 in FIG. 1. Nielson, Methods Enzymol. 313, 156-164 (1999); Elayadi, et al, id.; Braasch et al., Biochemistry 41, 4503-4509 (2002), Nielsen et al., Science 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications*, Horizon Scientific Press, pages 1-19; Nielsen et al., Science 254: 1497-1500.) One example of an amino acid residue of a PNA moiety is N-(2-aminoethyl)-glycine.

Further examples of PNA moieties include cyclohexyl PNA, retro-inverso PNA, phosphone PNA, propionyl PNA and aminoproline PNA moieties. For a description of these PNA moieties, see FIG. 5 of Nielsen et al., *Peptide Nucleic Acids-Protocols and Applications*, Horizon Scientific Press, pages 1-19. FIG. 5 on page 7 of Nielsen et al. is hereby incorporated by reference.

PNA can be chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability.

Peptide nucleic acids are also commercially available from Applied Biosystems (Foster City, Calif., USA).

In another example of a modified microRNA molecule, the molecule comprises at least one morpholino phosphoroamidate nucleotide moiety. Molecules comprising morpholino phosphoroamidate nucleotide moieties are generally referred to as morpholino (MF) nucleic acids. See structure 8 in FIG. 1. Heasman, Dev. Biol. 243, 209-214 (2002). Morpholino oligonucleotides are commercially available from Gene Tools LLC (Corvallis, Oreg., USA).

In a further example of a modified microRNA molecule, the molecule comprises at least one cyclohexene nucleotide moiety. Molecules comprising cyclohexene nucleotide moieties are generally referred to as cyclohexene nucleic acids (CeNA). See structure 10 in FIG. 1. Wang et al., J. Am. Chem. Soc. 122, 8595-8602 (2000), Verbeure et al., Nucleic Acids Res. 29, 4941-4947 (2001).

In a final example of a modified microRNA molecule, the molecule comprises at least one tricyclo nucleotide moiety. Molecules comprising tricyclo nucleotide moieties are generally referred to as tricyclo nucleic acids (tcDNA). See structure 9 in FIG. 1. Steffens et al., J. Am. Chem. Soc. 119, 11548-11549 (1997), Renneberg et al., J. Am. Chem. Soc. 124, 5993-6002 (2002).

The molecule can be a chimeric modified microRNA molecule. Chimeric molecules containing a mixture of any of the moieties mentioned above are also known, and may be made by methods known, in the art. See, for example, references cited above, and Wang et al, Proc. Natl. Acad. Sei. USA 96, 13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

The modified microRNA molecules of the invention comprise at least ten, preferably at least thirteen, more preferably at least fifteen, and even more preferably at least twenty contiguous bases having any of the contiguous base sequences of a naturally occurring microRNA molecule shown in SEQ ID NOs:1-94, SEQ. ID. NOs: 281-374, SEQ. ID NOs:467-481, SEQ. ID. NOs:497-522, or SEQ. ID. NO:549; except that the modified molecule comprises at least one modified moiety. In a preferred embodiment, the modified microRNA molecules comprise the entire sequence of any of the microRNA molecule shown in SEQ ID NOs:1-94, SEQ. ID, NOs: 281-374, SEQ. ID. NOs:467-481, SEQ. ID. NOs:497-522, or SEQ. ID. NO:549.

Any number of additional moieties, up to a maximum of forty moieties, having any base sequence can be added to the moieties comprising the contiguous base sequence, as long as the total number of moieties in the molecule does not exceed fifty. The additional moieties can be added to the 5' end, the 3' end, or to both ends of the contiguous sequence. The additional moieties can include a sequence of bases at the 5' end and/or a sequence of bases at the 3' end present in the hairpin precursor from which the microRNA is present or any fragment thereof. The additional moieties in the molecule, if any, can be any modified or unmodified moiety described above.

The modified microRNA molecules include equivalents thereof. Equivalents include wobble bases and non-complementary bases as described above.

Further, no more than fifty percent, and preferably no more than thirty percent, of the contiguous moieties contain deoxyribonucleotide backbone units. For example, Table C and D show maximum numbers of deoxyribonucleotide backbone units for 19-23 contiguous bases.

In another embodiment, in addition to the wobble base pairs and non-complementary bases described above, the moiety corresponding to position 11 in a naturally occurring microRNA sequence can be an addition, deletion or mismatch.

The modified microRNA molecule is preferably isolated, more preferably purified, as defined above.

TABLE C

Fifty Percent of the Contiguous Moieties containing Deoxyribonucleotide Backbone Units

| No. of Contiguous Bases | 10 | 11 | 12 | 13 | 14 | 15 | 16 | 17 | 18 | 19 | 20 | 21 | 22 | 23 |
|---|---|---|---|---|---|---|---|---|---|---|---|---|---|---|
| Max. No. of Deoxyribonucleotide Backbone Units | 5 | 5 | 6 | 6 | 7 | 7 | 8 | 8 | 9 | 9 | 10 | 10 | 11 | 11 |

TABLE D

Thirty Percent of the Contiguous Moieties Containing Deoxyribonucleotide Backbone Units

| No. of Contiguous Bases | 10 | 11 | 12 | 13 | 14 | 15 | 16 | 17 | 18 | 19 | 20 | 21 | 22 | 23 |
|---|---|---|---|---|---|---|---|---|---|---|---|---|---|---|
| Max. No. of Deoxyribonucleotide Backbone Units | 3 | 3 | 3 | 3 | 4 | 4 | 4 | 5 | 5 | 5 | 6 | 6 | 6 | 6 |

In yet another embodiment, caps can be attached to one end, to both ends, and/or between the ends of the molecule in order to increase resistance to nucleases of the modified microRNA molecules or isolated DNA or RNA molecules of the present invention described above. Increasing resistance to, for example, exonucleases and/or endonucleases is desirable. Any cap known to those in the art for increasing nuclease resistance can be employed.

Examples of such caps include inverted nucleotide caps and chemical caps. Inverted nucleotide caps can be attached at the 5' and/or 3' end. Chemical caps can be attached to one end, both ends, and/or between the ends of the molecule.

An inverted nucleotide cap refers to a 3'→5' sequence of nucleic acids attached to the modified microRNA molecule or DNA or RNA molecules at the 5' and/or the 3' end. There is no limit to the maximum number of nucleotides in the inverted cap just as long as it does not interfere with binding of the microRNA molecule or isolated DNA or RNA molecule to its target mRNA. Any nucleotide can be used in the inverted nucleotide cap. Usually, the nucleotide cap is less than about forty nucleotides in length, preferably less than about thirty nucleotides in length, more preferably less than about twenty nucleotides in length, and even more preferably less than about ten nucleotides in length. Typically, the inverted nucleotide cap is one nucleotide in length. The nucleotide for the inverted cap is generally thymine, but can be any nucleotide such as adenine, guanine, uracil, or cytosine.

A chemical cap refers to any chemical group known to those in the art for increasing nuclease resistance of nucleic acids. Examples of such chemical caps include hydroxyalkyl groups (alkyl hydroxides) or aminoalkyl groups (alkyl amines). Hydroxyalkyl groups are sometimes referred to as alkyl glycoyl groups (e.g., ethylene glycol). Aminoalkyl groups are sometimes referred to as amino linkers.

The alkyl chain in the hydroxyalkyl group or aminoalkyl groups can be a straight chain or branched chain. The minimum number of carbon atoms present in the alkyl chain is one, preferably at least two, and more preferably at least about three carbon atoms.

The maximum number of carbon atoms present in the alkyl chain is about eighteen, preferably about sixteen, and more preferably about twelve. Typical alkyl groups include methyl, ethyl, and propyl. The alkyl groups can be further substituted with one or more hydroxyl and/or amino groups.

Some examples of amino linkers are shown in Table E. The amino linkers listed in Table E are commercially available from TriLink Biotechnologies, San Diego, Calif.

Isolated MicroRNP

In another aspect, the invention provides an isolated microRNP comprising any of the isolated DNA or RNA molecules described above or modified microRNA molecules described above. The isolated DNA or RNA molecules or modified microRNA molecules described above in the microRNP can be bound to a protein.

Examples of such proteins include those proteins belonging to the Ago family. Examples of proteins of the Ago family include Ago 1, 2, 3, and 4. Typically, the Ago 2 protein and microRNA complex guides target mRNA cleavage in RNAi, while Ago 1, 3 and 4 represses translation of target mRNAs.

Anti-MicroRNA Molecules

In another aspect, the invention provides an anti-microRNA molecule. The anti-microRNA molecule may be any of the isolated DNA or RNA molecules described above or modified microRNA molecules described above, except that the sequence of bases of the anti-microRNA molecule is complementary to the sequence of bases in an isolated DNA or RNA molecule or modified microRNA molecule.

Examples of sequences of anti-microRNA molecules are shown in Tables F, F1, F2, F3 and F4.

TABLE E

Amino Linkers from TriLink Biotechnologies

2'-Deoxycytidine-5-C6 Amino Linker (3' Terminus)
2'-Deoxycytidine-5-C6 Amino Linker (5' or Internal)
3' C3 Amino Linker
3' C6 Amino Linker
3' C7 Amino Linker
5' C12 Amino Linker
5' C3 Amino Linker
5' C6 Amino Linker
C7 Internal Amino Linker
Thymidine-5-C2 Amino Linker (5' or Internal)
Thymidine-5-C6 Amino Linker (3' Terminus)
Thymidine-5-C6 Amino Linker (Internal)

TABLE F

Anti-microRNA Sequences for microRNAs in Table A

| MicroRNA | Anti-microRNA Sequence (5' → 3') |
|---|---|
| miR-18b-5p | CUAACUGCACUAGAUGCACCUUA (SEQ. ID. NO: 188) |
| miR-20b-3p | CUGGAAGUGCCCAUACUACAGU (SEQ. ID. NO: 189) |
| miR-20b-5p | CUACCUGCACUAUGAGCACUUUG (SEQ. ID. NO: 190) |
| miR-301b | UGCUUUGACAAUAUCAUUGCACUG (SEQ. ID. NO: 191) |
| miR-329 | AAAGAGGUUAACCAGGUGUGUU (SEQ. ID. NO: 192) |
| miR-374b | CACUUAGCAGGUUGUAUUAUAU (SEQ. ID. NO: 193) |
| miR-421 | CGCCCAAUUAAUGUCUGUUGAU (SEQ. ID. NO: 194) |
| miR-500 | ACCCUAUAAGCAAUAUUGCACUA (SEQ. ID. NO: 195) |
| miR-504 | GCAAUGCAACAGCAAUGCAC (SEQ. ID. NO: 196) |
| miR-604 | UGCUGUUAGCCCUAGCCCCGCA (SEQ. ID. NO: 197) |
| miR-610 | ACGGUCCUACACUCAAGGCAUG (SEQ. ID. NO: 198) |
| miR-618 | ACGCUUUGUCAGUACAUAUAA (SEQ. ID. NO: 199) |
| miR-619 | ACACACCCACGCGAGCCGGAAA (SEQ. ID. NO: 200) |
| miR-620 | CCAACCUGCCCGCUCCCAACAU (SEQ. ID. NO: 201) |
| miR-631 | AAGAGGGAGACCCAGGCUCGGA (SEQ. ID. NO: 202) |
| miR-720a | ACCAGCUAACAAUACACUGCCA (SEQ. ID. NO: 203) |
| miR-720b | GCCAGCUAACAAUACACUGCCU (SEQ. ID. NO: 204) |
| miR-723-3p | CCAGCACCACAUCAGGCCCACG (SEQ. ID. NO: 205) |
| miR-723-5p | UGUGGCCCUGACACGUGGUACU (SEQ. ID. NO: 206) |
| miR-730 | AAGAAGUGCACCGCGAAUGUUU (SEQ. ID. NO: 207) |
| miR-732 | GGGACCGACAGCAGAAUCCUUU (SEQ. ID. NO: 208) |
| miR-734 | ACGGUUUUACCAGACAGUAUUA (SEQ. ID. NO: 209) |
| miR-755 | UCACAUUUGCCUGCAGAGAUUU (SEQ. ID. NO: 210) |
| miR-800a | AAGUGGAUGACCCUGUACGAUU (SEQ. ID. NO: 211) |
| miR-800b | AACUGGAUGUCCCUGUAUGAUU (SEQ. ID. NO: 212) |
| miR-803 | CGAUGUAGUCCAAAGGCACAUA (SEQ. ID. NO: 213) |
| miR-805 | AUAUUAGGAACACAUCGCAAAA (SEQ. ID. NO: 214) |
| miR-806 | ACUCAGUAAUGGUAACGGUUU (SEQ. ID. NO: 215) |
| miR-809 | ACACCGAGGAGCCCAUCAUGAU (SEQ. ID. NO: 216) |
| miR-810 | CUGCAUGACGGCCUGCAAGACA (SEQ. ID. NO: 217) |
| miR-811 | GUCUCAGUUUCCUCUGCAAACA (SEQ. ID. NO: 218) |
| miR-812 | GCGAACUCACCACGGACAACCU (SEQ. ID. NO: 219) |
| miR-814 | GGAGACUCACAAGUUCCUGC (SEQ. ID. NO: 220) |
| miR-815 | GCACAACCCUAGUGGCGCCAUU (SEQ. ID. NO: 221) |
| miR-816 | CACUCAGCGGCCGUUUCCCAA (SEQ. ID. NO: 222) |
| miR-817 | GCUGAGCGGUGAGGGCAUACAG (SEQ. ID. NO: 223) |
| miR-818 | AGGACUAUAGAACUUUCCCCCU (SEQ. ID. NO: 224) |
| miR-819 | AGAGGCAGGGUAGUGUAAUGGA (SEQ. ID. NO: 225) |
| miR-821 | CAGCAGCCUCCGCCGCCGCCGC (SEQ. ID. NO: 226) |
| miR-822 | UAGCAGAAGCAUUCCGCACAC (SEQ. ID. NO: 227) |
| miR-824 | ACACACCAAGGAUAAUUUCUCC (SEQ. ID. NO: 228) |
| miR-825-3p | UUCAGUUAUCAAUCUGUCACAA (SEQ. ID. NO: 229) |
| miR-825-5p | CUCGUGACAUGAUGAUCCCCGA (SEQ. ID. NO: 230) |
| miR-826 | CUCUACUCACAGAAGUGUCAAU (SEQ. ID. NO: 231) |
| miR-828-3p | UUCGACUGCCACUCUUACUAGA (SEQ. ID. NO: 232) |
| miR-828-5p | CCUCUAGUAAAUAUGUCAGCAU (SEQ. ID. NO: 233) |
| miR-829-5p | CUGCACUUUUAUGAAUAAGCUC (SEQ. ID. NO: 234) |
| miR-829-3p | GACUAGCUUAUACAUAAAAUUA (SEQ. ID. NO: 235) |
| miR-831 | GGCCUCCGGAAGCUCCGCCCCA (SEQ. ID. NO: 236) |
| miR-832 | UGACCCACCUGGAGAUCCAUGG (SEQ. ID. NO: 237) |
| miR-834 | CCUGGCACACAGUAGACCUUCA (SEQ. ID. NO: 238) |
| miR-835-5p | UCCAGCCCCUCCAGGGCUUCCU (SEQ. ID. NO: 239) |
| miR-835-3p | AGGUGGAGCCCUGAGAACCGGA (SEQ. ID. NO: 240) |
| miR-837 | UGAGGGGCCUCAGCCUCCUGGU (SEQ. ID. NO: 241) |
| miR-838 | AUCGGGAGGGGACUGAGCCUGA (SEQ. ID. NO: 242) |
| miR-839-5p | UCGGGGCAGCUCAGUACAGGA (SEQ. ID. NO: 243) |
| miR-839-3p | AUCCUGUACUGAGCUGCCCG (SEQ. ID. NO: 244) |
| miR-840-3p | CCACGACCGACGCCACGCCGAG (SEQ. ID. NO: 245) |
| miR-840-5p | AGCCGGUCGAGGUCCGGUCGA (SEQ. ID. NO: 246) |
| miR-841 | GACCAAGAAAUAGCCUUUCAAA (SEQ. ID. NO: 247) |
| miR-842 | GCAAAGGUAAUUGCUGUUUUCG (SEQ. ID. NO: 248) |
| miR-843 | CUAGAAGCUCACAGUCUAGUUG (SEQ. ID. NO: 249) |
| miR-845 | UGCGCCACUGGAGCAUGCUUU (SEQ. ID. NO: 250) |
| miR-846 | GCUCCCCACAGACCCAGAGCCG (SEQ. ID. NO: 251) |
| miR-847 | CCCGCCAUAGUGGUCCUCUCUG (SEQ. ID. NO: 252) |
| miR-848 | CUGGUCCAUAGGGGAUGGCAAU (SEQ. ID. NO: 253) |
| miR-849 | CCAGUGUCUCCAGUAGUAGACA (SEQ. ID. NO: 254) |

TABLE F-continued

Anti-microRNA Sequences for microRNAs in Table A

| MicroRNA | Anti-microRNA Sequence (5' → 3') |
|---|---|
| miR-850 | GGAGAUGGAGCCAGGGCCCUAA (SEQ. ID. NO: 255) |
| miR-851 | CCUCGGGAUGGCGCCCGUUCAC (SEQ. ID. NO: 255) |
| miR-852 | GCACACAAUAAAUGUUUGCUGA (SEQ. ID. NO: 256) |
| miR-853 | AACCAAGACCCCGGAGAUCCCA (SEQ. ID. NO: 257) |
| miR-854 | UCGGUCCCUCGGGCCAGGGCAG (SEQ. ID. NO: 258) |
| miR-855-3p | UGUGGGUGUGUGCAUGAGCGUG (SEQ. ID. NO: 259) |
| miR-855-5p | CACACUCACACACACACACUCA (SEQ. ID. NO: 260) |
| miR-857 | CGGGGAGCGGGGCCCUGCCUU (SEQ. ID. NO: 261) |
| miR-864 | CCCUCUCAACUCAGCUUUU (SEQ. ID. NO: 262) |
| miR-867 | GUCUAGACUGUGAGCUCCUCGA (SEQ. ID. NO: 263) |
| miR-869 | GCACAUGUUCUGCGGCCCACCA (SEQ. ID. NO: 264) |
| miR-871-3p | CAGCACAGAGAUGGACAGAUAG (SEQ. ID. NO: 265) |
| miR-871-5p | CCGCUUGAGCUAACUCCGACCCG (SEQ. ID. NO: 266) |
| miR-92b | GGAGGCCGGGACGAGUGCAAUA (SEQ. ID. NO: 267) |
| miR-896 | GCUGCCGUAUAUGUGAUGUCAC (SEQ. ID. NO: 268) |
| miR-883 | GAGGUUUCCCGUGUAUGUUUCA (SEQ. ID. NO: 269) |
| miR-884 | GAACUUGCUAAAAAUGCAGAAU (SEQ. ID. NO: 270) |
| miR-885 | ACUGAAACCAAGUAUGGGUCGC (SEQ. ID. NO: 271) |
| miR-886 | AGCACAGACUUGCUGUGAUGUU (SEQ. ID. NO: 272) |
| miR-887 | CACCUGAUAAAACUGAGGUAUA (SEQ. ID. NO: 273) |
| miR-888 | ACACAACCUCAGUGUUUCCAGG (SEQ. ID. NO: 274) |
| miR-889 | GAUAGAGUGCAGACCAGGGUCU (SEQ. ID. NO: 275) |
| miR-890 | CCUCAUGGAAGGGUUCCCCACU (SEQ. ID. NO: 276) |
| miR-891 | UCAGUAGAGAUUGUUUCAACAC (SEQ. ID. NO: 277) |
| miR-892 | GGUGAUUCACAAAGAAAUCCAU (SEQ. ID. NO: 278) |
| miR-893 | ACAGCCGCCGCCGCCGCCGCCG (SEQ. ID. NO: 279) |
| miR-894 | UUCCCUUCUUUCCUCCCGUCUU (SEQ. ID. NO: 280) |

TABLE F1

Anti-microRNA sequences for microRNAs in Table A2

| MicroRNA | Anti-microRNA Sequence (5' → 3') |
|---|---|
| hsa-miR-100516 | UGACUGACAGCUUUUUGAGUA (SEQ. ID. NO: 551) |
| hsa-miR-100604 | UGCUGUUAGCCCUAGCCCCGCA (SEQ. ID. NO: 552) |
| hsa-miR-100610-5p | ACGGUCCUACACUCAAGGCAUG (SEQ. ID. NO: 553) |
| hsa-miR-100631 | AAGAGGGAGACCCAGGCUCGGA (SEQ. ID. NO: 554) |
| hsa-miR-100701 | CCUGAACUAACAAGUACCUU (SEQ. ID. NO: 555) |
| hsa-miR-100723 | CCAGCACCACAUCAGGCCCACG (SEQ. ID. NO: 556) |
| hsa-miR-100730 | AAGAAGUGCACCGCGAAUGUUU (SEQ. ID. NO: 557) |
| hsa-miR-100732 | GGGACCGACAGCAGAAUCCUU (SEQ. ID. NO: 558) |
| hsa-miR-100754 | AACCCAAUAUCAAACAUAUCA (SEQ. ID. NO: 559) |
| hsa-miR-100760 | UACACCACUCCCAUCUCAGUGC (SEQ. ID. NO: 560) |
| hsa-miR-100814 | AGGAGACUCACAAGUUCCUGC (SEQ. ID. NO: 561) |
| hsa-miR-100815 | ACACAACCCUAGUGGCGCCAUU (SEQ. ID. NO: 562) |
| hsa-miR-100818 | GGACUAUAGAACUUUCCCCCU (SEQ. ID. NO: 563) |
| hsa-miR-100819 | AGAGGCAGGGUAGUGUAAUGGA (SEQ. ID. NO: 564) |
| hsa-miR-100824 | ACACACCAAGGAUAAUUUCUCC (SEQ. ID. NO: 565) |
| hsa-miR-100825-3p | UUUCAGUUAUCAAUCUGUCACA (SEQ. ID. NO: 566) |
| hsa-miR-100825-5p | UCUCGUGACAUGAUGAUCCCCGA (SEQ. ID. NO: 567) |

TABLE F1-continued

Anti-microRNA sequences for microRNAs in Table A2

| MicroRNA | Anti-microRNA Sequence (5' → 3') |
|---|---|
| hsa-miR-100829-3p | ACUAGCUUAUACAUAAAAUUA (SEQ. ID. NO: 568) |
| hsa-miR-100835-5p | CUCCAGCCCCUCCAGGGCUUCCU (SEQ. ID. NO: 569) |
| hsa-miR-100842 | GCAAAGGUAAUUGCUGUUUUCG (SEQ. ID. NO: 570) |
| hsa-miR-100843-3p | CUAGAAGCUCACAGUCUAGUUG (SEQ. ID. NO: 571) |
| hsa-miR-100843-5p | CCCAGCUAGAUUGUAAGCUCCUU (SEQ. ID. NO: 572) |
| hsa-miR-100846 | CUCCCCACAGACCCAGAGCCG (SEQ. ID. NO: 573) |
| hsa-miR-100851 | CCUCGGGAUGGCGCCCGUUCAC (SEQ. ID. NO: 574) |
| hsa-miR-100852 | GCACACAAUAAAUGUUUGCUGA (SEQ. ID. NO: 575) |
| hsa-miR-100854 | UCGGUCCCUCGGGCCAGGGCAG (SEQ. ID. NO: 576) |
| hsa-miR-100855-3p | UGUGGGUGUGUGCAUGAGCGUG (SEQ. ID. NO: 577) |
| hsa-miR-100855-5p | ACACACUCACACACACACACUCA (SEQ. ID. NO: 578) |
| hsa-miR-100869-3p | AAGGUGAUGGUCAGCAGACAUA (SEQ. ID. NO: 579) |
| hsa-miR-100869-5p | GCACAUGUUCUGCGGCCCACCA (SEQ. ID. NO: 580) |
| hsa-miR-100871-3p | AAGGGUCAGUAAGCACCCGCG (SEQ. ID. NO: 581) |
| hsa-miR-100871-5p | CCGCUUGAGCUAACUCCGACCCG (SEQ. ID. NO: 582) |
| hsa-miR-100885 | CUGAAACCAAGUAUGGGUCGC (SEQ. ID. NO: 583) |
| hsa-miR-100887-3p | ACACAACCUCAGUGUUUCCAGG (SEQ. ID. NO: 584) |
| hsa-miR-100887-5p | CACCUGAUAAAACUGAGGUAUA (SEQ. ID. NO: 585) |
| hsa-miR-100891-3p | UGAAUUACUUUGUAAACCACCA (SEQ. ID. NO: 586) |
| hsa-miR-100891-5p | UGGUGAUUCACAAAGAAAUCCA (SEQ. ID. NO: 587) |
| hsa-miR-101001 | AGGGGCCUCAGCCUCCUGGU (SEQ. ID. NO: 588) |
| hsa-miR-146b | AGCCUAUGGAAUUCAGUUCUCA (SEQ. ID. NO: 589) |
| hsa-miR-147b | UAGCAGAAGCAUUUCCGCACAC (SEQ. ID. NO: 590) |
| hsa-miR-181d | ACCCACCGACAACAAUGAAUGUU (SEQ. ID. NO: 591) |
| hsa-miR-18b | CUAACUGCACUAGAUGCACCUUA (SEQ. ID. NO: 592) |
| hsa-miR-193b | AGCGGGACUUUGAGGGCCAGUU (SEQ. ID. NO: 593) |
| hsa-miR-200001 | UCAGUGGCUCAGGUUCGUUGCA (SEQ. ID. NO: 594) |
| hsa-miR-200002 | AAAGAGGUUAACCAUGUAUUAU (SEQ. ID. NO: 595) |
| hsa-miR-200003 | CAACUGAUGCCUUUCCAAGUA (SEQ. ID. NO: 596) |
| hsa-miR-200004 | UCAAUGACUCAGGUAAGUUGCA (SEQ. ID. NO: 597) |
| hsa-miR-200007 | CCCUGCGCCAUCUCCUCUAC (SEQ. ID. NO: 598) |

TABLE F1-continued

Anti-microRNA sequences for microRNAs in Table A2

| MicroRNA | Anti-microRNA Sequence (5' → 3') |
|---|---|
| hsa-miR-200008 | AACUCCGAUAUGCAAUGGGUA (SEQ. ID. NO: 599) |
| hsa-miR-20b | CUACCUGCACUAUGAGCACUUUG (SEQ. ID. NO: 600) |
| hsa-miR-20b-3p | CUGGAAGUGCCCAUACUACAGU (SEQ. ID. NO: 601) |
| hsa-miR-216b | UCACAUUUGCCUGCAGAGAUUU (SEQ. ID. NO: 602) |
| hsa-miR-301b | UGCUUUGACAAUAUCAUUGCACUG (SEQ. ID. NO: 603) |
| hsa-miR-329 | AAAGAGGUUAACCAGGUGUGUU (SEQ. ID. NO: 604) |
| hsa-miR-33b | GCAAUGCAACAGCAAUGCAC (SEQ. ID. NO: 605) |
| hsa-miR-374b | CACUUAGCAGGUUGUAUUAUAU (SEQ. ID. NO: 606) |
| hsa-miR-375 | UCACGCGAGCCGAACGAACAAA (SEQ. ID. NO: 607) |
| hsa-miR-376a | ACGUGGAUUUUCCUCUAUGAU (SEQ. ID. NO: 608) |
| hsa-miR-376b | AACAUGGAUUUUCCUCUAUGAU (SEQ. ID. NO: 609) |
| hsa-miR-376c | AAGUGGAUGACCCUGUACGAUU (SEQ. ID. NO: 610) |
| hsa-miR-376c | AAGUGGAUGACCCUGUACGAUU (SEQ. ID. NO: 611) |
| hsa-miR-377 | ACAAAAGUUGCCUUUGUGUGAU (SEQ. ID. NO: 612) |
| hsa-miR-378 | CCUUCUGACUCCAAGUCCAGU (SEQ. ID. NO: 613) |
| hsa-miR-379 | CCUACGUUCCAUAGUCUACCA (SEQ. ID. NO: 614) |
| hsa-miR-380 | AAGAUGUGGACCAUAUUACAUA (SEQ. ID. NO: 615) |
| hsa-miR-410 | ACAGGCCAUCUGUGUUAUAUU (SEQ. ID. NO: 616) |
| hsa-miR-421-3p | CGCCCAAUUAAUGUCUGUUGAU (SEQ. ID. NO: 617) |
| hsa-miR-429 | ACGGUUUUACCAGACAGUAUUA (SEQ. ID. NO: 618) |
| hsa-miR-431 | UGCAUGACGGCCUGCAAGACA (SEQ. ID. NO: 619) |
| hsa-miR-432 | CCACCCAAUGACCUACUCCAAGA (SEQ. ID. NO: 620) |
| hsa-miR-433 | ACACCGAGGAGCCCAUCAUGAU (SEQ. ID. NO: 621) |
| hsa-miR-449a | ACCAGCUAACAAUACACUGCCA (SEQ. ID. NO: 622) |
| hsa-nniR-449b | GCCAGCUAACAAUACACUGCCU (SEQ. ID. NO: 623) |
| hsa-miR-450a | AUAUUAGGAACACAUCGCAAAA (SEQ. ID. NO: 624) |
| hsa-miR-451 | AACUCAGUAAUGGUAACGGUUU (SEQ. ID. NO: 625) |
| hsa-miR-452 | UCAGUUUCCUCUGCAAACAGUU (SEQ. ID. NO: 626) |
| hsa-miR-453 | UGCGAACUCACCACGGACAACCU (SEQ. ID. NO: 627) |
| hsa-miR-454 | ACCCUAUAAGCAAUAUUGCACUA (SEQ. ID. NO: 628) |
| hsa-miR-455-5p | CGAUGUAGUCCAAAGGCACAUA (SEQ. ID. NO: 629) |
| hsa-miR-484 | AUCGGGAGGGGACUGAGCCUGA (SEQ. ID. NO: 630) |
| hsa-miR-485-3p | AGAGAGGAGAGCCGUGUAUGAC (SEQ. ID. NO: 631) |
| hsa-miR-485-5p | GAAUUCAUCACGGCCAGCCUCU (SEQ. ID. NO: 632) |
| hsa-mir-486_os | AUCCUGUACUGAGCUGCCCCG (SEQ. ID. NO: 633) |
| hsa-miR-487 | AACUGGAUGUCCCUGUAUGAUU (SEQ. ID. NO: 634) |
| hsa-miR-488 | AGACCAAGAAAUAGCCUUUCAA (SEQ. ID. NO: 635) |
| hsa-miR-490 | ACCCACCUGGAGAUCCAUGG (SEQ. ID. NO: 636) |

TABLE F1-continued

Anti-microRNA sequences for microRNAs in Table A2

| MicroRNA | Anti-microRNA Sequence (5' → 3') |
|---|---|
| hsa-miR-493 | CCUGGCACACAGUAGACCUUCA (SEQ. ID. NO: 637) |
| hsa-miR-497 | ACAAACCACAGUGUGCUGCUG (SEQ. ID. NO: 638) |
| hsa-miR-502 | UGAAUCCUUGCCCAGGUGCAUU (SEQ. ID. NO: 639) |
| hsa-miR-503 | CUGCAGAACUGUUCCCGCUGCUA (SEQ. ID. NO: 640) |
| hsa-miR-505 | AGGAAACCAGCAAGUGUUGACG (SEQ. ID. NO: 641) |
| hsa-miR-509-3p | CUACCCACAGACGUACCAAUCA (SEQ. ID. NO: 642) |
| hsa-miR-514 | UCUACUCACAGAAGUGUCAAU (SEQ. ID. NO: 643) |
| hsa-miR-92b | GAGGCCGGGACGAGUGCAAUA (SEQ. ID. NO: 644) |

TABLE F2

Anti-microRNA sequences for microRNAs in Table A4

| MicroRNA | Anti-microRNA Sequence (5' → 3') |
|---|---|
| hsa-miR-100516 | UGACUGACAGCUUUUUGAGUA (SEQ. ID. NO: 645) |
| hsa-miR-100701 | CCUGAACUAACAAGUAACCUU (SEQ. ID. NO: 646) |
| hsa-miR-100760 | UACACCACUCCCAUCUCAGUGC (SEQ. ID. NO: 647) |
| hsa-miR-100885 | CUGAAACCAAGUAUGGGUCGC (SEQ. ID. NO: 648) |
| hsa-miR-100887-3p | ACACAACCUCAGUGUUUCCAGG (SEQ. ID. NO: 649) |
| hsa-miR-100887-5p | CACCUGAUAAAACUGAGGUAUA (SEQ. ID. NO: 650) |
| hsa-miR-100891-3p | UGAAUUACUUUGUAAACCACCA (SEQ. ID. NO: 651) |
| hsa-miR-100891-5p | UGGUGAUUCACAAAGAAAUCCA (SEQ. ID. NO: 652) |
| hsa-miR-200001 | UCAGUGGCUCAGGUUCGUUGCA (SEQ. ID. NO: 653) |
| hsa-miR-200002 | AAAGAGGUUAACCAUGUAUUAU (SEQ. ID. NO: 654) |
| hsa-miR-200003 | CAACUGAUGCCUUUCCAAGUA (SEQ. ID. NO: 655) |
| hsa-miR-200004 | UCAAUGACUCAGGUAAGUUGCA (SEQ. ID. NO: 656) |
| hsa-miR-200007 | CCCUGCGCCAUCUCCUCUAC (SEQ. ID. NO: 657) |
| hsa-miR-200008 | AACUCCGAUAUGCAAUGGGUA (SEQ. ID. NO: 658) |
| hsa-mir-486_os | UCCUGUACUGAGCUGCCCCG (SEQ. ID. NO: 659) |

TABLE F3

Anti-microRNA sequences for microRNAs in Table A6

| MicroRNA | Anti-microRNA Sequence (5' → 3') |
|---|---|
| hsa-mir-18b-3p | GCCAGAAGGGGCAUUUAGGGCAG (SEQ. ID. NO: 660) |
| hsa-miR-618 | ACGCUUUGUCAGUACAUAUUAA (SEQ. ID. NO: 661) |
| hsa-miR-619 | ACACACCCACGCGAGCCGGAAA (SEQ. ID. NO: 662) |
| hsa-miR-620 | CCAACCUGCCCGCUCCCAACAU (SEQ. ID. NO: 663) |
| hsa-miR-723-5p | UCAUGUGGCCCUGACACGUGGUACU (SEQ. ID. NO: 664) |
| hsa-mir-816 | UCACUCAGCGGCCGUUUCCCAA (SEQ. ID. NO: 665) |
| hsa-mir-817 | GCUGAGCGGUGAGGGCAUACAG (SEQ. ID. NO: 666) |

TABLE F3-continued

Anti-microRNA sequences for microRNAs in Table A6

| MicroRNA | Anti-microRNA Sequence (5' → 3') |
|---|---|
| hsa-mir-821-1 | AGCCUCCGCCGCCGCCGC (SEQ. ID. NO: 667) |
| hsa-mir-821-2/3 | AGCCUCCGCCGCCGCCGC (SEQ. ID. NO: 668) |
| hsa-mir-828-3p | UCGACUGCCACUCUUACUAGA (SEQ. ID. NO: 669) |
| hsa-mir-828-5p | CCUCUAGUAAAUAUGUCAGCAU (SEQ. ID. NO: 670) |
| hsa-mir-831-1 | GGCCUCCGGAAGCUCCGCCCCA (SEQ. ID. NO: 671) |
| hsa-mir-831-2 | GGCCUCCGGAAGCUCCGCCCCA (SEQ. ID. NO: 672) |
| hsa-mir-831-3/-4/-5 | GGCCUCCGGAAGCUCCGCCCCA (SEQ. ID. NO: 673) |
| hsa-mir-840-3p | CCACGACCGACGCCACGCCGAGU (SEQ. ID. NO: 674) |
| hsa-mir-840-5p | GAGCCGGUCGAGGUCCGGUCGA (SEQ. ID. NO: 675) |
| hsa-mir-845-1 | GCGCCACUGGAGCAUGCUUU (SEQ. ID. NO: 676) |
| hsa-mir-845-2 | GCGCCACUGGAGCAUGCUUU (SEQ. ID. NO: 677) |
| hsa-mir-847 | CCCGCCAUAGUGGUCCUCUCUG (SEQ. ID. NO: 678) |
| hsa-mir-848 | CUGGUCCAUAGGGGAUGGCAAU (SEQ. ID. NO: 679) |
| hsa-mir-849 | CCAGUGUCUCCAGUAGUAGACA (SEQ. ID. NO: 680) |
| hsa-mir-850 | GGAGAUGGAGCCAGGGCCCUAA (SEQ. ID. NO: 681) |
| hsa-mir-853 | AACCAAGACCCCGGAGAUCCCA (SEQ. ID. NO: 682) |
| hsa-mir-857 | CCGGGGAGCGGGGCCCUGCCUU (SEQ. ID. NO: 683) |
| hsa-mir-864 | CCUCUCAACUCAGCUUUU (SEQ. ID. NO: 684) |
| hsa-mir-151 | CUAGACUGUGAGCUCCUCGA (SEQ. ID. NO: 685) |

TABLE F4

Anti-microRNA sequences for microRNA in Table A8

| MicroRNA | Anti-microRNA Sequence (5' → 3') |
|---|---|
| hsa-miR-544 | AUUCUGCAUUUUUAGCAAGUUC (SEQ. ID. NO: 686) |

The anti-microRNA molecule can be modified as described above for modified microRNA molecules. In one embodiment, the contiguous moieties in the anti-microRNA molecule are complementary to the corresponding microRNA molecule. The degree of complementarity of the anti-microRNA molecules are subject to the same restrictions described above for modified microRNA molecules, including the restriction relating to wobble base pairs, as well as those relating to additions, deletions and mismatches.

In a preferable embodiment, if the anti-microRNA molecule comprises only unmodified moieties, then the anti-microRNA molecule comprises at least one base, in the at least ten contiguous bases, which is non-complementary to the microRNA and/or comprises a chemical cap.

In another preferable embodiment, if the at least ten contiguous bases in an anti-microRNA molecule is perfectly (i.e., 100%) complementary to a microRNA molecule, then the anti-microRNA molecule contains at least one modified moiety in the at least ten contiguous bases and/or comprises a chemical cap.

In yet another embodiment, the moiety in the anti-microRNA molecule at the position corresponding to position 11 of a naturally occurring microRNA is non-complementary. The moiety in the anti-microRNA molecule corresponding to position 11 of a naturally occurring microRNA can be rendered non-complementary by the introduction of an addition, deletion or mismatch, as described above.

Utility

The microRNA molecules and anti-microRNA molecules of the present invention have numerous in vitro, ex vivo, and in vivo applications.

For example, the microRNA molecules and/or anti-microRNA molecules of the present invention can be introduced into a cell to study the function of the microRNA, and microRNA molecules in general.

In one embodiment, a microRNA in a cell is inhibited with a suitable anti-microRNA molecule. Alternatively, the activity of a microRNA molecule in a cell can be enhanced by introducing into the cell one or more additional microRNA molecules. The function of the microRNA can be inferred by observing changes associated with inhibition and/or enhanced activity of the microRNA in the cell.

In one aspect of the invention, the invention relates to a method for inhibiting microRNP activity in a cell. The method for inhibiting microRNP activity in a cell comprises introducing into the cell a single-stranded anti-microRNA molecule of the invention. The microRNP comprises a microRNA molecule. Any anti-microRNA molecule can be used in the method for inhibiting microRNP activity in a cell, as long as the anti-microRNA molecule is complementary, subject to the restrictions described above, to the microRNA present in the microRNP.

The anti-microRNA molecules of the present invention are capable of inhibiting microRNP activity by binding to the microRNA in the microRNP in a host cell. MicroRNP activity refers to the cleavage or the repression of translation of a target sequence. The target sequence may be any sequence which is partially or perfectly complementary to the sequence of bases in a microRNA.

For example, the microRNA molecules and anti-microRNA molecules of the present invention may be used as a modulator of the expression of genes which are at least partially complementary to the anti-microRNA molecules or microRNA. For instance, if a particular microRNA is beneficial for the survival of a cell, an appropriate isolated microRNA of the present invention may be introduced into the cell to promote survival. Alternatively, if a particular microRNA is harmful (e.g., induces apoptosis, induces cancer, etc.), an appropriate anti-microRNA molecule can be introduced into the cell in order to inhibit the activity of the microRNA and reduce the harm.

The microRNA molecules and/or anti-microRNA molecules can be introduced into a cell by any method known to those skilled in the art. For example, the microRNA molecules and/or anti-microRNA molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule or an anti-microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In *Antisense Technology in the Central Nervous System* (Leslie, R. A., Hunter, A. J. & Robertson, H. A., eds), pp. 147-157, Oxford University Press.

Targeting of a microRNA molecule or an anti-microRNA molecule to a particular cell can be performed by any method known to those skilled in the art. For example, the microRNA molecule or anti-microRNA molecule can be conjugated to an antibody or ligand specifically recognized by receptors on the cell.

The molecules can be administered to a mammal by any method known to those skilled in the art. Some examples of suitable modes of administration include oral and systemic administration. Systemic administration can be enteral or parenteral. Liquid or solid (e.g., tablets, gelatin capsules) formulations can be employed.

Parenteral administration of the molecules include, for example intravenous, intramuscular, and subcutaneous injections. For instance, a molecule may be administered to a mammal by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a molecule of the present invention can be accomplished by a nebulizer or liquid mist.

The molecules of the present invention can be in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical carrier may also comprise one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the molecules.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the molecules of the present invention in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The pharmaceutical carrier may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the molecules may be stored under nitrogen gas in vials sealed with impermeable stoppers.

Another in vitro application of the microRNA molecules and/or anti-microRNA molecules of the present invention is their use as diagnostic tools. For this purpose, the microRNA molecules and/or anti-microRNA molecules can be labeled.

The molecules of the present invention can be labeled in accordance with any method known in the art. For example, methods for labeling oligonucleotides have been described, for example, by Leary et al., 1983. *Proc. Natl. Acad. Sci. USA* 80:4045; Renz and Kurz 1984. *Nucl. Acids Res.* 12:3435; Richardson and Gumport 1983. *Nucl. Acids Res.* 11:6167;

Smith et al. 1985. *Nucl. Acids Res.* 13:2399; Meinkoth and Wahl, Anal. 1984. *Biochem.* 138:267; and Ausubel, F. M. et al. (Eds.) Current Protocols in Molecular Biology, John Wiley & Sons, Inc., New York, 1999, each of which is incorporated herein by reference.

The label may be radioactive. Some examples of useful radioactive labels include $^{32}P$, $^{125}I$, $^{131}I$, $^{35}S$, $^{14}C$, and $^{3}H$. Use of radioactive labels have been described in U.K. 2,034,323, U.S. Pat. No. 4,358,535, and U.S. Pat. No. 4,302,204.

Some examples of non-radioactive labels include enzymes and chromophores. Useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, in Ausubel, F. M. et al. (Eds.), Rotman 1961. *Proc. Natl. Acad, Sci, USA* 47:1981-1991, and by Current Protocols in Molecular Biology, John Wiley & Sons, Inc., New York (1999).

Useful chromophores include, for example, fluorescent, chemiluminescent, and bioluminescent molecules, as well as dyes. Some specific chromophores useful in the present invention include, for example, fluorescein, rhodamine, Cy3, Cy5, Texas red, phycoerythrin, umbelliferone, luminol.

The labels may be conjugated to the molecules of the present invention by methods that are well known in the art. The labels may be directly attached through a functional group on the molecule. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the molecules by means of coupling agents, such as dialdehydes, carbodiimides, dimaleimides, and the like. The label may also be conjugated to the molecule by means of a ligand attached to the molecule by a method described above and a receptor for that ligand attached to the label. Any of the known ligand-receptor combinations is suitable. Some suitable ligand-receptor pairs include, for example, biotin-avidin or -streptavidin, and antibody-antigen. The biotin-avidin combination is preferred.

Some microRNAs are expressed in specific tissues or cells. The expression of the microRNAs of the present invention in various tissues is shown below in Table G and Table G1. Table G and Table G1 show the relative cloning frequency in percent relative to total number of identified microRNAs for each given library. In Table G and Table G1, the expression of a given microRNA continues across several pages.

The expression of a microRNA is considered to be specifically enriched in a tissue- or cell type if its expression is more than about three-fold, preferably more than about four-fold, and more preferably more than about five-fold more than its expression in other tissue- or cell-types. For example, microRNA hsa-mir-20b is expressed in the B-cell derived lymphoma BL41 (0.05% expression); in the embryonal derived cell line/tumor NT2/D 1 (0.37% expression) NCCIT (0.72% expression), and Hek (0.13% expression); small cell adreno-carcinoma cell line SW13 (without and with yellow fever virus infection; 2.01% and 2.93% expression, respectively); and ductile breast carcinoma HCC38 (0.09% expression). The expression of microRNA hsa-mir-20b is considered to be enriched in small cell adreno-carcinoma cell line SW13 since its expression is about three-fold more than that of its expression in other tissue- and cell-types.

Thus, for instance, anti-microRNA molecules of the present invention can be used as a probe to identify a particular tissue- or cell type.

In addition, the microRNA molecules and/or anti-microRNA molecules of the present invention can be used in microarrays for microRNA expression analysis. For example, the anti-microRNA molecules of the present invention can be labeled in a microarray. Samples containing microRNAs can be added and the hybridization detected. Such microarrays may be used in, for example, diagnostic assays to survey microRNA expression in clinical samples of cancer patients and contribute to the diagnosis and staging for risk evaluation for certain cancer types.

TABLE G

Relative Cloning Frequency in % Relative to Total Number of Identified MicroRNA for Each Given Library.

| miRNA | Adult brain | | |
| --- | --- | --- | --- |
| | cerebellum | frontalcortex | midbrain |
| hsa-mir-20b | — | — | — |
| hsa-mir-301b | — | — | — |
| hsa-mir-302b | — | — | — |
| hsa-mir-302c | — | — | — |
| hsa-mir-302d | — | — | — |
| hsa-mir-329 | — | — | 0.07 |
| hsa-mir-367 | — | — | — |
| hsa-mir-368 | 0.13 | 0.26 | — |
| hsa-mir-369 | — | — | — |
| hsa-mir-374a | — | 0.07 | 0.07 |
| hsa-mir-374b | — | — | 0.07 |
| hsa-mir-410 | — | — | 0.07 |
| hsa-mir-421 | — | — | — |
| hsa-mir-423 | — | — | 0.07 |
| hsa-mir-425 | — | 0.20 | 0.40 |
| hsa-mir-500 | 0.13 | — | 0.07 |
| hsa-mir-502 | — | — | — |
| hsa-mir-504 | — | — | — |
| hsa-mir-519 | — | — | — |
| hsa-mir-604 | 0.13 | 0.26 | 0.61 |
| hsa-mir-610 | — | — | — |
| hsa-mir-615 | — | — | — |
| hsa-mir-618 | — | — | — |

TABLE G-continued

Relative Cloning Frequency in % Relative to Total Number of Identified MicroRNA for Each Given Library.

| miRNA | | | |
|---|---|---|---|
| hsa-mir-619 | — | — | — |
| hsa-mir-620 | — | — | — |
| hsa-mir-631 | — | — | — |
| hsa-mir-720a | — | — | — |
| hsa-mir-720b | — | — | — |
| hsa-mir-800a | — | 0.07 | 0.07 |
| hsa-mir-800b | — | — | 0.07 |
| hsa-mir-803 | — | — | — |
| hsa-mir-805 | — | — | — |
| hsa-mir-451 | 0.13 | 0.53 | 0.88 |
| hsa-mir-433 | — | — | 0.07 |
| hsa-mir-431 | — | 0.13 | — |
| hsa-mir-452 | — | — | — |
| hsa-mir-453 | — | — | — |
| hsa-mir-813 | — | — | 0.07 |
| hsa-mir-814 | — | — | — |
| hsa-mir-815 | — | 0.07 | 0.13 |
| hsa-mir-816 | — | — | — |
| hsa-mir-817 | — | — | — |
| hsa-mir-818 | — | — | — |
| hsa-mir-819 | 0.13 | 0.20 | — |
| hsa-mir-821 | — | — | — |
| hsa-mir-822 | — | — | — |
| hsa-mir-823 | 0.13 | — | — |
| hsa-mir-824 | — | 0.07 | 0.07 |
| hsa-mir-825 | — | — | — |
| hsa-mir-826 | — | — | — |
| hsa-mir-827 | — | — | — |
| hsa-mir-828 | — | 0.13 | 0.07 |
| hsa-mir-829 | — | — | — |
| hsa-mir-831 | — | — | — |
| hsa-mir-832 | — | — | — |
| hsa-mir-834 | — | — | — |
| hsa-mir-835 | — | — | — |
| hsa-mir-837 | — | — | — |
| hsa-mir-838 | — | — | — |
| hsa-mir-839 | — | — | 0.07 |
| hsa-mir-841 | 0.51 | — | — |
| hsa-mir-842 | — | — | — |
| hsa-mir-843 | — | 0.07 | — |
| hsa-mir-845 | — | — | — |
| hsa-mir-846 | — | — | 0.07 |
| hsa-mir-847 | — | — | — |
| hsa-mir-848 | — | — | — |
| hsa-mir-849 | — | — | — |
| hsa-mir-850 | 0.13 | — | — |
| hsa-mir-851 | — | — | — |
| hsa-mir-852 | — | — | — |
| hsa-mir-853 | — | — | — |
| hsa-mir-854 | 0.26 | — | — |
| hsa-mir-855 | — | 0.13 | — |
| hsa-mir-857 | — | — | — |
| hsa-mir-864 | — | — | — |
| hsa-mir-867 | — | — | 0.07 |
| hsa-mir-869 | — | — | 0.07 |
| hsa-mir-871 | — | — | — |
| hsa-mir-883 | — | — | — |
| hsa-mir-884 | — | — | — |
| hsa-mir-885 | — | — | — |
| hsa-mir-886 | — | — | — |
| hsa-mir-887 | — | — | — |
| hsa-mir-888 | — | — | — |
| hsa-mir-889 | — | — | — |
| hsa-mir-890 | — | — | — |
| hsa-mir-891 | — | — | — |
| hsa-mir-892 | — | — | — |
| hsa-mir-893 | — | — | — |
| hsa-mir-894 | — | — | — |
| hsa-mir-92b | — | 0.07 | 0.07 |

| | | Neuroblastoma | | |
|---|---|---|---|---|
| miRNA | Medulloblastoma DAOY | BE(2)-M17 | SH-SY5Y | SH-SY5Y_retinoic acid |
| hsa-mir-20b | — | — | — | — |
| hsa-mir-301b | — | 0.62 | 0.32 | 0.74 |

TABLE G-continued

Relative Cloning Frequency in % Relative to Total Number of Identified MicroRNA for Each Given Library.

| | | | | |
|---|---|---|---|---|
| hsa-mir-302b | — | — | — | — |
| hsa-mir-302c | — | — | — | — |
| hsa-mir-302d | — | — | — | — |
| hsa-mir-329 | — | — | — | — |
| hsa-mir-367 | — | — | — | — |
| hsa-mir-368 | 0.90 | 0.31 | 0.16 | — |
| hsa-mir-369 | — | — | — | — |
| hsa-mir-374a | — | — | 0.08 | 0.54 |
| hsa-mir-374b | — | — | 0.89 | — |
| hsa-mir-410 | — | 0.31 | — | — |
| hsa-mir-421 | — | — | — | — |
| hsa-mir-423 | 0.90 | — | 1.13 | 0.40 |
| hsa-mir-425 | 0.23 | 0.16 | 0.81 | 2.02 |
| hsa-mir-500 | — | 0.16 | — | — |
| hsa-mir-502 | 0.23 | 0.93 | — | — |
| hsa-mir-504 | — | — | — | — |
| hsa-mir-519 | — | — | — | — |
| hsa-mir-604 | — | — | 1.62 | 0.94 |
| hsa-mir-610 | — | — | — | — |
| hsa-mir-615 | 0.11 | — | — | — |
| hsa-mir-618 | — | — | — | — |
| hsa-mir-619 | — | — | — | — |
| hsa-mir-620 | — | — | — | — |
| hsa-mir-631 | — | — | — | — |
| hsa-mir-720a | — | — | — | — |
| hsa-mir-720b | — | — | — | — |
| hsa-mir-800a | — | — | — | — |
| hsa-mir-800b | — | 0.31 | — | — |
| hsa-mir-803 | — | — | — | — |
| hsa-mir-805 | — | 0.16 | — | — |
| hsa-mir-451 | — | — | — | — |
| hsa-mir-433 | — | — | — | — |
| hsa-mir-431 | — | 0.47 | — | — |
| hsa-mir-452 | — | — | — | — |
| hsa-mir-453 | — | 0.16 | — | — |
| hsa-mir-813 | 0.23 | 0.16 | — | — |
| hsa-mir-814 | — | 0.31 | 0.32 | 0.67 |
| hsa-mir-815 | — | — | 0.48 | 0.40 |
| hsa-mir-816 | — | — | — | — |
| hsa-mir-817 | — | — | — | 0.13 |
| hsa-mir-818 | — | — | — | — |
| hsa-mir-819 | — | — | — | — |
| hsa-mir-821 | — | — | — | — |
| hsa-mir-822 | 0.23 | — | — | — |
| hsa-mir-823 | — | — | — | — |
| hsa-mir-824 | — | — | — | — |
| hsa-mir-825 | — | — | — | — |
| hsa-mir-826 | — | — | — | — |
| hsa-mir-827 | — | — | — | — |
| hsa-mir-828 | — | — | — | — |
| hsa-mir-829 | — | — | — | — |
| hsa-mir-831 | — | — | — | — |
| hsa-mir-832 | — | 0.62 | 0.32 | 0.40 |
| hsa-mir-834 | — | 0.93 | — | — |
| hsa-mir-835 | — | — | 0.32 | — |
| hsa-mir-837 | — | 0.16 | — | — |
| hsa-mir-838 | — | — | — | — |
| hsa-mir-839 | — | — | — | — |
| hsa-mir-841 | — | — | 0.65 | 0.40 |
| hsa-mir-842 | — | 0.16 | 0.16 | — |
| hsa-mir-843 | 0.45 | 0.93 | 2.10 | 2.02 |
| hsa-mir-845 | 0.23 | — | 0.32 | — |
| hsa-mir-846 | — | — | — | 0.13 |
| hsa-mir-847 | — | — | — | — |
| hsa-mir-848 | — | — | — | — |
| hsa-mir-849 | — | — | — | — |
| hsa-mir-850 | — | — | — | — |
| hsa-mir-851 | — | — | — | 0.13 |
| hsa-mir-852 | — | — | — | — |
| hsa-mir-853 | — | — | 0.32 | 0.13 |
| hsa-mir-854 | — | 0.16 | — | — |
| hsa-mir-855 | — | — | — | — |
| hsa-mir-857 | — | — | 0.32 | 0.27 |
| hsa-mir-864 | — | — | — | — |
| hsa-mir-867 | — | — | — | — |
| hsa-mir-869 | — | 0.16 | — | — |
| hsa-mir-871 | 0.23 | — | — | — |

TABLE G-continued

Relative Cloning Frequency in % Relative to Total Number of Identified MicroRNA for Each Given Library.

| | | | | | |
|---|---|---|---|---|---|
| hsa-mir-883 | — | — | — | — | — |
| hsa-mir-884 | — | 0.16 | — | — | — |
| hsa-mir-885 | — | — | — | — | — |
| hsa-mir-886 | — | — | — | — | — |
| hsa-mir-887 | — | — | — | — | — |
| hsa-mir-888 | — | — | — | — | — |
| hsa-mir-889 | — | — | — | — | — |
| hsa-mir-890 | — | — | — | — | — |
| hsa-mir-891 | — | — | — | — | 0.13 |
| hsa-mir-892 | — | — | — | — | — |
| hsa-mir-893 | — | — | — | — | — |
| hsa-mir-894 | — | — | — | — | — |
| hsa-mir-92b | — | — | — | — | — |

| | Skin | Liver | Hepatocellular carcinoma | | Hepatoblastoma |
|---|---|---|---|---|---|
| miRNA | fibroblasts_CMV | liver | Huh7.5 | Huh7.5_HCV | PLC |
| hsa-mir-20b | — | — | — | — | — |
| hsa-mir-301b | — | — | — | — | — |
| hsa-mir-302b | — | — | — | — | — |
| hsa-mir-302c | — | — | — | — | — |
| hsa-mir-302d | — | — | — | — | — |
| hsa-mir-329 | — | — | — | — | — |
| hsa-mir-367 | — | — | — | — | — |
| hsa-mir-368 | 0.60 | — | — | — | — |
| hsa-mir-369 | 0.40 | — | — | — | — |
| hsa-mir-374a | 0.40 | — | 0.52 | 3.33 | 0.94 |
| hsa-mir-374b | — | — | — | — | 1.96 |
| hsa-mir-410 | — | — | — | — | — |
| hsa-mir-421 | — | — | 0.26 | — | 0.29 |
| hsa-mir-423 | — | — | 0.26 | — | 0.22 |
| hsa-mir-425 | — | 0.07 | — | — | 1.81 |
| hsa-mir-500 | 0.20 | — | — | — | 0.07 |
| hsa-mir-502 | 0.20 | 0.07 | — | — | — |
| hsa-mir-504 | — | — | — | — | 0.44 |
| hsa-mir-519 | 0.20 | 0.07 | — | — | — |
| hsa-mir-604 | 0.60 | — | 0.52 | — | 0.22 |
| hsa-mir-610 | 0.20 | — | — | 1.67 | — |
| hsa-mir-615 | — | — | — | — | — |
| hsa-mir-618 | — | — | — | — | — |
| hsa-mir-619 | — | — | — | — | — |
| hsa-mir-620 | — | — | — | — | — |
| hsa-mir-631 | — | — | — | — | — |
| hsa-mir-720a | — | — | — | — | — |
| hsa-mir-720b | — | — | — | — | — |
| hsa-mir-800a | — | — | — | — | — |
| hsa-mir-800b | — | — | — | — | — |
| hsa-mir-803 | — | — | — | — | — |
| hsa-mir-805 | — | — | — | — | 0.07 |
| hsa-mir-451 | — | 0.50 | — | — | — |
| hsa-mir-433 | — | — | — | — | — |
| hsa-mir-431 | — | — | — | — | — |
| hsa-mir-452 | — | — | — | — | — |
| hsa-mir-453 | — | — | — | — | — |
| hsa-mir-813 | 0.20 | — | — | — | — |
| hsa-mir-814 | — | — | — | — | — |
| hsa-mir-815 | — | — | — | — | — |
| hsa-mir-816 | — | — | — | — | 0.07 |
| hsa-mir-817 | — | 0.07 | — | — | — |
| hsa-mir-818 | — | — | — | — | — |
| hsa-mir-819 | — | 0.07 | — | — | — |
| hsa-mir-821 | — | — | — | — | — |
| hsa-mir-822 | 0.40 | — | — | — | — |
| hsa-mir-823 | — | 0.07 | — | — | 0.07 |
| hsa-mir-824 | — | — | — | — | — |
| hsa-mir-825 | — | — | — | — | 0.07 |
| hsa-mir-826 | — | — | — | — | — |
| hsa-mir-827 | — | — | — | — | — |
| hsa-mir-828 | — | — | — | — | — |
| hsa-mir-829 | — | — | — | — | — |
| hsa-mir-831 | — | — | — | — | — |
| hsa-mir-832 | — | — | — | — | — |
| hsa-mir-834 | 0.20 | — | — | — | — |
| hsa-mir-835 | — | — | — | — | — |
| hsa-mir-837 | — | — | — | — | — |
| hsa-mir-838 | — | — | — | — | — |

TABLE G-continued

Relative Cloning Frequency in % Relative to Total Number of Identified MicroRNA for Each Given Library.

| | | | | | |
|---|---|---|---|---|---|
| hsa-mir-839 | — | 0.07 | — | — | — |
| hsa-mir-841 | — | — | — | — | — |
| hsa-mir-842 | — | — | — | — | — |
| hsa-mir-843 | 0.20 | — | — | — | — |
| hsa-mir-845 | — | — | — | — | — |
| hsa-mir-846 | — | — | — | — | — |
| hsa-mir-847 | — | — | — | — | — |
| hsa-mir-848 | 0.40 | — | — | — | — |
| hsa-mir-849 | — | — | — | — | — |
| hsa-mir-850 | 0.20 | — | — | — | — |
| hsa-mir-851 | — | — | — | — | — |
| hsa-mir-852 | — | — | — | — | 0.29 |
| hsa-mir-853 | — | — | — | — | 0.07 |
| hsa-mir-854 | — | 0.07 | — | — | — |
| hsa-mir-855 | — | — | 0.26 | — | — |
| hsa-mir-857 | — | — | — | — | — |
| hsa-mir-864 | — | — | — | — | — |
| hsa-mir-867 | — | — | 0.13 | — | — |
| hsa-mir-869 | — | — | — | — | — |
| hsa-mir-871 | 0.40 | — | 0.26 | — | — |
| hsa-mir-883 | — | — | — | — | — |
| hsa-mir-884 | — | — | — | — | — |
| hsa-mir-885 | — | — | — | — | — |
| hsa-mir-886 | — | — | — | — | — |
| hsa-mir-887 | — | — | — | — | — |
| hsa-mir-888 | — | — | — | — | — |
| hsa-mir-889 | — | — | — | — | — |
| hsa-mir-890 | — | — | — | — | — |
| hsa-mir-891 | — | — | — | — | — |
| hsa-mir-892 | 0.20 | — | — | — | — |
| hsa-mir-893 | — | — | — | — | — |
| hsa-mir-894 | — | — | — | — | — |
| hsa-mir-92b | — | — | — | — | 0.04 |

| | Activated B-cells | B-cell derived lymphomas | | | | |
|---|---|---|---|---|---|---|
| miRNA | primary B cells | BL41 | BL41/95 | LY3 | U266 | BCBL1 |
| hsa-mir-20b | — | 0.05 | — | — | — | — |
| hsa-mir-301b | — | 0.20 | — | — | — | 0.73 |
| hsa-mir-302b | — | — | — | — | — | — |
| hsa-mir-302c | — | — | — | — | — | — |
| hsa-mir-302d | — | — | — | — | — | — |
| hsa-mir-329 | — | — | — | — | — | — |
| hsa-mir-367 | — | — | — | — | — | — |
| hsa-mir-368 | — | — | — | — | — | — |
| hsa-mir-369 | — | — | — | — | — | — |
| hsa-mir-374a | — | 0.10 | — | — | — | 0.25 |
| hsa-mir-374b | — | 0.10 | — | — | 0.41 | 0.25 |
| hsa-mir-410 | — | — | — | — | — | — |
| hsa-mir-421 | — | — | — | — | — | 0.25 |
| hsa-mir-423 | — | 0.29 | — | — | — | — |
| hsa-mir-425 | 2.50 | 0.10 | 0.29 | 0.99 | 0.82 | 0.48 |
| hsa-mir-500 | — | 0.49 | 0.15 | — | 0.41 | — |
| hsa-mir-502 | — | — | — | — | — | — |
| hsa-mir-504 | — | — | — | — | — | 0.49 |
| hsa-mir-519 | — | — | 0.15 | — | — | — |
| hsa-mir-604 | — | — | — | — | — | — |
| hsa-mir-610 | — | 0.10 | — | — | — | — |
| hsa-mir-615 | — | — | — | — | — | — |
| hsa-mir-618 | — | — | — | — | — | — |
| hsa-mir-619 | — | — | — | — | — | — |
| hsa-mir-620 | — | — | — | — | — | — |
| hsa-mir-631 | — | — | — | — | — | — |
| hsa-mir-720a | — | — | — | — | — | 0.25 |
| hsa-mir-720b | — | — | — | — | — | — |
| hsa-mir-800a | — | — | — | — | — | — |
| hsa-mir-800b | — | — | — | — | — | — |
| hsa-mir-803 | — | — | — | — | — | — |
| hsa-mir-805 | — | — | — | — | — | — |
| hsa-mir-451 | — | — | — | — | — | — |
| hsa-mir-433 | — | — | — | — | — | — |
| hsa-mir-431 | — | — | — | — | — | — |
| hsa-mir-452 | — | — | — | — | — | — |
| hsa-mir-453 | — | — | — | — | — | — |
| hsa-mir-813 | — | — | — | — | — | — |
| hsa-mir-814 | — | — | — | — | — | — |

TABLE G-continued

Relative Cloning Frequency in % Relative to Total Number of Identified MicroRNA for Each Given Library.

| miRNA | | | | | | |
|---|---|---|---|---|---|---|
| hsa-mir-815 | — | 0.10 | — | — | — | — |
| hsa-mir-816 | — | — | — | — | — | — |
| hsa-mir-817 | — | — | — | — | — | — |
| hsa-mir-818 | — | 0.20 | — | — | — | — |
| hsa-mir-819 | — | — | — | — | — | — |
| hsa-mir-821 | — | — | 0.29 | — | — | — |
| hsa-mir-822 | — | — | — | — | — | — |
| hsa-mir-823 | — | — | — | — | — | 0.25 |
| hsa-mir-824 | — | — | — | — | — | — |
| hsa-mir-825 | — | — | — | — | — | — |
| hsa-mir-826 | — | — | — | — | — | — |
| hsa-mir-827 | — | — | — | — | — | — |
| hsa-mir-828 | — | — | — | — | — | — |
| hsa-mir-829 | — | — | — | 0.50 | — | — |
| hsa-mir-831 | — | — | — | — | — | — |
| hsa-mir-832 | — | — | — | — | — | — |
| hsa-mir-834 | — | — | — | — | — | — |
| hsa-mir-835 | — | — | — | — | — | — |
| hsa-mir-837 | — | — | — | — | — | — |
| hsa-mir-838 | — | — | 0.15 | — | — | — |
| hsa-mir-839 | — | — | — | — | — | — |
| hsa-mir-841 | — | — | — | — | — | — |
| hsa-mir-842 | — | — | — | — | — | — |
| hsa-mir-843 | — | — | — | — | — | — |
| hsa-mir-845 | — | — | — | — | — | — |
| hsa-mir-846 | — | — | — | — | — | — |
| hsa-mir-847 | — | — | — | — | — | — |
| hsa-mir-848 | — | — | — | — | — | — |
| hsa-mir-849 | — | — | — | — | — | — |
| hsa-mir-850 | — | — | — | — | — | — |
| hsa-mir-851 | — | — | — | — | — | — |
| hsa-mir-852 | — | — | — | — | — | — |
| hsa-mir-853 | — | — | — | — | — | — |
| hsa-mir-854 | — | — | — | — | — | — |
| hsa-mir-855 | — | — | — | — | — | — |
| hsa-mir-857 | — | — | — | — | — | — |
| hsa-mir-864 | — | — | — | — | — | — |
| hsa-mir-867 | — | — | — | — | — | — |
| hsa-mir-869 | — | — | — | — | — | — |
| hsa-mir-871 | — | — | — | — | — | 1.45 |
| hsa-mir-883 | — | — | — | — | — | — |
| hsa-mir-884 | — | — | — | — | — | — |
| hsa-mir-885 | — | — | — | — | — | — |
| hsa-mir-886 | — | — | — | — | — | — |
| hsa-mir-887 | — | — | — | — | — | — |
| hsa-mir-888 | — | — | — | — | — | — |
| hsa-mir-889 | — | — | — | — | 0.41 | — |
| hsa-mir-890 | — | — | — | — | — | — |
| hsa-mir-891 | — | — | — | — | — | — |
| hsa-mir-892 | — | — | — | — | — | — |
| hsa-mir-893 | — | — | — | — | — | — |
| hsa-mir-894 | — | — | — | — | — | — |
| hsa-mir-92b | — | — | — | 0.50 | — | 0.49 |

| | Spleen | Endocrine organs | | | | |
|---|---|---|---|---|---|---|
| miRNA | spleen | pituitary | SW13 | SW13-YFV | ovary | testis |
| hsa-mir-20b | — | — | 2.01 | 2.93 | — | — |
| hsa-mir-301b | — | — | 0.13 | 0.61 | — | — |
| hsa-mir-302b | — | — | — | — | — | — |
| hsa-mir-302c | — | — | — | — | — | — |
| hsa-mir-302d | — | — | — | — | — | — |
| hsa-mir-329 | — | 0.06 | — | — | — | — |
| hsa-mir-367 | — | — | — | — | — | — |
| hsa-mir-368 | 0.18 | 0.62 | — | — | 0.30 | 0.30 |
| hsa-mir-369 | — | 0.12 | — | — | — | — |
| hsa-mir-374a | — | 0.12 | 0.07 | — | 0.08 | — |
| hsa-mir-374b | — | 0.06 | 0.20 | — | 0.08 | — |
| hsa-mir-410 | — | 0.43 | — | — | — | — |
| hsa-mir-421 | — | — | — | — | — | — |
| hsa-mir-423 | 0.92 | — | — | 0.24 | 0.38 | 0.07 |
| hsa-mir-425 | 0.18 | 0.06 | 0.40 | 0.61 | 0.08 | 0.15 |
| hsa-mir-500 | — | 0.06 | — | 0.24 | — | — |
| hsa-mir-502 | — | 0.06 | — | 0.12 | — | 0.74 |
| hsa-mir-504 | — | — | 0.13 | 0.12 | — | — |
| hsa-mir-519 | 0.18 | — | — | — | 0.15 | — |

TABLE G-continued

Relative Cloning Frequency in % Relative to Total Number of Identified MicroRNA for Each Given Library.

| | | | | | | |
|---|---|---|---|---|---|---|
| hsa-mir-604 | 0.18 | 0.06 | — | — | 0.23 | 0.15 |
| hsa-mir-610 | — | — | 0.13 | 0.12 | 0.15 | 0.07 |
| hsa-mir-615 | — | — | — | 0.24 | — | — |
| hsa-mir-618 | — | — | — | 0.24 | — | — |
| hsa-mir-619 | — | 0.06 | — | 0.24 | — | — |
| hsa-mir-620 | — | — | — | — | — | — |
| hsa-mir-631 | — | — | — | — | — | — |
| hsa-mir-720a | — | — | — | — | — | 0.30 |
| hsa-mir-720b | — | — | 0.13 | — | — | — |
| hsa-mir-800a | — | 0.18 | — | — | — | — |
| hsa-mir-800b | — | — | — | — | — | — |
| hsa-mir-803 | — | — | — | — | — | — |
| hsa-mir-805 | — | — | — | — | — | — |
| hsa-mir-451 | 0.18 | 1.29 | — | — | 0.75 | 0.07 |
| hsa-mir-433 | — | 0.06 | — | — | — | — |
| hsa-mir-431 | — | — | — | — | — | — |
| hsa-mir-452 | — | — | — | — | — | — |
| hsa-mir-453 | — | — | — | — | — | — |
| hsa-mir-813 | — | 0.06 | — | — | — | — |
| hsa-mir-814 | — | — | — | — | — | — |
| hsa-mir-815 | — | 0.06 | — | — | — | — |
| hsa-mir-816 | — | 0.06 | 0.13 | 0.12 | — | — |
| hsa-mir-817 | — | — | — | — | — | — |
| hsa-mir-818 | — | — | — | — | — | — |
| hsa-mir-819 | — | — | — | — | — | — |
| hsa-mir-821 | — | — | — | — | — | — |
| hsa-mir-822 | — | — | — | — | — | — |
| hsa-mir-823 | 0.18 | — | — | — | — | — |
| hsa-mir-824 | — | — | — | — | — | — |
| hsa-mir-825 | — | 0.31 | — | — | — | — |
| hsa-mir-826 | — | 0.12 | — | — | 0.15 | 0.59 |
| hsa-mir-827 | — | 0.08 | — | — | — | 0.44 |
| hsa-mir-828 | — | — | — | 0.12 | — | — |
| hsa-mir-829 | — | — | — | 0.24 | — | — |
| hsa-mir-831 | — | — | 0.13 | 0.12 | — | — |
| hsa-mir-832 | — | — | — | — | — | — |
| hsa-mir-834 | — | — | — | — | — | — |
| hsa-mir-835 | — | — | 0.27 | — | — | — |
| hsa-mir-837 | — | 0.06 | — | — | — | 0.07 |
| hsa-mir-838 | — | — | — | — | — | — |
| hsa-mir-839 | 0.18 | — | — | — | — | — |
| hsa-mir-841 | — | — | — | — | — | — |
| hsa-mir-842 | — | — | — | — | — | — |
| hsa-mir-843 | — | 0.06 | — | — | 0.45 | — |
| hsa-mir-845 | — | — | — | 0.12 | — | — |
| hsa-mir-846 | — | — | — | — | — | — |
| hsa-mir-847 | — | — | — | — | — | — |
| hsa-mir-848 | — | — | — | — | — | — |
| hsa-mir-849 | — | — | — | — | — | — |
| hsa-mir-850 | — | — | — | — | — | — |
| hsa-mir-851 | — | — | — | — | — | — |
| hsa-mir-852 | — | — | — | — | — | — |
| hsa-mir-853 | 0.18 | — | — | — | — | — |
| hsa-mir-854 | — | — | — | — | 0.08 | — |
| hsa-mir-855 | 0.18 | 0.12 | — | — | 0.53 | 0.52 |
| hsa-mir-857 | — | — | 0.13 | — | — | — |
| hsa-mir-864 | — | — | — | — | — | — |
| hsa-mir-867 | 0.09 | — | 0.13 | 0.18 | — | 0.07 |
| hsa-mir-869 | — | — | — | — | — | — |
| hsa-mir-871 | — | — | 0.13 | — | — | — |
| hsa-mir-883 | — | 0.06 | — | — | — | — |
| hsa-mir-884 | — | — | — | — | — | — |
| hsa-mir-885 | — | — | 0.13 | 0.24 | — | — |
| hsa-mir-886 | — | — | — | — | — | — |
| hsa-mir-887 | — | — | — | 0.24 | — | — |
| hsa-mir-888 | — | — | — | — | — | 0.07 |
| hsa-mir-889 | — | — | — | — | — | — |
| hsa-mir-890 | — | — | — | — | — | — |
| hsa-mir-891 | — | — | — | — | — | — |
| hsa-mir-892 | — | — | — | — | — | — |
| hsa-mir-893 | 0.18 | — | — | — | — | — |
| hsa-mir-894 | — | — | — | — | — | — |
| hsa-mir-92b | 0.55 | 0.06 | 0.13 | 0.12 | — | — |

TABLE G-continued

Relative Cloning Frequency in % Relative to Total Number of Identified MicroRNA for Each Given Library.

| miRNA | Embryonal derived cell lines/tumors | | | | Cervic carcinoma | Epididymis |
|---|---|---|---|---|---|---|
| | NT2/D1 | Saos-2 | NCCIT | Hek | HeLa S3 | epididymis |
| hsa-mir-20b | 0.37 | — | 0.72 | 0.13 | — | — |
| hsa-mir-301b | — | — | — | — | — | — |
| hsa-mir-302b | 3.90 | — | 15.22 | — | — | — |
| hsa-mir-302c | 9.06 | — | 5.07 | — | — | — |
| hsa-mir-302d | 1.50 | — | 4.35 | — | — | — |
| hsa-mir-329 | — | — | — | — | — | — |
| hsa-mir-367 | 9.71 | — | 10.14 | — | — | — |
| hsa-mir-368 | — | — | — | — | — | — |
| hsa-mir-369 | — | — | — | — | — | — |
| hsa-mir-374a | 1.35 | — | — | 0.25 | 0.32 | 0.16 |
| hsa-mir-374b | 0.49 | — | 1.45 | 0.25 | 0.16 | — |
| hsa-mir-410 | — | — | — | — | — | — |
| hsa-mir-421 | — | — | — | — | 0.16 | 0.08 |
| hsa-mir-423 | — | 1.69 | 0.72 | — | 0.32 | — |
| hsa-mir-425 | 0.12 | — | — | 0.76 | 0.16 | — |
| hsa-mir-500 | 0.12 | — | — | 0.25 | — | — |
| hsa-mir-502 | — | — | — | 0.25 | 0.48 | — |
| hsa-mir-504 | — | — | — | 0.51 | 0.16 | — |
| hsa-mir-519 | — | — | — | 0.25 | 0.16 | — |
| hsa-mir-604 | 0.12 | — | — | 0.25 | — | — |
| hsa-mir-610 | 0.12 | — | — | 0.25 | — | 0.24 |
| hsa-mir-615 | — | — | — | — | — | — |
| hsa-mir-618 | — | — | — | — | — | — |
| hsa-mir-619 | — | — | — | — | — | — |
| hsa-mir-620 | — | — | — | — | — | — |
| hsa-mir-631 | — | — | — | — | — | — |
| hsa-mir-720a | — | — | — | — | — | 0.08 |
| hsa-mir-720b | — | — | — | — | — | — |
| hsa-mir-800a | — | — | — | — | — | — |
| hsa-mir-800b | — | — | — | — | — | — |
| hsa-mir-803 | 0.25 | — | — | 0.25 | — | — |
| hsa-mir-805 | — | — | — | — | — | — |
| hsa-mir-451 | — | — | — | — | — | 0.40 |
| hsa-mir-433 | — | — | — | — | — | — |
| hsa-mir-431 | — | — | — | — | — | — |
| hsa-mir-452 | — | — | — | — | — | — |
| hsa-mir-453 | — | — | — | — | — | — |
| hsa-mir-813 | — | — | — | — | — | — |
| hsa-mir-814 | 0.12 | — | — | — | — | — |
| hsa-mir-815 | 0.12 | — | — | 0.51 | — | — |
| hsa-mir-816 | — | — | — | 0.25 | — | — |
| hsa-mir-817 | — | — | — | — | — | — |
| hsa-mir-818 | — | — | 0.72 | — | 0.16 | — |
| hsa-mir-819 | — | — | — | — | — | — |
| hsa-mir-821 | — | — | — | — | — | — |
| hsa-mir-822 | — | — | — | — | — | — |
| hsa-mir-823 | — | — | — | — | — | — |
| hsa-mir-824 | — | — | — | — | — | — |
| hsa-mir-825 | — | — | — | 0.25 | — | — |
| hsa-mir-826 | — | — | — | — | — | — |
| hsa-mir-827 | — | — | — | — | — | — |
| hsa-mir-828 | — | — | — | — | — | — |
| hsa-mir-829 | — | — | — | — | 0.16 | — |
| hsa-mir-831 | — | — | — | — | — | — |
| hsa-mir-832 | — | — | — | — | — | — |
| hsa-mir-834 | — | — | — | — | — | 0.08 |
| hsa-mir-835 | — | — | — | — | — | — |
| hsa-mir-837 | 0.12 | — | — | — | — | — |
| hsa-mir-838 | — | — | — | — | 0.16 | — |
| hsa-mir-839 | — | 1.69 | — | — | — | — |
| hsa-mir-841 | 0.12 | — | — | — | — | — |
| hsa-mir-842 | 0.12 | — | — | — | — | — |
| hsa-mir-843 | 1.97 | — | — | 0.25 | — | — |
| hsa-mir-845 | 0.12 | — | — | — | — | — |
| hsa-mir-846 | — | — | — | — | — | — |
| hsa-mir-847 | — | — | — | — | — | — |
| hsa-mir-848 | — | — | — | — | — | — |
| hsa-mir-849 | — | — | — | — | — | — |
| hsa-mir-850 | — | — | — | — | — | — |
| hsa-mir-851 | 0.12 | — | — | — | — | — |
| hsa-mir-852 | 0.37 | — | — | — | — | — |
| hsa-mir-853 | — | — | — | — | — | — |
| hsa-mir-854 | — | — | — | — | — | — |

TABLE G-continued

Relative Cloning Frequency in % Relative to Total Number of Identified MicroRNA for Each Given Library.

| | | | | | | |
|---|---|---|---|---|---|---|
| hsa-mir-855 | — | — | — | — | 0.32 | 0.16 |
| hsa-mir-857 | 0.12 | — | — | — | — | — |
| hsa-mir-864 | 0.25 | — | — | — | — | — |
| hsa-mir-867 | — | — | — | — | — | — |
| hsa-mir-869 | — | — | — | — | — | — |
| hsa-mir-871 | — | — | 0.72 | — | 0.32 | — |
| hsa-mir-883 | — | — | — | — | — | — |
| hsa-mir-884 | — | — | — | — | — | — |
| hsa-mir-885 | — | — | — | — | — | — |
| hsa-mir-886 | — | — | — | — | — | — |
| hsa-mir-887 | — | — | — | — | — | — |
| hsa-mir-888 | — | — | — | — | — | — |
| hsa-mir-889 | — | — | — | — | — | — |
| hsa-mir-890 | — | — | — | — | — | — |
| hsa-mir-891 | — | — | — | — | — | — |
| hsa-mir-892 | — | — | — | — | — | — |
| hsa-mir-893 | — | — | — | — | — | — |
| hsa-mir-894 | — | — | — | — | — | — |
| hsa-mir-92b | 0.37 | — | — | — | 0.16 | — |

| | Breast carcinoma | | | | | |
|---|---|---|---|---|---|---|
| miRNA | MCF10A | MCF7 | HCC38 | SkBr3 | BT474 | T47 |
| hsa-mir-20b | — | — | 0.09 | — | — | — |
| hsa-mir-301b | — | — | — | — | — | 0.60 |
| hsa-mir-302b | — | — | — | — | — | — |
| hsa-mir-302c | — | — | — | — | — | — |
| hsa-mir-302d | — | — | — | — | — | — |
| hsa-mir-329 | — | — | — | — | — | — |
| hsa-mir-367 | — | — | — | — | — | — |
| hsa-mir-368 | — | 0.25 | — | — | — | — |
| hsa-mir-369 | — | — | — | — | — | — |
| hsa-mir-374a | — | — | 0.09 | 0.47 | — | 0.09 |
| hsa-mir-374b | — | — | 0.19 | — | 0.05 | 0.43 |
| hsa-mir-410 | — | — | — | — | — | — |
| hsa-mir-421 | — | 0.13 | — | — | — | 0.09 |
| hsa-mir-423 | 0.19 | 0.25 | 0.47 | 0.12 | 0.42 | 0.51 |
| hsa-mir-425 | — | 0.38 | 0.75 | 0.93 | 1.50 | 2.22 |
| hsa-mir-500 | — | — | 0.19 | — | 0.98 | 0.34 |
| hsa-mir-502 | — | 0.50 | — | — | — | — |
| hsa-mir-504 | 0.09 | 0.13 | 0.09 | 0.23 | 0.61 | 0.09 |
| hsa-mir-519 | 0.09 | 0.13 | — | 0.23 | 0.05 | 0.17 |
| hsa-mir-604 | 0.19 | — | 0.19 | — | 0.19 | 0.17 |
| hsa-mir-610 | — | — | — | — | — | — |
| hsa-mir-615 | — | — | — | — | — | — |
| hsa-mir-618 | — | — | — | — | — | — |
| hsa-mir-619 | — | — | — | — | — | — |
| hsa-mir-620 | — | 0.25 | — | — | — | — |
| hsa-mir-631 | — | 0.25 | — | — | — | — |
| hsa-mir-720a | — | — | — | — | — | — |
| hsa-mir-720b | — | — | — | — | — | — |
| hsa-mir-800a | — | — | — | — | — | — |
| hsa-mir-800b | — | — | — | — | — | — |
| hsa-mir-803 | — | — | — | — | — | — |
| hsa-mir-805 | — | — | — | — | — | — |
| hsa-mir-451 | — | — | — | — | — | — |
| hsa-mir-433 | — | — | — | — | — | — |
| hsa-mir-431 | — | — | — | — | — | — |
| hsa-mir-452 | — | — | — | 0.12 | 0.05 | — |
| hsa-mir-453 | — | — | — | — | — | — |
| hsa-mir-813 | — | — | — | — | — | — |
| hsa-mir-814 | — | — | — | — | — | — |
| hsa-mir-815 | — | 0.13 | 0.09 | — | 0.05 | — |
| hsa-mir-816 | 0.09 | 0.13 | — | — | — | — |
| hsa-mir-817 | — | — | — | — | — | — |
| hsa-mir-818 | — | — | — | — | 0.05 | — |
| hsa-mir-819 | — | — | — | — | — | — |
| hsa-mir-821 | — | — | — | — | — | — |
| hsa-mir-822 | — | — | — | — | — | — |
| hsa-mir-823 | — | — | — | — | — | — |
| hsa-mir-824 | — | — | — | — | — | — |
| hsa-mir-825 | — | — | — | — | — | — |
| hsa-mir-826 | — | — | — | — | — | — |
| hsa-mir-827 | — | — | — | — | — | — |
| hsa-mir-828 | — | — | — | — | — | — |
| hsa-mir-829 | — | — | 0.09 | — | 0.05 | 0.09 |

TABLE G-continued

Relative Cloning Frequency in % Relative to Total Number of Identified MicroRNA for Each Given Library.

| | | | | | | |
|---|---|---|---|---|---|---|
| hsa-mir-831 | — | — | — | — | — | — |
| hsa-mir-832 | — | — | — | — | — | — |
| hsa-mir-834 | — | 0.13 | — | — | — | — |
| hsa-mir-835 | — | — | — | — | 0.05 | — |
| hsa-mir-837 | — | — | — | — | — | — |
| hsa-mir-838 | — | — | — | — | — | 0.09 |
| hsa-mir-839 | — | — | — | — | — | — |
| hsa-mir-841 | — | — | — | — | — | — |
| hsa-mir-842 | — | — | — | — | — | — |
| hsa-mir-843 | — | 0.13 | — | — | 0.23 | — |
| hsa-mir-845 | — | — | — | — | — | — |
| hsa-mir-846 | — | — | — | — | — | — |
| hsa-mir-847 | — | — | — | 0.23 | — | — |
| hsa-mir-848 | — | — | — | — | — | — |
| hsa-mir-849 | — | — | — | 0.23 | — | — |
| hsa-mir-850 | — | — | — | — | — | — |
| hsa-mir-851 | — | — | — | — | — | — |
| hsa-mir-852 | — | — | — | 0.12 | — | — |
| hsa-mir-853 | — | 0.13 | — | — | — | — |
| hsa-mir-854 | — | — | — | — | — | — |
| hsa-mir-855 | — | — | 0.19 | — | — | — |
| hsa-mir-857 | — | — | — | — | — | — |
| hsa-mir-864 | — | — | — | — | — | — |
| hsa-mir-867 | — | — | — | — | — | 0.04 |
| hsa-mir-869 | — | — | — | — | — | — |
| hsa-mir-871 | — | — | 0.09 | — | — | — |
| hsa-mir-883 | — | — | — | — | — | — |
| hsa-mir-884 | — | — | — | — | — | — |
| hsa-mir-885 | — | — | — | — | — | — |
| hsa-mir-886 | — | — | — | — | 0.05 | — |
| hsa-mir-887 | — | — | — | — | — | — |
| hsa-mir-888 | — | — | — | — | — | — |
| hsa-mir-889 | — | — | — | — | — | — |
| hsa-mir-890 | — | — | — | — | 0.05 | — |
| hsa-mir-891 | — | — | — | — | — | — |
| hsa-mir-892 | — | — | — | — | — | — |
| hsa-mir-893 | — | — | — | — | — | — |
| hsa-mir-894 | — | — | — | — | — | 0.09 |
| hsa-mir-92b | — | 0.63 | — | 0.12 | — | — |

The "—" in the table indicates 0%.

TABLE G1

Relative Cloning Frequency in % Relative to Total Number of Identified MicroRNA for Each Given Library.

| miRNA | hsa_cerebellum | hsa_frontalcortex | Adult brain hsa_midbrain | hsa_hippocampus |
|---|---|---|---|---|
| hsa-miR-100516 | — | — | — | — |
| hsa-miR-100516 | 0.13 | — | — | — |
| hsa-miR-100604 | — | 0.26 | 0.60 | 0.09 |
| hsa-miR-100610-5p | — | — | — | — |
| hsa-miR-100631 | — | — | — | — |
| hsa-miR-100732 | — | — | — | — |
| hsa-miR-100814 | — | 0.07 | — | — |
| hsa-miR-100815 | — | — | 0.13 | 0.09 |
| hsa-miR-100818 | — | 0.20 | — | — |
| hsa-miR-100819 | 0.13 | 0.07 | — | — |
| hsa-miR-100824 | — | — | 0.07 | — |
| hsa-miR-100825-3p | — | — | — | — |
| hsa-miR-100825-5p | — | — | — | — |
| hsa-miR-100829-3p | — | — | — | — |
| hsa-miR-100835-5p | — | — | — | — |
| hsa-miR-100842 | — | — | — | — |
| hsa-miR-100843-3p | — | 0.07 | — | 0.26 |
| hsa-miR-100843-5p | — | 0.07 | — | 0.26 |
| hsa-miR-100846 | — | — | 0.07 | — |
| hsa-miR-100851 | — | — | — | — |
| hsa-miR-100852 | 0.25 | — | — | — |
| hsa-miR-100854 | — | — | — | — |
| hsa-miR-100855-3p | — | 0.13 | — | 0.09 |
| hsa-miR-100855-5p | — | 0.13 | — | 0.09 |
| hsa-miR-100869-3p | — | — | — | 0.09 |
| hsa-miR-100869-5p | — | — | — | — |
| hsa-miR-100871-3p | — | — | — | — |
| hsa-miR-100871-5p | — | — | — | — |
| hsa-miR-100855 | — | — | — | — |
| hsa-miR-100885 | — | — | — | — |
| hsa-miR-100887-3p | — | — | — | — |
| hsa-miR-100887-5p | — | — | — | — |
| hsa-miR-100891-3p | — | — | — | — |
| hsa-miR-100891-5p | — | — | — | — |
| hsa-miR-100891-5p | — | — | — | — |
| hsa-miR-101001 | — | — | — | — |
| hsa-miR-146b | — | — | — | — |
| hsa-miR-147b | — | — | — | — |
| hsa-miR-181d | — | 0.03 | — | — |
| hsa-miR-18b | — | — | — | — |
| hsa-mir-18b-3p | — | — | — | — |
| hsa-miR-193b | — | — | — | — |

TABLE G1-continued

Relative Cloning Frequency in % Relative to Total Number of Identified MicroRNA for Each Given Library.

| miRNA | | | | | |
|---|---|---|---|---|---|
| hsa-miR-20b | — | — | — | — | — |
| hsa-miR-20b-3p | — | — | — | — | — |
| hsa-miR-216b | — | — | — | — | — |
| hsa-miR-301b | — | — | — | — | — |
| hsa-miR-329 | — | — | 0.07 | — | 0.09 |
| hsa-miR-33b | — | — | — | — | 0.26 |
| hsa-miR-374b | — | — | 0.07 | — | — |
| hsa-miR-375 | — | — | — | — | — |
| hsa-miR-376a | — | — | — | — | — |
| hsa-miR-376b | — | 0.07 | 0.07 | — | — |
| hsa-miR-376c | — | 0.07 | 0.07 | — | 0.26 |
| hsa-miR-377 | — | 0.07 | — | — | — |
| hsa-miR-378 | — | 0.13 | 0.07 | — | 0.43 |
| hsa-miR-379 | — | — | 0.27 | — | — |
| hsa-miR-380 | — | — | 0.07 | — | 0.09 |
| hsa-miR-410 | — | — | — | — | — |
| hsa-miR-421-3p | — | 0.13 | — | — | — |
| hsa-miR-429 | — | — | 0.07 | — | — |
| hsa-miR-431 | — | — | 0.07 | — | — |
| hsa-miR-432 | — | — | — | — | — |
| hsa-miR-433 | — | — | — | — | — |
| hsa-miR-449a | — | — | — | — | — |
| hsa-miR-449b | 0.13 | 0.52 | — | — | — |
| hsa-miR-450a | — | — | 0.67 | — | — |
| hsa-miR-451 | — | — | — | — | — |
| hsa-miR-452 | 0.13 | — | 0.07 | — | — |
| hsa-miR-453 | — | — | — | — | — |
| hsa-miR-454 | — | — | — | — | 0.09 |
| hsa-miR-455-5p | — | — | — | — | 0.09 |
| hsa-miR-484 | 0.51 | — | — | — | — |
| hsa-miR-485-3p | — | — | 0.07 | — | — |
| hsa-miR-485-5p | — | — | — | — | 0.69 |
| hsa-miR-486_os | — | — | — | — | — |
| hsa-miR-487 | 0.13 | — | — | — | — |
| hsa-miR-488 | — | — | — | — | — |
| hsa-miR-490 | — | — | — | — | — |
| hsa-miR-493 | — | — | — | — | — |
| hsa-miR-497 | — | — | — | — | — |
| hsa-miR-502 | — | — | — | — | — |
| hsa-miR-503 | — | — | — | — | — |
| hsa-miR-505 | — | — | — | — | — |
| hsa-miR-509-3p | — | — | — | — | — |
| hsa-miR-514 | — | — | — | — | — |
| hsa-miR-544 | — | — | — | — | — |
| hsa-miR-618 | — | — | — | — | — |
| hsa-miR-619 | — | — | — | — | — |
| hsa-miR-620 | — | — | — | — | — |
| hsa-miR-816 | — | — | — | — | — |
| hsa-mir-817 | — | 0.13 | — | — | — |
| hsa-mir-828-3p | — | — | — | — | — |

TABLE G1-continued

Relative Cloning Frequency in % Relative to Total Number of Identified MicroRNA for Each Given Library.

| miRNA | Medulloblastoma hsa_DADY | Glioblastoma hsa_SNB19 | Neuroblastoma BE(2)-M17 | hsa_5H-SY5Y | 5H-SY5Y_retinoic acid |
|---|---|---|---|---|---|
| hsa-mir-828-5p | — | — | — | — | 0.07 |
| hsa-mir-831-1 | — | — | — | — | — |
| hsa-mir-840-3p | — | — | — | — | — |
| hsa-mir-840-5p | — | — | — | — | 0.13 |
| hsa-mir-847 | — | — | — | — | — |
| hsa-mir-848 | — | — | — | — | — |
| hsa-mir-849 | 0.13 | — | — | — | — |
| hsa-mir-850 | — | — | — | — | — |
| hsa-mir-853 | — | — | — | — | — |
| hsa-mir-857 | — | — | — | — | — |
| hsa-mir-92b | — | 0.07 | — | — | 0.07 |
| hsa-miR-100516 | 0.23 | — | — | — | — |
| hsa-miR-100516 | 0.23 | — | — | — | — |
| hsa-miR-100604 | — | — | — | 1.61 | 0.94 |
| hsa-miR-100610-5p | — | — | — | — | — |
| hsa-miR-100631 | — | — | — | — | — |
| hsa-miR-100732 | — | — | — | — | — |
| hsa-miR-100814 | — | — | 0.30 | 0.32 | 0.67 |
| hsa-miR-100815 | — | 0.20 | — | 0.48 | 0.40 |
| hsa-miR-100818 | — | — | — | — | — |
| hsa-miR-100819 | — | — | — | — | — |
| hsa-miR-100824 | — | — | — | — | — |
| hsa-miR-100825-3p | — | — | — | — | — |
| hsa-miR-100825-5p | — | — | 0.15 | 0.16 | — |
| hsa-miR-100829-3p | 0.46 | 0.20 | 0.76 | 1.61 | 1.89 |
| hsa-miR-100835-5p | 0.46 | 0.20 | 0.76 | 1.61 | 1.89 |
| hsa-miR-100842 | — | — | — | — | 0.13 |
| hsa-miR-100843-3p | — | 0.20 | — | — | 0.13 |
| hsa-miR-100843-5p | — | — | — | — | — |
| hsa-miR-100846 | — | — | 0.15 | — | — |
| hsa-miR-100851 | — | — | — | — | — |
| hsa-miR-100852 | — | — | — | — | — |
| hsa-miR-100854 | — | 0.20 | — | — | — |
| hsa-miR-100855-3p | — | — | 0.15 | — | — |
| hsa-miR-100855-5p | — | — | 0.15 | — | — |
| hsa-miR-100869-3p | — | 0.20 | — | — | — |
| hsa-miR-100869-5p | — | 0.20 | — | — | — |
| hsa-miR-100871-3p | 0.23 | — | — | — | — |
| hsa-miR-100871-5p | 0.23 | — | — | — | — |
| hsa-miR-100885 | — | — | — | — | — |
| hsa-miR-100887-3p | — | — | — | — | — |
| hsa-miR-100887-5p | — | — | — | — | — |
| hsa-miR-100891-3p | — | — | — | — | — |

TABLE G1-continued

Relative Cloning Frequency in % Relative to Total Number of Identified MicroRNA for Each Given Library.

| miRNA | C1 | C2 | C3 | C4 | C5 |
|---|---|---|---|---|---|
| hsa-miR-100891-3p | — | — | — | — | — |
| hsa-miR-100891-5p | — | — | — | — | — |
| hsa-miR-100891-5p | — | — | 0.15 | — | — |
| hsa-miR-101001 | — | — | — | — | — |
| hsa-miR-146b | 0.11 | — | — | — | — |
| hsa-miR-147b | 0.23 | — | — | — | — |
| hsa-miR-181d | — | — | — | — | 0.13 |
| hsa-miR-18b | 0.11 | — | — | — | — |
| hsa-mir-18b-3p | 0.11 | — | — | — | — |
| hsa-miR-193b | — | — | — | — | — |
| hsa-miR-20b | — | — | — | — | — |
| hsa-miR-20b-3p | — | — | — | — | — |
| hsa-miR-216b | — | — | — | — | — |
| hsa-miR-301b | — | — | 0.61 | 0.32 | 0.74 |
| hsa-miR-329 | — | 0.40 | — | — | — |
| hsa-miR-33b | — | 0.60 | — | — | — |
| hsa-miR-374b | — | — | — | 0.88 | — |
| hsa-miR-375 | — | — | 0.15 | 0.16 | — |
| hsa-miR-376a | — | — | — | — | — |
| hsa-miR-376b | — | — | 0.30 | — | — |
| hsa-miR-376c | — | — | — | — | — |
| hsa-miR-377 | — | — | 1.98 | — | — |
| hsa-miR-378 | — | — | 4.57 | — | — |
| hsa-miR-379 | — | — | — | — | — |
| hsa-miR-380 | — | — | 0.30 | — | — |
| hsa-miR-410 | — | — | — | — | — |
| hsa-miR-421-3p | — | — | — | — | — |
| hsa-miR-429 | — | — | 0.46 | — | — |
| hsa-miR-431 | 0.23 | — | 0.15 | — | — |
| hsa-miR-432 | — | — | — | — | — |
| hsa-miR-433 | — | — | — | — | — |
| hsa-miR-449a | — | — | 0.15 | — | — |
| hsa-miR-449b | — | — | — | — | — |
| hsa-miR-450a | — | — | — | — | — |
| hsa-miR-451 | — | — | — | — | — |
| hsa-miR-452 | — | — | 0.15 | — | — |
| hsa-miR-453 | — | — | 0.15 | — | — |
| hsa-miR-454 | — | — | — | — | — |
| hsa-miR-455-5p | — | — | — | — | — |
| hsa-miR-484 | — | — | — | — | — |
| hsa-miR-485-3p | — | — | — | — | — |
| hsa-miR-485-5p | — | — | — | — | — |
| hsa-miR-486_os | — | — | 0.30 | — | — |
| hsa-miR-487 | — | — | 0.61 | 0.64 | 0.40 |
| hsa-miR-488 | — | — | 0.91 | 0.32 | 0.40 |
| hsa-miR-490 | — | — | — | — | — |
| hsa-miR-493 | — | — | 0.91 | — | — |
| hsa-miR-497 | — | — | — | — | — |
| hsa-miR-502 | 0.23 | — | — | — | — |
| hsa-miR-503 | — | — | 0.91 | — | — |

TABLE G1-continued

Relative Cloning Frequency in % Relative to Total Number of Identified MicroRNA for Each Given Library.

| | Skin | Liver | Hepatocellular carcinoma | | | | Hepatoblastoma | |
|---|---|---|---|---|---|---|---|---|
| | fibroblasts_CMV | hsa_liver | Huh7_HCV | Huh7_Mock | hsa_PLC | | hsa_HepG2 | hsa_HepG2_2215 |
| hsa-miR-505 | — | — | — | — | — | — | — | — |
| hsa-miR-509-3p | — | — | — | — | — | — | — | — |
| hsa-miR-514 | — | — | — | — | — | — | — | — |
| hsa-miR-544 | — | — | — | — | — | — | — | — |
| hsa-miR-618 | — | — | — | — | — | — | — | — |
| hsa-miR-619 | — | — | — | — | — | — | — | — |
| hsa-miR-620 | — | — | — | — | — | — | — | — |
| hsa-mir-816 | — | — | — | — | — | — | — | — |
| hsa-mir-817 | — | — | — | — | — | — | — | 0.13 |
| hsa-mir-828-3p | — | — | — | — | — | — | — | — |
| hsa-mir-828-5p | — | — | — | — | — | — | — | — |
| hsa-mir-831-1 | — | — | — | — | — | — | — | — |
| hsa-mir-840-3p | — | — | — | — | — | 0.32 | — | 0.40 |
| hsa-mir-840-5p | 0.23 | 0.40 | — | — | — | 0.96 | — | 0.54 |
| hsa-mir-847 | — | — | — | — | — | — | — | — |
| hsa-mir-848 | — | — | — | — | — | — | — | — |
| hsa-mir-849 | — | — | — | — | — | — | — | — |
| hsa-mir-850 | — | — | — | — | — | — | — | — |
| hsa-mir-853 | — | — | — | — | — | 0.32 | — | 0.27 |
| hsa-mir-857 | — | — | — | — | — | 0.32 | — | — |
| hsa-mir-92b | — | — | — | — | — | — | — | — |

| | Skin | Liver | Hepatocellular carcinoma | | | Hepatoblastoma | |
|---|---|---|---|---|---|---|---|
| miRNA | fibroblasts_CMV | hsa_liver | Huh7_HCV | Huh7_Mock | hsa_PLC | hsa_HepG2 | hsa_HepG2_2215 |
| hsa-miR-100516 | — | — | — | — | — | — | — |
| hsa-miR-100516 | — | — | — | — | — | — | — |
| hsa-miR-100604 | 0.60 | — | — | — | — | 0.07 | — |
| hsa-miR-100610-5p | — | — | 1.67 | — | 0.22 | — | 0.06 |
| hsa-miR-100631 | — | — | — | — | — | — | — |
| hsa-miR-100732 | — | — | — | — | — | — | — |
| hsa-miR-100814 | — | — | — | — | — | 0.15 | — |
| hsa-miR-100815 | — | — | — | — | — | 0.07 | — |
| hsa-miR-100818 | — | 0.07 | — | — | — | — | — |
| hsa-miR-100819 | — | — | — | — | — | — | — |
| hsa-miR-100824 | — | — | — | — | — | — | — |
| hsa-miR-100825-3p | — | — | — | — | — | — | — |
| hsa-miR-100825-5p | — | — | — | — | — | — | — |
| hsa-miR-100829-3p | — | — | — | — | — | — | — |
| hsa-miR-100835-5p | — | — | — | — | — | — | — |
| hsa-miR-100842 | — | — | — | — | — | 0.07 | — |
| hsa-miR-100843-3p | 0.20 | — | — | — | — | — | — |
| hsa-miR-100843-5p | 0.20 | — | — | — | — | — | — |
| hsa-miR-100846 | — | — | — | — | — | — | — |
| hsa-miR-100851 | — | — | — | 0.52 | — | — | — |
| hsa-miR-100852 | — | — | — | — | 0.29 | — | — |
| hsa-miR-100854 | — | 0.07 | — | — | — | — | 0.06 |
| hsa-miR-100855-3p | — | — | — | — | — | 0.15 | 0.13 |
| hsa-miR-100855-5p | — | — | — | — | — | 0.15 | 0.13 |
| hsa-miR-100869-3p | — | — | — | — | — | — | — |

TABLE G1-continued

Relative Cloning Frequency in % Relative to Total Number of Identified MicroRNA for Each Given Library.

| miRNA | | | | | | | | | | |
|---|---|---|---|---|---|---|---|---|---|---|
| hsa-miR-100869-5p | — | — | — | — | — | — | — | — | — | — |
| hsa-miR-100871-3p | — | — | — | 0.26 | — | — | — | — | — | — |
| hsa-miR-100871-5p | — | — | — | 0.26 | — | — | — | — | — | — |
| hsa-miR-100885 | — | — | — | — | — | — | — | — | — | — |
| hsa-miR-100887-3p | — | — | — | — | — | — | — | — | — | — |
| hsa-miR-100887-5p | — | — | — | — | — | — | — | — | — | — |
| hsa-miR-100891-3p | — | — | — | — | — | — | — | — | — | — |
| hsa-miR-100891-3p | — | — | — | — | — | — | — | — | — | — |
| hsa-miR-100891-5p | — | — | — | — | — | — | — | — | — | — |
| hsa-miR-100891-5p | — | — | — | — | — | — | — | — | — | — |
| hsa-miR-101001 | — | — | — | — | — | — | — | — | — | — |
| hsa-miR-146b | 0.40 | — | — | — | — | — | — | — | — | — |
| hsa-miR-147b | — | — | — | — | — | — | — | — | 0.11 | 0.03 |
| hsa-miR-181d | — | — | — | — | — | — | — | — | 0.11 | 0.03 |
| hsa-miR-18b | 0.20 | — | — | 0.26 | — | — | 0.07 | — | 0.07 | 0.06 |
| hsa-mir-18b-3p | — | — | — | — | — | — | — | — | — | — |
| hsa-miR-193b | — | — | 0.07 | — | — | — | — | — | — | — |
| hsa-miR-20b | — | — | — | — | — | — | — | — | — | — |
| hsa-miR-20b-3p | — | — | — | — | — | — | — | — | — | — |
| hsa-miR-216b | — | — | — | — | — | — | — | — | — | — |
| hsa-miR-301b | — | — | — | — | — | — | — | — | 0.26 | 0.39 |
| hsa-miR-329 | — | — | — | — | — | — | — | — | — | — |
| hsa-miR-33b | — | — | — | — | 0.43 | — | — | — | 0.15 | — |
| hsa-miR-374b | — | — | — | — | 1.72 | — | — | — | 0.97 | 0.71 |
| hsa-miR-375 | — | — | — | — | — | — | — | — | — | — |
| hsa-miR-376a | 0.20 | — | — | — | — | — | — | — | — | — |
| hsa-miR-376b | — | — | — | — | — | — | — | — | — | — |
| hsa-miR-376c | — | — | — | — | — | — | — | — | — | — |
| hsa-miR-377 | — | — | 0.07 | — | — | — | — | — | — | — |
| hsa-miR-378 | — | — | 0.07 | 0.26 | — | — | — | — | 0.07 | 0.06 |
| hsa-miR-379 | 1.00 | — | — | — | — | — | — | — | — | — |
| hsa-miR-380 | — | — | — | — | — | — | — | — | — | — |
| hsa-miR-410 | — | — | — | — | — | — | — | — | — | — |
| hsa-miR-421-3p | — | — | — | 0.26 | 0.29 | — | — | — | — | 0.13 |
| hsa-miR-429 | — | — | — | — | — | — | — | — | — | — |
| hsa-miR-431 | 0.20 | — | — | — | — | — | — | — | — | — |
| hsa-miR-432 | — | — | — | — | — | — | — | — | — | — |
| hsa-miR-433 | — | — | — | — | — | — | — | — | — | — |
| hsa-miR-449a | — | — | — | — | — | — | — | — | — | — |
| hsa-miR-449b | — | — | — | — | — | — | — | — | — | — |
| hsa-miR-450a | — | — | — | — | 0.07 | — | — | — | 0.07 | — |
| hsa-miR-451 | — | — | 0.57 | — | — | — | — | — | — | — |
| hsa-miR-452 | — | — | — | — | — | — | — | — | 0.07 | 0.06 |
| hsa-miR-453 | — | — | — | — | — | — | — | — | — | — |
| hsa-miR-454 | 0.20 | — | — | — | 0.07 | — | — | — | 0.60 | 0.26 |
| hsa-miR-455-5p | — | — | — | — | — | — | — | — | — | — |
| hsa-miR-484 | — | — | — | — | — | — | — | — | 0.07 | 0.06 |

TABLE G1-continued

Relative Cloning Frequency in % Relative to Total Number of Identified MicroRNA for Each Given Library.

| miRNA | Heart | Spleen | T-cells | | B-cells | precursor B-ALL | | |
| --- | --- | --- | --- | --- | --- | --- | --- | --- |
| | hsa heart | hsa spleen | hsa CD4 | hsa CD8 | hsa CD19 | hsa_B-ALL2_d0 | hsa_B-ALL3_d0 | hsa_B-ALL4_d0 |
| hsa-miR-485-3p | — | — | — | — | — | — | — | — |
| hsa-miR-485-5p | — | — | — | — | — | — | — | — |
| hsa-mir-486_os | — | — | — | — | — | — | — | — |
| hsa-miR-487 | — | — | — | — | — | — | — | — |
| hsa-miR-488 | — | — | — | — | — | — | — | — |
| hsa-miR-490 | 0.20 | — | — | — | — | — | — | — |
| hsa-miR-493 | 0.20 | — | — | — | — | — | — | — |
| hsa-miR-497 | — | — | — | — | — | — | — | 0.06 |
| hsa-miR-502 | — | — | — | — | — | — | — | — |
| hsa-miR-503 | — | 0.07 | — | — | — | 0.07 | 0.07 | 0.06 |
| hsa-miR-509-3p | — | — | — | — | — | — | — | — |
| hsa-miR-514 | — | — | — | — | — | — | — | — |
| hsa-miR-544 | — | — | — | — | — | — | — | — |
| hsa-miR-618 | — | — | — | — | — | — | — | — |
| hsa-miR-619 | — | — | — | — | — | — | — | — |
| hsa-miR-620 | — | — | — | — | — | — | — | — |
| hsa-mir-816 | — | — | — | — | — | 0.07 | — | — |
| hsa-mir-817 | — | 0.07 | — | — | — | — | — | — |
| hsa-mir-828-3p | — | — | — | — | — | — | — | — |
| hsa-mir-828-5p | — | — | — | — | — | — | — | — |
| hsa-mir-831-1 | — | — | — | — | — | — | — | — |
| hsa-mir-840-3p | — | — | — | 0.26 | — | 0.07 | — | — |
| hsa-mir-840-5p | — | — | — | — | — | 0.22 | 0.37 | 0.71 |
| hsa-mir-847 | — | — | — | — | — | — | — | — |
| hsa-mir-848 | 0.40 | — | — | — | — | — | — | — |
| hsa-mir-849 | — | — | — | — | — | — | — | — |
| hsa-mir-850 | 0.20 | — | — | — | — | — | — | — |
| hsa-mir-853 | — | — | — | — | — | — | — | — |
| hsa-mir-857 | — | — | — | — | — | — | — | — |
| hsa-mir-92b | — | — | — | — | — | 0.04 | — | — |
| hsa-miR-100516 | — | — | — | — | — | — | — | — |
| hsa-miR-100516 | — | 0.18 | — | — | — | — | — | — |
| hsa-miR-100604 | — | — | — | 0.16 | — | — | — | — |
| hsa-miR-100610-5p | — | — | — | — | — | — | — | 0.10 |
| hsa-miR-100631 | — | — | — | — | — | — | — | — |
| hsa-miR-100732 | — | — | — | — | — | — | — | — |
| hsa-miR-100814 | — | — | 0.14 | — | — | — | — | — |
| hsa-miR-100815 | — | — | — | — | — | 0.15 | 0.12 | — |
| hsa-miR-100818 | — | — | — | — | — | — | — | — |
| hsa-miR-100819 | — | — | — | — | — | — | — | — |
| hsa-miR-100824 | — | — | — | — | — | — | — | — |
| hsa-miR-100825-3p | — | — | — | — | — | — | — | — |
| hsa-miR-100825-5p | — | — | — | — | — | — | — | — |
| hsa-miR-100829-3p | — | — | — | — | — | — | — | — |
| hsa-miR-100835-5p | — | — | — | 0.16 | — | — | — | — |

TABLE G1-continued

Relative Cloning Frequency in % Relative to Total Number of Identified MicroRNA for Each Given Library.

| microRNA | | | | | | | | | |
|---|---|---|---|---|---|---|---|---|---|
| hsa-miR-100842 | — | — | — | — | — | — | — | — | — |
| hsa-miR-100843-3p | — | — | — | 0.14 | — | — | — | — | 0.10 |
| hsa-miR-100843-5p | — | — | — | — | — | — | 0.12 | — | 0.10 |
| hsa-miR-100846 | — | — | — | — | — | — | 0.12 | — | 0.10 |
| hsa-miR-100851 | — | — | — | — | — | — | — | — | — |
| hsa-miR-100852 | — | — | — | — | — | — | — | — | — |
| hsa-miR-100854 | — | — | — | — | 0.16 | — | — | — | — |
| hsa-miR-100855-3p | 0.18 | — | — | — | — | — | — | — | — |
| hsa-miR-100855-5p | 0.18 | — | — | — | — | — | — | — | — |
| hsa-miR-100869-3p | — | — | — | — | — | — | — | — | — |
| hsa-miR-100869-5p | — | — | — | — | — | — | — | — | — |
| hsa-miR-100871-3p | — | — | — | — | — | — | — | — | — |
| hsa-miR-100871-5p | — | — | — | — | — | — | — | — | — |
| hsa-miR-100885 | — | — | — | — | — | — | — | — | — |
| hsa-miR-100885 | — | — | — | — | — | — | — | — | — |
| hsa-miR-100887-3p | — | — | — | — | — | — | — | — | — |
| hsa-miR-100887-3p | — | — | — | — | — | — | — | — | — |
| hsa-miR-100887-5p | — | — | — | — | — | — | — | — | — |
| hsa-miR-100891-3p | — | — | — | — | — | — | — | — | — |
| hsa-miR-100891-3p | — | — | — | — | — | — | — | — | — |
| hsa-miR-100891-5p | — | — | — | — | — | — | — | — | — |
| hsa-miR-100891-5p | — | — | — | — | — | — | — | — | — |
| hsa-miR-101001 | — | — | — | 0.21 | — | — | — | — | — |
| hsa-miR-146b | — | — | — | — | — | — | — | — | 0.10 |
| hsa-miR-147b | — | — | — | — | — | — | — | — | — |
| hsa-miR-181d | — | — | — | — | — | — | — | — | — |
| hsa-miR-18b | — | — | — | — | — | — | — | — | 0.10 |
| hsa-mir-18b-3p | 0.18 | — | — | — | — | — | — | — | 0.10 |
| hsa-miR-193b | — | — | — | — | — | — | — | — | 0.10 |
| hsa-miR-20b | — | — | — | — | — | — | — | — | 0.10 |
| hsa-miR-20b-3p | — | — | — | — | — | — | — | — | 0.05 |
| hsa-miR-216b | — | — | — | — | — | — | — | — | — |
| hsa-miR-301b | — | — | — | — | — | — | — | — | — |
| hsa-miR-329 | — | — | — | — | — | — | — | — | — |
| hsa-miR-33b | — | — | — | — | 0.48 | 0.45 | — | — | 0.10 |
| hsa-miR-374b | 0.18 | — | — | — | 0.16 | — | — | — | — |
| hsa-miR-375 | — | — | — | — | — | — | — | — | — |
| hsa-miR-376a | — | — | — | — | — | — | — | — | — |
| hsa-miR-376b | — | — | — | — | — | — | — | — | — |
| hsa-miR-376c | — | — | — | — | — | — | — | — | — |
| hsa-miR-377 | — | — | — | — | — | — | — | — | — |
| hsa-miR-378 | — | — | — | — | — | — | — | — | 0.10 |
| hsa-miR-379 | — | — | — | — | — | — | — | — | — |
| hsa-miR-380 | — | — | — | — | — | — | — | — | — |
| hsa-miR-410 | — | — | — | — | — | — | — | — | — |
| hsa-miR-421-3p | — | — | — | — | — | — | — | — | — |
| hsa-miR-429 | — | — | — | — | — | — | — | — | — |
| hsa-miR-431 | — | — | — | — | — | — | — | — | — |
| hsa-miR-432 | — | — | — | — | — | — | — | — | — |

TABLE G1-continued

Relative Cloning Frequency in % Relative to Total Number of Identified MicroRNA for Each Given Library.

| | T-ALL | | | T-ALL in remission | AML | | | | |
|---|---|---|---|---|---|---|---|---|---|
| miRNA | hsa_jurk | hsa_T-ALL3_d0 | hsa_T-ALL4_d0 | hsa_T-ALL4_d29 | hsa_kas1 | hsa_HL60 | hsa_AML1_d0 | hsa_AML2_d0 | hsa_AML3_d0 |
| hsa-miR-433 | — | — | — | — | — | — | — | — | — |
| hsa-miR-449a | — | — | — | — | — | — | — | — | — |
| hsa-miR-449b | — | — | — | — | — | — | — | — | — |
| hsa-miR-450a | — | 0.18 | — | — | — | — | — | — | — |
| hsa-miR-451 | 1.68 | — | — | — | — | — | — | 0.25 | 0.20 |
| hsa-miR-452 | — | — | — | — | 0.30 | — | — | — | — |
| hsa-miR-453 | — | — | — | — | — | — | — | — | — |
| hsa-miR-454 | — | — | — | 0.16 | — | — | — | 0.12 | 0.10 |
| hsa-miR-455-5p | — | — | — | — | — | — | — | — | — |
| hsa-miR-485-3p | — | — | — | — | — | — | — | — | — |
| hsa-miR-485-5p | — | — | — | — | — | — | — | — | — |
| hsa-mir-486_os | — | — | — | — | — | — | — | — | — |
| hsa-miR-487 | — | — | — | — | — | — | — | — | — |
| hsa-miR-488 | — | — | — | — | — | — | — | — | — |
| hsa-miR-490 | — | — | — | — | — | — | — | — | — |
| hsa-miR-493 | — | — | — | — | — | — | — | — | — |
| hsa-miR-497 | 0.30 | — | — | — | — | — | — | — | — |
| hsa-miR-502 | — | — | — | — | — | — | — | — | — |
| hsa-miR-503 | — | 0.18 | — | 0.16 | — | — | — | — | — |
| hsa-miR-505 | — | — | 0.14 | — | — | — | — | — | — |
| hsa-miR-509-3p | — | — | — | — | — | — | — | — | — |
| hsa-miR-514 | — | — | — | — | — | — | — | — | — |
| hsa-miR-544 | — | — | — | — | — | — | — | — | — |
| hsa-miR-618 | — | — | — | — | — | — | — | — | — |
| hsa-miR-619 | — | — | — | — | — | — | — | — | — |
| hsa-miR-620 | — | — | — | — | — | — | — | — | — |
| hsa-mir-816 | — | — | — | — | — | — | — | — | — |
| hsa-mir-817 | — | — | — | — | — | — | — | — | — |
| hsa-mir-828-3p | — | — | — | — | — | — | — | — | — |
| hsa-mir-828-5p | — | — | — | — | — | — | — | — | — |
| hsa-mir-831-1 | — | — | — | — | — | — | — | — | — |
| hsa-mir-840-3p | — | 0.18 | — | — | — | — | — | — | — |
| hsa-mir-840-5p | — | — | — | — | — | — | — | — | — |
| hsa-mir-847 | — | — | — | — | — | — | — | — | — |
| hsa-mir-848 | — | — | — | — | — | — | — | — | — |
| hsa-mir-849 | — | — | — | — | — | — | — | — | — |
| hsa-mir-850 | — | 0.18 | — | — | — | — | — | — | — |
| hsa-mir-853 | — | — | — | — | — | — | 0.15 | — | — |
| hsa-mir-857 | — | — | — | — | — | — | — | — | — |
| hsa-miR-92b | — | 0.36 | — | 0.65 | — | 0.28 | — | 0.14 | 0.15 |
| hsa-miR-100516 | — | — | — | — | — | — | 0.10 | — | — |
| hsa-miR-100516 | — | — | — | — | — | — | 0.10 | — | 0.15 |
| hsa-miR-100604 | — | — | — | — | — | — | — | — | — |
| hsa-miR-100610-5p | — | 0.15 | — | — | — | — | — | — | — |
| hsa-miR-100631 | — | — | — | — | — | — | — | — | — |

TABLE G1-continued

Relative Cloning Frequency in % Relative to Total Number of Identified MicroRNA for Each Given Library.

| | | | | | | | | | |
|---|---|---|---|---|---|---|---|---|---|
| hsa-miR-100732 | — | — | — | — | — | — | — | — | — |
| hsa-miR-100814 | — | — | — | — | — | — | — | — | — |
| hsa-miR-100815 | 0.17 | 0.36 | 0.26 | — | — | — | — | — | — |
| hsa-miR-100818 | — | — | — | — | — | 0.29 | — | 0.14 | — |
| hsa-miR-100819 | — | — | — | — | — | — | — | — | — |
| hsa-miR-100824 | — | — | — | — | — | — | — | — | — |
| hsa-miR-100825-3p | — | 0.07 | — | — | — | — | — | — | — |
| hsa-miR-100825-5p | — | 0.07 | — | — | — | — | — | — | — |
| hsa-miR-100829-3p | — | — | — | — | — | — | — | — | — |
| hsa-miR-100835-5p | 0.17 | — | — | 0.41 | — | — | — | — | — |
| hsa-miR-100842 | — | — | — | — | — | — | — | — | — |
| hsa-miR-100843-3p | — | — | — | 0.08 | — | — | — | — | — |
| hsa-miR-100843-5p | — | — | — | 0.08 | — | — | — | — | — |
| hsa-miR-100846 | — | — | — | — | — | — | — | — | — |
| hsa-miR-100851 | — | — | — | — | — | — | — | — | — |
| hsa-miR-100852 | — | — | — | — | — | — | — | — | — |
| hsa-miR-100854 | — | — | — | — | — | — | — | — | — |
| hsa-miR-100855-3p | — | 0.15 | — | 0.16 | — | 0.20 | — | — | — |
| hsa-miR-100855-5p | — | 0.15 | — | 0.16 | — | 0.20 | — | — | — |
| hsa-miR-100869-3p | — | — | — | — | — | — | — | — | — |
| hsa-miR-100869-5p | — | — | — | — | — | — | — | — | — |
| hsa-miR-100871-3p | — | — | — | — | — | — | — | — | — |
| hsa-miR-100871-5p | — | — | — | — | — | — | — | — | — |
| hsa-miR-100885 | — | — | — | — | — | — | — | — | — |
| hsa-miR-100887-3p | — | — | — | — | — | — | — | — | — |
| hsa-miR-100887-5p | — | — | — | — | — | — | — | — | — |
| hsa-miR-100891-3p | — | — | — | — | — | — | — | — | — |
| hsa-miR-100891-5p | — | — | — | — | — | — | — | — | — |
| hsa-miR-101001 | — | — | — | — | — | — | — | — | — |
| hsa-miR-146b | — | — | — | — | — | — | — | — | — |
| hsa-miR-147b | — | — | — | — | — | — | — | — | — |
| hsa-miR-181d | — | 0.07 | — | — | — | 0.20 | — | — | — |
| hsa-miR-18b | — | 0.07 | — | — | — | 0.20 | — | — | — |
| hsa-mir-18b-3p | — | — | — | — | — | — | — | — | — |
| hsa-miR-193b | — | — | — | — | — | — | — | — | — |
| hsa-miR-20b | — | — | — | — | — | — | — | — | — |
| hsa-miR-20b-3p | — | — | — | — | — | — | — | — | — |
| hsa-miR-216b | 0.67 | 0.07 | — | — | 0.71 | — | — | 0.07 | — |
| hsa-miR-301b | — | — | — | — | 0.71 | — | — | — | — |
| hsa-miR-329 | — | — | 0.26 | — | — | — | — | — | — |
| hsa-miR-33b | — | — | — | 0.16 | — | 0.10 | 0.28 | — | — |
| hsa-miR-374b | — | — | — | — | — | — | — | — | — |
| hsa-miR-375 | — | — | — | — | — | — | — | — | — |
| hsa-miR-376a | — | — | — | — | — | — | — | 0.14 | — |
| hsa-miR-376b | — | — | — | — | — | — | — | — | — |
| hsa-miR-376c | — | — | — | — | — | — | — | — | — |

TABLE G1-continued

Relative Cloning Frequency in % Relative to Total Number of Identified MicroRNA for Each Given Library.

| miRNA | | | | | | | |
|---|---|---|---|---|---|---|---|
| hsa-miR-376c | — | — | — | — | — | — | — |
| hsa-miR-377 | — | 0.07 | 0.78 | — | — | — | — |
| hsa-miR-378 | — | — | 0.78 | — | — | 0.14 | — |
| hsa-miR-379 | — | — | 0.08 | — | 0.56 | — | — |
| hsa-miR-380 | — | — | 0.08 | — | — | — | — |
| hsa-miR-410 | — | — | — | — | — | — | — |
| hsa-miR-421-3p | — | — | — | — | — | — | — |
| hsa-miR-429 | — | — | — | — | — | — | — |
| hsa-miR-431 | — | — | — | — | — | — | — |
| hsa-miR-432 | — | — | — | — | — | — | — |
| hsa-miR-433 | — | — | — | — | — | — | — |
| hsa-miR-449a | — | 0.07 | 0.08 | — | — | — | — |
| hsa-miR-449b | — | — | — | — | — | — | — |
| hsa-miR-450a | — | — | — | — | — | — | — |
| hsa-miR-451 | — | — | — | — | — | — | 0.31 |
| hsa-miR-452 | — | — | — | — | — | — | — |
| hsa-miR-453 | — | — | — | — | — | — | — |
| hsa-miR-454 | 0.17 | — | — | — | — | — | — |
| hsa-miR-455-5p | — | — | 0.08 | — | — | 0.14 | — |
| hsa-miR-484 | — | — | — | — | — | — | — |
| hsa-miR-485-3p | — | — | — | — | — | — | — |
| hsa-miR-485-5p | — | — | — | — | — | — | — |
| hsa-mir-486_os | — | — | — | — | — | — | — |
| hsa-miR-487 | — | — | — | — | — | — | — |
| hsa-miR-488 | — | — | — | — | — | — | — |
| hsa-miR-490 | — | — | — | — | — | — | — |
| hsa-miR-493 | — | 0.22 | — | 0.26 | — | — | — |
| hsa-miR-497 | — | — | 0.08 | — | — | 0.14 | — |
| hsa-miR-502 | — | — | — | — | — | — | — |
| hsa-miR-503 | — | 0.07 | 0.24 | — | — | — | — |
| hsa-miR-505 | — | — | — | — | — | — | — |
| hsa-miR-509-3p | — | — | — | — | — | — | — |
| hsa-miR-514 | — | — | — | — | — | — | — |
| hsa-miR-544 | — | — | — | — | — | — | — |
| hsa-miR-618 | — | — | — | — | — | — | — |
| hsa-miR-619 | — | — | — | — | — | — | — |
| hsa-miR-620 | — | — | — | — | — | — | — |
| hsa-mir-816 | — | — | — | — | — | — | — |
| hsa-mir-817 | — | — | — | — | — | — | — |
| hsa-miR-828-3p | — | — | — | — | — | — | — |
| hsa-miR-828-5p | — | — | — | — | — | — | — |
| hsa-mir-831-1 | — | — | — | — | — | — | — |
| hsa-miR-840-3p | — | — | — | — | — | — | — |
| hsa-miR-840-5p | — | — | — | — | — | 0.27 | — |
| hsa-mir-847 | — | — | — | — | — | — | — |
| hsa-mir-848 | — | — | — | — | — | — | — |
| hsa-mir-849 | — | — | — | — | — | — | — |
| hsa-mir-850 | — | — | — | — | — | — | — |
| hsa-mir-853 | — | — | — | — | — | — | — |
| hsa-mir-857 | — | — | — | — | — | — | — |
| hsa-miR-92b | — | — | — | — | — | — | — |

TABLE G1-continued

Relative Cloning Frequency in % Relative to Total Number of Identified MicroRNA for Each Given Library.

| miRNA | hsa_pituitary | SW13 | SW13_YFV | Endocrine organs hsa_ovary | hsa_testis | hsa_thyroid | hsa_pancreatic_islet | Unrestricted somatic stem cells hsa_USSC_d1 |
|---|---|---|---|---|---|---|---|---|
| hsa-miR-100516 | — | — | — | — | — | — | — | — |
| hsa-miR-100516 | — | — | — | — | — | — | — | — |
| hsa-miR-100604 | 0.06 | — | — | — | — | — | — | — |
| hsa-miR-100610-5p | — | 0.13 | 0.12 | 0.23 | — | — | — | — |
| hsa-miR-100631 | — | — | — | — | — | — | — | 0.07 |
| hsa-miR-100732 | — | — | — | — | 0.15 | — | — | — |
| hsa-miR-100814 | — | — | — | — | 0.07 | — | — | — |
| hsa-miR-100815 | 0.06 | — | — | — | — | — | 0.09 | — |
| hsa-miR-100818 | — | — | — | — | — | — | — | 0.07 |
| hsa-miR-100819 | — | — | — | — | — | — | — | — |
| hsa-miR-100824 | — | — | — | — | — | — | — | — |
| hsa-miR-100825-3p | 0.18 | — | — | — | — | — | — | — |
| hsa-miR-100825-5p | 0.18 | — | — | — | — | — | — | — |
| hsa-miR-100829-3p | — | — | 0.24 | — | — | — | — | — |
| hsa-miR-100835-5p | — | 0.27 | — | — | — | — | — | — |
| hsa-miR-100842 | — | — | — | — | — | — | — | — |
| hsa-miR-100843-3p | 0.06 | — | — | 0.46 | — | — | — | — |
| hsa-miR-100843-5p | 0.06 | — | — | 0.46 | — | — | — | — |
| hsa-miR-100846 | — | — | — | — | — | — | — | — |
| hsa-miR-100851 | — | — | — | — | — | — | — | — |
| hsa-miR-100852 | — | — | — | 0.08 | — | — | — | — |
| hsa-miR-100854 | — | — | — | 0.53 | — | — | — | — |
| hsa-miR-100855-3p | 0.12 | — | — | 0.53 | 0.51 | — | 0.19 | 0.07 |
| hsa-miR-100855-5p | 0.12 | — | — | — | 0.51 | — | 0.19 | 0.07 |
| hsa-miR-100869-3p | — | — | — | — | — | — | — | 0.07 |
| hsa-miR-100869-5p | — | — | — | — | — | — | — | 0.07 |
| hsa-miR-100871-3p | — | 0.13 | 0.24 | — | — | — | — | 0.14 |
| hsa-miR-100871-5p | — | 0.13 | 0.24 | — | — | — | — | 0.14 |
| hsa-miR-100885 | — | 0.13 | 0.12 | — | — | — | 0.09 | — |
| hsa-miR-100885 | — | 0.13 | 0.12 | — | — | — | 0.09 | — |
| hsa-miR-100887-3p | — | — | 0.12 | — | — | — | — | — |
| hsa-miR-100887-5p | — | — | 0.12 | — | — | — | — | — |
| hsa-miR-100891-3p | — | — | — | — | — | — | — | — |
| hsa-miR-100891-3p | — | — | — | — | — | — | — | — |
| hsa-miR-100891-5p | — | — | — | — | — | — | — | — |
| hsa-miR-100891-5p | — | — | — | — | — | — | — | — |
| hsa-miR-101001 | 0.06 | — | — | — | 0.07 | — | — | 0.07 |
| hsa-miR-146b | — | — | 0.24 | — | — | — | — | — |
| hsa-miR-147b | — | — | — | — | — | — | 0.09 | — |
| hsa-miR-181d | — | 0.20 | 0.12 | — | — | — | — | — |
| hsa-miR-18b | — | 0.20 | 1.09 | — | — | — | — | — |
| hsa-mir-18b-3p | — | — | 1.09 | — | — | — | — | — |
| hsa-miR-193b | — | — | — | 0.23 | — | — | — | 0.07 |

TABLE G1-continued

Relative Cloning Frequency in % Relative to Total Number of Identified MicroRNA for Each Given Library.

| miRNA | Lib1 | Lib2 | Lib3 | Lib4 | Lib5 | Lib6 | Lib7 |
|---|---|---|---|---|---|---|---|
| hsa-miR-20b | — | 1.87 | — | 2.91 | — | — | 0.04 |
| hsa-miR-20b-3p | — | 1.87 | — | 2.91 | — | — | 0.04 |
| hsa-miR-216b | — | — | — | 0.61 | — | — | — |
| hsa-miR-301b | 0.06 | 0.13 | — | — | — | — | 0.07 |
| hsa-miR-329 | — | — | — | — | — | — | — |
| hsa-miR-33b | 0.06 | 0.13 | — | — | — | — | — |
| hsa-miR-374b | 0.06 | 0.20 | 0.08 | — | — | — | 0.21 |
| hsa-miR-375 | 3.05 | — | — | — | — | 5.07 | — |
| hsa-miR-376a | 0.18 | — | 0.08 | — | — | 0.09 | 0.07 |
| hsa-miR-376b | 0.18 | — | — | — | — | 0.09 | 0.07 |
| hsa-miR-376c | 0.18 | — | — | — | — | 0.19 | 0.07 |
| hsa-miR-377 | 0.24 | — | 0.23 | — | — | 0.19 | 0.07 |
| hsa-miR-378 | 0.06 | 0.53 | — | — | — | 0.19 | 0.35 |
| hsa-miR-379 | 0.24 | — | 0.22 | — | — | 0.38 | 0.14 |
| hsa-miR-380 | — | — | — | — | — | — | — |
| hsa-miR-410 | 0.43 | — | — | — | — | 0.19 | 0.07 |
| hsa-miR-421-3p | 0.12 | — | — | — | — | — | — |
| hsa-miR-429 | — | — | — | — | — | 0.09 | — |
| hsa-miR-431 | 0.06 | — | 0.08 | — | — | 0.19 | 0.14 |
| hsa-miR-432 | 0.06 | — | — | — | — | 0.09 | 0.14 |
| hsa-miR-433 | — | — | — | — | — | — | — |
| hsa-miR-449a | — | — | — | — | — | — | — |
| hsa-miR-449b | — | 0.13 | — | — | — | 0.29 | — |
| hsa-miR-450a | — | — | — | — | — | 0.07 | — |
| hsa-miR-451 | 1.28 | — | 0.76 | — | 1.92 | — | — |
| hsa-miR-452 | — | — | — | — | — | — | 0.07 |
| hsa-miR-453 | — | — | — | — | — | — | 0.07 |
| hsa-miR-454 | 0.06 | 0.24 | — | — | — | — | — |
| hsa-miR-455-5p | — | — | — | — | — | 0.19 | — |
| hsa-miR-484 | — | — | — | — | — | — | — |
| hsa-miR-485-3p | — | — | — | — | — | — | 0.07 |
| hsa-miR-485-5p | — | — | — | — | — | — | 0.07 |
| hsa-mir-486_os | — | — | — | — | — | — | — |
| hsa-miR-487 | — | — | — | — | — | — | — |
| hsa-miR-488 | — | — | — | — | — | — | — |
| hsa-miR-490 | — | — | — | — | — | — | — |
| hsa-miR-493 | — | — | — | — | — | — | 0.14 |
| hsa-miR-497 | — | — | 0.15 | — | 0.52 | 0.15 | — |
| hsa-miR-502 | 0.06 | 0.12 | — | — | — | 0.58 | — |
| hsa-miR-503 | — | — | — | — | — | — | — |
| hsa-miR-505 | — | — | — | — | — | 0.73 | — |
| hsa-miR-509-3p | 0.12 | — | 0.15 | — | — | 0.58 | — |
| hsa-miR-514 | — | — | — | — | — | — | — |
| hsa-miR-544 | — | — | — | — | — | — | — |
| hsa-miR-618 | — | 0.24 | — | — | — | — | — |
| hsa-miR-619 | 0.06 | 0.24 | — | — | — | — | 0.07 |
| hsa-miR-620 | — | — | — | — | — | — | — |
| hsa-mir-816 | — | 0.12 | — | — | — | — | — |
| hsa-mir-817 | — | — | — | — | — | — | — |
| hsa-mir-828-3p | — | — | — | — | — | — | — |

TABLE G1-continued

Relative Cloning Frequency in % Relative to Total Number of Identified MicroRNA for Each Given Library.

| | Embryonal derived cell lines/tumors | | | Placenta | Cervix carcinoma | | Epididymis | Prostate |
|---|---|---|---|---|---|---|---|---|
| miRNA | hsa_NT2/D1 | NCCIT | hsa_Hela exp | hsa_placenta | hsa_HeLa_susp | HeLa_HIV infected | hsa_epididymis | hsa_prostate |
| hsa-mir-828-5p | — | — | — | — | — | — | — | — |
| hsa-mir-831-1 | — | — | 0.13 | 0.12 | — | — | — | — |
| hsa-mir-840-3p | — | — | — | 0.12 | — | — | — | — |
| hsa-mir-840-5p | — | — | — | — | — | — | — | 0.08 |
| hsa-mir-847 | — | — | — | 0.12 | — | — | — | — |
| hsa-mir-848 | — | — | — | — | — | — | — | — |
| hsa-mir-849 | — | — | — | — | — | — | — | — |
| hsa-mir-850 | — | — | — | — | — | — | — | — |
| hsa-mir-853 | — | — | 0.13 | — | — | — | — | — |
| hsa-miR-92b | 0.06 | — | 0.13 | 0.12 | — | — | — | — |
| hsa-miR-100516 | — | — | — | — | — | — | 1.18 | — |
| hsa-miR-100516 | — | — | — | — | — | — | 1.18 | — |
| hsa-miR-100604 | 0.12 | — | — | — | — | — | — | — |
| hsa-miR-100610-5p | 0.12 | — | 0.25 | 0.06 | — | — | 0.08 | 0.08 |
| hsa-miR-100631 | — | — | — | — | — | — | — | — |
| hsa-miR-100732 | 0.12 | — | — | — | — | — | — | — |
| hsa-miR-100814 | 0.12 | — | — | — | — | — | — | — |
| hsa-miR-100815 | — | 0.73 | 0.51 | — | — | — | — | — |
| hsa-miR-100818 | — | — | — | — | — | — | — | — |
| hsa-miR-100819 | — | — | — | — | — | — | — | — |
| hsa-miR-100824 | — | — | — | — | — | — | — | — |
| hsa-miR-100825-3p | 0.12 | — | 0.25 | — | — | — | — | — |
| hsa-miR-100825-5p | 1.70 | — | 0.25 | — | — | — | — | — |
| hsa-miR-100829-3p | 1.70 | — | — | — | — | — | — | — |
| hsa-miR-100835-5p | — | — | — | — | — | 1.22 | — | — |
| hsa-miR-100842 | — | — | — | — | — | — | — | — |
| hsa-miR-100843-3p | 0.12 | — | — | — | — | — | — | — |
| hsa-miR-100843-5p | 0.36 | — | — | — | — | — | — | — |
| hsa-miR-100846 | — | — | — | — | — | — | — | — |
| hsa-miR-100851 | — | — | — | — | — | — | — | — |
| hsa-miR-100852 | — | — | — | — | — | — | — | — |
| hsa-miR-100854 | — | — | — | — | — | — | — | — |
| hsa-miR-100855-3p | — | — | — | — | — | — | 0.16 | 0.23 |
| hsa-miR-100855-5p | — | — | — | — | — | — | 0.16 | 0.23 |
| hsa-miR-100869-3p | — | — | — | — | — | — | — | — |
| hsa-miR-100869-5p | — | — | — | — | — | — | — | — |
| hsa-miR-100871-3p | — | 0.73 | — | — | 0.22 | — | — | — |
| hsa-miR-100871-5p | — | 0.73 | — | — | 0.22 | — | — | — |
| hsa-miR-100885 | — | — | — | 0.06 | — | — | — | — |
| hsa-miR-100885 | — | — | — | 0.06 | — | — | — | — |
| hsa-miR-100887-3p | — | — | — | — | — | — | — | — |
| hsa-miR-100887-5p | — | — | — | — | — | — | — | — |
| hsa-miR-100891-3p | — | — | — | — | — | — | — | — |

TABLE G1-continued

Relative Cloning Frequency in % Relative to Total Number of Identified MicroRNA for Each Given Library.

| miRNA | | | | | | | | |
|---|---|---|---|---|---|---|---|---|
| hsa-miR-100891-3p | — | — | — | — | — | — | — | — |
| hsa-miR-100891-5p | — | — | — | — | — | — | — | — |
| hsa-miR-100891-5p | — | — | — | — | — | — | — | — |
| hsa-miR-101001 | 0.12 | — | — | — | — | — | — | — |
| hsa-miR-1466 | — | — | — | — | — | — | — | — |
| hsa-miR-147b | — | — | — | — | — | — | — | — |
| hsa-miR-181d | — | — | — | — | — | — | — | — |
| hsa-miR-18b | — | 0.73 | 0.13 | — | — | — | — | — |
| hsa-mir-18b-3p | — | 0.73 | 0.13 | — | — | — | — | — |
| hsa-miR-193b | 0.36 | 0.73 | 0.25 | 0.06 | 0.43 | — | — | 0.16 |
| hsa-miR-20b | 0.36 | 0.73 | 0.13 | — | — | — | — | 0.08 |
| hsa-miR-20b-3p | — | — | 0.13 | — | — | — | — | 0.08 |
| hsa-miR-216b | — | — | — | — | — | — | — | — |
| hsa-miR-301b | — | — | — | — | — | — | — | — |
| hsa-miR-329 | — | — | 0.51 | — | — | — | — | — |
| hsa-miR-33b | 0.48 | 1.46 | 0.25 | — | 0.43 | 0.41 | — | 0.08 |
| hsa-miR-374b | — | — | — | — | — | — | — | 0.08 |
| hsa-miR-375 | — | — | — | — | — | — | — | — |
| hsa-miR-376a | — | — | — | 0.06 | — | — | — | — |
| hsa-miR-376b | — | — | — | 0.06 | — | — | — | — |
| hsa-miR-376c | — | — | — | 0.06 | — | — | — | — |
| hsa-miR-376c | — | — | — | 0.19 | — | — | — | — |
| hsa-miR-377 | — | — | 0.25 | — | — | — | — | — |
| hsa-miR-378 | — | — | — | 0.06 | — | — | — | — |
| hsa-miR-379 | — | — | — | — | — | — | — | — |
| hsa-miR-380 | — | — | — | — | — | — | — | — |
| hsa-miR-410 | — | — | — | — | — | — | 0.08 | — |
| hsa-miR-421-3p | — | — | — | 0.19 | — | — | — | — |
| hsa-miR-429 | — | — | — | — | — | — | — | — |
| hsa-miR-431 | — | — | — | — | — | — | — | — |
| hsa-miR-432 | — | — | — | — | — | — | — | — |
| hsa-miR-433 | — | — | — | — | — | — | 0.08 | — |
| hsa-miR-449a | — | — | — | — | — | — | — | — |
| hsa-miR-449b | — | — | — | — | — | — | — | — |
| hsa-miR-450a | — | — | — | 0.51 | — | — | 0.39 | 0.16 |
| hsa-miR-451 | — | — | — | — | — | — | — | — |
| hsa-miR-452 | — | — | 0.25 | — | — | — | — | — |
| hsa-miR-453 | — | — | 0.25 | — | — | — | — | — |
| hsa-miR-454 | 0.12 | — | — | — | — | — | — | 0.08 |
| hsa-miR-455-5p | — | — | — | — | — | 0.41 | — | — |
| hsa-miR-484 | — | — | — | — | — | — | — | — |
| hsa-miR-485-3p | — | — | — | — | — | — | — | — |
| hsa-miR-485-5p | — | — | — | — | — | 0.41 | — | — |
| hsa-mir-486_os | 0.12 | — | — | — | — | — | — | — |
| hsa-miR-487 | — | — | — | — | — | — | — | — |
| hsa-miR-488 | — | — | — | — | — | — | — | — |
| hsa-miR-490 | — | — | — | — | — | — | — | 0.08 |
| hsa-miR-493 | — | — | — | 0.11 | — | — | — | — |
| hsa-miR-497 | — | — | — | — | — | — | — | — |
| hsa-miR-502 | — | — | 0.25 | 0.25 | — | — | — | — |
| hsa-miR-503 | — | — | — | — | — | — | — | — |

TABLE G1-continued

Relative Cloning Frequency in % Relative to Total Number of Identified MicroRNA for Each Given Library.

| | hsa_MCF10A | hsa_MCF7 | hsa_HCC38 | hsa_SkBr3 | hsa_BT474 | hsa_T47 | hsa_A673 |
|---|---|---|---|---|---|---|---|
| hsa-miR-505 | — | — | — | — | — | — | 0.08 |
| hsa-miR-509-3p | — | — | — | — | — | — | — |
| hsa-miR-514 | — | — | — | — | — | — | — |
| hsa-miR-544 | — | — | — | — | — | — | — |
| hsa-miR-618 | — | — | — | — | — | — | — |
| hsa-miR-619 | — | — | — | — | — | — | — |
| hsa-miR-620 | — | — | — | — | — | — | — |
| hsa-mir-816 | — | 0.25 | — | — | — | — | — |
| hsa-mir-817 | — | — | — | — | 0.82 | — | — |
| hsa-mir-828-3p | — | — | — | — | — | — | — |
| hsa-mir-828-5p | — | — | — | — | — | — | — |
| hsa-mir-831-1 | — | — | — | — | — | — | — |
| hsa-mir-840-3p | 0.73 | — | — | — | 0.41 | — | — |
| hsa-miR-840-5p | 0.36 | — | 0.06 | — | 0.22 | — | — |
| hsa-mir-847 | — | — | — | — | — | — | — |
| hsa-mir-848 | — | — | — | — | — | — | — |
| hsa-mir-849 | — | — | — | — | — | — | — |
| hsa-mir-850 | — | — | — | — | — | — | — |
| hsa-mir-853 | 0.12 | — | — | — | — | — | — |
| hsa-mir-857 | 0.36 | — | — | — | — | — | — |
| hsa-miR-92b | — | — | — | — | — | — | — |

| | Breast Carcinoma | | | | | | Ewing Sarcoma |
|---|---|---|---|---|---|---|---|
| miRNA | hsa_MCF10A | hsa_MCF7 | hsa_HCC38 | hsa_SkBr3 | hsa_BT474 | hsa_T47 | hsa_A673 |
| hsa-miR-100516 | — | — | — | — | — | — | — |
| hsa-miR-100516 | 0.18 | — | — | — | — | — | — |
| hsa-miR-100604 | — | — | 0.18 | — | 0.18 | — | — |
| hsa-miR-100610-5p | — | 0.25 | — | — | — | 0.17 | 0.09 |
| hsa-miR-100631 | — | — | — | — | — | — | — |
| hsa-miR-100732 | — | — | — | — | — | — | — |
| hsa-miR-100814 | — | 0.13 | 0.09 | — | 0.05 | — | — |
| hsa-miR-100815 | — | — | — | — | 0.05 | — | 0.09 |
| hsa-miR-100818 | — | — | — | — | — | — | — |
| hsa-miR-100819 | — | — | — | — | — | — | — |
| hsa-miR-100824 | — | — | — | — | — | — | — |
| hsa-miR-100825-3p | — | — | — | — | — | — | — |
| hsa-miR-100825-5p | — | — | — | — | — | — | — |
| hsa-miR-100829-3p | — | 0.13 | — | — | 0.05 | — | — |
| hsa-miR-100835-5p | — | 0.13 | — | — | 0.23 | — | 0.09 |
| hsa-miR-100843-3p | — | — | — | — | 0.23 | — | 0.09 |
| hsa-miR-100843-5p | — | — | — | — | — | — | — |
| hsa-miR-100846 | — | — | — | — | — | — | — |
| hsa-miR-100851 | — | — | — | 0.12 | — | — | — |
| hsa-miR-100852 | — | — | — | — | — | — | — |
| hsa-miR-100854 | — | — | — | — | — | — | — |
| hsa-miR-100855-3p | — | — | 0.18 | — | — | — | — |
| hsa-miR-100855-5p | — | — | 0.18 | — | — | — | — |
| hsa-miR-100869-3p | — | — | — | — | — | — | — |

TABLE G1-continued

Relative Cloning Frequency in % Relative to Total Number of Identified MicroRNA for Each Given Library.

| | | | | | | | |
|---|---|---|---|---|---|---|---|
| hsa-miR-100869-5p | — | — | — | — | — | — | — |
| hsa-miR-100871-3p | — | — | — | — | — | — | — |
| hsa-miR-100871-5p | — | — | — | — | — | — | — |
| hsa-miR-100885 | — | — | — | — | — | — | — |
| hsa-miR-100887-3p | — | — | — | — | — | — | — |
| hsa-miR-100887-5p | — | — | — | — | — | — | — |
| hsa-miR-100891-3p | — | — | — | — | — | — | 0.18 |
| hsa-miR-100891-3p | — | — | — | — | — | — | 0.18 |
| hsa-miR-100891-5p | — | — | — | — | — | — | 0.18 |
| hsa-miR-100891-5p | — | — | — | — | — | — | 0.18 |
| hsa-miR-101001 | — | — | — | — | — | — | — |
| hsa-miR-146b | — | — | — | — | — | — | — |
| hsa-miR-147b | — | — | — | 0.02 | — | — | — |
| hsa-miR-181d | — | — | 0.18 | 0.02 | — | — | — |
| hsa-miR-18b | — | — | 0.18 | 0.02 | — | — | — |
| hsa-mir-18b-3p | 0.09 | 0.25 | — | 0.05 | — | — | — |
| hsa-miR-193b | — | — | — | — | 0.23 | 0.17 | 0.09 |
| hsa-miR-20b | — | — | — | — | — | — | 0.03 |
| hsa-miR-20b-3p | — | — | — | — | — | — | 0.03 |
| hsa-miR-216b | — | — | — | — | — | 0.59 | 0.45 |
| hsa-miR-301b | — | — | — | — | — | — | — |
| hsa-miR-329 | 0.09 | 0.13 | 0.09 | 0.60 | — | 0.08 | — |
| hsa-miR-33b | — | — | 0.18 | 0.05 | — | 0.42 | 0.63 |
| hsa-miR-374b | — | 4.26 | — | — | 0.12 | 0.17 | — |
| hsa-miR-375 | — | — | — | — | — | — | — |
| hsa-miR-376a | — | — | — | — | — | — | 0.09 |
| hsa-miR-376b | — | — | — | — | — | — | — |
| hsa-miR-376c | — | — | — | — | — | — | — |
| hsa-miR-377 | 0.46 | — | — | 0.28 | 0.23 | — | 0.72 |
| hsa-miR-378 | — | 0.13 | — | — | — | — | 0.09 |
| hsa-miR-379 | — | — | — | — | — | — | — |
| hsa-miR-380 | — | — | — | — | — | — | — |
| hsa-miR-410 | — | 0.13 | — | — | — | 0.08 | 0.18 |
| hsa-miR-421-3p | — | 0.25 | — | 0.09 | — | 0.25 | 0.18 |
| hsa-miR-429 | — | — | — | — | — | — | — |
| hsa-miR-431 | — | — | — | — | — | — | — |
| hsa-miR-432 | — | — | — | — | — | — | — |
| hsa-miR-433 | — | — | — | — | — | — | 0.09 |
| hsa-miR-449a | — | — | — | — | — | — | — |
| hsa-miR-449b | — | — | — | — | — | — | — |
| hsa-miR-450a | — | — | — | — | — | — | — |
| hsa-miR-451 | — | — | — | — | 0.12 | — | — |
| hsa-miR-452 | — | — | — | 0.05 | — | — | 0.09 |
| hsa-miR-453 | — | — | — | 0.97 | — | — | — |
| hsa-miR-454 | — | — | 0.18 | — | — | 0.34 | — |
| hsa-miR-455-5p | — | — | — | — | — | — | — |
| hsa-miR-484 | — | — | — | — | — | 0.05 | — |

TABLE G1-continued

Relative Cloning Frequency in % Relative to Total Number of Identified MicroRNA for Each Given Library.

| | | | | | | | |
|---|---|---|---|---|---|---|---|
| hsa-miR-485-3p | — | — | — | — | — | — | — |
| hsa-miR-485-5p | — | — | — | — | — | — | — |
| hsa-miR-486_os | — | — | — | — | — | — | — |
| hsa-miR-487 | — | — | — | — | — | — | 0.27 |
| hsa-miR-488 | — | — | — | — | — | — | — |
| hsa-miR-490 | — | 0.13 | — | — | — | — | 0.09 |
| hsa-miR-493 | — | 0.13 | — | — | — | — | — |
| hsa-miR-497 | — | — | — | 0.05 | — | 0.08 | — |
| hsa-miR-502 | — | 0.50 | — | — | — | — | — |
| hsa-miR-503 | — | — | — | — | — | — | 1.53 |
| hsa-miR-505 | — | — | — | — | — | — | — |
| hsa-miR-509-3p | — | — | — | — | — | — | — |
| hsa-miR-514 | — | — | — | — | — | — | — |
| hsa-miR-544 | — | — | — | — | — | — | — |
| hsa-miR-618 | — | — | — | — | — | — | — |
| hsa-miR-619 | — | 0.25 | — | — | — | — | — |
| hsa-miR-620 | — | 0.13 | — | — | — | — | — |
| hsa-miR-816 | 0.09 | — | — | — | — | — | — |
| hsa-miR-817 | — | — | — | — | — | — | — |
| hsa-miR-828-3p | — | — | — | — | — | — | — |
| hsa-miR-828-5p | — | — | — | — | — | — | — |
| hsa-miR-831-1 | — | — | — | — | — | — | — |
| hsa-miR-840-3p | — | — | — | 0.05 | — | — | — |
| hsa-miR-840-5p | — | — | — | 0.55 | — | 0.51 | 0.18 |
| hsa-miR-847 | — | — | 0.23 | — | — | — | — |
| hsa-miR-848 | — | — | 0.23 | — | — | — | — |
| hsa-miR-849 | — | — | — | — | — | — | — |
| hsa-miR-850 | — | — | — | — | — | — | — |
| hsa-miR-853 | — | — | — | — | — | — | 0.09 |
| hsa-miR-857 | — | — | — | — | — | — | — |
| hsa-miR-92b | — | 0.50 | 0.12 | — | — | — | 0.09 |

EXAMPLES

Example 1

Materials and Methods

Total RNA Isolation, Cloning and Annotation

Small RNAs were isolated from 100-200 µg of total RNA and cloned as described previously. The annotation was based on information from GenBank (http://www.ncbi.nih.gov/Genbank/), a dataset of human tRNA sequences (http://ma.wustl.edu/GtRDB/Hs/Hs-seqs.html), a dataset of human sn/snoRNA sequences (http://mbcr.bcm.tmc.edu/smallRNA/Database, snoRNA-LBME-db at http://www-snorna.biotoul.fr/index.php and NONCODE v1 at http://noncode.bioinfo.org.cn/), the microRNA registry release version 5.1, and the repeat element annotation of version 17 of the human genome assembly from UCSC (http://genome.ucse.edu).

Cell Lines and Tissues

Pituitary gland was dissected 2 hours postmortal following the written consent of the person's relatives. The identity of the person was obscured for privacy reasons. The human breast cancer cell lines MCF7 and SkBr3 were gifts of Dr. Neal Rosen (Memorial Sloan-Kettering Cancer Center, NY), and were maintained in 1:1 mixture of DME:F12 medium supplemented with 100 units/ml penicillin, 100 µg/ml streptomycin, 4 mM glutamine, and 10% heat inactivated fetal bovine serum, and incubated at 37° C. in 5% CO2. The human neuroblastoma cell line BE(2)-M17 (ATCC:CRL-2267) was maintained in 1:1 mixture of OptiMem:F12 medium supplemented with non essential amino acids, 10% heat inactivated fetal bovine serum, and incubated at 37° C. in 5% $CO_2$.

Example 2

Prediction of Novel miRNA Genes

We predicted microRNA precursors by using conservation filters as well as structural features of the hairpin and folding energy. We compared these predicted sequences to cloning results from human tissues and cell lines, as well as to sequences of experimentally verified microRNAs in other mammals. In applying similarity considerations we followed Rfam, where more than 45% of the human entries are supported by similarity to microRNAs in other mammals. Table 1 demonstrates the verified predictions. FIG. 2A shows the extension of the cluster of miR-200 to include an additional member that was verified by cloning from human tissues, located approximately 1000 nucleotides downstream to miR-200a (Table 1). FIG. 2B demonstrates the identification of two additional microRNA genes in the vicinity of miR-369, one verified by cloning and one supported by its sequence similarity to the mouse homolog (Table 1).

TABLE 1

Supporting evidence for the predicted microRNA genes in the vicinity of known microRNAs
Predicted microRNA genes supported by cloning

| Cluster founding microRNAs | Coordinates of cluster founding microRNAs[1] | | | Predicted microRNA precursor coordinates | | Supporting evidence | |
|---|---|---|---|---|---|---|---|
| | Chromosome[2] | Start | End | Start[3] | end | By cloning (this study)[4] | By similarity[5] |
| miR-200b, miR-200a | 1 (+) | 1008542 | 1009390 | 1010452 | 1010518 | miR-734-3p | miR-429 |
| miR-191(MH) | 3 (−) | 49017063 | 49017154 | 49016591 | 49016681 | miR-425-3p, 5p | Rfam: hsa-miR-425 |
| miR-127, miR-136 | 14 (+) | 99339357 | 99341161 | 99337372 | 99337503 | miR-810 | |
| | | | | 99338264 | 99338356 | miR-809 | |
| miR-299, miR-323 | 14 (+) | 99480172 | 99482195 | 99483163 | 99483242 | miR-807 | |
| miR-368 | 14 (+) | 99496068 | 99496133 | 99497151 | 99497236 | miR-376a-3p | |
| miR-134 | 14 (+) | 99511065 | 99511137 | 99512568 | 99512647 | miR-812 | |
| miR-369 | 14 (+) | 99521976 | 99522045 | 99521669 | 99521773 | miR-409-3p, 5p | Rfam: mmu-miR-409 |
| miR-144 | 17 (−) | 27334114 | 27334199 | 27333954 | 27334017 | miR-806 | cand919 |
| miR-224 (MH) | X (−) | 149744663 | 149744743 | 149745713 | 149745797 | miR-811 | |

[1] The precursor coordinates are listed. When the predicted miRNA is in the vicinity of an already known miRNA cluster, the coordinates of the whole cluster are listed, from the initial coordinate of the precursor of the first miRNA to the end coordinate of the precursor of the last miRNA.
[2] The chromosome number, strand and coordinates are taken from the UCSC July 2003 human genome assembly build 34 (hg16) (http://genome.ucsc.edu).
[3] The coordinates of predicted miRNAs are on the same chromosome and strand as the known cluster member/s.
[4] Cloned miRNAs were given new names. When miRNAs from both sides of the precursor stem were identified and matched our predictions they are designated with 3p and 5p.
[5] There are three types of supporting evidence by similarity:

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Aug. 5, 2013. The sequence listing.txt file is 145 kb in size.

What is claimed is:

1. An isolated nucleic acid molecule comprising a microRNA having SEQ ID NO: 294, said molecule having no more than 50 nucleotides, wherein the molecule is modified for increased nuclease resistance.

2. An isolated nucleic acid molecule comprising a hairpin precursor microRNA having SEQ ID NO: 388, said molecule having no more than 300 nucleotides, wherein the molecule is modified for increased nuclease resistance.

3. An isolated molecule according to claim 1, wherein the isolated molecule is a DNA molecule.

4. An isolated molecule according to claim 1, wherein the isolated molecule is a RNA molecule.

5. An isolated molecule according to claim 1, wherein the isolated molecule further comprises a cap.

6. An isolated molecule according to claim 1, wherein the cap is an inverted nucleotide cap, or a chemical cap.

7. An isolated molecule according to claim 1, wherein the isolated molecule consists of SEQ ID NO: 294.

8. An isolated molecule according to claim 2, wherein the isolated molecule consists of SEQ ID NO: 388.

9. An isolated single stranded nucleic acid molecule comprising an anti-microRNA having SEQ ID NO: 564, said molecule having no more than 50 nucleotides, wherein the molecule is modified for increased nuclease resistance.

10. A molecule according to claim 9, wherein at least one of the nucleotides is a modified deoxyribonucleotide or ribonucleotide moiety.

11. A molecule according to claim 10 wherein the modified deoxyribonucleotide is a phosphorothioate deoxyribonucleotide moiety, or a N'3-N'5 phosphoroamidate deoxyribonucleotide moiety.

12. A molecule according to claim 10, wherein the modified ribonucleotide is substituted at the 2' position.

13. A molecule according to claim 12, wherein the substituent at the 2' position is a $C_1$ to $C_4$ alkoxy-$C_1$ to $C_4$ alkyl group.

14. A molecule according to claim 13, wherein the $C_1$ to $C_4$ alkoxy-$C_1$ to $C_4$ alkyl group is methoxyethyl.

15. A molecule according to claim 10, wherein the modified ribonucleotide has a methylene bridge between the 2'-oxygen atom and the 4'-carbon atom.

16. A molecule according to claim 9, wherein at least one of the nucleotides is a peptide nucleic acid moiety.

17. A molecule according to claim 16, wherein at least one of the moieties is a T-fluororibonucleotide moiety and/or wherein at least one of the moieties is a morpholino phosphoroamidate nucleotide moiety and/or wherein at least one of the moieties is a tricyclo nucleotide moiety and/or, wherein at least one of the moieties is a cyclohexene nucleotide moiety.

18. A molecule according to claim 9, wherein the molecule is a chimeric molecule.

19. A molecule according to claim 9, wherein the molecule comprises at least one modified moiety for increased nuclease resistance.

20. A molecule according to claim 19, wherein the nuclease is an exonuclease.

21. A molecule according to claim 20, wherein the molecule comprises at least one or at least two modified moieties at the 5' end and/or at the 3' end.

22. A molecule according to claim 20, wherein the molecule comprises a cap at the 5' end, the 3' end, or both ends of the molecule.

23. A molecule according to claim 22, wherein the molecule comprises a chemical cap or an inverted nucleotide cap.

24. A molecule according to claim 19, wherein the nuclease is an endonuclease.

25. A molecule according to claim 9, wherein all of the nucleotides are nuclease resistant.

26. A molecule according to claim 9, wherein the isolated molecule consists of SEQ ID NO: 564.

27. A vector comprising the isolated nucleic acid molecule according to claim 1.

28. A vector comprising the isolated nucleic acid molecule according to claim 2.

29. A vector comprising the isolated nucleic acid molecule according to claim 9.

* * * * *